United States Patent
White et al.

(10) Patent No.: US 10,961,266 B2
(45) Date of Patent: Mar. 30, 2021

(54) CHEMOSELECTIVE METHYLENE HYDROXYLATION IN AROMATIC MOLECULES

(71) Applicant: The Board of Trustees of the University of Illinois, Urbana, IL (US)

(72) Inventors: M. Christina White, Champaign, IL (US); Jinpeng Zhao, Indianapolis, IN (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 16/569,492

(22) Filed: Sep. 12, 2019

(65) Prior Publication Data
US 2020/0087331 A1   Mar. 19, 2020

Related U.S. Application Data

(60) Provisional application No. 62/730,795, filed on Sep. 13, 2018, provisional application No. 62/814,663, filed on Mar. 6, 2019.

(51) Int. Cl.

| | | |
|---|---|---|
| *C07D 209/48* | (2006.01) | |
| *C07F 13/00* | (2006.01) | |
| *C07C 67/42* | (2006.01) | |
| *C07C 67/22* | (2006.01) | |
| *C07C 67/313* | (2006.01) | |
| *C07D 317/60* | (2006.01) | |
| *C07D 211/64* | (2006.01) | |
| *C07D 211/32* | (2006.01) | |
| *C07D 221/20* | (2006.01) | |
| *C07D 213/50* | (2006.01) | |
| *C07D 233/64* | (2006.01) | |
| *C07D 235/08* | (2006.01) | |
| *C07D 215/14* | (2006.01) | |
| *C07J 9/00* | (2006.01) | |
| *B01J 31/18* | (2006.01) | |
| *C07C 253/30* | (2006.01) | |

(52) U.S. Cl.
CPC ............ *C07F 13/005* (2013.01); *B01J 31/184* (2013.01); *C07C 67/22* (2013.01); *C07C 67/313* (2013.01); *C07C 67/42* (2013.01); *C07C 253/30* (2013.01); *C07D 209/48* (2013.01); *C07D 211/32* (2013.01); *C07D 211/64* (2013.01); *C07D 213/50* (2013.01); *C07D 215/14* (2013.01); *C07D 221/20* (2013.01); *C07D 233/64* (2013.01); *C07D 235/08* (2013.01); *C07D 317/60* (2013.01); *C07J 9/005* (2013.01); *B01J 2231/70* (2013.01); *B01J 2531/72* (2013.01); *C07B 2200/07* (2013.01); *C07C 2601/08* (2017.05)

(58) Field of Classification Search
CPC .................................................. C07F 13/005
See application file for complete search history.

(56) References Cited

U.S. PATENT DOCUMENTS

| 5,817,877 A | 10/1998 | Hartwig et al. |
|---|---|---|
| 6,307,087 B1 | 10/2001 | Buchwald et al. |
| 7,829,342 B2 | 11/2010 | White et al. |
| 7,871,855 B2 | 1/2011 | Yan et al. |
| 9,770,711 B2 | 9/2017 | White et al. |
| 9,925,528 B2 | 3/2018 | White et al. |
| 2004/0087820 A1 | 5/2004 | Fuchs et al. |
| 2009/0093638 A1 | 4/2009 | Doyle et al. |
| 2010/0063277 A1 | 3/2010 | Zhang et al. |
| 2011/0015397 A1 | 1/2011 | White et al. |
| 2012/0190635 A1 | 7/2012 | Li et al. |
| 2013/0184494 A1 | 7/2013 | Kurosawa et al. |

FOREIGN PATENT DOCUMENTS

| EP | 2099749 B1 | 9/2015 |
|---|---|---|
| JP | 2006057014 A | 3/2006 |
| WO | 2007059015 A1 | 5/2007 |
| WO | 2010028159 A2 | 3/2010 |

OTHER PUBLICATIONS

Zhao et al. (Nature Chemistry, 2019, 11, 213-221).*
Bigi et al., "Cafestol to Tricalysiolide B and Oxidized Analogues: Biosynthetic and Derivatization Studies Using Non-heme Iron Catalyst Fe(PDP)," Synlett., 23(19):2768-2772, Dec. 2012.
Bigi et al., "Directed Metal (Oxo) Aliphatic C—H Hydroxylations: Overriding Substrate Bias," J. Am. Chem. Soc., 134 (23):9721-9726, May 2012.
Chen et al., "A Predictably Selective Aliphatic C—H Oxidation Reaction for Complex Molecule Synthesis," Science, 318 (5851):783-787, Nov. 2007.
Chen et al., "Combined Effects on Selectivity in Fe-Catalyzed Methylene Oxidation," Science, 327(5965):566-571, Jan. 2010.
Dolotova et al., Zhumal Obshchei Khimii (Russian Journal of General Chemistry), 58(9):2173,1988.
Dolotova et al., Zhumal Obshchei Khimii (Russian Journal of General Chemistry), 62(9):2064-75, 1992.
Fürstner, A., "Alkene Metathesis in Organic Synthesis (Topics in Organometallic Chemistry)," 1, 1998, 7pgs.
Gormisky et al., "Catalyst-Controlled Aliphatic C—H Oxidations with a Predictive Model for Site Selectivity," J. Am. Chem. Soc., 135(38):14052-14055, Sep. 2013.
Groves et al., "Hydrocarbon Oxidations with Oxometalloporphinates. Isolation and Reactions of a (porphinato) Manganese(V) Complex," J. Am. Chem. Soc., 102(20):6375-6377, Sep. 1980.
Groves et al., "Synthesis, Characterization, and Reactivity of Oxomanganese(IV) Porphyrin Complexes," J. Am. Chem. Soc., 110(26):8628-8638, Dec. 1988.

(Continued)

*Primary Examiner* — Brian E McDowell
(74) *Attorney, Agent, or Firm* — Haukaas Fortius PLLC; Michael H. Haukaas

(57) ABSTRACT

A chemoselective and reactive Mn(CF$_3$-PDP) catalyst system that enables for the first time the strategic advantages of late-stage aliphatic C—H hydroxylation to be leveraged in aromatic compounds. This discovery will benefit small molecule therapeutics by enabling the rapid diversification of aromatic drugs and natural products and identification of their metabolites.

19 Claims, 1 Drawing Sheet

(56) References Cited

OTHER PUBLICATIONS

Gustafson et al., "Linear Free Energy Relationship Analysis of a Catalytic Desymmetrization Reaction of a Diarylmethane-Bis(Phenol)," Org. Lett., 12(12):2794-2797, May 2010.

Harper et al., "Three-Dimensional Correlation of Steric and Electronic Free Energy Relationships Guides Asymmetric Propargylation," Science, 333(6051):1875-1878, Sep. 2011.

Howell et al., "Remote Oxidation of Aliphatic C—H Bonds in Nitrogen-Containing Molecules," J Am Chem Soc., 137 (46):14590-14593, Nov. 2015.

Hung et al., "Development of a Terpene Feedstock-based Oxidative Synthetic Approach to the Illicium Sesquiterpenes," J Am Chem Soc., 141(7):3083-3099, Feb. 2019.

International Search Report and Written Opinion of the ISA/US dated Dec. 4, 2014 in International Application No. PCT/US2014/054835; 10pgs.

Knecht et al., "Synthesis and Properties of Soluble Phthalocyaninatomanganese(III) Complexes," J. Porphyrins Phthalocyanines; 3:292-298; Apr. 1999.

Liu et al., "Cyclopropanation of Alkenes Catalyzed by Metallophthalocyanines," J Mol Catal A: Chem., 246(1-2):49-52, Mar. 2006.

Nanjo et al., "Remote, Late-Stage Oxidation of Aliphatic C—H Bonds in Amide-Containing Molecules," J. Am. Chem. Soc., 139(41):14586-14591, Sep. 2017.

Olivo et al., "Supramolecular Recognition Allows Remote, Site-Selective C—H Oxidation of Methylenic Sites in Linear Amines," Angew Chem Int Ed Engl., 56(51):16347-16351, Dec. 2017.

Osberger et al., "Oxidative Diversification of Amino Acids and Peptides by Small-molecule Iron Catalysis," Nature, 537(7619):214-219, Sep. 2016.

Ottenbacher et al., "Highly Efficient, Regioselective, and Stereospecific Oxidation of Aliphatic C—H Groups with H2O2, Catalyzed by Aminopyridine Manganese Complexes," Org. Lett., 14(17):4310-4313, Jul. 2012.

Ottenbacher et al., "Highly Enantioselective Bioinspired Epoxidation of Electron-Deficient Olefins with H2O2 on Aminopyridine Mn Catalysts," ACS Catal., 4(5):1599-1606, Apr. 2014.

Paradine et al., "A Manganese Catalyst for Highly Reactive yet Chemoselective Intramolecular C(Sp3)-H Amination," Nat. Chem., 7:987-994, Oct. 2015.

Paradine et al., "Iron-Catalyzed Intramolecular Allylic C—H Amination," J. Am. Chem. Soc., 134(4):2036-2039, Jan. 2012.

Petkov et al., "Functionalization of Nanocrystalline Diamond Films with Phthalocyanines," Applied Surface Science, (Apr. 2016), vol. 379, pp. 415-423.

Ruppel et al., "Cobalt-Catalyzed Intramolecular C—H Amination with Arylsulfonyl Azides," Org. Lett., 9(23):4889-4892, Oct. 2007.

White et al., "A Synthetically Useful, Self-Assembling MMO Mimic System for Catalytic Alkene Epoxidation with Aqueous H2O2," J Am Chem Soc., 123(29):7194-7195, Jul. 2001.

White et al., "Adding Aliphatic C—H Bond Oxidations to Synthesis," Science, 335(6070):807-809, Feb. 2012.

White et al., "Aliphatic C—H Oxidations for Late-Stage Functionalization," J. Am. Chem. Soc., 140(43):13988-14009, Sep. 2018.

* cited by examiner

CHEMOSELECTIVE METHYLENE HYDROXYLATION IN AROMATIC MOLECULES

RELATED APPLICATIONS

This application claims priority under 35 U.S.C. § 119(e) to U.S. Provisional Patent Application Nos. 62/730,795 filed Sep. 13, 2018 and 62/814,663 filed Mar. 6, 2019, which applications are incorporated herein by reference.

GOVERNMENT SUPPORT

This invention was made with government support under Grant No. R35 GM122525 awarded by the National Institutes of Health. The government has certain rights in the invention.

BACKGROUND OF THE INVENTION

The majority of small molecule therapeutics are comprised of functionalized hydrocarbon scaffolds containing a mixture of $C(sp^2)$-H bonds and increasingly more $C(sp^3)$-H bonds. Reactions that effect the direct atomistic exchange of hydrogen with oxygen remote from such aromatic groups would avoid lengthy de novo synthesis for generating analogues and identifying metabolites; however, because of the challenges of hydroxylating an inert C—H bond in the presence of oxidatively more labile π-functionality, such transformations have not been fully realized in the laboratory. Iron enzymes are the only known catalysts capable of hydroxylation of strong aliphatic C—H bonds in the presence of π-functionality by means of restricted substrate access to the oxidant (FIG. 1), however, these enzymes are challenging to use on preparative scales (vide infra) and this supramolecular approach for achieving chemoselectivity has not been successful with small molecule catalysts.

Despite recent advances in small molecule catalysts for site-selective aliphatic C—H hydroxylations, none of these catalysts can effect strong aliphatic methylene C—H bond oxidation (BDE=98 kcal/mol) in the presence of a range of aromatic groups. Whereas C—H aminations, alkylations and halogenation reactions tolerate aromatic functionality, the only aromatic groups tolerated in higher energy methylene C—H hydroxylations have been electronically deactivated with strong electron withdrawing groups (that is nitro, trifluoromethyl, triflate with >0.5 $\sigma_p$ values). Ruthenium and manganese catalysts and stoichiometric oxidant TFDO are tolerant of benzoate ($\sigma_p$=0.45) and in a few cases phenyl functionality however only in the hydroxylation of weaker benzylic C—H (BDE=85 kcal/mol) or tertiary $C(sp^3)$-H bonds (BDE=96 kcal/mol).

To divert oxidation of labile aromatic functionalities, a catalyst's capacity for aliphatic hydroxylations may need to be reduced. Accordingly, there is a need for a catalyst system that enables the strategic advantages of late-stage aliphatic C—H hydroxylation to be leveraged in aromatic and other useful compounds.

SUMMARY

The present disclosure provides a chemoselective and reactive manganese catalyst that enables the strategic advantages of late-stage aliphatic C—H hydroxylation to be leveraged in aromatic compounds. This discovery will, for example, benefit small molecule therapeutics by enabling the rapid diversification of aromatic drugs and natural products and identification of their metabolites.

Accordingly, this disclosure provides a manganese complex of Formula I:

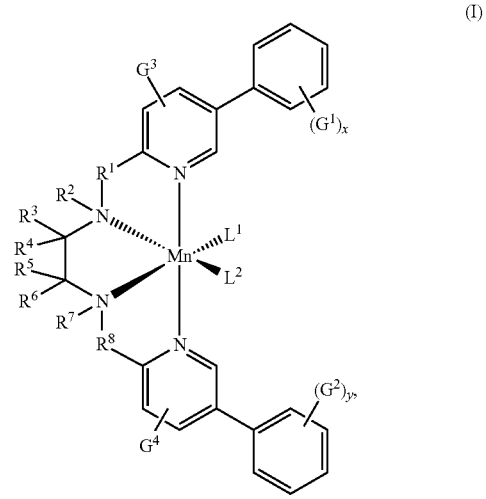

or a salt thereof;
wherein
$L^1$ and $L^2$ are each independently halo or a ligand;
each $G^1$ and each $G^2$ is independently halo, —$(C_1$-$C_6)$alkyl, —$O(C_1$-$C_6)$alkyl, or —$C(=O)O(C_1$-$C_6)$alkyl, wherein the $(C_1$-$C_6)$alkyl moiety of —$(C_1$-$C_6)$alkyl, —$O(C_1$-$C_6)$alkyl and —$C(=O)O(C_1$-$C_6)$alkyl are optionally substituted with one or more halo groups;
x and y are each independently 1-5;
$G^3$ and $G^4$ are independently H, halo, —$(C_1$-$C_6)$alkyl, —$O(C_1$-$C_6)$alkyl, —$C(=O)O(C_1$-$C_6)$alkyl, —$NO_2$, —CN, —$CF_3$, —$CF_2CH_3$, —$CF_2CF_3$, or —$NR^aR^b$ wherein $R^a$ and $R^b$ are independently H, or $(C_1$-$C_6)$alkyl;
$R^1$ and $R^8$ are each independently —$(C_1$-$C_6)$alkylene-; and
$R^2$, $R^3$, $R^4$, $R^5$, $R^6$, and $R^7$ are each independently H or $(C_1$-$C_6)$alkyl; or
$R^2$ and $R^3$ taken together with the carbon and nitrogen atoms to which they are attached form a 5- or 6-membered heterocycle;
$R^4$ and $R^5$ are each independently H or $(C_1$-$C_6)$alkyl; and
$R^6$ and $R^7$ taken together with the carbon and nitrogen atoms to which they are attached form a 5- or 6-membered heterocycle;
wherein each $(C_1$-$C_6)$alkyl is unbranched or optionally branched.

This disclosure also provides a composition comprising a complex described above in combination with one or more counter ions.

Additionally, this disclosure provides a method of oxidizing a substrate comprising contacting a substrate with an effective amount of a composition according to the compositions described herein, wherein the substrate comprises an aromatic moiety and methylene moiety, and the methylene moiety is selectively oxidized.

The disclosure further provides novel compounds of Formulas I-III, intermediates for the synthesis of compounds of Formulas I-III, as well as methods of preparing compounds of Formulas I-III. The invention also provides compounds of Formulas I-III that are useful as intermediates for the synthesis of other useful compounds. The disclosure also provides products of the oxidized compounds, as generally and specifically described herein.

In some preferred embodiments demonstrated herein, the combination of Mn(CF$_3$-PDP) 1 catalyst and chloroacetic acid additive achieves C(sp$^3$)-H oxidation with an unprecedented combination of high chemoselectivity, i.e. tolerates medicinally important aromatic functionalities, and high reactivity, i.e. preparatively oxidizes aliphatic methylene C—H bonds in the absence of directing groups or molecular recognition elements (Scheme 1).

BRIEF DESCRIPTION OF THE DRAWINGS

The following drawing forms part of the specification and is included to further demonstrate certain embodiments or various aspects of the invention. In some instances, embodiments of the invention can be best understood by referring to the accompanying drawing in combination with the detailed description presented herein.

DETAILED DESCRIPTION

Despite significant progress in the development of site-selective aliphatic C—H oxidations over the past decade, the ability to oxidize strong methylene C—H bonds in the presence of more oxidatively labile aromatic functionalities remains a major unsolved problem. Such chemoselective reactivity is highly desirable for enabling late stage oxidative derivatizations of pharmaceuticals and medicinally important natural products that often contain such functionality. Herein is reported a simple manganese small molecule catalyst Mn(CF$_3$-PDP) 1 system that achieves such chemoselectivity via an unexpected synergy of catalyst design and acid additive.

Preparative remote methylene oxidation was obtained in 50 aromatic compounds housing medicinally relevant halogen, oxygen, heterocyclic, and biaryl moieties. Late stage methylene oxidation is demonstrated on four drug scaffolds, including the ethinylestradiol scaffold where other non-directed C—H oxidants that tolerate aromatic groups effect oxidation at only activated tertiary benzylic sites. Rapid generation of a known metabolite (piragliatin) from an advanced intermediate is demonstrated.

Figure 1:
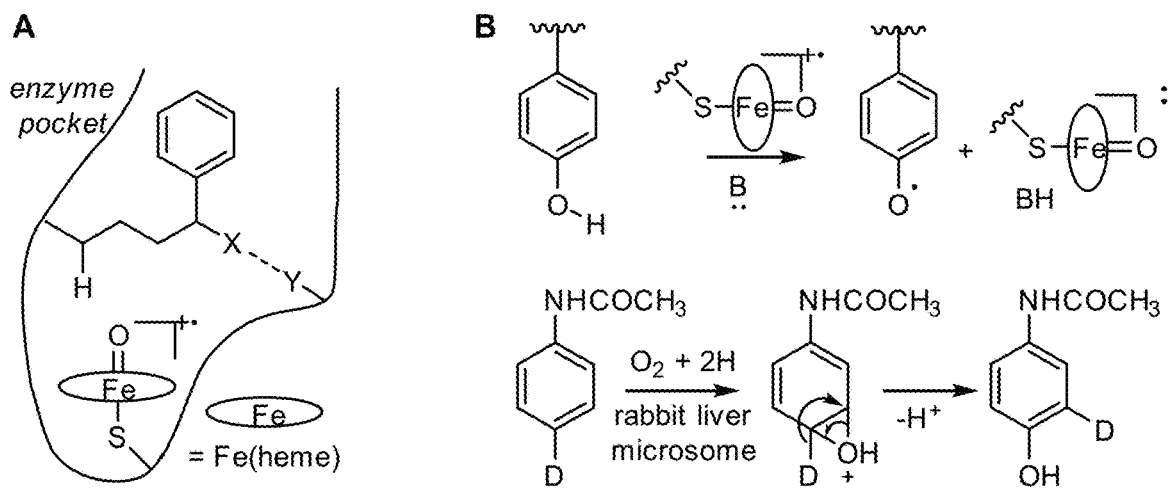
FIG. 1. A. Cytochrome P450 enzymes (CYPs) achieve such chemoselective oxidation of methylene C—H bonds by restricting the substrate's approach to the iron oxidant, however these enzymes are challenging to use preparatively. B. The two major pathways of aromatic oxidation with the iron(oxo) oxidants generated in CYPs are electron transfer (top) or epoxidation followed by hydride shift (e.g., the "NIH shift", bottom).

Enzymatic and small molecule approaches for C—H oxidation are shown in FIG. 1 and Scheme 1 below. A chemoselective small molecule catalyst capable of strong methylene C—H bond oxidations in the presence of the more oxidatively labile π-functionality of aromatic groups was previously unknown.

Scheme 1.
A. Small molecule catalyst Mn(CF$_3$-PDP) 1 achieves chemoselective hydroxylation of strong methylene C—H bonds in presence of aromatic functionalities. This reactivity is orthogonal to other oxidants that perform weaker bond oxidants (for example benzylic C—H) in the presence of aromatic functionality as demonstarted with an ethinylestradiol derivative. R$_1$-R$_4$ can be H, OH, alkyl, or a value defined herein for substituents and/or R$_1$-R$_4$ groups.
B. The crystal structure of the Mn(CF$_3$-PDP)Cl$_2$ precatalyst shows the bulky ligand framework thought to be critical for the high chemoselectivity achieved with Mn(CF$_3$-PDP)(CH$_3$CN)$_2$•(SbF$_6$)$_2$ catalyst [Mn(CF$_3$-PDP)] 1.

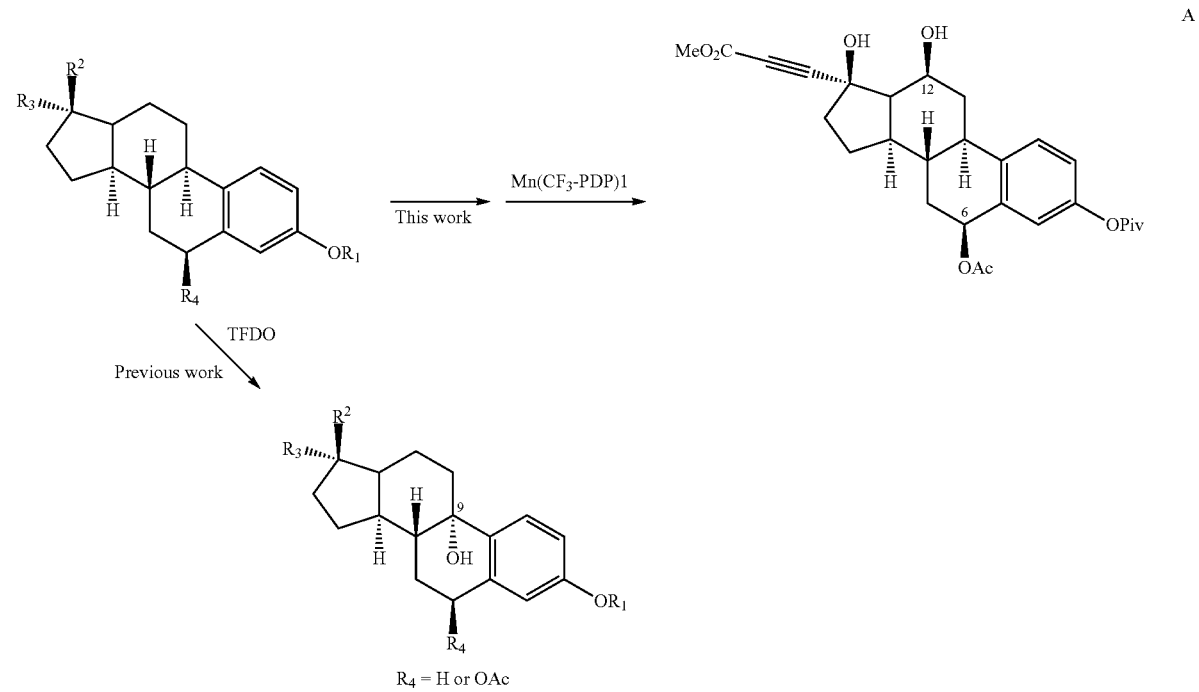

-continued

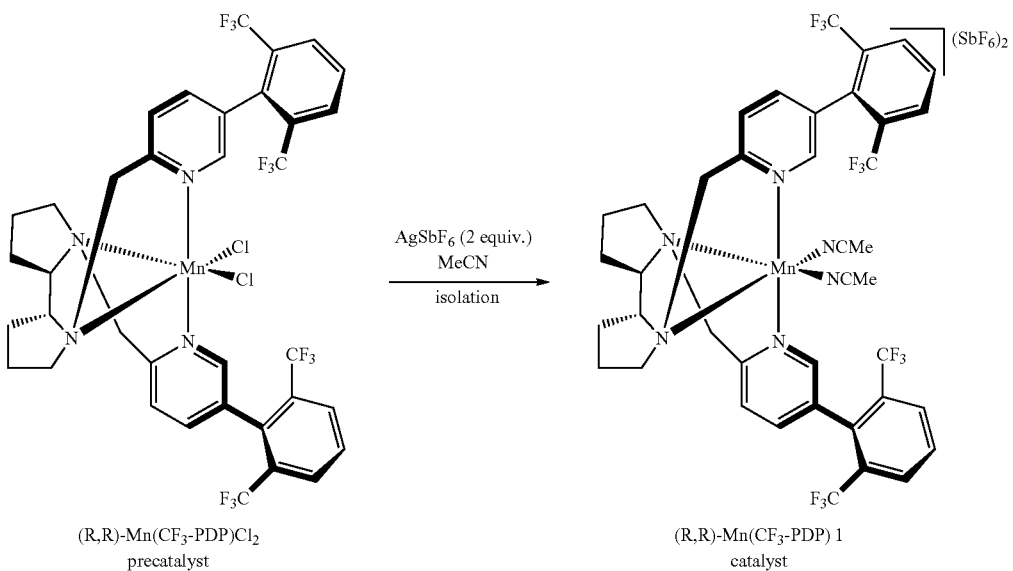

(R,R)-Mn(CF$_3$-PDP)Cl$_2$
precatalyst (R,R)-Mn(CF$_3$-PDP) 1
catalyst

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or terths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into subranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms; or for example, a range between 1-20 carbon atoms, such as 2-6, 3-6, 2-8, or 3-8 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings that can be oxidized by the methods disclosed herein. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" or "heterocycle" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aromatic" refers to either an aryl or heteroaryl group or substituent described herein. Additionally, an aromatic moiety may be a bisaromatic moiety, a trisaromatic moiety, and so on. A bisaromatic moiety has a single bond between two aromatic moieties such as, but not limited to, biphenyl, or bipyridine. Similarly, a trisaromatic moiety has a single bond between each aromatic moiety.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. In other embodiments, the aryl group can have 6 to 60 carbons atoms, 6 to 120 carbon atoms, or 6 to 240 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof Such as racemic mixtures, form part of the present invention. Many organic compounds exist in optically active forms, i.e., they have the ability to rotate the plane of plane-polarized light. In describing an optically active compound, the prefixes D and L, or R and S. are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate (defined below), which may occur where there has been no stereoselection or stereospecificity in a chemical reaction or process.

In a molecule, the term "stereocenter" refers to a particular instance of a stereogenic element that is geometrically a point. A stereocenter or stereogenic center is any point in a molecule, though not necessarily an atom, bearing groups, such that an interchanging of any two groups leads to a stereoisomer. A chiral center is a stereocenter consisting of an atom holding a set of ligands (atoms or groups of atoms) in a spatial arrangement which is not superimposable on its mirror image.

The terms "racemic mixture" and "racemate" refer to an equimolar mixture of two enantiomeric species, devoid of optical activity.

The term "enantiomerically enriched" ("ee") as used herein refers to mixtures that have one enantiomer present to a greater extent than another. Reactions that provide one enantiomer present to a greater extent than another would therefore be "enantioselective" (or demonstrate "enantioselectivity"). In one embodiment, the term "enantiomerically enriched" refers to a mixture having at least about 2% ee; in another embodiment of the invention, the term "enantiomerically enriched" refers to a mixture having at least about 5% ee; in another embodiment of the invention, the term "enantiomerically enriched" refers to a mixture having at least about 20%; in another embodiment of the invention, the term "enantiomerically enriched" refers to a mixture having at least about 50%; in another embodiment of the invention, the term "enantiomerically enriched" refers to a mixture having at least about 80%; in another embodiment of the invention, the term "enantiomerically enriched" refers to a mixture having at least about 90%; in another embodiment of the invention, the term "enantiomerically enriched" refers to a mixture having at least about 95%; in another embodiment of the invention, the term "enantiomerically enriched" refers to a mixture having at least about 98%; in another embodiment of the invention, the term "enantiomerically enriched" refers to a mixture having at least about 99%. The term "enantiomerically enriched" includes enantiomerically pure mixtures which are mixtures that are substantially free of the species of the opposite optical activity or one enantiomer is present in very low quantities, for example, 0.01%, 0.001% or 0.0001%.

The term "sp$^3$ hybridization" means that an atom is bonded and/or coordinated in a configuration having a tetrahedral character. The term "unactivated sp$^3$-hybridized C—H bond" typically refers to aliphatic C—H bonds which are unreactive. Conversely, electron withdrawing groups or groups that can stabilize the breakage of the C—H bond by conjugation, for example a phenyl group, to some extent activate the C—H bond, thereby increasing its propensity for reacting when contacting certain reagents. In this disclosure, benzylic C—H bonds in a substrate are activated relative to non-benzylic C—H bonds.

The term "oxo bridge" refers to a transition metal coordination complex comprising an oxo ligand. Formally O$^{2-}$, an oxo ligand can be bound to one or more metal centers, i.e., it can exist as a) a terminal ligand, or b) a bridging ligand, as shown below:

a)

b)
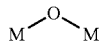

wherein M is a transition metal. The oxo ligands disclosed herein are typically terminal oxo ligands.

The term "product selectivity" or just "selectivity" is the ability to favor a certain product over others in an organic reaction where multiple products could potentially be generated from one substrate. Product selectivity includes stereoselectivity and regioselectivity; the former refers to the selectivity for a stereoisomer and the later for constitutional isomer. Product selectivity is usually observed when one reaction pathway is preferred and is often expressed as the ratio of product isomers or the ratio of rate constants for reaction pathways that generate those product isomers.

Embodiments of the Invention

This disclosure provides a manganese complex of Formula I:

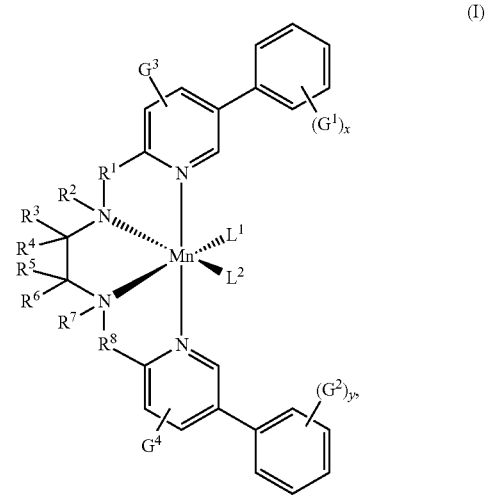

(I)

or a salt thereof;
wherein
L$^1$ and L$^2$ are each independently halo or a ligand;
each G$^1$ and each G$^2$ is independently halo, —(C$_1$-C$_6$)alkyl, —O(C$_1$-C$_6$)alkyl, or —C(=O)O(C$_1$-C$_6$)alkyl, wherein the (C$_1$-C$_6$)alkyl moiety of —(C$_1$-C$_6$)alkyl, —O(C$_1$-C$_6$)alkyl and —C(=O)O(C$_1$-C$_6$)alkyl are optionally substituted with one or more halo groups;
x and y are each independently 1-5;
G$^3$ and G$^4$ are independently H, halo, —(C$_1$-C$_6$)alkyl, —O(C$_1$-C$_6$)alkyl, —C(=O)O(C$_1$-C$_6$)alkyl, —NO$_2$, —CN, —CF$_3$, —CF$_2$CH$_3$, —CF$_2$CF$_3$, or —NR$^a$R$^b$ wherein R$^a$ and R$^b$ are independently H, or —(C$_1$-C$_6$)alkyl;
R$^1$ and R$^8$ are each independently —(C$_1$-C$_6$)alkylene-; and
R$^2$, R$^3$, R$^4$, R$^5$, R$^6$, and R$^7$ are each independently H or —(C$_1$-C$_6$)alkyl; or
R$^2$ and R$^3$ taken together with the carbon and nitrogen atoms to which they are attached form a 5- or 6-membered heterocycle;
R$^4$ and R$^5$ are each independently H or (C$_1$-C$_6$)alkyl; and
R$^6$ and R$^7$ taken together with the carbon and nitrogen atoms to which they are attached form a 5- or 6-membered heterocycle;
wherein each —(C$_1$-C$_6$)alkyl is unbranched or optionally branched.

In some embodiments, the complex is an (S,S) enantiomer. In some other embodiments, the complex is an (R,R) enantiomer. The stereocenters being referred to in Formula I that define the (S,S) and (R,R) enantiomers are the carbon atoms at the —(R$^3$)(R$^4$)C— moiety and the —(R$^5$)(R$^6$)C— moiety. In additional embodiments, the complex is a salt and the anion of the salt is Cl$^-$, Br$^-$, AcO$^-$, TfO$^-$, CF$_3$CO$_2^-$, BF$_4^-$, ClO$_4^-$, ReO$_4^-$, AsF$_6^-$, PF$_6^-$, or SbF$_6^-$. In further embodiments, L$^1$ and L$^2$ are each independently chloro, acetone, acetonitrile, or a terminal oxo bridge; or L$^1$ and L$^2$ together are a carboxylate group.

In various embodiments, each G$^1$ and each G$^2$ is independently —(C$_1$-C$_6$)alkyl substituted with one or more halo groups. In other various embodiments, each G$^1$ is independently chloro, methyl, ethyl, isopropyl, tert-butyl, —OCH$_3$, —C(=O)OCH$_3$, —C(=O)OC(CH$_3$)$_3$, —CF$_3$, —CF$_2$CH$_3$, or —CF$_2$CF$_3$. In some further embodiments, each G$^2$ is independently chloro, methyl, ethyl, isopropyl, tert-butyl, —OCH$_3$, —C(=O)OCH$_3$, —C(=O)OC(CH$_3$)$_3$, —CF$_3$, —CF$_2$CH$_3$, or CF$_2$CF$_3$. In yet other embodiments, x and y are each independently 2 or 3. In additional embodiments, G$^3$ and G$^4$ are at the 4-position of the pyridyl moiety of Formula I. In certain embodiments, G$^3$ and G$^4$ are electron withdrawing groups or electron donation groups. In certain other embodiments, G$^3$ and G$^4$ are electron withdrawing groups, for example when the (C$_1$-C$_6$)alkyl moiety of —(C$_1$-C$_6$)alkyl, —O(C$_1$-C$_6$)alkyl and —C(=O)O(C$_1$-C$_6$)alkyl are optionally substituted with one or more halo groups.

This disclosure also provides a complex of Formula I is a complex of Formula II:

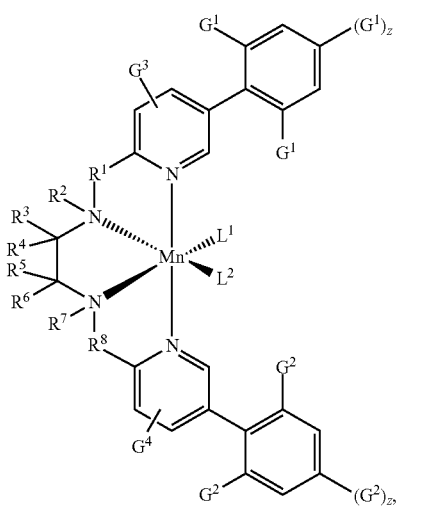

(II)

or salt thereof; wherein z is 0 or 1. In some embodiments, each G$^1$ and each G$^2$ is independently chloro, methyl, ethyl, isopropyl, tert-butyl, —OCH$_3$, —C(=O)OCH$_3$, —C(=O)OC(CH$_3$)$_3$, —CF$_3$, —CF$_2$CH$_3$, or —CF$_2$CF$_3$. In other embodiments, z is 0, therefore G$^1$ and G$^2$ at the para-positions are absent. In additional embodiments, R$^1$ and R$^8$ are each —CH$_2$—.

Additionally, this disclosure provides a complex of Formula I is a complex of Formula III:

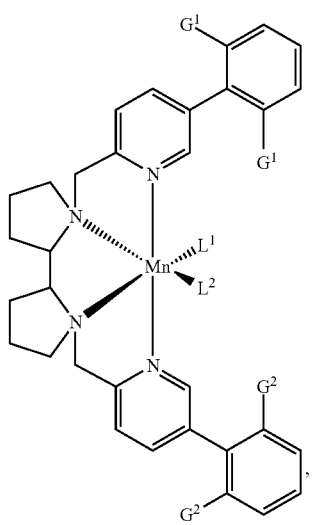

(III)

or salt thereof. In some embodiments, each G$^1$ and each G$^2$ is independently chloro, methyl, ethyl, isopropyl, tert-butyl, —OCH$_3$, —C(=O)OCH$_3$, —C(=O)OC(CH$_3$)$_3$, —CF$_3$, —CF$_2$CH$_3$, or —CF$_2$CF$_3$. In other embodiments, the complex is (R,R)—Mn(CF$_3$-PDP):

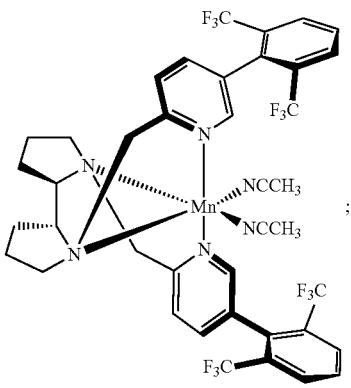

or the (S,S) enantiomer thereof or salt thereof.

This disclosure also provides a composition comprising a complex of disclosed above in combination with one or more counter ions. In various embodiments, the one or more counter ions are Cl$^-$, Br$^-$, AcO$^-$, TfO$^-$, CF$_3$CO$_2^-$, BF$_4^-$, ClO$_4^-$, ReO$_4^-$, AsF$_6^-$, PF$_6^-$, or SbF$_6^-$. In additional embodiments, the disclosed composition is in combination with an oxidant and optionally an acid. In other embodiments, the oxidant comprises hydrogen peroxide, ozone, a peracid, an alkyl hydroperoxide, a periodinane, or a combination thereof.

This disclosure further provides a method of oxidizing a substrate comprising contacting a substrate with an effective amount of a composition according to the compositions described herein, wherein the substrate comprises an aromatic moiety and methylene moiety, and the methylene moiety is selectively oxidized. In other embodiments, the substrate comprises an organic molecule, wherein the organic molecule comprises carbon and hydrogen atoms, and may further comprise heteroatoms and metals. The substrate may also be a polymer or copolymer.

In additional embodiments, contacting the substrate with an effective amount of an oxidant and a complex are performed under suitable conditions, as defined herein. Suitable conditions refer to reaction conditions such as, but not limited to, the reaction temperature, the type of solvent, the concentration (or equivalents) of each different molecule, reagent, additive, etc. that is in the reaction mixture, the order or method of adding reagents to the reaction mixture, the type of recation vessel, the reaction pressure, the presence or absence of an inert atmosphere and/or moisture, and the reaction time. In further embodiments, the reaction temperature is about −80° C. to about 80° C., about −40° C. to about 40° C., or −20° C. to about 20° C.

In some embodiments, said method further comprising contacting the substrate with an effective amount of a Lewis acid, a halogenated organic acid, or a combination thereof. In various other embodiments, selective oxidation of a substrate is performed when the substrate comprises a basic amine. In some other embodiments the amine of an oxidizable substrate is complexed to an acid, such as a Lewis acid.

In other embodiments, the methylene moiety of the substrate comprises an unactivated sp$^3$-hybridized C—H bond, wherein the C—H bond is selectively oxidized (Table 1)

because the oxidation potential of manganese is sufficiently low to make it oxidatively less promiscuous, and the steric interactions of the catalyst ligands and the substrate favor remote oxidation of more sterically accessible methylene sites on the substrate. In further embodiments, a sterically unhindered C—H bond in a substrate is selectively oxidized over a sterically hindered C—H bond (e.g. oxidation of gamma-methylene favored over beta-methylene; Table 1). In other embodiments, a primary or secondary aliphatic C—H bond is selectively oxidized over a benzylic C—H bond, for example compounds 35 (Table 2) and 45 (Scheme 2). In additional embodiments, the more acidic C—H bond in a molecule is oxidized (e.g., compound 64; Scheme 3), or the less acidic C—H bond (e.g., compound 52, Scheme 2). In some other embodiments, the C—H bond in a substrate (e.g., a natural product) that is most accessible to the reactive site of metal catalyst described herein is the C—H bond that is selectively oxidized (e.g., compound 73 and 74; Scheme 3).

In yet other embodiments, the C—H bond is a sterically unhindered C—H bond and is selectively oxidized to an alcohol moiety or a carbonyl moiety. In other embodiments, hyperconjugative activation of an alcohol formed by an oxidation method disclosed herein promotes subsequent oxidation to the ketone. In additional embodiments, the oxidation of a substrate such as a natural product is diasteroselective. In further embodiments, the oxidation of a substrate such as a natural product is steroselective (Scheme 3). In various other embodiments, the composition is enantiomerically enriched and matched or mismatched to the substrate, the substrate has at least one stereocenter and the C—H bond is selectively oxidized to an alcohol moiety, and the alcohol moiety has the (S)- or (R)-configuration.

In various aspects, this disclosure provides a composition comprising a complex of Formula IB:

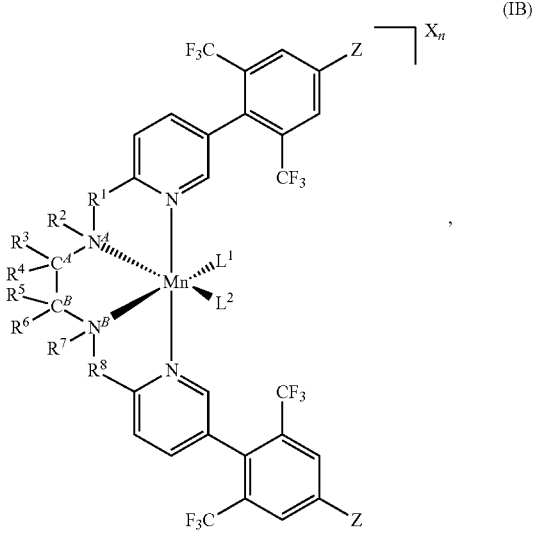

(IB)

or a salt thereof; wherein
X is a counterion;
n is 2 or 3;
$L^1$ and $L^2$ are ligands;
each Z is independently H or $CF_3$;
$R^1$, $R^2$, $R^7$ and $R^8$ are each independently an alkyl group, a heteroalkyl group, an aryl group, and a heteroaryl group;

$R^3$, $R^4$, $R^5$ and $R^6$ are each independently hydrogen, halo, alkyl, heteroalkyl, aryl, and heteroaryl;

$C^A$ and $C^B$ are carbon atoms and $N^A$ and $N^B$ are nitrogen atoms, where the superscript on the atoms denote their separate locations;

$C^A$ and $N^A$, in combination with at least one pair of groups selected from the group consisting of $R^1$ and $R^3$, $R^1$ and $R^4$, $R^2$ and $R^3$, and $R^2$ and $R^4$, form a pyrrolidine ring; and $C^B$ and $N^B$, in combination with one pair of groups selected from the group consisting of $R^8$ and $R^6$, $R^8$ and $R^5$, $R^7$ and $R^6$, and $R^7$ and $R^5$, form a pyrrolidine ring; and wherein $C^A$ and $C^B$, together with at least one pair of groups selected from the group consisting of $R^3$ and $R^5$, $R^4$ and $R^6$, $R^4$ and $R^5$, and $R^3$ and $R^6$, optionally form a cyclopentenyl ring.

In other aspects, the complex of Formula IB is Formula IC:

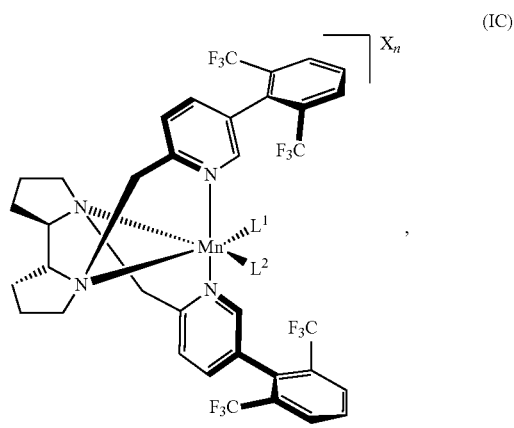

(IC)

or its (S,S) enantiomer;
wherein
$L^1$ and $L^2$ are each independently halo or a ligand;
X is a counterion selected from the group consisting of $Cl^-$, $Br^-$, $AcO^-$, $TfO^-$, $CF_3CO_2^-$, $BF_4^-$, $ClO_4^-$, $ReO_4^-$, $AsF_6^-$, and $SbF_6^-$; and n is 2 or 3. In some other embodiments, $L^1$ and $L^2$ are acetonitrile.

In yet additional aspects, this disclosure provides a method of oxidizing an organic substrate comprising contacting the organic substrate and an oxidant in a first reaction mixture, wherein the first reaction mixture comprises a composition disclosed above, thereby oxidizing the organic substrate to provide an oxidized product. In other aspects, said oxidized product in a second reaction mixture contacts an oxidant and a composition disclosed above, thereby further oxidizing the oxidized product to provide a second oxidized product.

In other embodiments, any one of the manganese catalysts disclosed herein is useful for selective oxidation of a marketed compound, a regulatory approved compound, a biologically active pharmaceutical ingredient. In further embodiments, any one of the manganese catalysts disclosed herein is useful for selective oxidation of a compound, wherein compound has a steroid structure or steroid core structure. In various embodiments, the compound is an antiinflamitory drug, an anticancer drug, a pain reliever, a drug for the central nervous system, a drug for metabolic or immune disorders, an antibiotic, an antiviral, an antiinfective, or a cardiovasucar drug.

Results and Discussion

Reaction development. An initial investigation performed was the oxidation of secondary methylene substrate 2 having a mildly electron withdrawing bromo-substituted aryl moiety ($\sigma_p$=0.23) with oxidants capable of oxidizing benzylic and tertiary C(sp$^3$)H bonds in the presence of benzoates. Stoichiometric oxidant TFDO [methyl(trifluoromethyl)dioxirane] was evaluated under low temperature conditions that prevent free-radical formation (*J. Org. Chem.* 1996, 61, 5564) as well as more forcing conditions. Only the later were effective at producing methylene oxidized product albeit in poor yields and chemoselectivity (Table 1, entries 1-2). Ruthenium catalysts purported to be highly chemoselective for benzylic and tertiary C(sp$^3$)H oxidations [Ru(Me$_3$TACN)] and cis-[Ru(dtbyp)$_2$Cl$_2$] were not effective in oxidizing stronger methylene bonds (entry 3-4). Known manganese catalysts Mn(OTf)$_2$/bipyridine, Mn(PDP)(OTf)$_2$ (*Org. Lett.* 2015, 17, 6066), were evaluated under their previously reported conditions for C(sp$^3$)-H bond oxidation and found to furnish 3 in poor yields but encouraging chemoselectivities (entries 5-6).

The two primary mechanisms for aromatic oxidation with iron oxo enzymes (CYP450s) are single electron pathways at aromatic protein residues to generate radicals and epoxidation of aromatic substrates followed by a rearrangement/hydride shift ("NIH shift') to generate phenols (FIG. 1B). It is well-precedented that a switch from iron to manganese in catalysts that oxidize C—H bonds via high-valent metal heteroatom species (that is, metal oxos and nitrenes) leads to a reduction in their oxidation potential that may alter their reactivity and chemoselectivity. Studies disclosed herein evaluated the non-heme FePDP 4 catalyst [Fe(PDP)(SbF$_6$)$_2$], previously demonstrated to hydroxylate strong aliphatic C—H bonds (*Science* 2007, 318, 783), and its direct manganese analogue MnPDP 5 [Mn(PDP)(SbF$_6$)$_2$], each thought to proceed via metal(oxo) intermediates (Table 1, entries 7-8).

Under analogous conditions, both catalysts proceeded with poor yields of desired methylene oxidized products. However, in the case of the manganese catalyst, the chemoselectivity for 2° oxidized product was significantly higher than that of its iron counterpart (entries 7-8). Although increased reactivity with similar chemoselectivity is observed by switching from the iterative addition protocol to the more forcing slow addition protocol, a preparatively useful yield could not be achieved (36% yield, entry 9).

It was hypothesized that the restricted approach trajectory and enhanced electrophilicity provided to the metal(oxo) by appropriate ligand modifications could enhance chemoselectivity. A bulky, electrophilic metal(oxo) should prefer an electron rich methylene C—H bond over a relatively electron deficient and more sterically demanding π-system. The sterically and electronically modified non-heme catalyst Fe(CF$_3$-PDP) 6 [Fe(CF$_3$-PDP)(SbF$_6$)$_2$] was reported to have preferential reactivity for methylene versus tertiary aliphatic C—H bonds (*J. Am. Chem. Soc.* 2013, 135, 14052). The catalysts Fe(CF$_3$-PDP) 6 and its manganese analogue Mn(CF$_3$-PDP) 1 [Mn(CF$_3$-PDP)(SbF$_6$)$_2$] were evaluated. It was found that both catalysts gave lower yields of 3 than Mn(PDP) 5 (entry 9), whereas novel catalyst Mn(CF$_3$-PDP) 1 was unique in affording very high chemoselectivity (Table 1, entries 10-11). Analogous site-selectivity trends to those previously reported with Fe(CF$_3$-PDP) were observed, with Mn(CF$_3$-PDP) 1 favoring remote oxidation on the more sterically accessible methylene site (vide infra). Hyperconjugative activation by the alcohol of the methine C—H bond promotes subsequent oxidation to the ketone.

The electrophilicity of the presumed manganese oxo intermediate may additionally be tuned with the inclusion of acid additives, previously shown to modulate reactivity and selectivity with metal(oxo) species. Acetic acid in non-heme iron-catalyzed C—H oxidations enhances reactivity, likely by binding and delivery of a proton to the H$_2$O$_2$ at the metal center to promote metal(oxo) carboxylate formation. Carboxylic acid containing substrates are able to direct C—H hydroxylations to electronically and sterically disfavored sites, providing compelling evidence for carboxylate as an ancillary ligand to Fe(PDP) 4 during oxidation. To probe this effect on the electronics of Mn(CF$_3$-PDP) 1, electron deficient carboxylic acids in combination with 1 was examined. It was found that both chloro- and dichloroacetic acid significantly increased yields for methylene oxidation, however only chloroacetic acid maintained good chemoselectivities (Table 1, entries 12-13).

TABLE 1

Reaction development of Mn(CF$_3$-PDP) 1 catalysis.

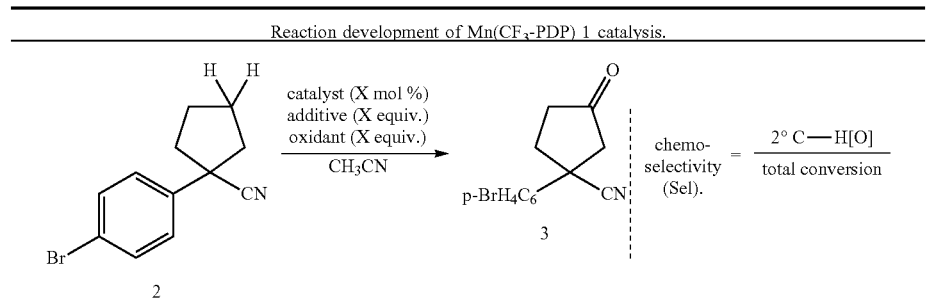

| Entry | Catalyst | Additive | Oxidant | Temperature | Yield | Sel. |
|---|---|---|---|---|---|---|
| 1 | — | — | TFDO 3 equiv. | −20° C. | trace | N.D. |
| 2 | — | — | TFDO 3 (6) equiv. | 0° C. | trace (11%) | N.D. (18%) |
| 3 | Ru(Me$_3$TACN) (2%) | — | CAN 2 × 3 equiv. | RT | trace | N.D. |
| 4 | cis-Ru(dtbpy)$_2$Cl$_2$ (5%) | — | H$_5$IO$_6$ 2 equiv. | RT | 0% | N.D. |
| 5 | Mn(OTf)$_2$, 0.1%; bipy, 1% | — | AcOOH 3 equiv. | RT | 26% | 43% |

TABLE 1-continued

Reaction development of Mn(CF$_3$-PDP) 1 catalysis.

$$\text{substrate 2} \xrightarrow[\text{CH}_3\text{CN}]{\substack{\text{catalyst (X mol \%)}\\ \text{additive (X equiv.)}\\ \text{oxidant (X equiv.)}}} \text{product 3} \quad \text{chemo-selectivity (Sel).} = \frac{2°\text{C}-\text{H[O]}}{\text{total conversion}}$$

| Entry | Catalyst | Additive | Oxidant | Temperature | Yield | Sel. |
|---|---|---|---|---|---|---|
| 6 | Mn(PDP)(OTf)$_2$ (0.1%) | CH$_3$COOH 14 equiv. | H$_2$O$_2$ 2.5 equiv. | 0° C. | 9% | 69% |
| 7 | Fe(PDP) 4 (3 × 5%) | CH$_3$COOH 3 × 0.5 equiv. | H$_2$O$_2$ 3 × 1.2 equiv. | RT$^a$ | 1% | 2% |
| 8 | Mn(PDP) 5 (3 × 5%) | CH$_3$COOH 3 × 0.5 equiv. | H$_2$O$_2$ 3 × 1.2 equiv. | RT$^a$ | 7% | 59% |
| 9 | 5 (25%) | CH$_3$COOH 5 equiv. | H$_2$O$_2$ 9 equiv. | RT$^b$ | 36% | 71% |
| 10 | Fe(CF$_3$—PDP) 6 (25%) | CH$_3$COOH 5 equiv. | H$_2$O$_2$ 9 equiv. | RT$^b$ | 24% | 27% |
| 11 | Mn(CF$_3$—PDP) 1 (25%) | CH$_3$COOH 5 equiv. | H$_2$O$_2$ 9 equiv. | RT$^b$ | 21% | 95% |
| 12 | 1 (25%) | ClCH$_2$CO$_2$H (5 equiv.) | H$_2$O$_2$ 9 equiv. | RT$^b$ | 73% | 90% |
| 13 | 1 (25%) | Cl$_2$CHCO$_2$H (5 equiv.) | H$_2$O$_2$ 9 equiv. | RT$^b$ | 66% | 77% |
| 14 | 5 (25%) | ClCH$_2$CO$_2$H (5 equiv.) | H$_2$O$_2$ 9 equiv. | RT$^b$ | 32% | 65% |
| 15 | 1 (10%) | ClCH$_2$COOH (15 equiv.) | H$_2$O$_2$ 10 equiv. | 0° C.$^c$ | 86% | 94% |
| 16 | 5 (10%) | ClCH$_2$COOH (15 equiv.) | H$_2$O$_2$ 10 equiv. | 0° C.$^c$ | 38% | 85% |
| 17 | 6 (10%) | ClCH$_2$COOH (15 equiv.) | H$_2$O$_2$ 10 equiv. | 0° C.$^c$ | 5% | 7% |
| 18 | 1 (10%) | CH$_3$COOH (15 equiv.) | H$_2$O$_2$ 10 equiv. | 0° C.$^c$ | 20% | 75% |

Isolated yields are an average of two (TFDO) or three (all catalytic reactions) runs. TFDO, Methyl(trifluoromethyl) dioxirane; Me3TACN, N,N',N''-trimethyl-1,4,7-triazacyclononane; CAN, ceric ammonium nitrate; dtbpy, 4,4'-di-tert-butyl-2,2'-bipyridine; bipy, 2,2'-bipyridine; PDP, 1,1'-bis(pyridin-2-ylmethyl)-2,2'-bipyrrolidine; CF$_3$-PDP, 1,1'-bis((5-(2,6-bis(trifluoro-methyl)phenyl)pyridin-2-yl)methyl)-2,2'-bipyrrolidine; RT, room temperature. SbF$_6$-[hexafluoroantimony(V)] is used as counterion for catalyst 1, 4-6. $^a$Iterative addition protocol. $^b$Slow addition protocol. $^c$Single catalyst addition (method A), standard procedure for Mn(CF$_3$-PDP) 1 used unless otherwise noted: substrate (0.3 mmol) with Mn(CF$_3$-PDP) 1 (0.03 mmol) and ClCH2CO2H (4.5 mmol) dissolved in MeCN (0.6 mL) maintained at 0° C., a solution of H$_2$O$_2$ (50% wt., 3.0 mmol) in MeCN (3.75 mL, 0.8 M) was added via syringe pump over 3 hours.

Interestingly, chloroacetic acid did not show the same beneficial effect with the Mn(PDP) 5 catalyst for methylene oxidations (entry 14). Catalyst 1 loadings were decreased (25 mol %→10 mol %) and the yield was enhanced by increasing acid and H$_2$O$_2$ equivalents, decreasing reaction temperature (room temperature→0° C.) and modifying the addition protocol (entry 15, see Table 3 in Examples section for details). Under these optimized conditions, neither Mn(PDP) 5 nor Fe(CF$_3$-PDP) 6 showed significant improvements (entries 16-17), indicating that the catalyst is one critical component; however, switching back to acetic acid under these optimized conditions with 1 also led to significant diminishments in the yield and chemoselectivity for this oxidation (entry 18). Collectively, these results suggest a synergy between the acid additive and catalyst to furnish a remarkable amalgamation of reactivity and chemoselectivity.

Reaction scope. To assess the ability of aromatic groups to tolerate methylene oxidation reactions with 1, a cyclopentane substrate with electronically and sterically varied aromatic substituents (Table 2) was evaluated. A cyclopentane substrate with a phenyl substituent afforded poor yields of remote oxidation product 7 due competitive aromatic oxidation. Consistent with the hypothesis that π-oxidation is more sterically demanding than C(sp$^3$)-H hydroxylation oxidation, introduction of an electron rich but bulky tert-butyl (t-Bu) substituent blocks aromatic oxidation to afford desired methylene oxidation product 8 in 65% yield. Significantly, electron rich and unsubstituted aromatic groups are also susceptible to CYP450 oxidations and this source of metabolic instability may account the observation that approximately 50% of top leading drugs on the market are halogenated. Mildly electron withdrawing halogen substituted aromatic groups, are all well tolerated in this reaction: bromine ($\sigma_p$=0.23), chlorine ($\sigma_p$=0.23) and even fluorine ($\sigma_p$=0.06) substituted substrates all afford synthetically useful yields of methylene oxidation products 3 (86%, Table 1, entry 15), 9 (81%, Table 2) and 10 (56%).

TABLE 2
Substrate scope of Mn(CF₃—PDP) 1 catalyzed chemoselective C—H hydroxylation.
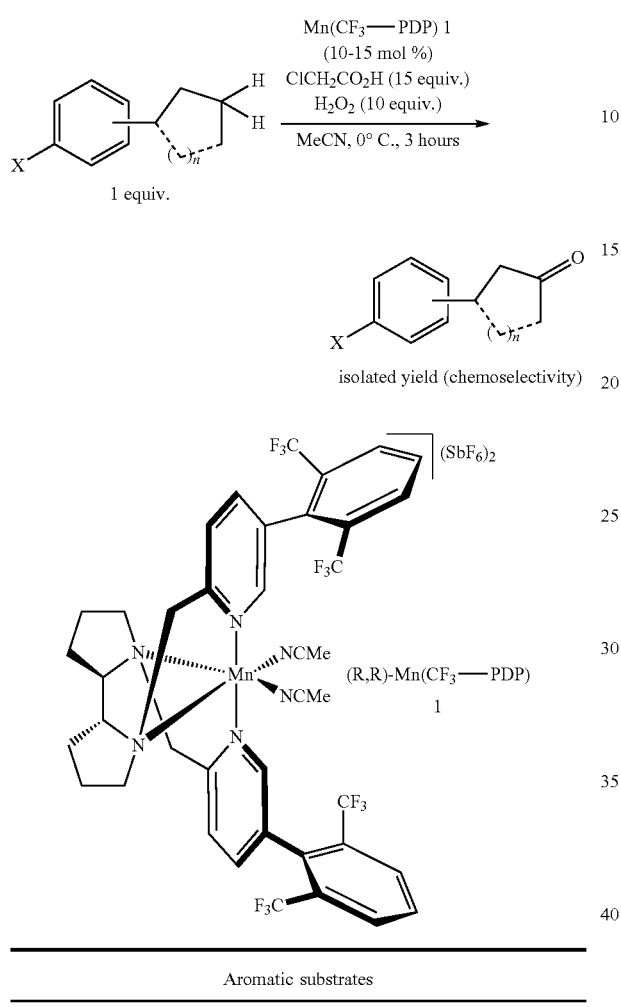
Aromatic substrates
| X = H | 7, 10% (12%) |
| t-Bu | 8, 65% (73%) |
| Cl | 9, 81% (89%) |
| gram scale (5 mol % 1) | 72% (84%) |
| F | 10, 56%$^a$ (63%) |
| NPhth | 11, 63% (78%) |
12, 73% (87%)
cat. 6$^b$: 11% (11%)
TABLE 2-continued
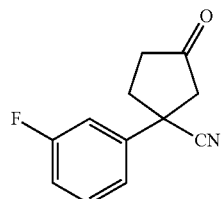
13, 66% (82%)
cat. 6$^b$: 11% (18%)
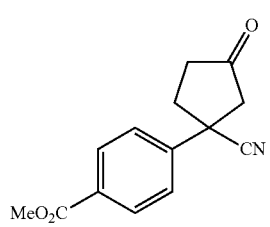
14, 84% (95%)
cat. 6$^b$: 28% (30%)
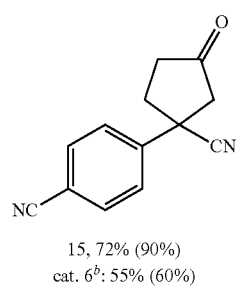
15, 72% (90%)
cat. 6$^b$: 55% (60%)
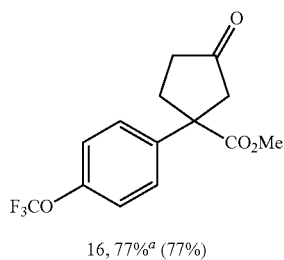 [SMILES: COC(=O)C1(c2ccc(OC(F)(F)F)cc2)CCC(=O)C1]
16, 77%$^a$ (77%)
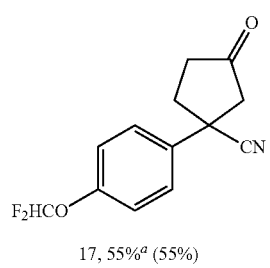 [SMILES: N#CC1(c2ccc(OC(F)F)cc2)CCC(=O)C1]
17, 55%$^a$ (55%)

TABLE 2-continued
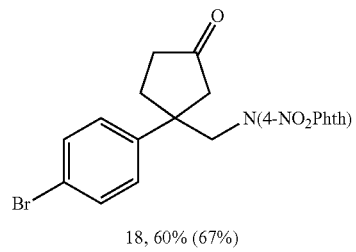
18, 60% (67%)
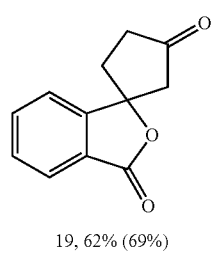 [SMILES: O=C1CCC2(C1)OC(=O)c1ccccc12]
19, 62% (69%)
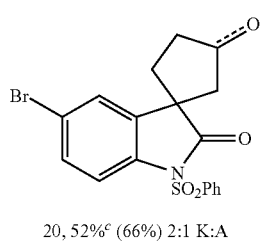
20, 52%[c] (66%) 2:1 K:A
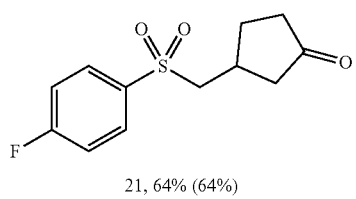 [SMILES: O=C1CCC(CS(=O)(=O)c2ccc(F)cc2)C1]
21, 64% (64%)
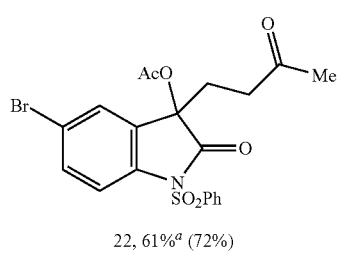
22, 61%[a] (72%)
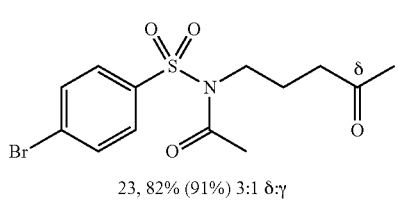 [SMILES: CC(=O)CCCN(C(C)=O)S(=O)(=O)c1ccc(Br)cc1]
23, 82% (91%) 3:1 δ:γ
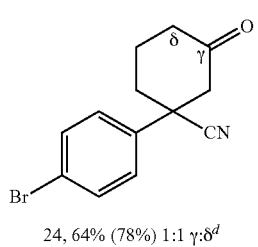
24, 64% (78%) 1:1 γ:δ[d]
TABLE 2-continued
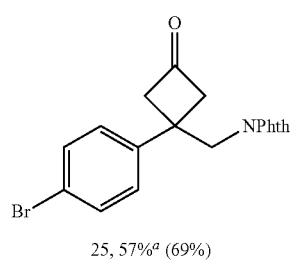
25, 57%[a] (69%)
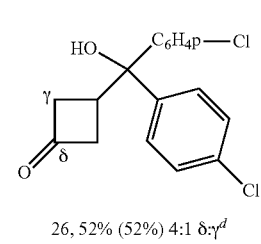
26, 52% (52%) 4:1 δ:γ[d]
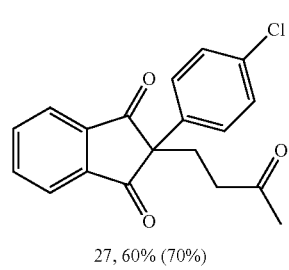 [SMILES: CC(=O)CCC1(c2ccc(Cl)cc2)C(=O)c2ccccc2C1=O]
27, 60% (70%)
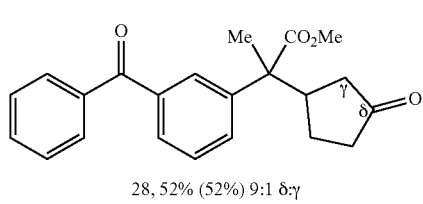 [SMILES: COC(=O)C(C)(c1cccc(C(=O)c2ccccc2)c1)C1CCC(=O)C1]
28, 52% (52%) 9:1 δ:γ
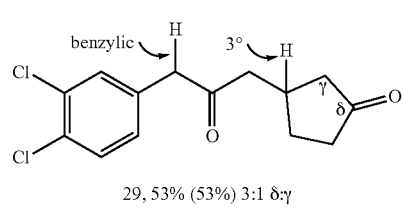 [SMILES: O=C1CCC(CC(=O)Cc2ccc(Cl)c(Cl)c2)C1]
29, 53% (53%) 3:1 δ:γ
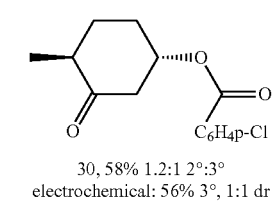
30, 58% 1.2:1 2°:3°
electrochemical: 56% 3°, 1:1 dr
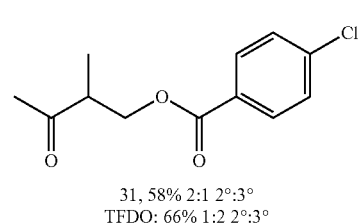 [SMILES: CC(=O)C(C)COC(=O)c1ccc(Cl)cc1]
31, 58% 2:1 2°:3°
TFDO: 66% 1:2 2°:3°

TABLE 2-continued

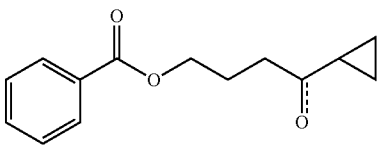

32, 54%[e] 4.5:1 K:A
Mn(PDP(OTf)$_2$: 0%; Mn(OTf)$_2$/bipy:17%

Aromatic substrates with multiple
substitutions of varied electronic and steric properties

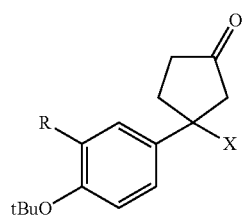

R = H  X = CN    33, 0% (0%)
    Cl     CO$_2$Me  34, 73% (73%)

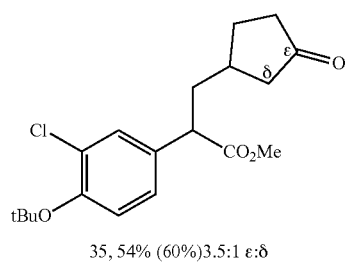 [SMILES: COC(=O)C(CC1CCC(=O)C1)c1ccc(OC(C)(C)C)c(Cl)c1]

35, 54% (60%) 3.5:1 ε:δ

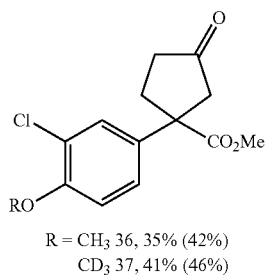

R = CH$_3$ 36, 35% (42%)
    CD$_3$ 37, 41% (46%)

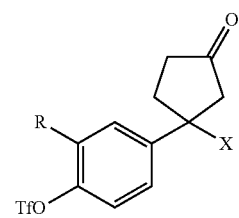

R = OMe X = CO$_2$Me 38, 52% (57%)
    CH$_3$    CN     39, 59% (75%)

TABLE 2-continued

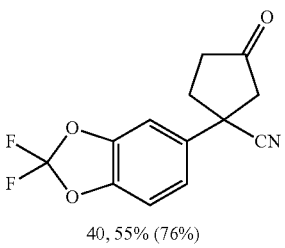 [SMILES: N#CC1(c2ccc3c(c2)OC(F)(F)O3)CCC(=O)C1]

40, 55% (76%)

[a]Iterative catalyst addition protocol (method B): a total of 15 mol % Mn(CF3—PDP) 1 was added in 3 portions (5 mol %, 3 times). See the Examples section for additional details.
[b]25 mol % Fe(CF3—PDP) 6, slow addition protocol.
[c]Starting material recycled once.
[d]Ratios are statistically corrected.
[e]7% chloroacetic ester, 8% recovered starting material also observed.

In Table 2 above, Method A is used unless otherwise noted. Isolated yields are average of two-three runs. Chemoselectivity (2° C.—H [O]/total conversion) in parenthesis. NPhth, phthalimide; N(4-NO2Phth), 4-nitrophthalimide.

It is worth noting that in gram-scale reactions, catalyst and acid loadings can be reduced to 5 mol % and 7.5 equiv. (respectively) to afford products with comparable isolated yields and chemoselectivities (9, 72% yield, 84% chemoselectivity). The phthalimide group diminishes resonance donation of aniline enabling effective remote methylene oxidation to furnish 11 in 63% yield. Compounds with meta-ester ($\sigma_m$=0.23) and 3,5-difluoro-substituents are oxidized with Mn(CF$_3$-PDP) 1 to give 12 (73%) and 13 (66%) in useful yields. When evaluating aromatic substrates with stronger electron withdrawing substituents such as para-esters and nitriles, somewhat tolerated with Fe(CF$_3$-PDP) 6, it was observed that 1 affords higher yields of methylene oxidized products 14 and 15 with excellent chemoselectivity. Underscoring the unprecedented level of chemoselectivity with the new Mn(CF$_3$-PDP) 1, direct comparisons made with Fe(CF$_3$-PDP) 6 under previously reported optimal conditions (Table 1, entry 10) show 1 gives significant improvements in yields and selectivities relative to 6 (11% for 12 and 13, 28% for 14, 55% for 15). Substrates with trifluoromethyl and difluoromethyl aromatic groups, increasingly found in pharmaceuticals, afford remote methylene oxidation in 77% (16) and 55% (17) yield, respectively.

Cyclopentanes with a nitrophthalimide masked primary amine as well as isobenzofuranone and oxindole cores, seen in fluorescein and sunitinib, afforded remote methylene oxidation products 18, 19, and 20 in good yields and chemoselectivities. Spirocycle substrates are not uniquely effective, methylene oxidations of analogous aromatic compounds containing remotely appended cyclopentane rings and linear aliphatic chains afford products in good yields (64% for 21, 61% for 22, 82% for 23, and vide infra). Following site-selectivity rules established with analogous non-heme iron catalysts, oxidation by 1 of a 3-butyl 3-acetoxy oxindole substrate gave only one observed methylene oxidized product at the most sterically accessible and electron rich δ site remote from the tertiary acetoxyl moiety (22). When the alkyl chain was extended by one carbon in an N-pentyl benzenesulfonamide substrate, a 3:1 δ:γ mixture of oxidized products (23) was observed still favoring the most remote δ site.

Small ring carbocycles are increasingly utilized in pharmaceutical compounds to address the physicochemical and pharmacological challenges in classic sp$^2$-hybridized planar structures. Cyclohexyl rings are oxidized in good yields, however poor site-selectivities (Table 2, 24, 1:1 γ:δ ratio) due to competing electronic effects favoring the remote δ site and stereoelectronic effects, that is relief of ring strain, favoring the γ site. Despite their prevalence in natural products and pharmaceutical molecules, cyclobutanes are rarely demonstrated in intermolecular C—H oxidations due to the partial sp²-hybridized character of the C—H bonds.

Under Mn(CF₃-PDP) 1 catalysis, remote cyclobutyl groups are effectively oxidized in preparative yields with excellent site-selectivity (25). The chemoselectivity and high yield of remote oxidation are maintained in reactions with a series of biaryl bioactive molecule derivatives, further highlighting the generality of this method. A cyclobutyl analogue of the pesticide proclonol is oxidized on the cyclobutyl ring in good yield and site-selectivity (26, 52% yield, 4:1 δ:γ). A derivative of clorindione, a vitamin K antagonist, is oxidized with 1 to afford 60% isolated yield of ketone product 27. A derivative of nonsteroidal anti-inflammatory drug ketoprofen affords remote ketone products 28 in 52% yield and 9:1 site-selectivity.

The site-selectivity of Mn(CF₃-PDP) 1 catalysis, analogous to that reported for Fe(PDP) and Fe(CF₃-PDP) catalysis, is not solely dependent on bond dissociation energies of the C—H bond: in the 1 catalyzed oxidation of dichlorobenzylketone derivative, C—H oxidation of the remote methylene sites on the cyclopentyl ring are preferred over oxidation of weaker benzylic and tertiary sites that are electronically deactivated by the proximal carbonyl (Table 2, 29). Highlighting the orthogonality of Mn(CF₃-PDP) 1 catalysis to alternative methods, 1 preferentially oxidizes at the less electron rich but more sterically accessible methylene sites to afford 30 and 31, whereas electrochemical radical methods and TFDO both afford the tertiary alcohol as the exclusive or major product. Cyclopropanes effectively activate α-methylene sites towards oxidation with 1 to afford 54% combined yield of ketone and alcohol products 32 with no detectable ring-opened products. In contrast, other Mn catalysts, including Mn(PDP)(OTf)₂ give no product or trace yields.

Medicinally interesting compounds often contain aromatic rings with varied electronic and steric properties (Table 2). Whereas tert-butoxybenzene moiety in the precursor of 33 is oxidized, addition of a bulky, electronegative chlorine substituent to the aromatic group affords methylene oxidized product 34 in 73% yield. A compound of alternate topology with the same aromatic substitution is also oxidized in preparative yields to afford 35 in 54% yield, albeit in diminished site-selectivity (3.5:1 ε:δ). Replacing Ot-Bu with OMe in the substrate followed by oxidation with 1 provides product 36 in diminished yield and selectivity. Consistent with the lability of the ethereal site, oxidation by 1 of an analogous deuterated anisole compound affords 37 with a slightly higher yield and chemoselectivity. As the aromatic ring is made more electron deficient, ethereal and benzylic C—H bonds are shielded from oxidation with 1: in triflate protected phenol substrates with methyl and methoxyl substituents higher yields and selectivities are obtained for methylene oxidized products 38 and 39, respectively. In a difluorobenzodioxole substrate where the ethereal C—H bonds are replaced with fluorine and the π-donation of the oxygen into the aromatic ring is attenuated, remote oxidized product 40 is furnished in preparative yields.

A cursory glance at pharmaceutical molecules reveals that the combination of halogenated aromatics and nitrogen heterocycles (e.g. piperidines, pyridines, imidazoles) is ubiquitous in their structures. The Mn(CF₃-PDP) 1 catalysis with the known HBF₄ protection strategy for enabling remote methylene C—H oxidations in the presence of basic nitrogen heterocycles that additionally contain aromatic moieties (Scheme 2a) was explored.

Scheme 2. Chemoselective methylene C—H oxidation.

a Aromatic substrates with heteroaromatic or 3° amine substituents[a]

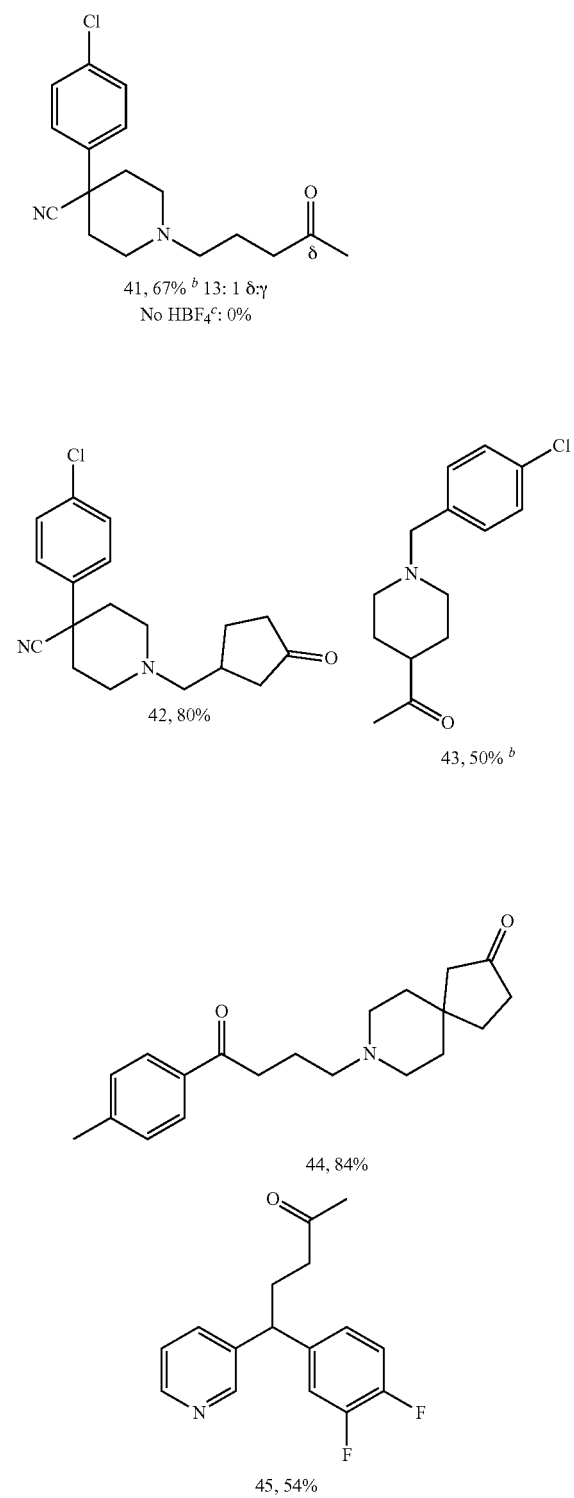

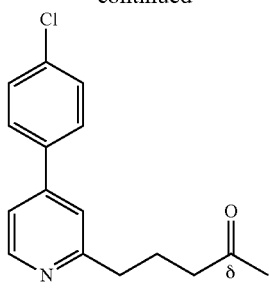
46, 78% 5: 1 δ: γ
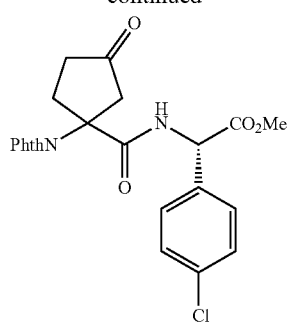
51, 59%
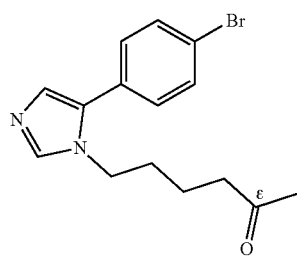
47, 50% 2: 1 ε: mixture
no HBF₄ᶜ: 0%
cat. 6ᵈ: <5%
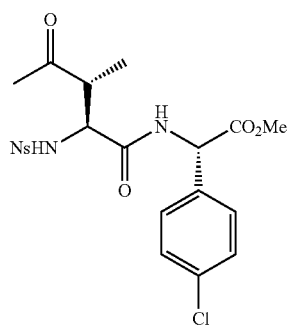
(+)-52, 44% ᵉ,ᶠ
2°: 3° = 9: 1
48, 55% ᵉ 10: 1 δ: γ
no HBF₄ᶜ: <5%
cat. 6ᵈ: <5%
49, 84% 4: 1 δ: γ
no HBF₄ᶜ: <5%
cat. 6ᵈ: <5%
X = Br 53, 69% ᵍ
F 54, 61% ᵍ
Cl 55, 70% ᵍ
with 6: 0% ᵍ
OPiv 56, 69% ᵍ
with 6: <5% ᵍ
b Aromatic dipeptides
(+)-50, 55% ᵉ
with 6ᵈ: <5%
1) Mn(CF₃-PDP) 1
2) TfOH
→
(-)-57

-continued

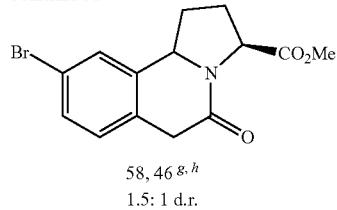

58, 46 [g, h]
1.5: 1 d.r.

a. Mn(CF$_3$-PDP) 1 catalyzed remote 2° C—H oxidation in the presence of aromatic functionality with basic nitrogen containing heterocycles or heteroaromatics. b. Mn(CF$_3$-PDP) 1 oxidation of peptides containing amino acids with mildly deactivated aromatic groups. This enables for the first time intramolecular functionalizations with arene π-nucleophiles to furnish medicinally relevant tricyclic cores. Isolated yields are average of two-three runs. Ns, 4-nitrophenylsulfonyl. [a]HBF$_4$•OEt$_2$ protection followed by slow catalyst addition protocol (method C): both H$_2$O$_2$ (10 equiv.) and Mn(CF$_3$-PDP) 1 (10 mol%) were simultaneously added over 3 hours. See Examples section for more details. [b]Method C used at 0° C. [c]Without HBF$_4$ complexation under optimal condition with 1. [d]25 mol% Fe(CF$_3$-PDP) 6, slow addition protocol. [e]Method B used. [f]Starting material recycled once. [g]Method A used with AcOH (15 equiv.) and H$_2$O$_2$ (5.0 or 7.5 equiv.) at -36° C. [h]Crude hemiaminal, TfOH (2.0 equiv.), 90° C., 2 hours.

4-Arylpiperidines and benzyl derived piperidines, prevalent motifs in opioid analgesics and cognition enhancing drugs (e.g. ketobemidone and donepezil), were tolerated and afforded remote methylene oxidized products in good yields (41-43). In the absence of HBF$_4$, no desired remote oxidation was observed, indicating the chloroacetic acid alone is not effective in protecting the basic amine functionality. An analogue of haloperidol bearing 4-fluorophenyl butyl ketone and piperidine pharmacophores undergoes remote oxidation with 1 in 84% isolated yield to afford 44. An aliphatic motif with a 1,1-disubstituted pyridine-aryl pharmacophore is effectively oxidized to afford ketone product 45 in 54% yield. Mn(CF$_3$-PDP) 1 oxidation of a chloro-phenylpyridine substrate shows excellent yields (46, 78%) and good site-selectivity (5:1 δ:γ). Additionally, imidazole, benzimidazole and quinoline derivatives are successfully oxidized to afford remote ketone in 50% (47), 55% (48) and 84% (49) yield, respectively. Significantly, without the combination of HBF$_4$ protection and Mn(CF$_3$-PDP) 1 catalysis, no significant remote oxidized products were observed: 1 affords enhanced heterocycle tolerance relative to iron catalyst 6, however, the protonation strategy is still necessary in oxidations with 1 for less basic heterocycles to access 47, 48, and 49.

Previous reports demonstrated an impressive ability of iron catalysts to afford remote aliphatic C—H hydroxylations on peptides (Nature 2016, 537, 214); however, the aromatic side chains present were restricted to strongly electron withdrawing triflate (σ=0.53) protected tyrosine. Using Mn(CF$_3$-PDP) 1 catalysis, dipeptide containing chlorophenylglycin residues can be oxidized at aliphatic norleucine and cyclopentyl residues to afford single oxidation product in 55% (50) and 59% (51) yield respectively (Scheme 2b). An isoleucine residue is selectively oxidized at the more sterically accessible methylene site to furnish 52 with 9:1 secondary:tertiary ratio. Mn(CF$_3$-PDP) 1 selectively installs the diversifiable C5-hydroxyl group onto proline in dipeptide settings containing halogenated phenylalanine and now readily removable pivalate protected tyrosine amino acid residues in good yields (53-56). Arene π-nucleophiles can now be linked directly to an amide nitrogen (57) prior to C—H hydroxylation to enable N-acyl iminium intramolecular cyclization to furnish tricyclic isoquinolone derivative 58. Importantly, in all cases examined Fe(CF$_3$-PDP) 6 oxidations run under reported optimal conditions do not tolerate these aromatic functionalities and afford only trace remote oxidized products (e.g., 50, 55 and 56).

Late-stage oxidation of pharmaceuticals. The unprecedented chemoselectivity and reactivity of Mn(CF$_3$-PDP) 1 for remote methylene oxidations in the presence of pharmaceutically relevant aromatics and heteroaromatic moieties, provides an opportunity to effect late-stage diversification of drug leads (Scheme 3a). The atomistic change of C—H to C—O is a validated way to impact physiological responses of small molecules due to altered interactions with proteins and/or changes to physical properties. Evaluation of the hexanoyl derivative 59 of efavirenz, a WHO essential medicine for HIV-1, demonstrates that the singular chemoselectivity of 1-catalyzed aliphatic C—H oxidation persists in the presence of the π-system of an aromatic and an alkyne moiety to furnish 60 in 58% yield with no observed products from oxidation of the aromatic or alkyne functionality.

Compound 61, a γ-secretase modulator analogue, was effectively oxidized by 1/HBF$_4$ strategy to give remote ketone product 62 in 55% yield. The activated tertiary benzylic sites, generally susceptible to TFDO and radical-mediated C—H abstraction, did not undergo oxidation or epimerization with 1. Antidepressant citalopram 63, housing two aromatic rings and a tertiary amine, underwent selective C—H hydroxylation alpha to the ethereal oxygen. Treatment of the hemiacetal with BF$_3$.Et$_2$O furnished a reactive oxocarbenium ion intermediate that underwent diastereoselective nucleophilic attack by an electron rich arene to furnish the 2-naphthol adduct 64 in 42% overall yield (2 steps, 3:1 d.r.). Significantly, generation of hemiacetals has not been described under iron catalysis, likely because the highly reactive hemiacetal rapidly undergoes further oxidation to a carbonyl.

Oxidative metabolism of pharmaceuticals via CYP450 enzyme mediated C—H hydroxylation is a major pathway for drug clearance in vivo and their identification is crucial for the evaluation of their safety and effectiveness. Piragliatin, a drug candidate advanced in the clinic for type 2 diabetes, was discovered via in vivo metabolite studies (MetID) of lead compound 65 (Scheme 3b). Since MetID studies only generate analytical amounts of the metabolite, piragliatin, its diastereomer as well as several other potential cyclopentyl ring metabolites were produced in quantities needed for identification and in vivo safety and efficacy profiling via independent total syntheses that each proceeded with a higher step counts than that of the lead 65 (8 steps). Advanced synthetic intermediate 66 whose acid was used in the synthesis of 65 can be intercepted and directly oxidized with 1 to afford the C3 ketone 67 (1:1 d.r.) in 54% yield. Hydrolysis of methyl ester followed by amide coupling with 2-aminopyrazine rapidly affords piragliatin and its diastereomer (54% yield, 1:1 d.r.). Mn(CF$_3$-PDP) 1 catalysis may provide a powerful means for rapidly accessing aliphatic metabolites of aromatic drugs in preparative quantities.

Sequential C—H oxidation of complex natural products. Natural products (e.g. polyketides, steroids, flavonoids) containing aromatic moieties showcase a wide range of biological activities and serve as impacting starting points for generating new pharmaceuticals. Chemical modifications to these complex structures is generally limited to manipulations of native functionality. It was envisioned that Mn(CF$_3$-PDP) 1 may be used on such medicinally important aromatic steroids like estrogen supplement ethinylestradiol, containing a sensitive aromatic ring and an alkyne, to enable the rapid, sequential buildup of remote hydroxylation on a steroid core (Scheme 3c). In contrast to TFDO which hydroxylates the doubly activated tertiary benzylic site on estrone derivatives (e.g. 68), performing oxidation with 1 on ethinylestradiol derivative 69 effectively oxidizes the sterically more accessible secondary benzylic C—H site in high yields.

The oxidation state of the newly formed C—O bond is controlled by the amount of hydrogen peroxide oxidant: 10 equivalents affords the benzylic ketone product 70 (72% yield; gram-scale synthesis with 2% of 1, 74% yield) whereas 2 equivalents affords a mixture of ketone 70 and alcohol 71 formed as a single diastereomer. Further hydroxylation at the non-activated methylene $Cl_2$ position can be effected with 1 in to afford diastereomerically pure alcohol products: oxidation of ketone 70 and the protected benzylic alcohol 72 afford single diastereomers of $Cl_2$ β-alcohol in 47% yield of 73 and 32% yield of 74. The observed diastereoselectivity and absence of over-oxidized $Cl_2$ ketone products is likely due to the inability of bulky catalyst 1 to access the sterically hindered $Cl_2$ hydrogen. In sharp contrast, TFDO oxidation of 72 led to hydroxylation at the tertiary benzylic site to afford 75 in 84% yield.

The ability to access hydroxylation of methylene sites on steroids has been primarily limited to enzymes and engineered directing group approaches. Despite the fact that $Cl_2$ hydroxylation occurs in numerous classes of natural steroids (e.g. polyoxypregnanes, digoxigenin, cholic acid), it is significant to note that the only non-directed C—H hydroxylations at this position have been effected with (PDP)-inspired small molecule catalysts.

Scheme 3. Late-stage methylene hydroxylation of synthetic and natural product, aromatic drugs derivatives.

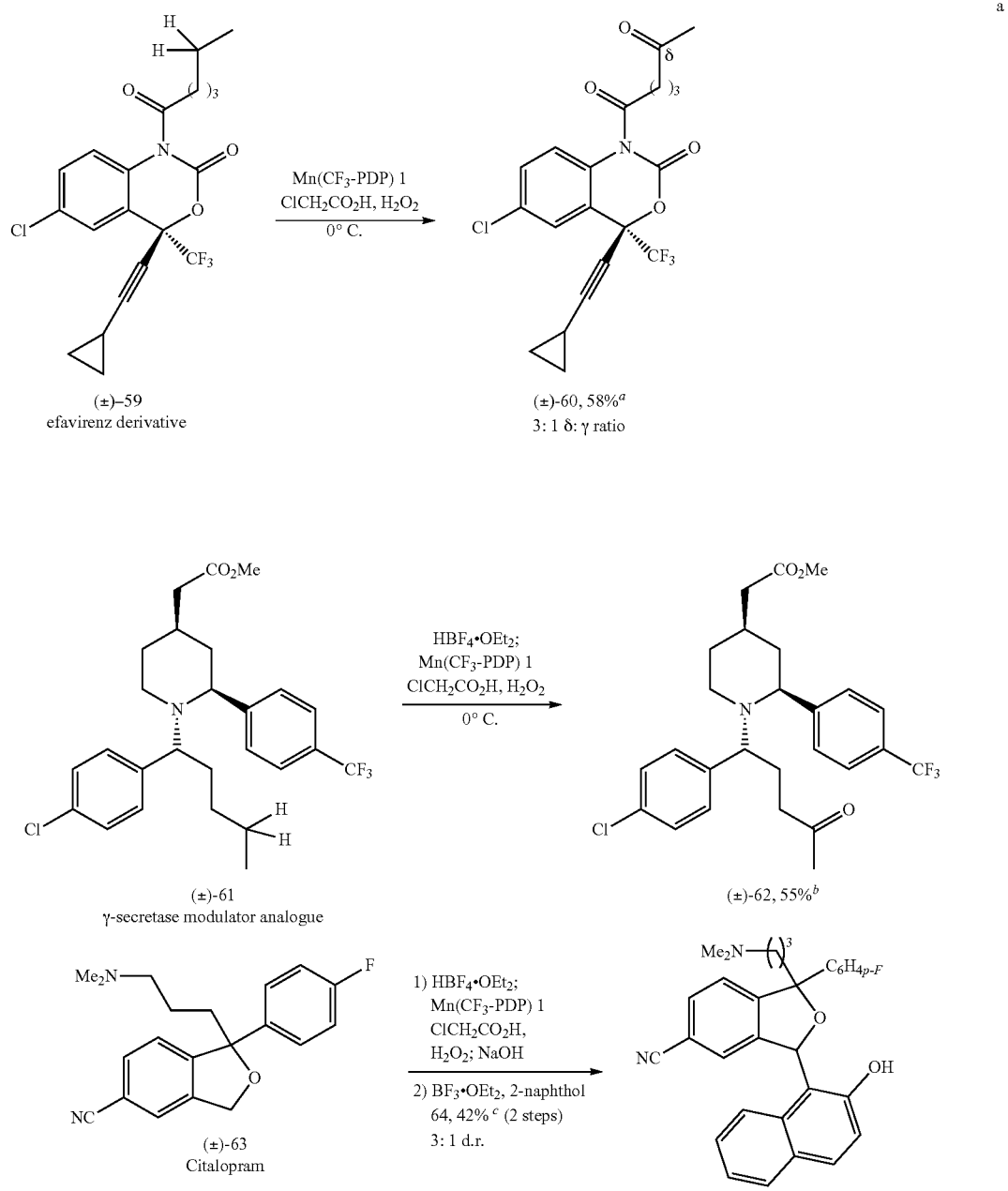

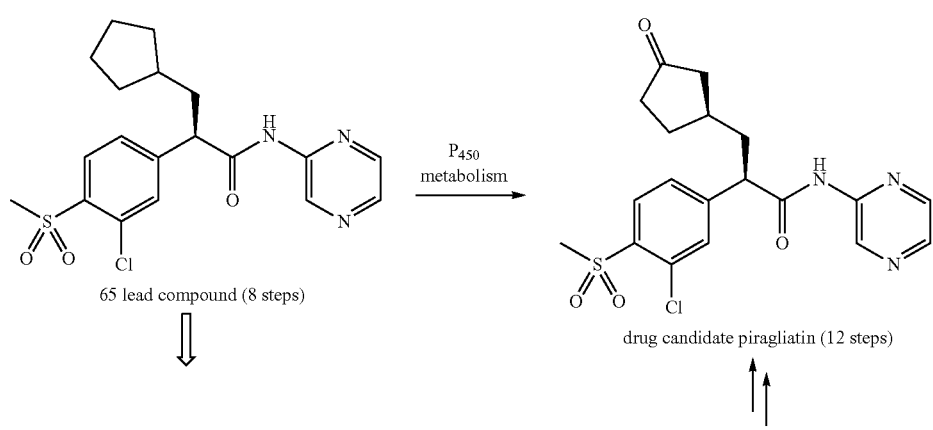
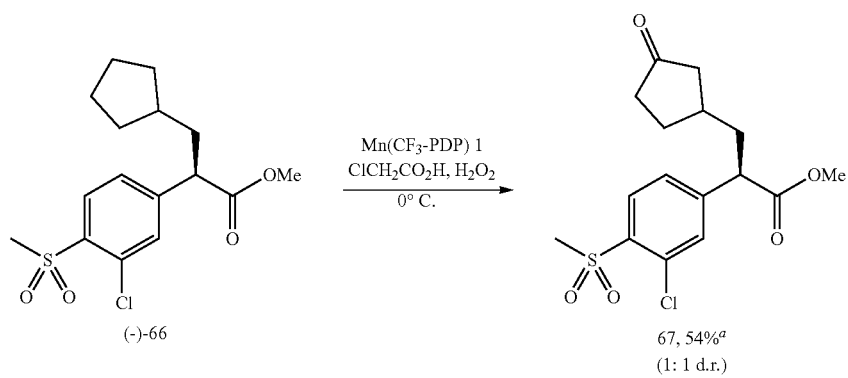
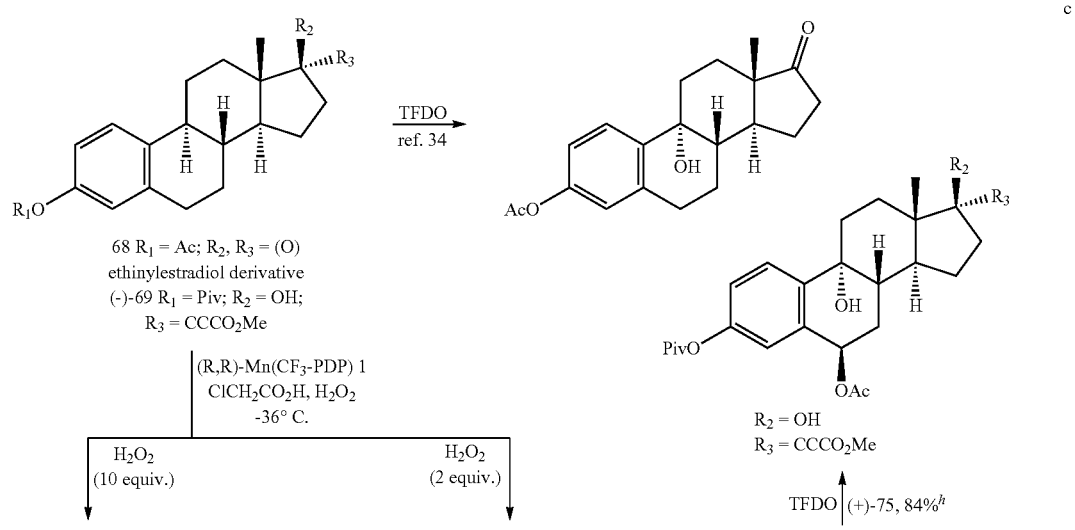

-continued

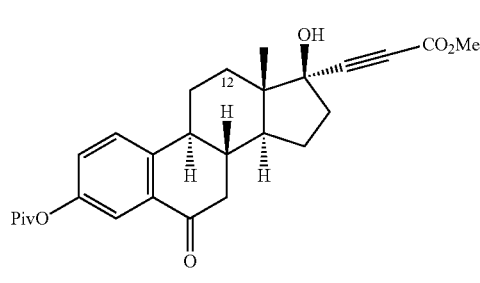

(−)-70, 72% [e]
gram scale: 74% [e]

(R,R)-Mn(CF$_3$-PDP) 1
ClCH$_2$CO$_2$H, H$_2$O$_2$
0° C.

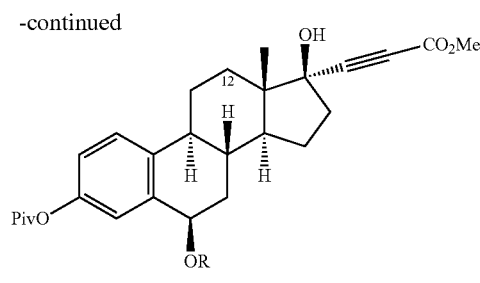

R = H (−)-71,
69% [e] single diastereomer 1.4:1 A:K
R = Ac (+)-72, 86% [f]

(R,R)-Mn(CF$_3$-PDP) 1
ClCH$_2$CO$_2$H, H$_2$O$_2$
0° C.

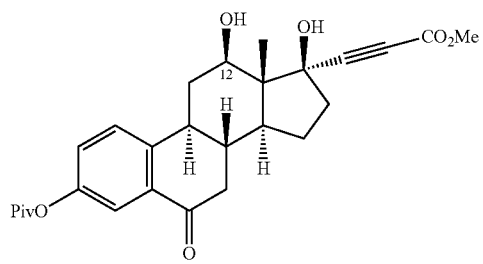

(−)-73, 47% [g]

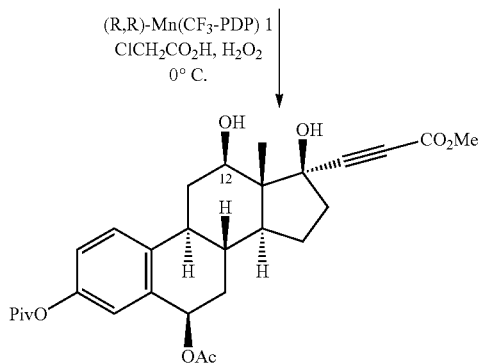

(+)-74, 32% [g]

a. Derivatives of the HIV-1 drug efavirenz and a γ-secretase modulator analogue that house oxidatively sensitive π-functionality such as aryl halides, acetylenes, piperidine, and tertiary amines are oxidized with Mn(CF$_3$-PDP) 1 at remote methylene sites in preparative yields. Antidepressant citalopram is oxidized to a hemiacetal and arylated with an arene π-nucleophiles via an intermediate oxocarbenium.

b. Drug candidate piragliatin, identified as a metabolite of drug lead 65, required de novo synthesis to furnish quantities for further evaluation. Mn(CF$_3$-PDP) 1 catalysis enables an advanced lead intermediate to be rapidly transformed to piragliatin.

c. Sequential Mn(CF$_3$-PDP) 1 catalyzed 2° benzylic/2° aliphatic C—H oxidation of an ethinylestradiol derivative. 2° benzylic oxidation can be tuned with oxidant to give ketone 70 or diastereomerically pure alcohol 71 that undergo further diastereoselective C12 β methylene hydroxylation to alcohols 73 and 74 (crystal structures confirm the 12β configuration). In contrast, TFDO furnishes oxidation at the doubly activated 3° benzylic site. All reactions run with limiting substrate and isolated yields reported as an average (2-3 reactions, using 1). See Example 8 and Example 9 for more details. Ac, acetyl; Piv, pivaloyl.

[a] Method A used at 0° C. [b] HBF$_4$•OEt$_2$ protection followed by method C at 0° C. [c] Method A using 2 equiv. H$_2$O$_2$; arylation protocol. [d] LiOH•H$_2$O (5 equiv.); oxalyl chloride(1.1 equiv.); 2-aminopyrazine (2.2 equiv.), pyridine (2.2 equiv.). [e] Method A with modifications: 1 (5 mol%; 2 mol% for gram scale), ClCH$_2$CO$_2$H (7.5 equiv.), H$_2$O$_2$ (10 equiv. for 70 or 2 equiv. for 71), 4:1 MeCN: CH$_2$Cl$_2$ at −36° C. [f] Ac$_2$O (2.4 quiv.), NEt$_3$ (2.4 equiv.), CH$_2$Cl$_2$, 86%. [g] Method A with 4: 1 MeCN: CH$_2$Cl$_2$ at 0° C. [h] TFDO: 72 (0.05 mmol) in CH$_2$Cl$_2$ (0.5 mL) at −20° C. TFDO (0.4 M solution, 0.25 mL, 2 equiv.) added at −20° C. and stirred for 40 minutes in dark.

Conclusion. Recognition of the benefits of moving away from flat architectures in drug design is stimulating the incorporation of increasing C(sp$^3$)-H bonds into aromatic medicinal compounds. The development of the chemoselective and reactive Mn(CF$_3$-PDP) 1 catalyst system described herein enables for the first time the strategic advantages of late-stage aliphatic C—H oxidation to be leveraged in these settings. Following the same predictable selectivity rules first established with Fe(PDP) and Fe(CF$_3$-PDP) catalysts, the Mn(CF$_3$-PDP) 1 catalyst system site-selectively oxidizes methylene sites distinguished by subtle differences in electronic, steric, and stereoelectronic environments in a range of carbocyclic and linear alkane structures.

In sharp contrast to all previous small molecule C—H oxidation systems, Mn(CF$_3$-PDP) 1 affords preparative methylene oxidations in medicinally relevant aromatic compounds substituted with halogen, oxygen, nitrogen, heterocyclic, and biaryl moieties. It is anticipated that this discovery will benefit future catalyst design in developing chemoselective and reactive aliphatic C—H oxidation catalysts. Additionally, small-molecule therapeutics will be empowered with 1 to rapidly diversify aromatic drugs and natural products and quickly identify their metabolites. Future studies will probe the mechanism that biases the relatively simple Mn(CF$_3$-PDP) 1 catalyst system towards methylene C—H oxidation and impedes non-productive aromatic oxidation.

General Synthetic Methods

The invention also relates to methods of making the compounds and compositions of the invention. The compounds and compositions can be prepared by any of the applicable techniques of organic synthesis, for example, the techniques described herein. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure*, 5$^{th}$ Ed. by M. B. Smith and J. March (John Wiley & Sons, New York, 2001), *Comprehensive Organic Synthesis; Selec-* tivity, Strategy & Efficiency in Modern Organic Chemistry, in 9 Volumes, Barry M. Trost, Ed.-in-Chief (Pergamon Press, New York, 1993 printing)); *Advanced Organic Chemistry, Part B: Reactions and Synthesis*, Second Edition, Cary and Sundberg (1983); *Protecting Groups in Organic Synthesis*, Second Edition, Greene, T. W., and Wutz, P. G. M., John Wiley & Sons, New York; and *Comprehensive Organic Transformations*, Larock, R.C., Second Edition, John Wiley & Sons, New York (1999).

A number of exemplary methods for the preparation of the compounds of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically, the temperatures will be −100° C. to 200° C., solvents will be aprotic or protic depending on the conditions required, and reaction times will be 1 minute to 10 days. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Protecting Groups. The term "protecting group" refers to any group which, when bound to a hydroxy or other heteroatom prevents undesired reactions from occurring at this group and which can be removed by conventional chemical or enzymatic steps to reestablish the hydroxyl group. The particular removable protecting group employed is not always critical and preferred removable hydroxyl blocking groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

Suitable hydroxyl protecting groups are known to those skilled in the art and disclosed in more detail in T. W. Greene, *Protecting Groups In Organic Synthesis*; Wiley: New York, 1981 ("Greene") and the references cited therein, and Kocienski, Philip J.; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Methods

General Methods. All C—H oxidations were carried out under air with magnetic stirring, with no precautions to exclude oxygen or moisture. All other reactions were performed with oven dried or flame dried glassware under inert atmosphere of dry nitrogen or argon. Fe(PDP), Fe(CF$_3$-PDP), (Me$_3$tacn)RuCl$_3$ and cis-[Ru(dtbpy)$_2$Cl$_2$] catalysts were synthesized according to literature procedures. Preparation of Mn(PDP)(MeCN)$_2$(SbF$_6$)$_2$ 5 and Mn(CF$_3$-PDP)(MeCN)$_2$(SbF$_6$)$_2$ 1 catalysts are described in Example 2. All catalysts were stored at 0° C. The catalysts were warmed to room temperature prior to use and weighted out in air. Chloroacetic acid was purchased from Sigma-Aldrich and broke into small pieces before use. H$_2$O$_2$ (50% wt. aqueous solution) was purchased from Sigma-Aldrich and used as received. AgSbF$_6$ used for catalyst metathesis was purchased from Strem Chemicals and stored in the glove box to avoid light prior to use. Solvents including THF, DCM, diethyl ether, DMF, toluene and benzene were dried by passing through a bed of activated alumina (Glass Contour, Laguna Beach, Calif.). Triethylamine and pyridine were distilled over calcium hydride prior to use. All other commercially available reagents were purchased from common sources (e.g. Sigma-Aldrich, Strem Chemicals, Oakwood, Alfa-Aesar, TCI America, etc.) and were used as received.

Thin-layer chromatography was conducted with E. Merck silica gel 60 F254 precoated plates (0.25 mm) and visualized with UV and/or staining including potassium permanganate, ceric ammonium molybdate, or phosphomolybdic acid/cerium sulfate. Flash column chromatography was performed using EM reagent silica gel 60 (230-400 mesh).

$^1$H NMR were recorded using a Varian Unity-500 (500 MHz), Varian Unity Inova-500 (500 MHz), Bruker Avance-500 (500 MHz) and Agilent VNMRS NMR (750 MHz) spectrometer, using solvent as internal standard (CDCl$_3$ at 7.26 ppm). Data are reported as: s=singlet, d=doublet, t=triplet, q=quartet, p=pentat, oct=octet, m=multiplet, br=broad, app=apparent; coupling constants in Hz; integration. Proton-decoupled $^{13}$C NMR were recorded using a Varian Unity-500 (500 MHz), Bruker Avance-500 (500 MHz) and Agilent VNMRS NMR (750 MHz) spectrometer, using solvent as internal standard (CDCl$_3$ at 77.16 ppm). $^{19}$F NMR were recorded using a Varian Unity-500 (470 MHz), Bruker Avance-500 (500 MHz) and Agilent VNMRS NMR (750 MHz) spectrometer, using external standard (CFCl$_3$ at 0 ppm). High resolution mass spectrometry (HRMS) was performed with a Waters Q-TOF Ultima spectrometer or Waters GCT Premier EI spectrometer. Optical rotations were obtained using a JASCO P2000 polarimeter (cell dimensions: 3.5×50 mm) and were reported as $[\alpha]_D^{T/°C.}$ concentration (c=g/100 mL, solvent).

Method A: Single Catalyst Addition Protocol. A 40 mL vial was charged with substrate (0.3 mmol, 1.0 equiv.), Mn(CF$_3$-PDP) 1 (0.03 mmol, 10 mol %), ClCH$_2$CO$_2$H (425 mg, 4.5 mmol, 15.0 equiv.) and a stir bar. Acetonitrile (MeCN, 0.6 mL, 0.50 M) was added along the wall to ensure all compounds were washed beneath the solvent level and the vial was sealed with a screw cap fitted with a PTFE/Silicone septum. The vial was cooled to 0° C. with an ice/water bath. A separate solution of H$_2$O$_2$ [(204 mg, 3.0 mmol, 10.0 equiv.), 50% wt. in H$_2$O, purchased from Sigma-Aldrich] in MeCN (3.75 mL) was loaded into a 10 mL syringe fitted with a 25 G needle and was added dropwise to the stirring reaction over 3 hours via a syringe pump (1.25 mL/h addition rate) while maintaining the reaction vial at 0° C. Upon completion, the reaction mixture was concentrated to a minimum amount of solvent. The residue was dissolved in ~20 mL dichloromethane (DCM) and washed with 9 mL sat. NaHCO$_3$ solution (CAUTION: CO$_2$ released) to remove ClCH$_2$CO$_2$H. The aqueous layer was extracted with ~15 mL DCM two times and the combined organic layer was dried with Na$_2$SO$_4$. The filtrate was concentrated and purified by flash chromatography on silica gel.

Method B: Iterative Catalyst Addition Protocol. A 40 mL vial was charged with substrate (0.3 mmol, 1.0 equiv.), Mn(CF$_3$-PDP) 1 (0.015 mmol, 5 mol %), ClCH$_2$CO$_2$H (425 mg, 4.5 mmol, 15.0 equiv.) and a stir bar. MeCN (0.6 mL, 0.50 M) was added along the wall to ensure all compounds were washed beneath the solvent level and the vial was sealed with a screw cap fitted with a PTFE/Silicone septum. The vial was cooled to −36° C. with a 1,2-dichloroethane/dry ice bath or to 0° C. with ice/water bath. A separate solution of H$_2$O$_2$ [(204 mg, 3.0 mmol, 10.0 equiv.), 50% wt. in H$_2$O, purchased from Sigma-Aldrich] in MeCN (3.75 mL) was loaded into a 10 mL syringe fitted with a 25 G needle and was added dropwise to the stirring reaction over 3 hours via a syringe pump (1.25 mL/h addition rate) while maintain at the corresponding temperature. The initial time is recorded as the time the first drop of H$_2$O$_2$ solution was added into the reaction. One hour after the initial time, another batch of catalyst (0.015 mmol, 5 mol %) was dissolved with 0.1 mL MeCN in a 0.5-dram vial and added dropwise into the reaction via syringe followed directly by another 0.1 mL MeCN that was used to rinse the vial. The addition of 5 mol % catalyst was repeated at two hours after the initial time using the same procedure. A total of 15 mol % of catalyst was used in this protocol. Upon completion, the reaction was worked up and purified as described in Method A.

Method C: Slow Catalyst Addition Protocol. A 40 mL vial was charged with substrate (0.3 mmol, 1.0 equiv.), ClCH$_2$CO$_2$H (425 mg, 4.5 mmol, 15.0 equiv.) and a stir bar. MeCN (0.6 mL, 0.50 M) was added along the wall to ensure all compounds were washed beneath the solvent level and the vial was sealed with a screw cap fitted with a PTFE/Silicone septum. The vial was cooled to −36° C. with 1,2-dichloroethane/dry ice bath or to 0° C. with ice/water bath. A 1.0 mL syringe was filled with a solution of Mn(CF$_3$-PDP) 1 (0.03 mmol, 10 mol %) in MeCN (0.375 mL, 0.083 M). A few drops of this solution were added to the reaction. A 10 mL syringe was filled with a solution of H$_2$O$_2$ (204 mg, 3.0 mmol, 10.0 equiv., 50% wt. in H$_2$O, purchased from Sigma-Aldrich) in MeCN (3.75 mL, 0.8 M). Both syringes were fitted with 25 G needles and loaded to a syringe pump resulting a slow simultaneous addition of catalyst and oxidant solutions over 3 hours while maintain at the corresponding temperature (1.25 mL/h addition rate for the H$_2$O$_2$ syringe; 0.125 mL/h for the catalyst syringe). Upon completion, the reaction was worked up and purified as described in Method A.

Synthetic procedures for Mn(CF$_3$-PDP) 1 and for all substrates in the manuscript are available in the Examples Section. Crystallographic data for the structures reported in this disclosure have been deposited at the Cambridge Crystallographic Data Centre (CCDC), under deposition number CCDC 1869257 for (S,S)-5, CCDC 1869258 for 73, CCDC 1869259 for 74 and CCDC 1869260 for (R,R)—S2. Copies of the data can be obtained from www.ccdc.cam.ac.uk/structures/. All other data supporting the findings of this study are provided by this disclosure.

Example 2

Synthesis and Characterization of Catalysts

Synthesis and Characterization of Mn(PDP)(MeCN)$_2$ (SbF$_6$)$_2$

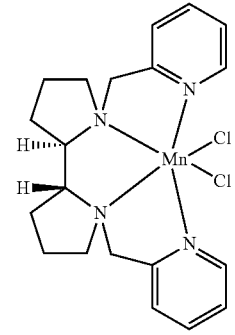

(R,R)—Mn(PDP)Cl$_2$[S1]. In a 50 mL recovery flask was charged (2R,2'R)-1,1'-bis(pyridin-2-ylmethyl)-2,2'-bipyrrolidine ligand (1.0684 g, 3.31 mmol) synthesized according to literature procedure (Science 2007, 318, 783), a stir bar and MeCN (20 mL, 0.166 M). Freshly grinded MnCl$_2$.4H$_2$O (purchased from Strem, 655.7 mg, 3.313 mmol, 1.0 equiv.) was added and the reaction was allowed to stir vigorously for 24 hours under nitrogen atmosphere. Fine white solid was formed during the course of reaction and there should be no pink non-ligated manganese salt remained. Diethyl ether freshly taken from solvent delivery system was added to the reaction to precipitate out the complex. The solvent was removed via pipette and the remaining solids were washed thoroughly with diethyl ether five times and dried under a stream of dry nitrogen gas overnight to yield (R,R)—Mn(PDP)Cl$_2$ (1.3566 g, 3.03 mmol, 91% yield) as white solid. HRMS (TOF ESI+) m/z calculated for C$_{20}$H$_{26}$N$_4$ClMn [M−Cl]$^+$: 412.1226, found 412.1213.

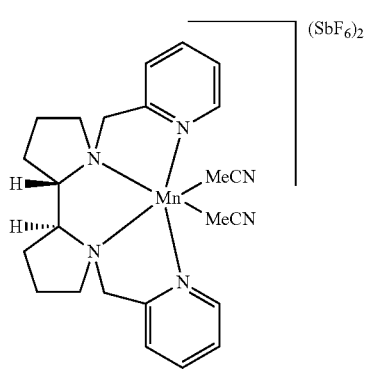

(R,R)—Mn(PDP)(MeCN)$_2$(SbF$_6$)$_2$ [5]. In a flamed dried 100 mL recovery flask was charged (R,R)—Mn(PDP)Cl$_2$ S1 (1.2073 g, 2.69 mmol), a stir bar and 35 mL anhydrous MeCN. AgSbF$_6$ (purchased from Strem, 1.8508 g, 5.39 mmol, 2.0 equiv.) was weighed under argon atmosphere in glove box and then added to the reaction under a stream of nitrogen. The flask was wrapped with aluminum foil to protect from light and the reaction was vigorously stirred for 24 hours. AgCl precipitated out and the reaction was filtered through a pad of Celite® and concentrated under vacuum to a minimum amount of MeCN remaining. The residue was redissolved in a minimum amount of MeCN and filtered through a 0.22 μm Acrodisc® LC PVDF filter (HPLC certified) and concentrated. The filtration-concentration process was repeated two more times and the residue was concentrated to a minimum amount of MeCN remaining and then dried under a positive stream of nitrogen for 24 hours. (R,R)—Mn(PDP)(MeCN)$_2$(SbF$_6$)$_2$ 5 was obtained as a white solid (2.3795 g, 2.56 mmol, 95% yield). HRMS (TOF ESI+) m/z calculated for C$_{20}$H$_{26}$N$_4$F$_6$MnSb [M-SbF$_6$-2(MeCN)]$^+$: 612.0480, found 612.0469.

The (S,S)—Mn(PDP)(MeCN)$_2$(SbF$_6$)$_2$ can be synthesized with the same procedure from (2S,2'S)-1,1'-bis(pyridin-2-ylmethyl)-2,2'-bipyrrolidine ligand.

A single crystal for X-ray crystallography was obtained by dissolving 20 mg (S,S)—Mn(PDP)(MeCN)$_2$(SbF$_6$)$_2$ (S,S)-5 in 0.2 mL MeCN and 0.1 mL benzene, followed by diethyl ether diffuse into the catalyst solution at room temperature. Crystallographic data for 5 can be obtained with deposit number CCDC 1869257.

Synthesis and Characterization of Mn(CF$_3$-PDP)(MeCN)$_2$(SbF$_6$)$_2$

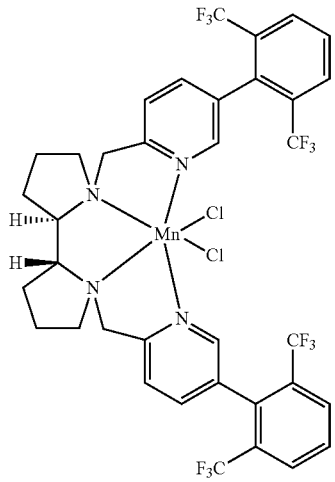

(R,R)—Mn(CF$_3$-PDP)Cl$_2$ [S2]. In a 50 mL recovery flask was charged (2R,2'R)-1,1'-bis((5-(2,6-bis(trifluoromethyl)phenyl)pyridin-2-yl)methyl)-2,2'-bipyrrolidineligand (1.5076 g, 2.02 mmol) synthesized according to literature procedure (J. Am. Chem. Soc. 2013, 135, 14052), a stir bar and MeCN (12 mL, 0.166 M). Freshly grinded MnCl$_2$.4H$_2$O (purchased from Strem, 399.6 mg, 2.02 mmol, 1.0 equiv.) was added and the reaction was allowed to stir vigorously for 24 hours under nitrogen atmosphere. Fine white solid was formed during the course of reaction and there should be no pink non-ligated manganese salt remained. Diethyl ether freshly taken from solvent delivery system was added to the reaction to precipitate out the complex. The solvent was removed via pipette and the remaining solids were washed thoroughly with diethyl ether five times and dried under a stream of dry nitrogen gas overnight to yield (R,R)—Mn(CF$_3$-PDP)Cl$_2$ (1.6075 g, 1.84 mmol, 91% yield) as white solid. HRMS (TOF ESI+) m/z calculated for C$_{36}$H$_{30}$N$_4$ClMnF$_{12}$ [M−Cl]$^+$: 836.1348, found 836.1353.

A single crystal for X-ray crystallography was obtained by dissolving ~20 mg (R,R)—Mn(CF$_3$-PDP)Cl$_2$ S2 in 0.2 mL MeCN and 0.1 mL benzene, followed by diethyl ether diffuse into the catalyst solution at room temperature. Crystallographic data for S2 can be obtained with deposit number CCDC 1869260.

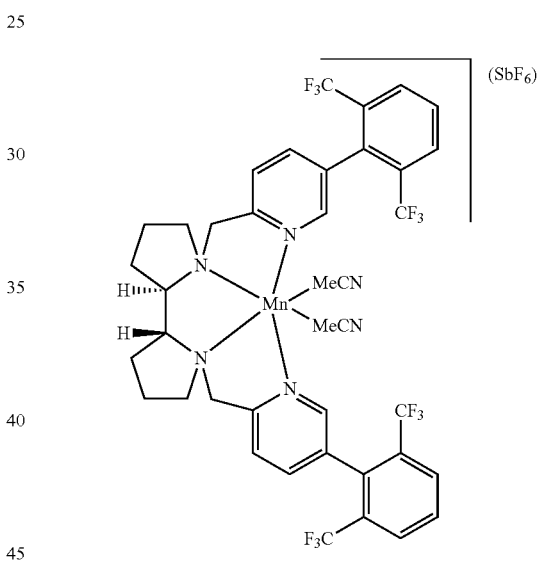

(R,R)—Mn(CF$_3$-PDP)(MeCN)$_2$(SbF$_6$)$_2$ [1]. In a flamed dried 100 mL recovery flask was charged (R,R)—Mn(CF$_3$-PDP)Cl$_2$ S2 (1.6075 g, 1.84 mmol), a stir bar and 24 mL dry MeCN. AgSbF$_6$ (purchased from Strem, 1.2662 g, 3.68 mmol, 2.0 equiv.) was weighed under argon atmosphere in glove box and then added to the reaction under nitrogen protection. The flask was wrapped with aluminum foil to protect from light and the reaction was vigorously stirred for 24 hours. AgCl was precipitated out and the reaction was filtered through a pad of Celite® and concentrated under vacuum to a minimum amount of MeCN remaining. The residue was redissolved in a minimum amount of MeCN and filtered through a 0.22 μm Acrodisc® LC PVDF filter (HPLC certified) and concentrated. The filtration-concentration process was repeated two more times and the residue was concentrated to a minimum amount of MeCN remaining and dried under a positive stream of nitrogen for 24 hours. (R,R)—Mn(CF$_3$-PDP)(MeCN)$_2$(SbF$_6$)$_2$ was obtained as a white solid (2.3420 g, 1.73 mmol, 94% yield). HRMS (TOF ESI+) m/z calculated for C$_{36}$H$_{30}$N$_4$F$_{18}$MnSb [M-SbF$_6$-2(MeCN)]$^+$: 1036.0602, found 1036.0624.

The (S,S)—Mn(CF$_3$-PDP)(MeCN)$_2$(SbF$_6$)$_2$ can be synthesized with the same procedure. A single crystal for X-ray crystallography was obtained by dissolving ~20 mg (S,S)—Mn(CF$_3$-PDP)(MeCN)$_2$(SbF$_6$)$_2$ in 0.2 mL MeCN and 0.1 mL benzene, followed by diethyl ether diffuse into the catalyst solution at room temperature. However, a concise resolved structure from the single crystal cannot be obtained due to heavy modulation.

Figure 2:
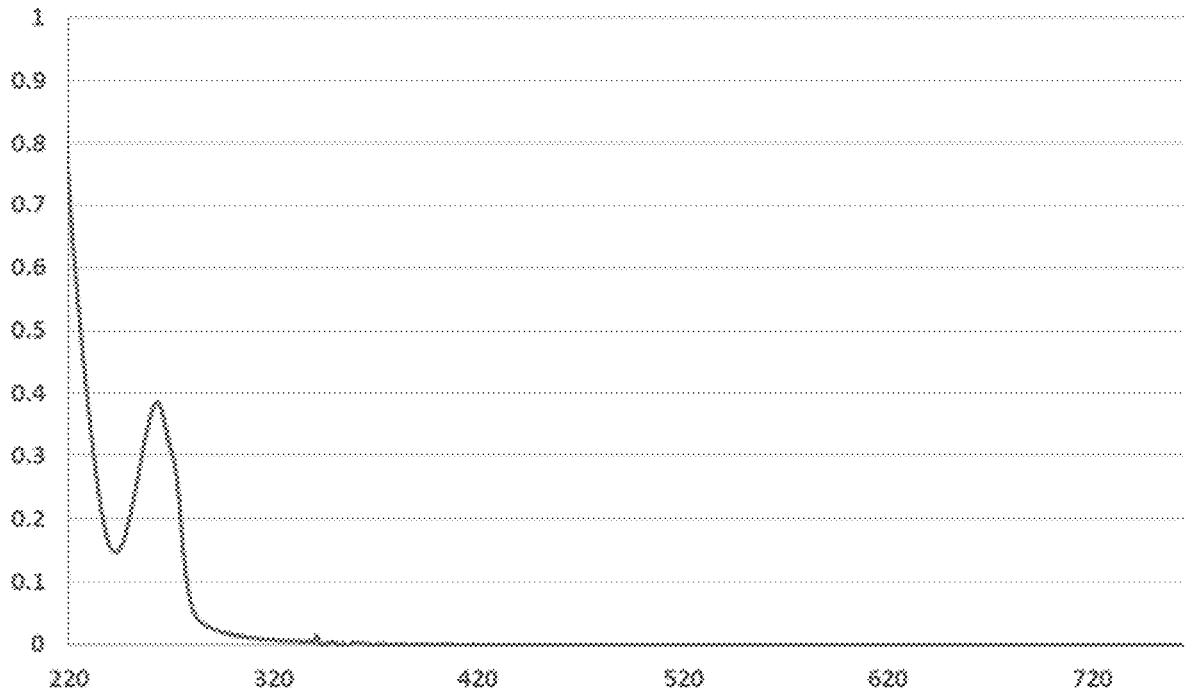
FIG. 2. UV-Visible spectrum for Mn(CF$_3$-PDP) 1.

UV-Vis spectra for Mn(CF$_3$-PDP) 1: In a 10 mL volumetric flask, 19.8 mg (0.0146 mmol) of (R,R)—Mn(CF$_3$-PDP) 1 was dissolved in MeCN to make a 10 mL solution (1.46 M). 250 μL of this solution was diluted to a 10 mL solution (0.0365 M) in a 10 mL volumetric flask. A UV-Vis spectrum (FIG. 2) was taken from 800-220 nm in a quartz cuvette (path length=1 cm).

Example 3

Optimization of C—H Oxidation Protocol (see Table 3)

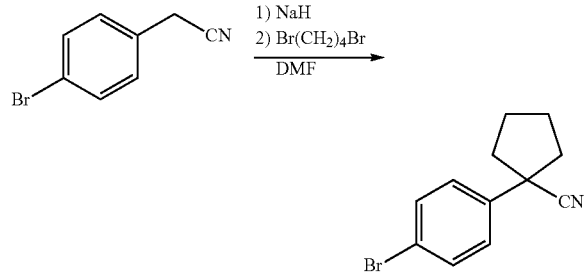

Synthesis of 1-(4-bromophenyl)cyclopentane-1-carbonitrile [2]. In a flamed dried 50 mL flask, 1.9604 g (10.0 mmol) of 2-(4-bromophenyl)acetonitrile was dissolved in 15 mL anhydrous DMF. 632.0 mg (95% purity, 25.0 mmol, 2.5 equiv.) of NaH was added in portions at 0° C. and the reaction was allowed to stir for 1 hour at 0° C. 2.1593 g (1.18 mL, 10.0 mmol, 1.0 equiv.) of 1,4-dibromobutane was added dropwise at 0° C. and the reaction was allowed to stir overnight at room temperature. The reaction was quenched carefully with ~10 mL water and extracted with 30 mL EtOAc three times. The combined organic layer was washed with 50 mL brine, dried with MgSO$_4$, filtered, and concentrated. Flash column chromatography on silica (50 mm fritted glass column, 300 mL SiO$_2$) using 5% EtOAc/hexanes→10% EtOAc/hexanes as eluent gave 2.1143 g (8.45 mmol) of pure product as a white solid (85% yield).

$^1$H-NMR (500 MHz, CDCl$_3$) δ 7.50 (d, J=8.6 Hz, 2H), 7.33 (d, J=8.5 Hz, 2H), 2.49-2.43 (m, 2H), 2.08-1.89 (m, 6H). $^{13}$C-NMR (126 MHz, CDCl$_3$) δ 139.0, 132.0, 127.9, 124.0, 121.9, 47.5, 40.6, 24.3. HRMS (TOF ESI+) m/z calculated for C$_{11}$H$_{12}$Br [M−CN]$^+$: 223.0122, found 223.0123.

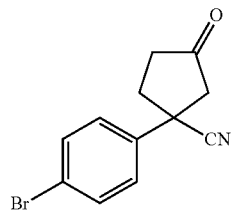 [SMILES: N#CC1(c2ccc(Br)cc2)CCC(=O)C1]

Characterization of 1-(4-bromophenyl)-3-oxocyclopentane-1-carbonitrile [3]. $^1$H-NMR (500 MHz, CDCl$_3$) δ 7.59-7.57 (m, 2H), 7.35-7.32 (m, 2H), 3.05 (d, J=18.1 Hz, 1H), 2.83 (ddd, J=10.3, 8.5, 3.9 Hz, 1H), 2.75 (d, J=18.2 Hz, 1H), 2.70-2.64 (m, 1H), 2.56-2.50 (m, 1H), 2.41 (ddd, J=12.9, 9.9, 8.2 Hz, 1H). $^{13}$C-NMR (126 MHz, CDCl$_3$) δ 211.6, 136.6, 132.7, 127.6, 123.1, 122.1, 49.8, 43.9, 36.7, 36.3. HRMS (TOF ESI+) m/z calculated for C$_{11}$H$_{10}$OBr [M−CN]$^+$: 236.9915, found 236.9915. Enantiomeric excess (ee) of cyclic ketone oxidation products were not evaluated due to the generally low ee (11% for 17, vide infra).

Generation of TFDO: Methyl(trifluoromethyl)dioxirane (TFDO) was synthesized according to the literature. Titration shows the concentration of the TFDO trifluoroacetone solution is about 0.4M. The TFDO solution was stored at −78° C. and was used up within a week. The quality of TFDO was checked by oxidizing 2-methylpentyl 4-chlorobenzoate. Reported: 60% combined yield, 1.9:1 δ:β ratio. Observed with TFDO prepared in-house: 60% combined yield, 2.1:1 δ:β ratio.

General precautions of reactions using TFDO: All solvents and TFDO transfer during the reaction setup was done with a plastic syringe equipped with plastic micropipette tips to avoid any metal contamination. Due to the sensitivity of TFDO to light, the reaction was wrapped with aluminum foil during the course of reaction.

Entry 1. The reaction was proceeded with under low temperature that prevent free-radical formation. In a 1-dram vial charged with 1-(4-bromophenyl)cyclopentane-1-carbonitrile 2 (12.5 mg, 0.05 mmol, 1.0 equiv.) and a stir bar. 0.5 mL dichloromethane (DCM) freshly obtained from SDS was transferred into the vial via plastic syringe equipped with micropipette tip. The reaction was cooled to −20° C., and 0.38 mL 0.4M TFDO solution was added into the vial in 1-2 portions and the reaction was kept at −20° C. for 48 h. The reaction was concentrated on rotvap to remove all volatiles and the crude mixture was analyzed by quantitative $^1$H NMR with nitrobenzene added as internal standard. Run 1: <5% product, (10.0 mg, 0.040 mmol, 80.0% rsm). Run 2: <5% product, (10.3 mg, 0.041 mmol, 82.0% rsm). Average: <5% product, 81.0% rsm.

Entry 2. The reaction was proceeded at 0° C. In a 1-dram vial charged with 1-(4-bromophenyl)cyclopentane-1-carbonitrile 2 (25.0 mg, 0.10 mmol, 1.0 equiv.) and a stir bar. 1.0 mL DCM freshly obtained from SDS was transferred into the vial via plastic syringe equipped with micropipette tip. The reaction was cooled to 0° C., and 0.75 mL 0.4M TFDO solution was added into the vial in 2-3 portions and the reaction was kept at 0° C. for 6 h. The reaction was concentrated on rotvap to remove all volatiles and the crude mixture was analyzed by quantitative $^1$H NMR with nitrobenzene added as internal standard. Run 1: <5% product, (18.6 mg, 0.075 mmol, 74.5% rsm). Run 2: <5% product, (18.8 mg, 0.075 mmol, 75.1% rsm). Average: <5% product, 74.8% rsm.

TFDO oxidation with 3+3 equiv. oxidant: The reaction was proceeded at 0° C. with an extra addition of TFDO to push the conversion. In a 1-dram vial charged with 1-(4-bromophenyl)cyclopentane-1-carbonitrile 2 (12.5 mg, 0.05 mmol, 1.0 equiv.) and a stir bar. 0.5 mL DCM freshly obtained from SDS was transferred into the vial via plastic syringe equipped with micropipette tip. The reaction was cooled to −0° C., and 0.38 mL 0.4M TFDO solution was added into the vial in 1-2 portions and the reaction was kept at 0° C. for 6 h. Another portion of 0.38 mL 0.4M TFDO solution was added into the vial in 1-2 portions and the reaction was allowed to react at 0° C. for another 12 h.

The reaction was concentrated on rotvap to remove all volatiles and the crude mixture was analyzed by quantitative 1H NMR with nitrobenzene added as internal standard. Run 1: (1.6 mg, 0.006 mmol, 12.3% product), (5.0 mg, 0.020 mmol, 39.9% rsm). Run 2: (1.3 mg, 0.005 mmol, 10.1% product), (4.8 mg, 0.019 mmol, 38.3% rsm).

Average: 11.2% product, 39.1% rsm. Selectivity=11.2/(100-39.1)=18.4%.

See Table 3 below for variations and results of the C—H oxidation protocol.

TABLE 3

Optimization of C—H oxidation protocol.

| entry | catalyst | additive | oxidant | temperature | protocol | yield | selectivity |
|---|---|---|---|---|---|---|---|
| 1 | — | — | TFDO 3 equiv. | −20° C. | — | trace | N.D. |
| 2 | — | — | TFDO 3 equiv. (3 + 3 equiv.) | 0° C. | — | trace (11%) | N.D. (18%) |
| 3 | Ru(Me$_3$TACN) (2%) | — | CAN 2 × 3 equiv. | RT | — | trace | N.D. |
| 4 | cis-Ru(dtbpy)$_2$Cl$_2$ (5%) | — | H$_5$IO$_6$ 2 equiv. | RT | — | 0% | N.D. |
| 5 | Mn(OTf)$_2$, 0.1% bipy, 1% | — | AcOOH 3 equiv. | RT | — | 26% | 43% |
| 6 | Mn(PDP)(OTf)$_2$ (0.1%) | CH$_3$COOH 14 equiv. | H$_2$O$_2$ 2.5 equiv. | 0° C. | — | 9% | 69% |
| 7 | Fe(PDP) (3 × 5%) | CH$_3$COOH 3 × 0.5 equiv. | H$_2$O$_2$ 3 × 1.2 equiv. | RT | iterative | 1% | 2% |
| 8 | Mn(PDP) (3 × 5%) | CH$_3$COOH 3 × 0.5 equiv. | H$_2$O$_2$ 3 × 1.2 equiv. | RT | iterative | 7% | 59% |
| 9 | Mn(PDP) (25%) | CH$_3$COOH 5 equiv. | H$_2$O$_2$ 9 equiv. | RT | double slow | 36% | 71% |
| 10 | Fe(CF$_3$—PDP) (25%) | CH$_3$COOH 5 equiv. | H$_2$O$_2$ 9 equiv. | RT | double slow | 24% | 27% |
| 11 | Mn(CF$_3$—PDP) (25%) | CH$_3$COOH 5 equiv. | H$_2$O$_2$ 9 equiv. | RT | double slow | 21% | 95% |
| 12 | Mn(CF$_3$—PDP) (25%) | ClCH$_2$CO$_2$H (5 equiv.) | H$_2$O$_2$ 9 equiv. | RT | double slow | 73% | 90% |
| 13 | Mn(CF$_3$—PDP) (25%) | Cl$_2$CHCO$_2$H (5 equiv.) | H$_2$O$_2$ 9 equiv. | RT | double slow | 66% | 77% |
| 14 | Mn(PDP) (25%) | ClCH$_2$CO$_2$H (5 equiv.) | H$_2$O$_2$ 9 equiv. | RT | double slow | 32% | 65% |
| 15 | Mn(CF$_3$—PDP) (10%) | ClCH$_2$COOH (15 equiv.) | H$_2$O$_2$ 10 equiv. | 0° C. | single catalyst | 86% | 94% |
| 16 | Mn(PDP) (10%) | ClCH$_2$COOH (15 equiv.) | H$_2$O$_2$ 10 equiv. | 0° C. | single catalyst | 38% | 85% |
| 17 | Fe(CF$_3$—PDP) (10%) | ClCH$_2$COOH (15 equiv.) | H$_2$O$_2$ 10 equiv. | 0° C. | single catalyst | 5% | 7% |
| 18 | Mn(CF$_3$—PDP) (10%) | CH$_3$COOH (15 equiv.) | H$_2$O$_2$ 10 equiv. | 0° C. | single catalyst | 20% | 75% |

TFDO: methyl(trifluoromethyl)dioxirane. Abbreviation of catalysts: Ru(Me$_3$TACN) = Ru(Me$_3$TACN)(ClO$_4$)$_3$. Fe(PDP) = Fe(PDP)(MeCN)$_2$(SbF$_6$)$_2$. Fe(CF$_3$—PDP) = Fe(CF$_3$—PDP)(MeCN)$_2$(SbF$_6$)$_2$. Mn(PDP) = Mn(PDP)(MeCN)$_2$(SbF$_6$)$_2$. Mn(CF$_3$—PDP) = Mn(CF$_3$—PDP)(MeCN)$_2$(SbF$_6$)$_2$.

Chemoselectivity is defined as the yield of desired remote oxidation product over the conversion of starting material.

$$\text{chemoselectivity} = \frac{\text{yield of remote oxidation product}}{\text{conversion of starting material}}$$

Entry 3. In a 16×125 mm disposable test tube fitted with a stir bar and a rubber septum. 2 mg (5 µmol, 0.02 equiv.) Ru(Me₃TACN)Cl₃, 2.0 mL H₂O and 4 mg AgClO₄ (0.02 mmol, 0.08 equiv.) was added sequentially and stirred at 80° C. for 5 min. White AgCl participated was observed and the mixture was cooled to room temperature. 1-(4-bromophenyl)cyclopentane-1-carbonitrile 2 (62.5 mg, 0.25 mmol, 1.0 equiv.) was dissolved in 2.0 mL tert-butanol and added to the reaction followed by ceric ammonium nitrate (411 mg, 0.75 mmol, 3.0 equiv.). The dark red reaction was allowed to stir at room temperature for 30 min and another batch of ceric ammonium nitrate (411 mg, 0.75 mmol, 3.0 equiv.) was added. The reaction was further stirred for 14 hours and quenched with 1 mL of MeOH, diluted with water and extracted with 25 mL ×3 ethyl acetate. The combined organic layer was dried with MgSO₄, filtered and concentrated under reduced pressure. The crude mixture was analyzed by quantitative ¹H NMR analysis with nitrobenzene added as internal standard. Run 1: trace product, (58.2 mg, 0.233 mmol, 93.1% rsm). Run 2: trace product, (53.7 mg, 0.215 mmol, 85.9% rsm). Run 3: trace product, (54.9 mg, 0.220 mmol, 87.9% rsm). Average: trace product, 89.0% rsm±3.7%.

Entry 4. In a 20 mL vial charged with 1-(4-bromophenyl)cyclopentane-1-carbonitrile 2 (62.5 mg, 0.25 mmol, 1.0 equiv.), a magnetic stir bar and a solution of cis-Ru(dtbpy)₂Cl₂ (8.9 mg, 13 µmol, 0.05 equiv.) in 2.0 mL acetic acid. 2.0 mL water was added to the vial and the purple solution was stirred at room temperature for 2 min before a single portion of H₅IO₆ (114 mg, 0.50 mmol, 2.0 equiv.) was added. The reaction was wrapped with aluminum foil and stirred at room temperature for 4 hours. The reaction was transferred to a separatory funnel with 4 mL CH₂Cl₂ and 30 mL water. The aqueous layer was extracted with 3×15 mL CH₂Cl₂ and the combined organic layer was dried over Na₂SO₄. The crude reaction was concentrated and analyzed by quantitative ¹H NMR analysis with nitrobenzene added as internal standard. Run 1: 0% product, (57.9 mg, 0.231 mmol, 92.5% rsm). Run 2: 0% product, (52.4 mg, 0.209 mmol, 83.8% rsm). Run 3: 0% product, (54.2 mg, 0.217 mmol, 86.6% rsm). Average: 0% product, 87.6% rsm±4.4%.

Entry 5. To a 20 mL vial containing 1-(4-bromophenyl)cyclopentane-1-carbonitrile 2 (62.5 mg, 0.25 mmol, 1.0 equiv.), AcOH (1.25 mL), Mn(OTf)₂ solution (20 µL, 12.5 mM solution in 9:1 AcOH/H₂O, 0.25 µmol, 0.001 equiv.) and bipyridine solution (100 µL, 0.025 M solution in AcOH, 2.5 µmmol, 0.01 equiv.). The mixture was stirred for 10 minutes and modified peracetic acid solution (220 µL, prepared by mixing 1.0 mL of commercial peracetic acid (35% Sigma-Aldrich) with 0.3 mL of 10% KOH solution, 0.75 mmol, 3.0 equiv.) was added dropwise in 30 seconds. The reaction was stirred for another 60 seconds and then diluted with 5 mL acetone. After 30 seconds stirring, the mixture was filtered through Celite® and the filtrate was concentrated under reduced temperature. The crude mixture was analyzed by quantitative ¹H NMR analysis with nitrobenzene added as internal standard. Run 1: (18.7 mg, 0.071 mmol, 28.3% yield), (25.1 mg, 0.100 mmol, 40.1% rsm). Run 2: (16.2 mg, 0.061 mmol, 24.5% yield), (23.5 mg, 0.094 mmol, 37.6% rsm). Run 3: (17.1 mg, 0.065 mmol, 25.9% yield), (24.1 mg, 0.096 mmol, 38.5% rsm). Average: 26.2% yield±1.9%, 38.7% rsm±1.3%. Selectivity=26.2/(100-38.7)=42.7%.

Entry 6. Mn(PDP)(OTf)₂ was prepared by metathesis between Mn(PDP)Cl₂ and AgOTf according to a similar procedure as Mn(PDP)(MeCN)₂(SbF₆)₂ reported in Example 2. To a 20 mL vial containing 1-(4-bromophenyl)cyclopentane-1-carbonitrile 2 (75.0 mg, 0.30 mmol, 1.0 equiv.), AcOH (0.24 mL, 14 equiv.), Mn(PDP)(OTf)₂ solution (60 µL, 5 mM solution in MeCN, 0.30 µmol, 0.001 equiv.) and MeCN (1.14 mL). The mixture was thermostatted at 0° C. and a solution of H₂O₂ (50%, 51.0 mg, 0.75 mmol, 2.5 equiv.) in 0.3 mL MeCN was added via syringe pump over 1 h. The reaction was stirred for another 1 h at 0° C. before concentrated on rotvap. The crude mixture was analyzed by quantitative ¹H NMR analysis with nitrobenzene added as internal standard. Run 1: (7.6 mg, 0.029 mmol, 9.6% yield), (66.3 mg, 0.265 mmol, 88.4% rsm). Run 2: (6.5 mg, 0.025 mmol, 8.2% yield), (65.5 mg, 0.262 mmol, 87.3% rsm). Run 3: (7.2 mg, 0.027 mmol, 9.0% yield), (64.2 mg, 0.256 mmol, 85.5% rsm). Average: 8.9% yield±0.7%, 87.1% rsm±1.5%. Selectivity=8.9/(100-87.1)=69.0%.

Entry 7. The reaction was conducted according to the iterative addition protocol. In a 40 mL vial was charged with 1-(4-bromophenyl)cyclopentane-1-carbonitrile 2 (75.0 mg, 0.30 mmol, 1.0 equiv.), (R,R)—Fe(PDP) catalyst 4 (14.0 mg, 0.015 mmol, 0.05 equiv.), AcOH (9.0 mg, 0.15 mmol, 0.5 equiv.), MeCN (0.45 mL) and a stir bar. The vial was stirred vigorously and a solution of H₂O₂ (50 wt %, 24.5 mg, 1.2 equiv.) in MeCN (3.75 mL) in a 10 mL syringe equipped with 25 G needle was added dropwise over 60-75 seconds. The reaction was allowed to stir for 10 minutes at room temperature and a second batch of catalyst (14.0 mg, 0.015 mmol, 0.05 equiv.) and AcOH (9.0 mg, 0.15 mmol, 0.5 equiv.) dissolved in 0.3 mL MeCN was added via pipette. This was followed by a solution of H₂O₂ (50 wt %, 24.5 mg, 1.2 equiv.) in MeCN (3.75 mL) in a 10 mL syringe equipped with 25 G needle dropwise over 60-75 seconds. After another 10 minutes a third batch of catalyst and H₂O₂ was added in the same manner. The third addition was allowed to stir for 10 minutes for a total reaction time of 30 minutes. Significant decrease in yield was observed when the peroxide solution was added rapidly.

Upon completion of the reaction, the mixture was concentrated in vacuo to a minimum amount of MeCN. 20 mL ether was added to crush the iron complex out and the mixture was filtered via a Celite® plug. The filtrate was dried over Na₂SO₄, concentrated and analyzed by quantitative ¹H NMR analysis with nitrobenzene added as internal standard. Run 1: (1.2 mg, 0.005 mmol, 1.5% yield), (35.4 mg, 0.141 mmol, 47.1% rsm). Run 2: (1.3 mg, 0.005 mmol, 1.5% yield), (35.0 mg, 0.140 mmol, 46.5% rsm). Run 3: (0.6 mg, 0.002 mmol, 0.9% yield), (33.8 mg, 0.135 mmol, 45.1% rsm). Average: 1.3% yield±0.3%, 46.2% rsm±1.0%. Selectivity=1.3/(100-46.2)=2.4%.

Entry 8. The reaction was conducted according to the iterative addition protocol. In a 40 mL vial was charged with 1-(4-bromophenyl)cyclopentane-1-carbonitrile 2 (75.0 mg, 0.30 mmol, 1.0 equiv.), (R,R)—Mn(PDP) catalyst 5 (14.0 mg, 0.015 mmol, 0.05 equiv.), AcOH (9.0 mg, 0.15 mmol, 0.5 equiv.), MeCN (0.45 mL) and a stir bar. The vial was stirred vigorously and a solution of H₂O₂ (50 wt %, 24.5 mg, 1.2 equiv.) in MeCN (3.75 mL) in a 10 mL syringe equipped with 25 G needle was added dropwise over 60-75 seconds. The reaction was allowed to stir for 10 minutes at room temperature and a second batch of catalyst (14.0 mg, 0.015 mmol, 0.05 equiv.) and AcOH (9.0 mg, 0.15 mmol, 0.5 equiv.) dissolved in 0.3 mL MeCN was added via pipette. This was followed by a solution of $H_2O_2$ (50 wt %, 24.5 mg, 1.2 equiv.) in MeCN (3.75 mL) in a 10 mL syringe equipped with 25 G needle dropwise over 60-75 seconds. After another 10 minutes a third batch of catalyst and $H_2O_2$ was added in the same manner. The third addition was allowed to stir for 10 minutes for a total reaction time of 30 minutes. Significant decrease in yield was observed when the peroxide solution was added rapidly.

Upon completion of the reaction, the mixture was concentrated in vacuo to a minimum amount of MeCN. 20 mL ether was added, and the mixture was filtered via a Celite® plug. The filtrate was dried over $Na_2SO_4$, concentrated and analyzed by quantitative $^1H$ NMR analysis with nitrobenzene added as internal standard. Run 1: (5.6 mg, 0.021 mmol, 7.1% yield), (66.3 mg, 0.265 mmol, 88.4% rsm). Run 2: (4.5 mg, 0.017 mmol, 5.7% yield), (65.5 mg, 0.262 mmol, 87.3% rsm). Run 3: (5.5 mg, 0.021 mmol, 6.9% yield), (68.0 mg, 0.272 mmol, 90.6% rsm). Average: 6.6% yield±0.8%, 88.8% rsm±1.7%. Selectivity=6.6/(100-88.8)=58.9%.

Entry 9. The reaction was conducted in slow addition protocol. In a 40 mL vial was charged with 1-(4-bromophenyl)cyclopentane-1-carbonitrile 2 (75.0 mg, 0.30 mmol, 1.0 equiv), AcOH (90.1 mg, 1.5 mmol, 5.0 equiv.), MeCN (0.60 mL) and a stir bar. A 1 mL syringe was charged with a solution of (R,R)—Mn(PDP) catalyst 5 (69.9 mg, 0.075 mmol, 0.25 equiv.) in MeCN (0.375 mL). A 10 mL syringe was charged with a solution of $H_2O_2$ (183.6 mg, 2.7 mmol, 9.0 equiv.) in MeCN (3.75 mL). Both syringes were fitted with 25 G needles and the solution was added dropwise via syringe pump over 1 hour. Upon completion of addition, the reaction was concentrated in vacuo to a minimum amount of MeCN and purified by column chromatography on silica (35 mm fritted glass column, 150 mL $SiO_2$) using 20% acetone/hexanes→30% acetone/hexanes as eluent to give both recovered starting material and product. Run 1: (28.5 mg, 0.108 mmol, 36.0% yield), (38.0 mg, 0.152 mmol, 50.6% rsm). Run 2: (28.1 mg, 0.106 mmol, 35.5% yield), (38.7 mg, 0.155 mmol, 51.6% rsm). Run 3: (28.2 mg, 0.107 mmol, 35.6% yield), (35.6 mg, 0.142 mmol, 47.4% rsm). Average: 35.7% yield±0.3%, 49.9% rsm±2.2%. Selectivity=35.7/(100-49.9)=71.3%.

Entry 10. The reaction was conducted in slow addition protocol. In a 40 mL vial was charged with 1-(4-bromophenyl)cyclopentane-1-carbonitrile 2 (75.0 mg, 0.30 mmol, 1.0 equiv), AcOH (90.1 mg, 1.5 mmol, 5.0 equiv.), MeCN (0.60 mL) and a stir bar. A 1 mL syringe was charged with a solution of (R,R)—Fe(CF$_3$-PDP) catalyst 6 (101.6 mg, 0.075 mmol, 0.25 equiv.) in MeCN (0.375 mL). A 10 mL syringe was charged with a solution of $H_2O_2$ (183.6 mg, 2.7 mmol, 9.0 equiv.) in MeCN (3.75 mL). Both syringes were fitted with 25 G needles and the solution was added dropwise via syringe pump over 1 hour. Upon completion of addition, the reaction was concentrated in vacuo to a minimum amount of MeCN and purified by column chromatography on silica (35 mm fritted glass column, 150 mL $SiO_2$) using 20% acetone/hexanes→30% acetone/hexanes as eluent to give both recovered starting material and product. Run 1: (18.5 mg, 0.070 mmol, 23.3% yield), (7.2 mg, 0.029 mmol, 9.6% rsm). Run 2: (21.2 mg, 0.080 mmol, 26.8% yield), (7.5 mg, 0.030 mmol, 10.0% rsm). Run 3: (17.0 mg, 0.064 mmol, 21.5% yield), (7.5 mg, 0.030 mmol, 10.0% rsm). Average: 23.9% yield±2.7%, 9.9% rsm±0.2%. Selectivity=23.9/(100-9.9)=26.5%.

Entry 11. The reaction was conducted in slow addition protocol. In a 40 mL vial was charged with 1-(4-bromophenyl)cyclopentane-1-carbonitrile 2 (75.0 mg, 0.30 mmol, 1.0 equiv), AcOH (90.1 mg, 1.5 mmol, 5.0 equiv.), MeCN (0.60 mL) and a stir bar. A 1 mL syringe was charged with a solution of (R,R)—Mn(CF$_3$-PDP) catalyst 1 (101.6 mg, 0.075 mmol, 0.25 equiv.) in MeCN (0.375 mL). A 10 mL syringe was charged with a solution of $H_2O_2$ (183.6 mg, 2.7 mmol, 9.0 equiv.) in MeCN (3.75 mL). Both syringes were fitted with 25 G needles and the solution was added dropwise via syringe pump over 1 hour. Upon completion of addition, the reaction was concentrated in vacuo to a minimum amount of MeCN and purified by column chromatography on silica (35 mm fritted glass column, 150 mL $SiO_2$) using 20% acetone/hexanes→30% acetone/hexanes as eluent to give both recovered starting material and product. Run 1: (16.6 mg, 0.063 mmol, 20.9% yield), (58.6 mg, 0.234 mmol, 78.1% rsm). Run 2: (17.2 mg, 0.065 mmol, 21.7% yield), (57.3 mg, 0.229 mmol, 76.4% rsm). Run 3: (14.9 mg, 0.056 mmol, 18.8% yield), (60.4 mg, 0.241 mmol, 80.5% rsm). Average: 20.5% yield±1.5%, 78.3% rsm±2.1%. Selectivity=20.5/(100-78.3)=94.5%.

Entry 12. The reaction was conducted in slow addition protocol. In a 40 mL vial was charged with 1-(4-bromophenyl)cyclopentane-1-carbonitrile 2 (75.0 mg, 0.30 mmol, 1.0 equiv), ClCH$_2$COOH (141.7 mg, 1.5 mmol, 5.0 equiv.), MeCN (0.60 mL) and a stir bar. A 1 mL syringe was charged with a solution of (R,R)—Mn(CF$_3$-PDP) catalyst 1 (101.6 mg, 0.075 mmol, 0.25 equiv.) in MeCN (0.375 mL). A 10 mL syringe was charged with a solution of $H_2O_2$ (183.6 mg, 2.7 mmol, 9.0 equiv.) in MeCN (3.75 mL). Both syringes were fitted with 25 G needles and the solution was added dropwise via syringe pump over 1 hour. Upon completion of addition, the reaction was concentrated in vacuo to a minimum amount of MeCN. The residue was dissolved in ~20 mL DCM and washed with 9 mL sat. NaHCO$_3$ solution (CAUTION: CO$_2$ was released) to remove ClCH$_2$CO$_2$H. The aqueous layer was extracted with ~15 mL DCM twice and the combined organic layer was dried with Na$_2$SO$_4$. After filtration, the filtrate was concentrated and purified by column chromatography on silica (35 mm fritted glass column, 150 mL SiO$_2$) using 20% acetone/hexanes→30% acetone/hexanes as eluent to give both recovered starting material and product. Run 1: (55.6 mg, 0.210 mmol, 70.2% yield), (17.4 mg, 0.070 mmol, 23.2% rsm). Run 2: (58.7 mg, 0.222 mmol, 74.1% yield), (12.5 mg, 0.050 mmol, 16.7% rsm). Run 3: (58.1 mg, 0.220 mmol, 73.3% yield), (14.1 mg, 0.056 mmol, 18.8% rsm). Average: 72.5% yield±2.1%, 19.6% rsm±3.3%. Selectivity=72.5/(100-19.6)=90.2%.

Entry 13. The reaction was conducted in slow addition protocol. In a 40 mL vial was charged with 1-(4-bromophenyl)cyclopentane-1-carbonitrile 2 (75.0 mg, 0.30 mmol, 1.0 equiv), Cl$_2$CHCOOH (193.4 mg, 1.5 mmol, 5.0 equiv.), MeCN (0.60 mL) and a stir bar. A 1 mL syringe was charged with a solution of (R,R)—Mn(CF$_3$-PDP) catalyst 1 (101.6 mg, 0.075 mmol, 0.25 equiv.) in MeCN (0.375 mL). A 10 mL syringe was charged with a solution of $H_2O_2$ (183.6 mg, 2.7 mmol, 9.0 equiv.) in MeCN (3.75 mL). Both syringes were fitted with 25 G needles and the solution was added dropwise via syringe pump over 1 hour. Upon completion of addition, the reaction was concentrated in vacuo to a minimum amount of MeCN. The residue was dissolved in ~20 mL DCM and washed with 9 mL sat. NaHCO$_3$ solution (CAUTION: CO$_2$ was released) to remove Cl$_2$CHCO$_2$H. The aqueous layer was extracted with ~15 mL DCM twice and the combined organic layer was dried with Na$_2$SO$_4$. After filtration, the filtrate was concentrated and purified by column chromatography on silica (35 mm fritted glass column, 150 mL SiO$_2$) using 20% acetone/hexanes→30% acetone/hexanes as eluent to give both recovered starting material and product. Run 1: (53.9 mg, 0.204 mmol, 68.0% yield), (10.3 mg, 0.041 mmol, 13.7% rsm). Run 2: (50.8 mg, 0.192 mmol, 64.1% yield), (10.3 mg, 0.041 mmol, 13.7% rsm). Run 3: (53.0 mg, 0.201 mmol, 66.9% yield), (9.3 mg, 0.037 mmol, 12.4% rsm). Average: 66.3% yield±2.0%, 13.3% rsm±0.8%. Selectivity=66.3/(100-13.3)=76.5%.

Entry 14. The reaction was conducted in slow addition protocol. In a 40 mL vial was charged with 1-(4-bromophenyl)cyclopentane-1-carbonitrile 2 (75.0 mg, 0.30 mmol, 1.0 equiv), $ClCH_2COOH$ (141.7 mg, 1.5 mmol, 5.0 equiv.), MeCN (0.60 mL) and a stir bar. A 1 mL syringe was charged with a solution of (R,R)—Mn(PDP) catalyst 5 (69.8 mg, 0.075 mmol, 0.25 equiv.) in MeCN (0.375 mL). A 10 mL syringe was charged with a solution of $H_2O_2$ (183.6 mg, 2.7 mmol, 9.0 equiv.) in MeCN (3.75 mL). Both syringes were fitted with 25 G needles and the solution was added dropwise via syringe pump over 1 hour. Upon completion of addition, the reaction was concentrated in vacuo to a minimum amount of MeCN. The residue was dissolved in ~20 mL DCM and washed with 9 mL sat. $NaHCO_3$ solution (CAUTION: $CO_2$ was released) to remove $ClCH_2CO_2H$. The aqueous layer was extracted with ~15 mL DCM twice and the combined organic layer was dried with $Na_2SO_4$. After filtration, the filtrate was concentrated and purified by column chromatography on silica (35 mm fitted glass column, 150 mL $SiO_2$) using 20% acetone/hexanes→30% acetone/hexanes as eluent to give both recovered starting material and product. Run 1: (26.4 mg, 0.110 mmol, 33.3% yield), (39.2 mg, 0.157 mmol, 52.2% rsm). Run 2: (24.1 mg, 0.091 mmol, 30.4% yield), (39.6 mg, 0.158 mmol, 52.8% rsm). Run 3: (25.9 mg, 0.098 mmol, 32.7% yield), (35.2 mg, 0.141 mmol, 46.9% rsm). Average: 32.1% yield±1.5%, 50.6% rsm±3.2%. Selectivity=32.1/(100-50.6)=65.0%.

Entry 15. The reaction was conducted with Method A: single catalyst addition protocol (vide infra, Section IV). In a 40 mL vial was charged with 1-(4-bromophenyl)cyclopentane-1-carbonitrile 2 (75.0 mg, 0.30 mmol, 1.0 equiv), $ClCH_2COOH$ (425.3 mg, 4.5 mmol, 15.0 equiv.), (R,R)—Mn($CF_3$-PDP) catalyst 1 (40.7 mg, 0.03 mmol, 0.10 equiv.) MeCN (0.60 mL) and a stir bar. A 10 mL syringe was charged with a solution of $H_2O_2$ (204 mg, 3.0 mmol, 10.0 equiv.) in MeCN (3.75 mL), fitted with 25 G needles and the solution was added dropwise via syringe pump over 3 hours (1.25 mL/hour) while the reaction vial was maintained at 0° C. Upon completion of addition, the reaction was concentrated in vacuo to a minimum amount of MeCN. The residue was dissolved in ~20 mL DCM and washed with 9 mL sat. $NaHCO_3$ solution (CAUTION: $CO_2$ was released) to remove $ClCH_2CO_2H$. The aqueous layer was extracted with ~15 mL DCM twice and the combined organic layer was dried with $Na_2SO_4$. After filtration, the filtrate was concentrated and purified by column chromatography on silica (35 mm fitted glass column, 150 mL $SiO_2$) using 20% acetone/hexanes→30% acetone/hexanes as eluent to give both recovered starting material and product. Run 1: (67.8 mg, 0.257 mmol, 85.6% yield), (8.7 mg, 0.035 mmol, 11.6% rsm). Run 2: (68.3 mg, 0.259 mmol, 86.2% yield), (5.5 mg, 0.022 mmol, 7.3% rsm). Run 3: (67.2 mg, 0.254 mmol, 84.8% yield), (5.9 mg, 0.024 mmol, 7.9% rsm). Average: 85.5% yield±0.7%, 8.9% rsm±2.3%. Selectivity=85.5/(100-8.9)=93.9%.

Entry 16. The reaction was conducted with Method A: single catalyst addition protocol (vide infra, Section IV). In a 40 mL vial was charged with 1-(4-bromophenyl)cyclopentane-1-carbonitrile 2 (75.0 mg, 0.30 mmol, 1.0 equiv), $ClCH_2COOH$ (425.3 mg, 4.5 mmol, 15.0 equiv.), (R,R)—Mn(PDP) catalyst 5 (27.9 mg, 0.03 mmol, 0.10 equiv.) MeCN (0.60 mL) and a stir bar. A 10 mL syringe was charged with a solution of $H_2O_2$ (204 mg, 3.0 mmol, 10.0 equiv.) in MeCN (3.75 mL), fitted with 25 G needles and the solution was added dropwise via syringe pump over 3 hours (1.25 mL/hour) while the reaction vial was maintained at 0° C. Upon completion of addition, the reaction was concentrated in vacuo to a minimum amount of MeCN. The residue was dissolved in ~20 mL DCM and washed with 9 mL sat. $NaHCO_3$ solution (CAUTION: $CO_2$ was released) to remove $ClCH_2CO_2H$. The aqueous layer was extracted with ~15 mL DCM twice and the combined organic layer was dried with $Na_2SO_4$. After filtration, the filtrate was concentrated and purified by column chromatography on silica (35 mm fitted glass column, 150 mL $SiO_2$) using 20% acetone/hexanes→30% acetone/hexanes as eluent to give both recovered starting material and product. Run 1: (31.0 mg, 0.117 mmol, 39.1% yield), (41.6 mg, 0.166 mmol, 55.4% rsm). Run 2: (30.3 mg, 0.115 mmol, 38.2% yield), (40.4 mg, 0.162 mmol, 53.8% rsm). Run 3: (28.0 mg, 0.106 mmol, 35.3% yield), (43.5 mg, 0.174 mmol, 58.0% rsm). Average: 37.5% yield±2.0%, 55.7% rsm±2.1%. Selectivity=37.5/(100-55.7)=84.7%.

Entry 17. The reaction was conducted with Method A: single catalyst addition protocol (vide infra, Section IV). In a 40 mL vial was charged with 1-(4-bromophenyl)cyclopentane-1-carbonitrile 2 (75.0 mg, 0.30 mmol, 1.0 equiv), $ClCH_2COOH$ (425.3 mg, 4.5 mmol, 15.0 equiv.), (R,R)—Fe($CF_3$-PDP) catalyst 6 (40.7 mg, 0.03 mmol, 0.10 equiv.) MeCN (0.60 mL) and a stir bar. A 10 mL syringe was charged with a solution of $H_2O_2$ (204 mg, 3.0 mmol, 10.0 equiv.) in MeCN (3.75 mL), fitted with 25 G needles and the solution was added dropwise via syringe pump over 3 hours (1.25 mL/hour) while the reaction vial was maintained at 0° C. Upon completion of addition, the reaction was concentrated in vacuo to a minimum amount of MeCN. The residue was dissolved in ~20 mL DCM and washed with 9 mL sat. $NaHCO_3$ solution (CAUTION: $CO_2$ was released) to remove $ClCH_2CO_2H$. The aqueous layer was extracted with ~15 mL DCM twice and the combined organic layer was dried with $Na_2SO_4$. After filtration, the filtrate was concentrated and purified by column chromatography on silica (35 mm fitted glass column, 150 mL $SiO_2$) using 20% acetone/hexanes→30% acetone/hexanes as eluent to give both recovered starting material and product. Run 1: (4.2 mg, 0.016 mmol, 5.3% yield), (18.7 mg, 0.075 mmol, 24.9% rsm). Run 2: (4.5 mg, 0.017 mmol, 5.7% yield), (18.8 mg, 0.075 mmol, 25.1% rsm). Run 3: (4.2 mg, 0.016 mmol, 5.3% yield), (17.8 mg, 0.071 mmol, 23.7% rsm). Average: 5.4% yield±0.2%, 24.6% rsm±0.8%. Selectivity=5.4/(100-24.6)=7.2%.

Entry 18. The reaction was conducted with Method A: single catalyst addition protocol (vide infra, Section IV). In a 40 mL vial was charged with 1-(4-bromophenyl)cyclopentane-1-carbonitrile 2 (75.0 mg, 0.30 mmol, 1.0 equiv), $CH_3COOH$ (270.2 mg, 4.5 mmol, 15.0 equiv.), (R,R)—Mn($CF_3$-PDP) catalyst 1 (40.7 mg, 0.03 mmol, 0.10 equiv.) MeCN (0.60 mL) and a stir bar. A 10 mL syringe was charged with a solution of $H_2O_2$ (204 mg, 3.0 mmol, 10.0 equiv.) in MeCN (3.75 mL), fitted with 25 G needles and the solution was added dropwise via syringe pump over 3 hours (1.25 mL/hour) while the reaction vial was maintained at 0° C. Upon completion of addition, the reaction was concentrated in vacuo to a minimum amount of MeCN. The residue was dissolved in ~20 mL DCM and washed with 9 mL sat. $NaHCO_3$ solution (CAUTION: $CO_2$ was released) to remove $CH_3CO_2H$. The aqueous layer was extracted with ~15 mL DCM twice and the combined organic layer was dried with Na$_2$SO$_4$. After filtration, the filtrate was concentrated and purified by column chromatography on silica (35 mm fritted glass column, 150 mL SiO$_2$) using 20% acetone/hexanes→30% acetone/hexanes as eluent to give both recovered starting material and product. Run 1: (16.0 mg, 0.061 mmol, 20.2% yield), (56.3 mg, 0.225 mmol, 75.0% rsm). Run 2: (13.1 mg, 0.050 mmol, 16.5% yield), (55.9 mg, 0.223 mmol, 74.5% rsm). Run 3: (17.8 mg, 0.067 mmol, 22.5% yield), (53.5 mg, 0.214 mmol, 71.3% rsm). Average: 19.7% yield±3.0%, 73.6% rsm±2.0%. Selectivity=19.7/(100−73.6)=74.6%.

Example 4

Chemoselective Methylene Oxidation in Aromatic Substrates (Table 4)

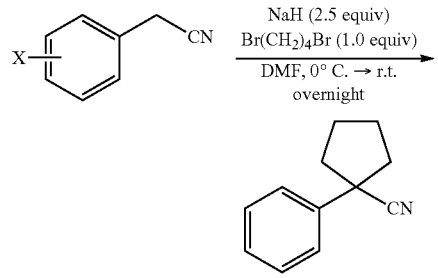

Scheme 4. General procedure for the synthesis of substrate S3-S6.

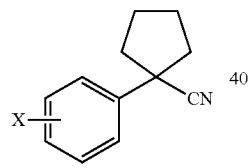

1-Phenylcyclopentane-1-carbonitrile [S3]. In a flamed dried 100 mL flask, 1.1715 g (10.0 mmol) of 2-phenylacetonitrile was dissolved in 15 mL anhydrous DMF. 632.0 mg (95% purity, 25.0 mmol, 2.5 equiv.) of NaH was added in portions at 0° C. and the reaction was allowed to stir for 1 hour at 0° C. 2.1593 g (1.18 mL, 10.0 mmol, 1.0 equiv.) of 1,4-dibromobutane was added dropwise at 0° C. and the reaction was stirred overnight at room temperature. The reaction was quenched carefully with ~10 mL water and extracted with 30 mL EtOAc three times. The combined organic layer was washed with 50 mL brine, dried with MgSO$_4$, filtered, and concentrated. Flash column chromatography on silica (50 mm fritted glass column, 300 mL SiO$_2$) using 3% EtOAc/hexanes→5% EtOAc/hexanes as eluent gave 1.2535 g (7.31 mmol) of pure product as a slightly yellowish oil (73% yield).

$^1$H-NMR (500 MHz, CDCl$_3$) 7.48-7.45 (m, 2H), 7.40-7.37 (m, 2H), 7.33-7.29 (m, 1H), 2.51-2.47 (m, 2H), 2.12-1.91 (m, 6H). $^{13}$C-NMR (126 MHz, CDCl$_3$) δ 139.9, 129.0, 127.9, 126.1, 124.5, 47.9, 40.6, 24.4. HRMS (EI+) m/z calculated for C$_{12}$H$_{12}$N [M−H]$^+$: 170.09697, found 170.09660.

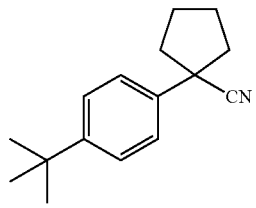 [SMILES: CC(C)(C)c1ccc(C2(C#N)CCCC2)cc1]

1-(4-(tert-Butyl)phenyl)cyclopentane-1-carbonitrile [S4]. In a flamed dried 100 mL flask, 1.7326 g (10.0 mmol) of 2-(4-tert-butylphenyl)acetonitrile was dissolved in 15 mL anhydrous DMF. 632.0 mg (95% purity, 25.0 mmol, 2.5 equiv.) of NaH was added in portions at 0° C. and the reaction was allowed to stir for 1 hour at 0° C. 2.1593 g (1.18 mL, 10.0 mmol, 1.0 equiv.) of 1,4-dibromobutane was added dropwise at 0° C. and the reaction was stirred overnight at room temperature. The reaction was quenched carefully with ~10 mL water and extracted with 30 mL EtOAc three times. The combined organic layer was washed with 50 mL brine, dried with MgSO$_4$, filtered, and concentrated. Flash column chromatography on silica (50 mm fritted glass column, 300 mL SiO$_2$) using 2% EtOAc/hexanes→5% EtOAc/hexanes as eluent gave 1.5612 g (6.87 mmol) of pure product as a slightly yellowish solid (69% yield).

$^1$H-NMR (500 MHz, CDCl$_3$) δ 7.41-7.37 (m, 4H), 2.49-2.44 (m, 2H), 2.11-1.91 (m, 6H), 1.33 (s, 9H). $^{13}$C-NMR (126 MHz, CDCl$_3$) δ 150.8, 136.9, 125.9, 125.8, 124.7, 47.5, 40.5, 34.6, 31.4, 24.3. HRMS (EI+) m/z calculated for C$_{16}$H$_{21}$N [M]$^+$: 227.1674, found 227.1678.

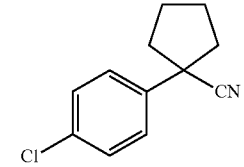 [SMILES: N#CC1(c2ccc(Cl)cc2)CCCC1]

1-(4-Chlorophenyl)cyclopentane-1-carbonitrile [S5]. In a flamed dried 50 mL flask, 1.5159 g (10.0 mmol) of 2-(4-chlorophenyl)acetonitrile was dissolved in 15 mL anhydrous DMF. 632.0 mg (95% purity, 25.0 mmol, 2.5 equiv.) of NaH was added in portions at 0° C. and the reaction was allowed to stir for 1 hour at 0° C. 2.1593 g (1.18 mL, 10.0 mmol, 1.0 equiv.) of 1,4-dibromobutane was added dropwise at 0° C. and the reaction was stirred overnight at room temperature. The reaction was quenched carefully with ~10 mL water and extracted with 30 mL EtOAc three times. The combined organic layer was washed with 50 mL brine, dried with MgSO$_4$, filtered, and concentrated. Flash column chromatography on silica (50 mm fritted glass column, 300 mL SiO$_2$) using 5% EtOAc/hexanes→10% EtOAc/hexanes as eluent gave 1.6928 g (8.23 mmol) of pure product as a clear oil (82% yield).

$^1$H-NMR (500 MHz, CDCl$_3$) δ 7.40-7.37 (m, 2H), 7.36-7.33 (m, 2H), 2.49-2.44 (m, 2H), 2.08-1.90 (m, 6H). $^{13}$C-NMR (126 MHz, CDCl$_3$) δ 138.5, 133.8, 129.1, 127.5, 124.1, 47.4, 40.6, 24.3. HRMS (TOF ESI+) m/z calculated for C$_{11}$H$_{12}$Cl [M−CN]$^+$: 179.0628, found 179.0635.

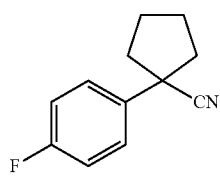 [SMILES: N#CC1(c2ccc(F)cc2)CCCC1]

1-(4-Fluorophenyl)cyclopentane-1-carbonitrile [S6]. In a flamed dried 100 mL flask, 2.7030 g (20.0 mmol) of 2-(4-fluorophenyl)acetonitrile was dissolved in 30 mL anhydrous DMF. 1.2630 g (95% purity, 50.0 mmol, 2.5 equiv.) of NaH was added in portions at 0° C. and the reaction was allowed to stir for 1 hour at 0° C. 4.3186 g (2.37 mL, 20.0 mmol, 1.0 equiv.) of 1,4-dibromobutane was added dropwise at 0° C. and the reaction was allowed to stir overnight at room temperature. The reaction was quenched carefully with 10 mL water and extracted with 60 mL EtOAc three times. The combined organic layer was washed with 50 mL brine, dried with MgSO$_4$, filtered, and concentrated. Flash column chromatography on silica (50 mm fritted glass column, 300 mL SiO$_2$) using 5% EtOAc/hexanes→10% EtOAc/hexanes as eluent gave 2.9857 g (15.8 mmol) of pure product as a clear oil (79% yield).

$^1$H-NMR (500 MHz, CDCl$_3$) δ 7.42 (dd, J=8.8, 5.1 Hz, 2H), 7.06 (t, J=8.6, 8.6 Hz, 2H), 2.50-2.43 (m, 2H), 2.08-1.89 (m, 6H). $^{13}$C-NMR (126 MHz, CDCl$_3$) δ 162.2 (d, J=247.1 Hz), 135.7 (d, J=3.2 Hz), 127.8 (d, J=8.2 Hz), 124.3, 115.8 (d, J=21.7 Hz), 47.2, 40.6, 24.2. $^{19}$F-NMR (470 MHz, CDCl$_3$) δ −114.93. HRMS (EI+) m/z calculated for C$_{12}$H$_{12}$NF [M]$^+$: 189.0954, found 189.0958.

TABLE 4

Chemoselective methylene oxidation in aromatic substrates.

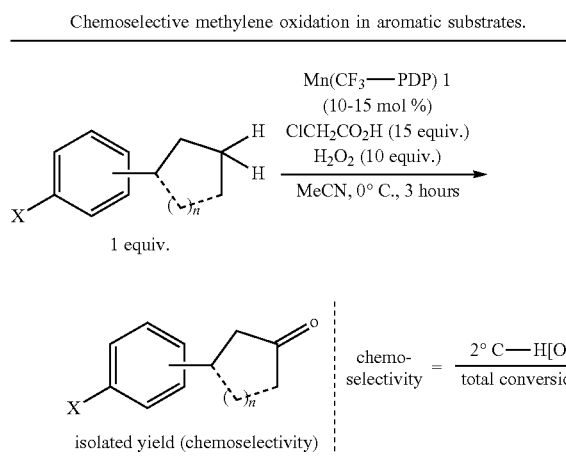

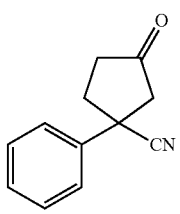

7, 10% (12%)

TABLE 4-continued

Chemoselective methylene oxidation in aromatic substrates.

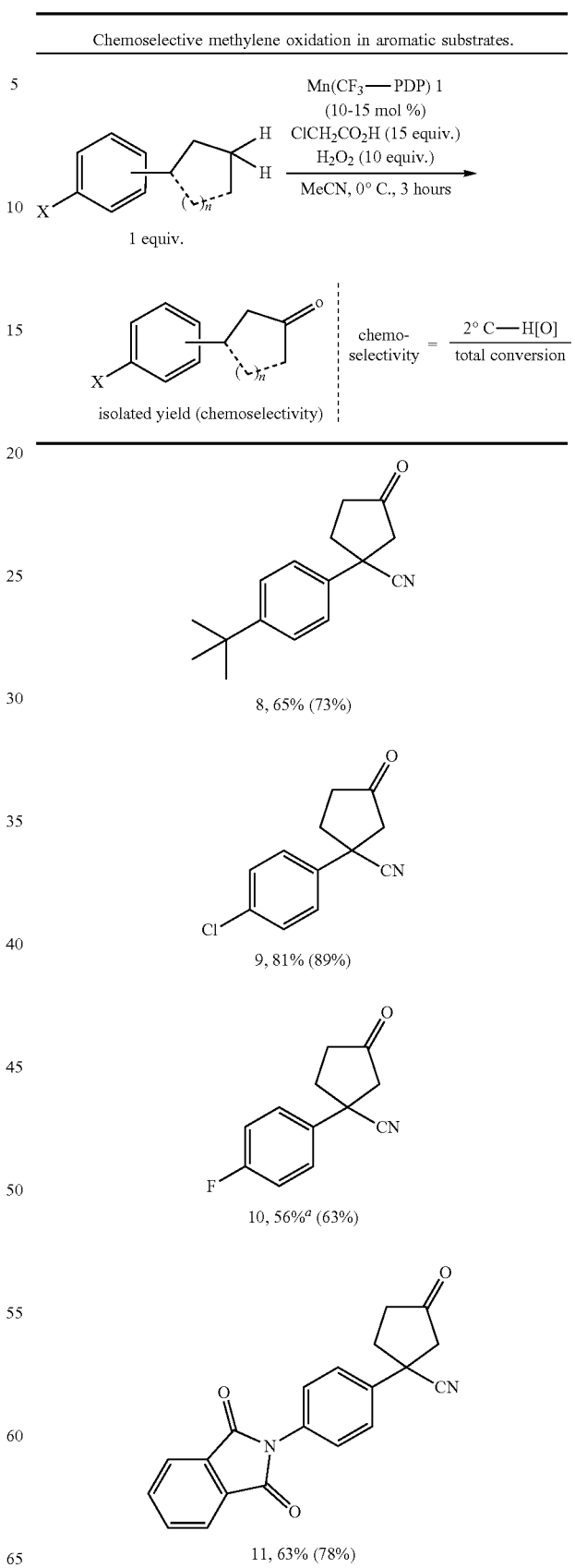

8, 65% (73%)

9, 81% (89%)

10, 56%$^a$ (63%)

11, 63% (78%)

TABLE 4-continued
Chemoselective methylene oxidation in aromatic substrates.
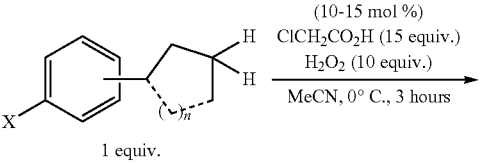
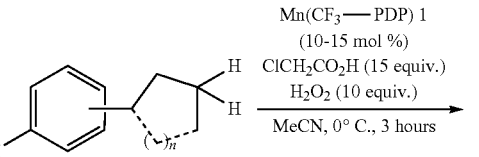

TABLE 4-continued
Chemoselective methylene oxidation in aromatic substrates.
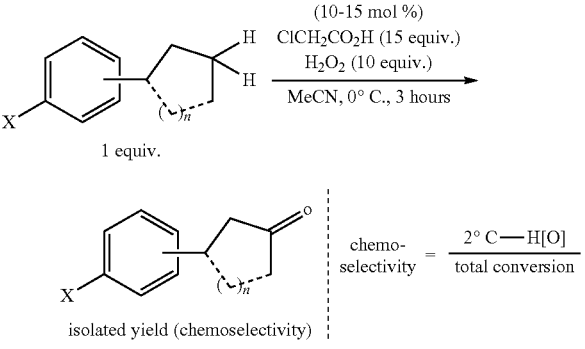
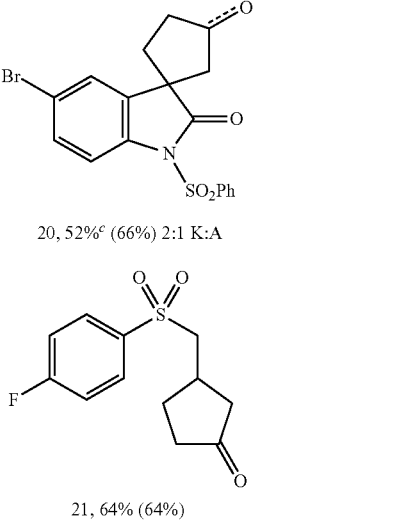
20, 52%[c] (66%) 2:1 K:A
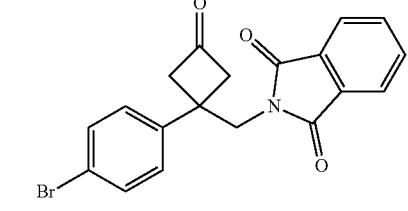
21, 64% (64%)
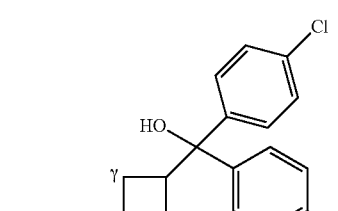
22, 61%[a] (72%)
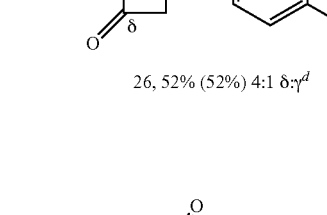
23, 82% (91%) 3:1 δ:γ
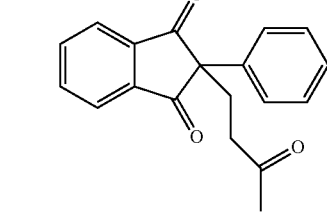
24, 64% (78%) 1:1 δ:γ[d]
TABLE 4-continued
Chemoselective methylene oxidation in aromatic substrates.
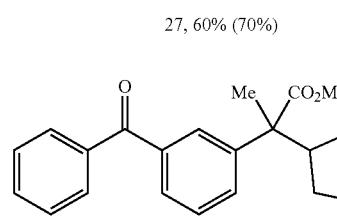
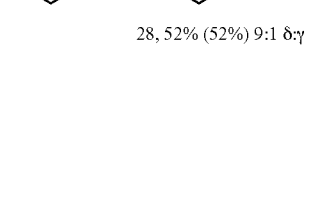
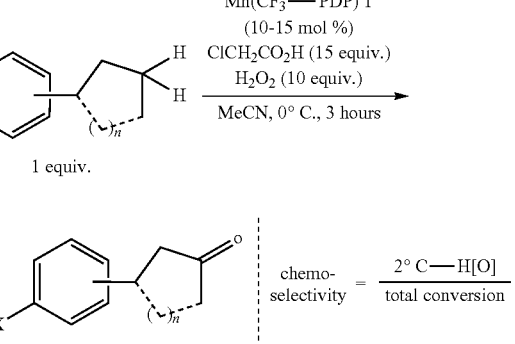
25, 57%[a] (69%)
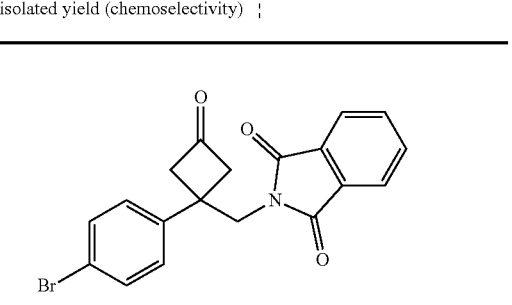
26, 52% (52%) 4:1 δ:γ[d]
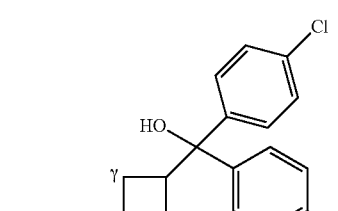
27, 60% (70%)
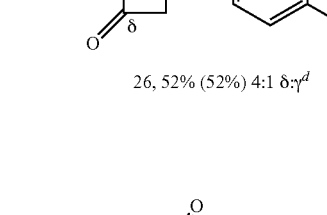
28, 52% (52%) 9:1 δ:γ

TABLE 4-continued

Chemoselective methylene oxidation in aromatic substrates.

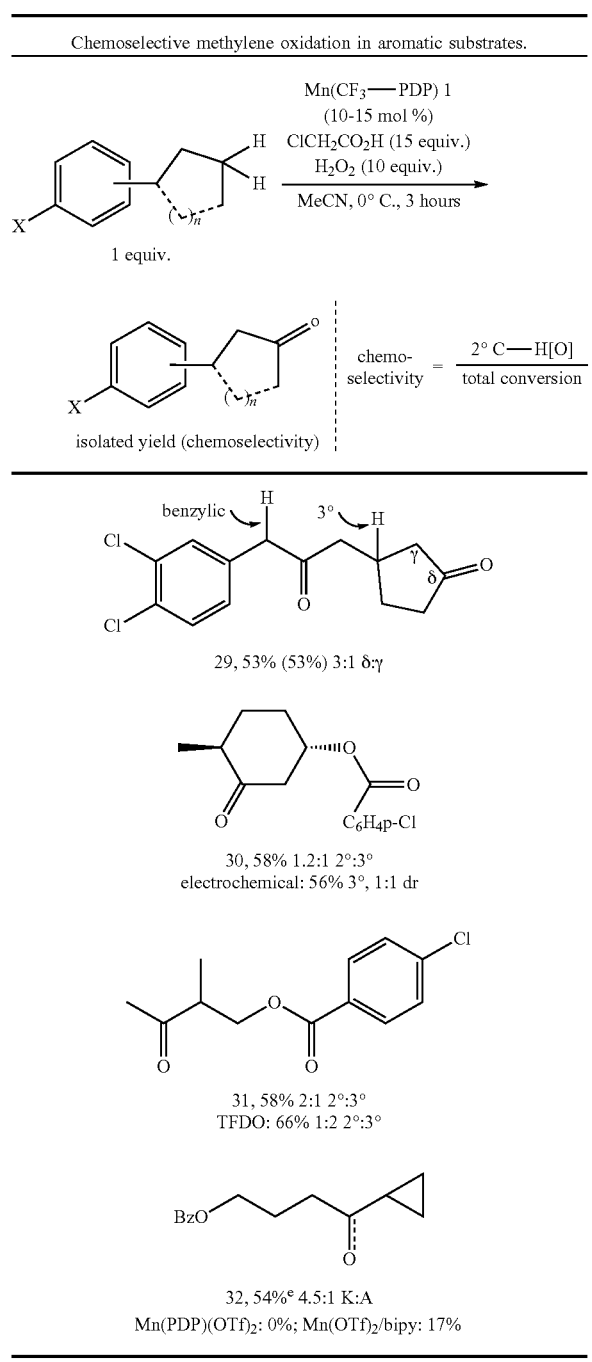

29, 53% (53%) 3:1 δ:γ

30, 58% 1.2:1 2°:3°
electrochemical: 56% 3°, 1:1 dr 31, 58% 2:1 2°:3°
TFDO: 66% 1:2 2°:3°

32, 54%[e] 4.5:1 K:A
Mn(PDP)(OTf)$_2$: 0%; Mn(OTf)$_2$/bipy: 17%

Method A: single catalyst addition protocol is used unless otherwise noted. Isolated yields are average of three runs. [a]Iterative catalyst addition protocol (method B): substrate (0.3 mmol) with Mn(CF$_3$-PDP) 1 (0.015 mmol) and ClCH$_2$CO$_2$H (4.5 mmol) dissolved in MeCN (0.6 mL) maintained 0° C., a solution of H$_2$O$_2$ (50% wt., 3.0 mmol) in MeCN (3.75 mL, 0.8 M) was added via syringe pump over 3 hours; two additional portions of Mn(CF$_3$-PDP) 1 (0.015 mmol each) in MeCN (0.2 mL each) were added to the reaction after one and two hours. [b]25 mol % Fe(CF$_3$-PDP) 6, slow addition protocol. [c]Starting material recycled 1×. [d]Ratios are statistically corrected. [e]7% chloroacetic ester, 8% recovered starting material.

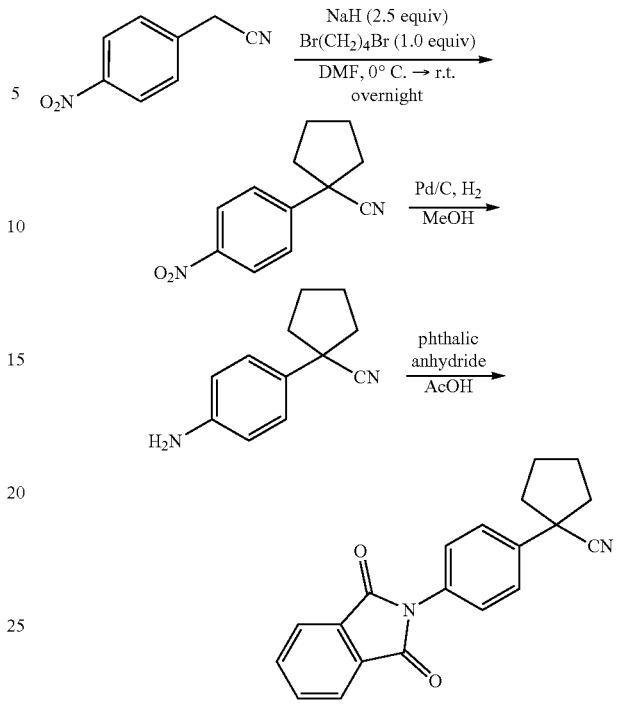

1-(4-(1,3-Dioxoisoindolin-2-yl)phenyl)cyclopentane-1-carbonitrile [S7]. In a flamed dried 100 mL flask, 4.0538 g (25.0 mmol) of 2-(4-nitrophenyl)acetonitrile was dissolved in 50 mL anhydrous DMF. 1.58 g (95% purity, 62.5 mmol, 2.5 equiv.) of NaH was added in portions at 0° C. and the reaction was allowed to stir for 1 hour at 0° C. 5.40 g (3.0 mL, 25.0 mmol, 1.0 equiv.) of 1,4-dibromobutane was added dropwise at 0° C. and the reaction was allowed to stir overnight at room temperature. The reaction was quenched carefully with ~20 mL water and extracted with 50 mL EtOAc three times. The combined organic layer was washed with 50 mL brine, dried with MgSO$_4$, filtered, and concentrated. Flash column chromatography on silica (50 mm fritted glass column, 300 mL SiO$_2$) using 10% EtOAc/hexanes→25% EtOAc/hexanes as eluent gave 2.2851 g (10.6 mmol) of 1-(4-nitrophenyl)cyclopentane-1-carbonitrile as a yellow solid (42% yield). $^1$H-NMR (500 MHz, CDCl$_3$) δ 8.28-8.22 (m, 2H), 7.69-7.61 (m, 2H), 2.55 (dt, J=7.1, 4.6 Hz, 2H), 2.17-1.92 (m, 6H). This solid was dissolved in 30 mL MeOH and charged with 228 mg Pd/C (5% wt.) and the reaction was stirred under a balloon of H$_2$ overnight to obtain 1-(4-aminophenyl)cyclopentane-1-carbonitrile in quantitative yield. $^1$H-NMR (500 MHz, CDCl$_3$) δ 7.24-7.18 (m, 2H), 6.71-6.64 (m, 2H), 3.69 (br. s, 2H), 2.48-2.34 (m, 2H), 2.09-1.79 (m, 6H). In a 50 mL flask was charged with 558.9 mg (3.0 mmol, 1 equiv.) of 1-(4-aminophenyl)cyclopentane-1-carbonitrile, 12 mL acetic acid and 533.2 mg (3.6 mmol, 1.2 equiv.) of phthalic anhydride. The reaction was refluxed overnight before concentrated. Flash column chromatography on silica (50 mm fritted glass column, 300 mL SiO$_2$) using 50% EtOAc/hexanes→100% Acetone as eluent gave 464.5 mg (1.47 mmol) of 1-(4-(1,3-dioxoisoindolin-2-yl)phenyl)cyclopentane-1-carbonitrile as a slightly brown solid (49% yield).

$^1$H-NMR (500 MHz, acetone-d$_6$) δ 7.97-7.92 (m, 4H), 7.71-7.69 (m, 2H), 7.60-7.57 (m, 2H), 2.53-2.48 (m, 2H), 2.25-2.18 (m, 2H), 2.03-2.00 (m, 4H). $^{13}$C-NMR (126 MHz, acetone-d$_6$) δ 167.7, 140.6, 135.4, 132.92, 132.86, 128.3, 127.5, 124.6, 124.2, 48.5, 40.9, 24.7. HRMS (TOF ESI+) m/z calculated for $C_{20}H_{17}N_2O_2$ $[M+H]^+$: 317.1290, found 317.1284.

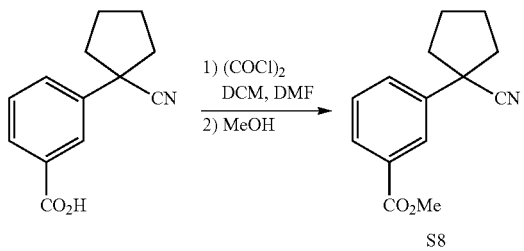

Methyl 3-(1-cyanocyclopentyl)benzoate [S8]. In a flamed dried 50 mL flask, 753.4 mg (3.5 mmol) of 3-(1-cyanocyclopentyl)benzoic acid was dissolved in 20 mL anhydrous DCM. 533.1 mg (355 μL, 4.2 mmol, 1.2 equiv.) of $(COCl)_2$ was dropwise at 0° C., followed by a drop of anhydrous DMF and the reaction was allowed to stir for 2 hours at room temperature before 10 mL anhydrous MeOH was added. The reaction was stirred overnight and concentrated. Flash column chromatography on silica (50 mm fritted glass column, 300 mL $SiO_2$) using 5% EtOAc/hexanes as eluent gave 721.3 mg (3.1 mmol) of pure product as a clear oil (90% yield).

$^1$H-NMR (500 MHz, $CDCl_3$) δ 8.09 (app. t, J=2.3 Hz, 1H), 7.98 (dt, J=7.7, 1.3 Hz, 1H), 7.69 (ddd, J=7.9, 2.1, 1.0 Hz, 1H), 7.46 (t, J=7.8, 1H), 3.93 (s, 3H), 2.53-2.49 (m, 2H), 2.11-1.95 (m, 6H). $^{13}$C-NMR (126 MHz, $CDCl_3$) δ 166.7, 140.4, 131.0, 130.9, 129.14, 129.12, 127.0, 124.1, 52.4, 47.8, 40.6, 24.3. HRMS (TOF ESI+) m/z calculated for $C_{14}H_{16}NO_2$ $[M+H]^+$: 230.1181, found 230.1179.

Scheme 5. General procedure for the synthesis of substrate S9-S13.

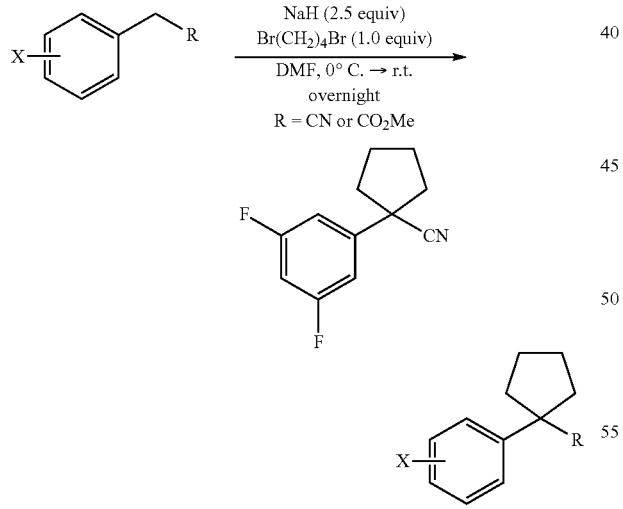

1-(3,5-Difluorophenyl)cyclopentane-1-carbonitrile [S9]. In a flamed dried 50 mL flask, 1.5313 g (10.0 mmol) of 2-(3,5-difluorophenyl)acetonitrile was dissolved in 15 mL anhydrous DMF. 632.2 mg (95% purity, 25.0 mmol, 2.5 equiv.) of NaH was added in portions at 0° C. and the reaction was allowed to stir for 1 hour at 0° C. 2.1593 g (1.18 mL, 10.0 mmol, 1.0 equiv.) of 1,4-dibromobutane was added dropwise at 0° C. and the reaction was allowed to stir overnight at room temperature. The reaction was quenched carefully with ~10 mL water and extracted with 30 mL EtOAc three times. The combined organic layer was washed with 50 mL brine, dried with $MgSO_4$, filtered, and concentrated. Flash column chromatography on silica (50 mm fritted glass column, 300 mL $SiO_2$) using 2% EtOAc/hexanes→5% EtOAc/hexanes as eluent gave 1.8752 g (9.05 mmol) of pure product as a white solid (91% yield).

$^1$H-NMR (500 MHz, $CDCl_3$) δ 7.02-6.97 (m, 2H), 6.78-6.74 (m, 1H), 2.51-2.43 (m, 2H), 2.07-1.93 (m, 6H). $^{13}$C-NMR (126 MHz, $CDCl_3$) δ 163.2 (dd, J=249.6, 12.9 Hz), 143.9 (t, J=8.9 Hz), 123.4, 109.6-109.5 (m), 103.5 (t, J=25.2 Hz), 47.7 (t, J=2.2 Hz), 40.6, 24.3. $^{19}$F-NMR (470 MHz, $CDCl_3$) δ −108.62--108.66 (m). HRMS (TOF ESI+) m/z calculated for $C_{11}H_{11}F_2$ $[M-CN]^+$: 181.0829, found 181.0831.

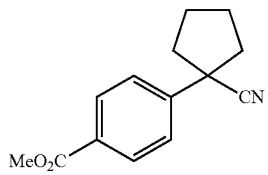 [SMILES: COC(=O)c1ccc(C2(C#N)CCCC2)cc1]

Methyl 4-(1-cyanocyclopentyl)benzoate [S10]. In a flamed dried 50 mL flask, 1.7519 g (10.0 mmol) of methyl 4-(cyanomethyl)benzoate was dissolved in 15 mL anhydrous DMF. 632.0 mg (95% purity, 25.0 mmol, 2.5 equiv.) of NaH was added in portions at 0° C. and the reaction was allowed to stir for 1 hour at 0° C. 2.1593 g (1.18 mL, 10.0 mmol, 1.0 equiv.) of 1,4-dibromobutane was added dropwise at 0° C. and the reaction was stirred overnight at room temperature. The reaction was quenched carefully with ~10 mL water and extracted with 30 mL EtOAc three times. The combined organic layer was washed with 50 mL brine, dried with $MgSO_4$, filtered, and concentrated. Flash column chromatography on silica (50 mm fritted glass column, 200 mL $SiO_2$) using 15% EtOAc/hexanes→30% EtOAc/hexanes as eluent gave 794.0 mg (3.46 mmol) of pure product as a clear oil (34% yield).

$^1$H-NMR (500 MHz, $CDCl_3$) δ 8.04 (dd, J=8.3, 1.4 Hz, 2H), 7.53 (dd, J=8.4, 1.4 Hz, 2H), 3.92 (s, 3H), 2.53-2.47 (m, 2H), 2.12-1.93 (m, 6H). $^{13}$C-NMR (126 MHz, $CDCl_3$) δ 166.6, 144.9, 130.3, 129.8, 126.2, 123.9, 52.4, 48.0, 40.8, 24.5. HRMS (TOF ESI+) m/z calculated for $C_{14}H_{16}NO_2$ $[M+H]^+$: 230.1181, found 230.1177.

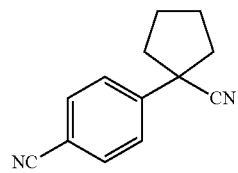 [SMILES: N#Cc1ccc(C2(C#N)CCCC2)cc1]

4-(1-Cyanocyclopentyl)benzonitrile [S11]. In a flamed dried 50 mL flask, 710.8 mg (5.0 mmol) of 2-(4-cyanophenyl)acetonitrile was dissolved in 7.5 mL anhydrous DMF. 316.0 mg (95% purity, 12.5 mmol, 2.5 equiv.) of NaH was added in portions at 0° C. and the reaction was allowed to stir for 1 hour at 0° C. 1.0797 g (0.59 mL, 5.0 mmol, 1.0 equiv.) of 1,4-dibromobutane was added dropwise at 0° C. and the reaction was allowed to stir overnight at room temperature. The reaction was quenched carefully with −10 mL water and extracted with 30 mL EtOAc three times. The combined organic layer was washed with 50 mL brine, dried with MgSO$_4$, filtered, and concentrated. Flash column chromatography on silica (50 mm fritted glass column, 300 mL SiO$_2$) using 5% EtOAc/hexanes→10% EtOAc/hexanes as eluent gave 880.1 mg (4.48 mmol) of pure product as a colorless oil (90% yield).

$^1$H-NMR (500 MHz, CDCl$_3$) δ 7.69-7.67 (m, 2H), 7.59-7.57 (m, 2H), 2.52-2.48 (m, 2H), 2.09-1.94 (m, 6H). $^{13}$C-NMR (126 MHz, CDCl$_3$) δ 145.2, 132.8, 127.0, 123.3, 118.3, 112.0, 48.0, 40.7, 24.5. HRMS (EI+) m/z calculated for C$_{13}$H$_{12}$N$_2$ [M]$^+$: 196.1000, found 196.1004.

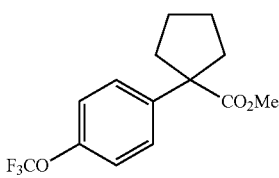

Methyl 1-(4-(trifluoromethoxy)phenyl)cyclopentane-1-carboxylate [S12]. In a flamed dried 50 mL flask, 468.3 mg (2.0 mmol) of methyl 2-(4-(trifluoromethoxy)phenyl)acetate was dissolved in 4 mL anhydrous DMF. 125.0 mg (95% purity, 5.0 mmol, 2.5 equiv.) of NaH was added in portions at 0° C. and the reaction was allowed to stir for 1 hour at 0° C. 431.8 mg (0.24 mL, 2.0 mmol, 1.0 equiv.) of 1,4-dibromobutane was added dropwise at 0° C. and the reaction was allowed to stir overnight at room temperature. The reaction was quenched carefully with ~10 mL water and extracted with 30 mL EtOAc three times. The combined organic layer was washed with 50 mL brine, dried with MgSO$_4$, filtered, and concentrated. Flash column chromatography on silica (50 mm fritted glass column, 300 mL SiO$_2$) using 2.5% EtOAc/hexanes→5% EtOAc/hexanes as eluent gave 260.8 mg (0.91 mmol) of pure product as a colorless oil (45% yield).

$^1$H-NMR (500 MHz, CDCl$_3$) δ 7.39-7.36 (m, 2H), 7.16-7.13 (m, 2H), 3.62 (s, 3H), 2.68-2.63 (m, 2H), 1.92-1.85 (m, 2H), 1.77-1.69 (m, 4H). $^{13}$C-NMR (126 MHz, CDCl$_3$) δ 176.2, 148.1 (q, J=1.9 Hz), 142.1, 128.4, 120.8, 120.6 (q, J=257.0 Hz), 58.8, 52.6, 36.4, 23.7. $^{19}$F-NMR (471 MHz, CDCl$_3$) δ -57.85. HRMS (TOF ESI+) m/z calculated for C$_{14}$H$_{16}$O$_3$F$_3$ [M+H]$^+$: 289.1052, found 289.1047.

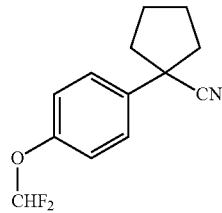 [SMILES: N#CC1(c2ccc(OC(F)F)cc2)CCCC1]

1-(4-(Difluoromethoxy)phenyl)cyclopentane-1-carbonitrile [S13]. In a flamed dried 50 mL flask, 1.000 g (5.46 mmol) of 2-(4-(difluoromethoxy)phenyl)acetonitrile was dissolved in 12 mL anhydrous DMF. 344.8 mg (95% purity, 13.7 mmol, 2.5 equiv.) of NaH was added in portions at 0° C. and the reaction was allowed to stir for 1 hour at 0° C. 1.179 g (0.65 mL, 5.46 mmol, 1.0 equiv.) of 1,4-dibromobutane was added dropwise at 0° C. and the reaction was allowed to stir overnight at room temperature. The reaction was quenched carefully with ~10 mL water and extracted with 30 mL EtOAc three times. The combined organic layer was washed with 50 mL brine, dried with MgSO$_4$, filtered, and concentrated. Flash column chromatography on silica (50 mm fritted glass column, 200 mL SiO$_2$) using 2% EtOAc/hexanes→5% EtOAc/hexanes as eluent gave 1.169 g (4.93 mmol) of pure product as a colorless oil (90% yield). Enantiomeric excess (ee) was determined by chiral HPLC (OJ-H, 90:10 hexanes:isopropanol, 1.0 mL/min, 30° C., 224 nm): 11%.

$^1$H-NMR (500 MHz, CDCl$_3$) δ 7.45 (d, J=8.7 Hz, 2H), 7.13 (d, J=8.7 Hz, 2H), 6.51 (t, J=73.6 Hz, 1H), 2.51-2.45 (m, 2H), 2.08-1.92 (m, 6H). $^{13}$C-NMR (126 MHz, CDCl$_3$) δ 150.6 (t, J=3.0 Hz), 137.1, 127.7, 124.2, 120.0, 115.8 (t, J=260.5 Hz), 47.4, 40.6, 24.3. $^{19}$F-NMR (470 MHz, CDCl$_3$) δ -81.4 (d, J=73.2 Hz). HRMS (TOF ESI+) m/z calculated for C$_{13}$H$_{13}$NONaF$_2$ [M+Na]$^+$: 260.0863, found 260.0862.

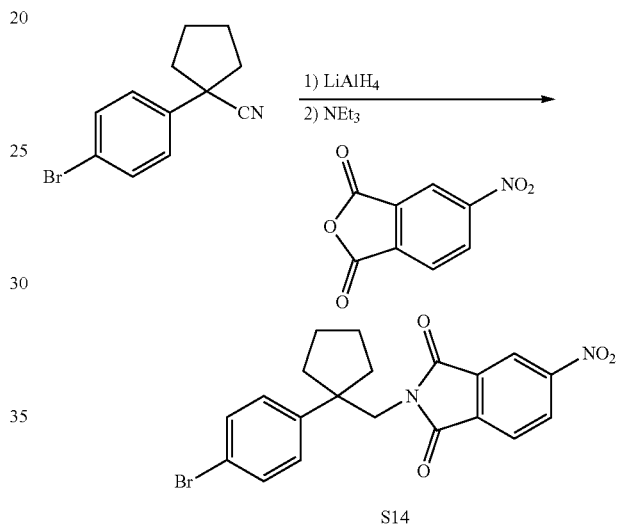

S14

2-((1-(4-Bromophenyl)cyclopentyl)methyl)-5-nitroisoindoline-1,3-dione [S14]. In a flamed dried 50 mL flask, 227.7 mg (6.0 mmol, 1.5 equiv.) LiAlH$_4$ was mixed with 12 mL anhydrous ether, a solution of 1.0006 g (4.0 mmol, 1.0 equiv.) of 1-(4-bromophenyl) cyclopentane-1-carbonitrile 2 in 6 mL anhydrous ether was added dropwise at 0° C. The reaction was allowed to reflux overnight before quenched with 250 μL water, 250 μL 15% NaOH and 750 μL water sequentially. After stirring for 1 h, MgSO$_4$ was added and the mixture was filtered through Celite. The filtrate was concentrated and redissovled in 20 mL toluene, 772.0 mg (4.0 mmol, 1.0 equiv.) of 4-nitrophthalic anhydride was added followed by 560 μL (4.0 mmol, 1.0 equiv.) NEt$_3$. The reaction was refluxed overnight and concentrated. Flash column chromatography on silica (35 mm fritted glass column, 150 mL SiO$_2$) using 10% EtOAc/hexanes→20% EtOAc/hexanes as eluent gave 790.2 mg (1.84 mmol) of pure product as a slightly yellow solid (46% yield over 2 steps).

$^1$H-NMR (500 MHz, CDCl$_3$) δ 8.57-8.55 (m, 2H), 7.95 (d, J=8.0 Hz, 1H), 7.35 (d, J=8.1 Hz, 2H), 7.14 (d, J=8.4 Hz, 2H), 3.85 (s, 2H), 2.08-1.87 (m, 6H), 1.74-1.66 (m, 2H). $^{13}$C-NMR (126 MHz, CDCl$_3$) δ 166.3, 166.1, 151.8, 144.3, 136.2, 133.2, 131.3, 129.3, 129.1, 124.6, 120.6, 118.8, 53.0, 47.5, 36.2, 22.9. HRMS (TOF ESI+) m/z calculated for C$_{20}$H$_{18}$N$_2$O$_4$Br [M+H]$^+$: 429.0450, found 429.0446.

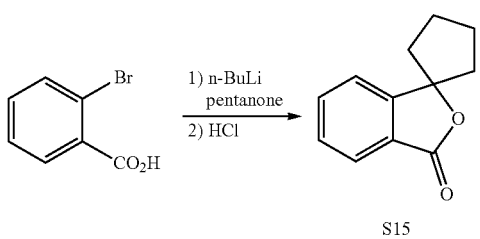 [SMILES: O=C(O)c1ccccc1Br ; O=C1OC2(CCCC2)c2ccccc21 ; "S15"]

3'H-Spiro[cyclopentane-1,1'-isobenzofuran]-3'-one [S15]. In a flamed dried 300 mL flask, 2.0102 g (10.0 mmol) of 2-bromobenzoic acid was dissolved in 50 mL anhydrous THF. n-Butyl lithium (1.6 M, 13.1 mL, 21.0 mmol) was added dropwise at −78° C. and the reaction was allowed to stir for 1 hour at −78° C. 841.2 mg (0.89 mL, 10.0 mmol, 1.0 equiv.) of cyclopentanone dissolved in 10 mL anhydrous THF was added dropwise at −78° C. and the reaction was allowed to warm to room temperature and stir overnight. The reaction was poured into 40 mL water and the aqueous layer was washed with 40 mL hexanes and 40 mL ether. The aqueous layer was adjusted to pH between 2-3 with 3M HCl. 50 mL DCM was added and the mixture was stirred for 1 hour before adjusted to neutral pH with 10% $K_2CO_3$ solution. Layers are separated and the aqueous layer was extracted with 30 mL DCM twice. The combined organic layer was washed with 50 mL brine, dried with $Na_2SO_4$, filtered, and concentrated. Flash column chromatography on silica (50 mm fritted glass column, 300 mL $SiO_2$) using 10% EtOAc/hexanes→20% EtOAc/hexanes as eluent gave 631.7 mg (3.36 mmol) of pure product as a white solid (34% yield).

$^1$H-NMR (500 MHz, CDCl$_3$) δ 7.84 (dt, J=8.0, 2.2 Hz, 1H), 7.66 (td, J=7.5, 1.4 Hz, 1H), 7.49 (td, J=7.5, 2.4 Hz, 1H), 7.41-7.39 (m, 1H), 2.11-2.06 (m, 6H), 1.97-1.94 (m, 2H). $^{13}$C-NMR (126 MHz, CDCl$_3$) δ 170.0, 152.8, 134.2, 129.0, 126.3, 125.5, 121.0, 95.6, 39.8, 25.0. HRMS (TOF ESI+) m/z calculated for $C_{12}H_{13}O_2$ [M+H]$^+$: 189.0916, found 189.0908.

(3.36 g, 30 mmol, 3.0 equiv.) in THF (24 mL) dropwise over 30 min, while the temperature was maintained below −15° C. then the mixture was stirred. After 10 min, 1,4-dibromobutane (1.43 mL, 12 mmol, 1.2 equiv.) was added dropwise over 15 min with the temperature being maintained between −10° C. and −5° C. then the mixture was stirred at 0° C. After 1 h, the reaction was quenched with 3.5% aqueous HCl solution (20 mL) and the mixture was stirred at room temperature for 1 h. The mixture was separated and the yellow organic layer was washed with brine (30 mL), dried with $Na_2SO_4$, and filtered. The resulting solution diluted with MeCN (10 mL) and THF was removed under reduced pressure. MeCN (5 mL) was added and the mixture was cooled to 0° C. The precipitate was collected by filtration and washed with cold MeCN (3×3 mL) to provide 1.87 g of 5'-bromospiro[cyclopentane-1,3'-indolin]-2'-one in 70% yield as a white solid. A 50 mL round bottom flask was charged with a stir bar, 5'-bromospiro[cyclopentane-1,3'-indolin]-2'-one (532 mg, 2.00 mmol, 1.0 equiv.), benzenesulfonyl chloride (307 μL, 2.40 mmol, 1.2 equiv.) and THF (8 mL) and cooled to 0° C. To the stirred mixture was added LHMDS (402 mg, 2.40 mmol, 1.2 equiv.) in THF (2.4 mL) dropwise and the mixture was stirred at the same temperature. After 3 hours, the reaction was quenched with $H_2O$ (20 mL) and extracted with EtOAc (3×15 mL). The combined organic layers were washed with brine (20 mL), dried over $Na_2SO_4$, filtered and concentrated under reduced pressure. The residue was diluted with DCM and concentrated onto silica gel (5 mL) for dry loading onto the column (SiO$_2$, 35 mL) and then eluted with 5% EtOAc/hexane to give 596 mg of the product in 73% yield as a white solid.

$^1$H-NMR (500 MHz, CDCl$_3$) δ 8.06 (dd, J=8.4, 1.2 Hz, 2H), 7.80 (d, J=8.7 Hz, 1H), 7.65 (t, J=7.5 Hz, 1H), 7.55-7.52 (m, 2H), 7.43 (dd, J=8.7, 2.1 Hz, 1H), 7.27 (d, J=2.1 Hz, 1H), 2.09-1.86 (m, 6H), 1.79-1.74 (m, 2H). $^{13}$C-NMR (126 MHz, CDCl$_3$) δ 179.8, 138.1, 137.5, 137.1, 134.6, 131.1, 129.3, 127.9, 126.0, 118.3, 115.2, 54.3, 39.8, 26.9. HRMS (TOF ESI+) m/z calculated for $C_{18}H_{17}BrNO_3S$ [M+H]$^-$: 406.0113, found 406.0110.

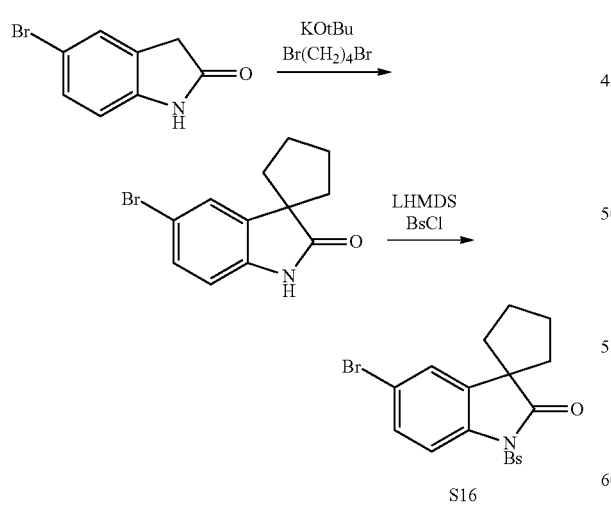

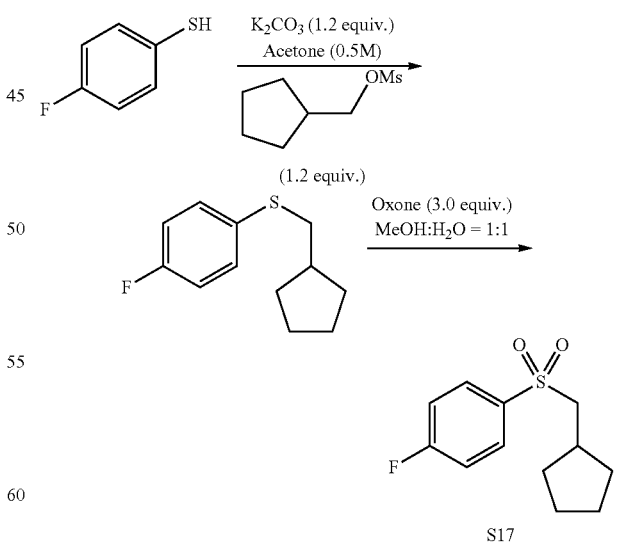

5'-Bromo-1'-(phenylsulfonyl)spiro[cyclopentane-1,3'-indolin]-2'-one [S16]. A 100 mL round bottom flask was charged with a stir bar, 5-Bromooxindole (2.12 g, 10 mmol, 1.0 equiv.) and THF (12 mL) under an Ar atmosphere and cooled −15° C. To the stirred mixture was added KO$^t$Bu 1-((Cyclopentylmethyl)sulfonyl)-4-fluorobenzene [S17]. 533 μL (5.0 mmol) of 4-flourothiophenol was dissolved in 10 mL (0.5 M) acetone. 1.0695 g (6.0 mmol, 1.2 equiv.) of cyclopentylmethyl methanesulfonate and 829.3 mg (6.0 mmol, 1.2 equiv.) of K$_2$CO$_3$ was added sequentially and the reaction was allowed to stir overnight. The reaction was diluted with 20 mL water and extracted with 30 mL EtOAc three times. The combined organic layer was dried with Na$_2$SO$_4$, filtered, and concentrated. Flash column chromatography on silica (50 mm fritted glass column, 150 mL SiO$_2$) using 1% EtOAc/hexanes→3% EtOAc/hexanes as eluent gave 746.6 mg (3.55 mmol) of (cyclopentylmethyl)(4-fluorophenyl)sulfane intermediate with minor impurity. The intermediate was dissolved in 32 mL 1:1 MeOH:H$_2$O and 3.274 g (10.65 mmol, 3.0 equiv.) Oxone® was added in portions at 0° C. The reaction was allowed to warm up to room temperature and stirred overnight. The reaction was diluted with 30 mL water and extracted with 40 mL ether TWICE. The combined organic layer was washed with 40 mL brine, dried with MgSO$_4$, filtered, and concentrated. Flash column chromatography on silica (50 mm fritted glass column, 150 mL SiO$_2$) using 10% EtOAc/hexanes→20% EtOAc/hexanes as eluent gave 788.2 mg (3.25 mmol) of pure product as a white solid in 65% yield over 2 steps.

$^1$H-NMR (500 MHz, CDCl$_3$) δ 7.96-7.92 (m, 2H), 7.27-7.22 (m, 2H), 3.14 (d, J=6.9 Hz, 2H), 2.30-2.21 (m, 1H), 1.92-1.86 (m, 2H), 1.64-1.51 (m, 4H), 1.26-1.18 (m, 2H). $^{13}$C-NMR (126 MHz, CDCl$_3$) δ 165.9 (d, J=255.9 Hz), 136.2, 131.0 (d, J=9.5 Hz), 116.7 (d, J=22.6 Hz), 62.3, 34.5, 32.8, 24.9. $^{19}$F-NMR (470 MHz, CDCl$_3$) δ -104.31. HRMS (TOF ESI+) m/z calculated for C$_{12}$H$_{16}$O$_2$SF [M+H]$^+$: 243.0855, found 243.0860.

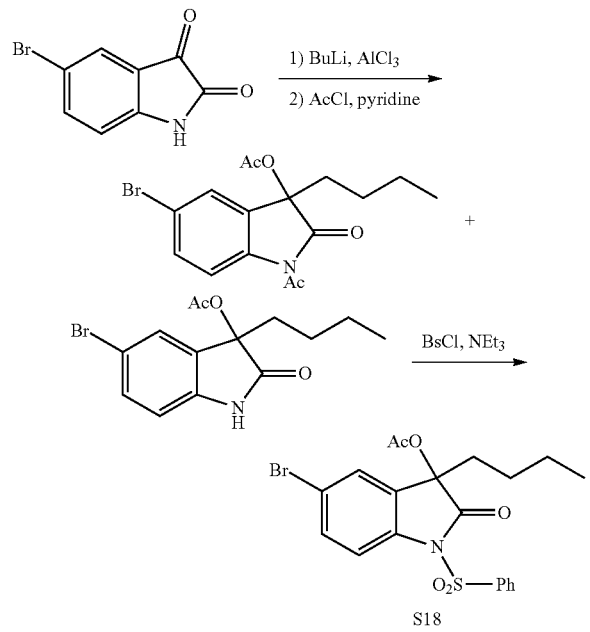

(±)-5-Bromo-3-butyl-2-oxo-1-(phenylsulfonyl)indolin-3-yl acetate [S18]. A 100 mL round bottom flask was charged with a stir bar and AlCl$_3$ (2.67 g, 20 mmol, 2.0 equiv.) under inert atmosphere and placed in an ice bath. THF (20 mL) was carefully added to dissolve AlCl$_3$ and the ice bath was replaced with a water bath. To the stirred solution was added n-BuLi (1.6 M in hexane, 37.5 mL, 60.0 mmol, 6.0 equiv.) dropwise over 30 minutes and the resulting suspension was stirred at room temperature. After 1 hour, THF was removed under the reduced pressure and the residue was dissolved with toluene (10 mL) under Ar atmosphere. A 20 mL syringe fitted with LC PVDF filter (HPLC certified) was used to remove white precipitate of LiCl, and the solid was rinsed with toluene (5 mL). A 300 mL round bottom flask was charged with a stir bar and 5-bromoisatin and toluene (50 mL) under Ar atmosphere. To the stirred suspension was added the prepared solution of Bu$_3$Al in toluene dropwise and the mixture was stirred at 70° C. After 3 hours, the mixture was concentrated under reduced pressure and cooled to 0° C., then quenched with saturated potassium sodium tartrate (100 mL), diluted with EtOAc (100 mL) and stirred at room temperature. After 1 hour, aqueous layer was separated and extracted with EtOAc (2×100 mL). The combined organic layers were washed with brine (50 mL), dried over Na$_2$SO$_4$ filtered and concentrated under reduced pressure to give 1.76 g of a crude product. A 100 mL round bottom flask was charged with a stir bar, the crude mixture (1.76 g, less than 6.19 mmol) and DCM (20 mL). To the stirred mixture were added pyridine (1.50 mL, 18.6 mmol, 3.0 equiv.), 4-(dimethylamino)pyridine (DMAP, 151 mg, 1.24 mmol, 0.20 equiv.), and acetic anhydride (1.76 mL, 18.6 mmol, 3.0 equiv.) and the mixture was stirred at room temperature overnight.

The reaction was quenched with H$_2$O and extracted with DCM (3×20 mL). The combined organic layers were washed with H$_2$O (20 mL) and brine (20 mL), dried over Na$_2$SO$_4$, filtered, and concentrated under reduced pressure. The residue was diluted with DCM and concentrated onto silica gel (15 mL) for dry loading onto the column (SiO$_2$, 150 mL) and then eluted with 5% EtOAc/Hexane to afford 1-acetyl-5-bromo-3-butyl-2-oxoindolin-3-yl acetate and 5-bromo-3-butyl-2-oxoindolin-3-yl acetate. 1-acetyl-5-bromo-3-butyl-2-oxoindolin-3-yl acetate (260 mg, 0.706 mmol) could be converted to 5-bromo-3-butyl-2-oxoindolin-3-yl acetate by treatment with Na$_2$CO$_3$ (15.0 mg, 0.142 mmol) in MeOH (5 mL) at 0° C. for 30 min. A 100 mL round bottom flask was charged with a stir bar, 5-bromo-3-butyl-2-oxoindolin-3-yl acetate (638 mg, 1.96 mmol, 1.0 equiv.), benzenesulfonyl chloride (375 μL, 2.94 mmol, 1.5 equiv.), and DCM (10 mL). To the stirred mixture was added Et$_3$N (546 μL, 3.92 mmol, 2.0 equiv.) and the mixture was stirred at 30° C. overnight. The reaction was quenched with H$_2$O and extracted with DCM (3×20 mL). The combined organic layers were dried over Na$_2$SO$_4$, filtered, and concentrated under reduced pressure. The residue was diluted with DCM and concentrated onto silica gel (5 mL) for dry loading onto the column (SiO$_2$, 100 mL) and then eluted with 5%→EtOAc/Hexane to afford 544 mg (1.17 mmol) of the 5-bromo-1-((4-bromophenyl)sulfonyl)-3-butyl-2-oxoindolin-3-yl acetate in 60% yield as a white solid.

$^1$H-NMR (500 MHz, CDCl$_3$) δ 8.06 (d, J=7.5 Hz, 2H), 7.83 (d, J=8.7 Hz, 1H), 7.65 (t, J=7.5 Hz, 1H), 7.54-7.49 (m, 3H), 7.28 (d, J=2.1 Hz, 1H), 1.91 (s, 3H), 1.97-1.86 (m, 2H), 1.27-1.19 (m, 2H), 1.15-1.00 (m, 2H), 0.80 (t, J=7.3 Hz, 3H). $^{13}$C-NMR (125 MHz, CDCl$_3$) δ 172.4, 168.9, 138.4, 137.3, 134.8, 133.2, 129.7, 129.1, 128.2, 126.0, 118.3, 115.3, 79.0, 36.9, 23.8, 22.6, 20.3, 13.8. HRMS (TOF ESI+) m/z calculated for C$_{20}$H$_{20}$BrNNaO$_5$S [M+Na]$^+$: 488.0143, found 488.0130.

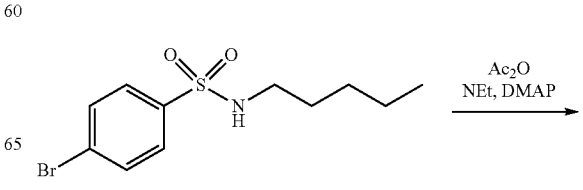

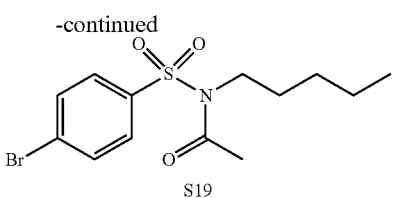

S19

N-((4-Bromophenyl)sulfonyl)-N-pentylacetamide [S19]. In a flamed dried 50 mL flask, 995 mg (3.25 mmol, 1.0 equiv.) of 4-bromo-N-pentylbenzenesulfonamide, 2.27 mL (16.25 mmol, 5.0 equiv.) of triethylamine and 39.7 mg (0.33 mmol, 10 mol %) of DMAP was dissolved in 14 mL DCM. 0.7 mL (9.75 mmol, 3.0 equiv.) acetic chloride was added dropwise at 0° C. and the reaction was allowed to warm to RT and stir overnight. 14 mL of water was added to quench the reaction and the aqueous layer was extracted with 14 mL DCM twice. The combined organic layer was washed with 30 mL brine and was dried with $Na_2SO_4$. Flash column chromatography on silica (150 mm fritted glass column, 200 mL $SiO_2$) using 5% EtOAc/hexanes→15% EtOAc/hexanes as eluent gave 1.122 g (3.16 mmol) of pure product as a sticky colorless oil (97% yield).

$^1$H-NMR (500 MHz, $CDCl_3$) δ 7.78-7.75 (m, 2H), 7.70-7.67 (m, 2H), 3.77-3.74 (m, 2H), 2.29 (s, 3H), 1.74-1.68 (m, 2H), 1.40-1.28 (m, 4H), 0.91 (t, J=7.0 Hz, 3H). $^{13}$C-NMR (126 MHz, $CDCl_3$) δ 170.0, 138.9, 132.6, 129.3, 129.0, 47.6, 29.9, 29.0, 24.9, 22.4, 14.1. HRMS (TOF ESI+) m/z calculated for $C_{13}H_{19}NO_3SBr$ [M+H]$^+$: 348.0269, found 348.0268.

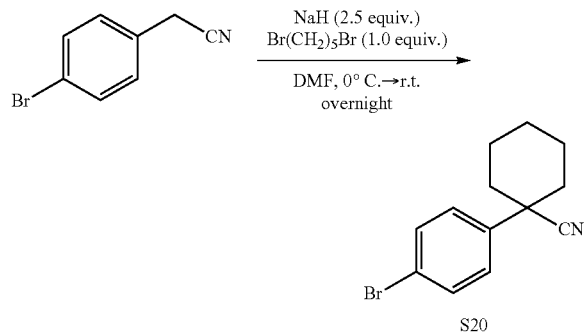

1-(4-Bromophenyl)cyclohexane-1-carbonitrile [S20]. In a flamed dried 50 mL flask, 1.9604 g (10.0 mmol) of 2-(4-bromophenyl)acetonitrile was dissolved in 15 mL anhydrous DMF. 632.0 mg (95% purity, 25.0 mmol, 2.5 equiv.) of NaH was added in portions at 0° C. and the reaction was allowed to stir for 1 hour at 0° C. 2.2994 g (1.36 mL, 10.0 mmol, 1.0 equiv.) of 1,5-dibromopentane was added dropwise at 0° C. and the reaction was allowed to stir overnight at room temperature. The reaction was quenched carefully with ~10 mL water and extracted with 30 mL EtOAc three times. The combined organic layer was washed with 50 mL brine, dried with $MgSO_4$, filtered, and concentrated. Flash column chromatography on silica (50 mm fritted glass column, 300 mL $SiO_2$) using 5% EtOAc/hexanes→10% EtOAc/hexanes as eluent gave 1.9307 g (7.3 mmol) of pure product as a white solid (73% yield).

$^1$H-NMR (500 MHz, $CDCl_3$) δ 7.53-7.50 (m, 2H), 7.38-7.35 (m, 2H), 2.15-2.11 (m, 2H), 1.90-1.78 (m, 5H), 1.72 (ddd, J=13.0, 12.8, 4.1 Hz, 2H), 1.32-1.22 (m, 1H). $^{13}$C-NMR (126 MHz, $CDCl_3$) δ 140.7, 132.1, 127.5, 122.4, 121.9, 44.2, 37.4, 25.0, 23.7. HRMS (EI+) m/z calculated for $C_{13}H_{14}NBr$ [M]$^+$: 263.0310, found 263.0313.

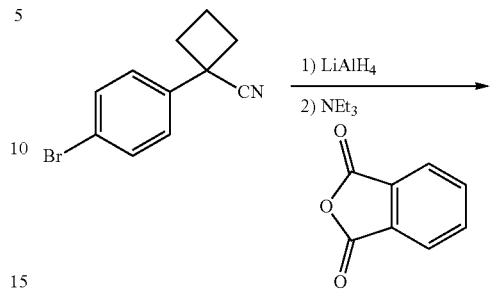

S21

2-((1-(4-Bromophenyl)cyclobutyl)methyl)isoindoline-1,3-dione [S21]. In a flamed dried 50 mL flask, 232.0 mg (6.12 mmol, 1.5 equiv.) $LiAlH_4$ was mixed with 12 mL anhydrous ether, a solution of 963.0 mg (4.08 mmol, 1.0 equiv.) of 1-(4-bromophenyl)cyclobutane-1-carbonitrile in 6 mL anhydrous ether was added dropwise at 0° C. The reaction was allowed to reflux overnight before quenched with 250 μL water, 250 μL 15% NaOH and 750 μL water sequentially. After stirring for 1 h, $MgSO_4$ was added and the mixture was filtered through Celite. The filtrate was concentrated and redissovled in 20 mL toluene, 604.2 mg (4.08 mmol, 1.0 equiv.) of phthalic anhydride was added followed by 570 μL (4.08 mmol, 1.0 equiv.) triethylamine. The reaction was refluxed overnight and concentrated. Flash column chromatography on silica (50 mm fritted glass column, 200 mL $SiO_2$) using 5% EtOAc/hexanes→15% EtOAc/hexanes as eluent gave 1.2621 g (3.41 mmol) of pure product as a white solid (84% yield over 2 steps).

$^1$H-NMR (500 MHz, $CDCl_3$) δ 7.77 (dd, J=5.4, 3.1 Hz, 2H), 7.69 (dd, J=5.5, 3.1 Hz, 2H), 7.36 (d, J=8.2 Hz, 2H), 7.02 (d, J=8.3 Hz, 2H), 3.95 (s, 2H), 2.51 (ddd, J=12.7, 8.7, 4.7 Hz, 2H), 2.39-2.33 (m, 2H), 2.08 (dp, J=11.4, 8.5 Hz, 1H), 1.87-1.79 (m, 1H). $^{13}$C-NMR (126 MHz, $CDCl_3$) δ 168.5, 146.3, 134.1, 131.8, 131.2, 128.1, 123.4, 120.0, 47.9, 47.8, 31.8, 16.1. HRMS (TOF ESI+) m/z calculated for $C_{19}H_{17}NO_2Br$ [M+H]$^+$: 370.0443, found 370.0442.

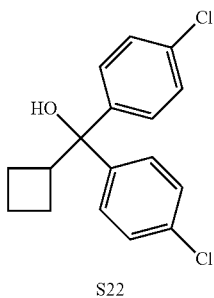

S22

Bis(4-chlorophenyl)(cyclobutyl)methanol [S22]. In a flamed dried 100 mL flask, 572.8 mg (4.0 mmol, 1.0 equiv.) of N-methoxy-N-methylcyclobutanecarboxamide was dissolved in 20 mL THF, 11 mL THF solution containing 12 mmol (3.0 equiv.) freshly made 4-Chlorophenylmagnesium bromide was added dropwise at −78° C. The reaction was allowed to stir at −78° C. for 1 h then at RT for 1.5 h. The reaction was quenched with saturated NH$_4$Cl solution, extracted with 20 mL ether three times. The combined organic layer was concentrated, dissolved in 20 mL DCM and washed with 20 mL brine. Followed by drying with MgSO$_4$, the crude reaction was transferred into a 100 mL flamed dried flask and dissolved in 20 mL THF. Another portion of 11 mL THF solution containing 10 mmol (2.5 equiv.) 4-Chlorophenyl magnesium bromide was added dropwise at −78° C. The reaction was allowed to warm up to RT and stirred overnight. The reaction was quenched with saturated NH$_4$Cl solution, extracted with 30 mL ether three times. The combined organic layer was washed with 30 mL brine and was dried with Na$_2$SO$_4$. Flash column chromatography on silica (150 mm fritted glass column, 200 mL SiO$_2$) using 5% EtOAc/hexanes→10% EtOAc/hexanes as eluent gave 905.8 mg (2.95 mmol) of pure product as a yellow solid (74% yield).

$^1$H-NMR (500 MHz, CDCl$_3$) δ 7.28-7.24 (m, 8H), 3.34-3.30 (m, 1H), 2.15 (br. s, 1H), 2.05-1.96 (m, 2H), 1.89-1.72 (m, 4H). $^{13}$C-NMR (126 MHz, CDCl$_3$) δ 144.3, 133.0, 128.4, 127.9, 78.0, 44.0, 22.9, 17.1. HRMS (EI+) m/z calculated for C$_{17}$H$_{16}$OCl$_2$ [M]$^+$: 306.0578, found 306.0575.

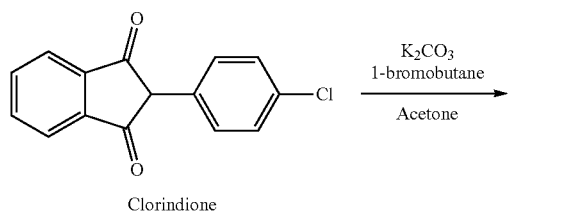

Clorindione

S23

2-Butyl-2-(4-chlorophenyl)-1H-indene-1,3(2H)-dione [S23]. In a 50 mL flask, 223.4 mg (0.87 mmol, 1.0 equiv.) of Clorindione was dissolved in 4.4 mL acetone followed by 360.7 mg (2.61 mmol, 3.0 equiv.) K$_2$CO$_3$ and 934 μL (8.70 mmol, 10 equiv.) 1-bromobutane. The flask was capped with polyethylene cap and sealed with electric tape and the reaction was allowed to stir under 60° C. for 24 hours. The reaction was concentrated, dissolved in 20 mL water and extracted with 20 mL EtOAc three times. The combined organic layer was dried with Na$_2$SO$_4$, filtered, and concentrated. Purification by CombiFlash on silica (40 g) using hexanes→10% EtOAc/hexanes as eluent gave 145.4 mg (0.47 mmol) of pure product as a yellow solid (54% yield).

$^1$H-NMR (500 MHz, CDCl$_3$) δ 8.07-8.02 (m, 2H), 7.89-7.87 (m, 2H), 7.39-7.36 (m, 2H), 7.28-7.25 (m, 2H), 2.24-2.19 (m, 2H), 1.28-1.21 (m, 2H), 1.13-1.07 (m, 2H), 0.79 (t, J=7.3 Hz, 3H). $^{13}$C-NMR (126 MHz, CDCl$_3$) δ 201.8, 142.0, 136.2, 135.7, 133.8, 129.0, 128.4, 123.7, 61.6, 36.6, 27.4, 23.2, 13.8. HRMS (TOF ESI+) m/z calculated for C$_{19}$H$_{18}$O$_2$Cl [M+H]$^+$: 313.0995, found 313.0991.

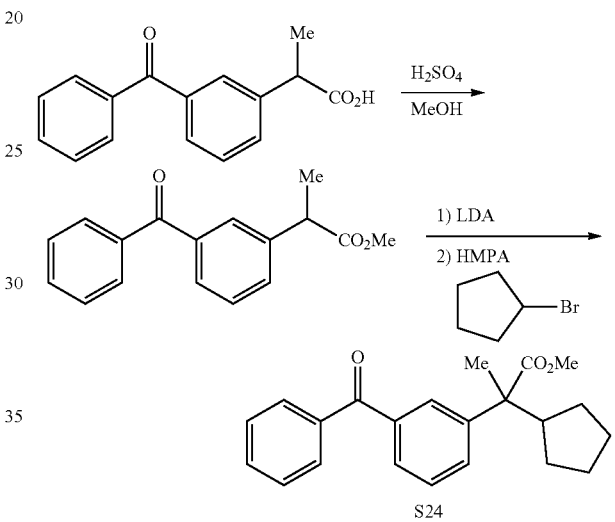

S24

(±)-Methyl 2-(3-benzoylphenyl)-2-cyclopentylpropanoate [S24]. In a 50 mL recovery flask was charged 3.814 g (15 mmol) ketoprofen, 25 mL MeOH and 1 mL concentrated H$_2$SO$_4$. The reaction was refluxed overnight. After cooled to room temperature, the reaction was poured into 100 mL water and extract with 50 mL DCM 3 times. Combined organic layer was washed with sat. NaHCO$_3$, dried with MgSO$_4$ then purified by a plug of silica. In a 300 mL flamed dried flask, 1.3416 g (5 mmol) of ketoprofen methyl ester was dissolved in 50 mL anhydrous THF, cooled to −78° C. and 5.5 mmol (1.1 equiv.) freshly made LDA solution and 0.87 mL (5.0 mmol, 1.0 equiv.) HMPA was added sequentially. After stirring at −78° C. for 10 minutes, 1.61 mL (2.2355 g, 15 mmol, 3.0 equiv.) of bromocyclopentane was added. The reaction was allowed to warm to room temperature and stirred overnight. The reaction was quenched with 10 mL saturated NH$_4$Cl, extracted with 30 mL ether 3 times and dried over MgSO$_4$. The crude mixture was purified by CombiFlash using a 40 g silica column and eluted with pure hexane→10% ethyl acetate/hexane to give product in 631.9 mg (1.96 mmol, 39% yield).

$^1$H-NMR (500 MHz, CDCl$_3$) 7.80-7.78 (m, 3H), 7.65 (ddd, J=7.6, 1.6, 1.1 Hz, 1H), 7.61-7.51 (m, 2H), 7.50-7.47 (m, 2H), 7.44-7.41 (m, 1H), 3.66 (s, 3H), 2.80 (tt, J=9.3, 7.9 Hz, 1H), 1.75-1.72 (m, 1H), 1.55 (s, 3H), 1.59-1.37 (m, 6H), 1.14 (ddt, J=12.5, 9.8, 7.8 Hz, 1H). $^{13}$C-NMR (126 MHz, CDCl$_3$) δ 196.8, 176.3, 144.2, 137.7, 137.6, 132.6, 130.8, 130.2, 128.6, 128.4, 128.31, 128.27, 53.0, 52.2, 47.0, 28.6, 27.9, 26.0, 25.8, 18.7. HRMS (TOF ESI+) m/z calculated for $C_{22}H_{25}O_3$ [M+H]$^+$: 337.1804, found 337.1793.

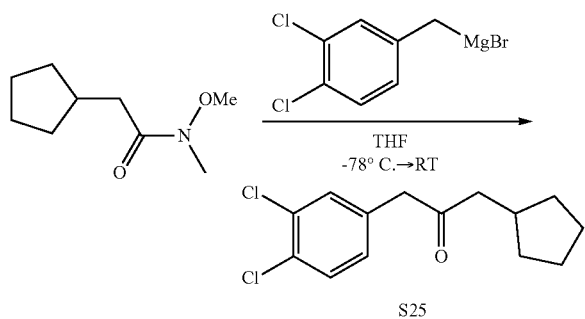

1-Cyclopentyl-3-(3,4-dichlorophenyl)propan-2-one [S25]. In a flamed dried 100 mL flask, 822.0 mg (4.8 mmol, 1.0 equiv.) of 2-cyclopentyl-N-methoxy-N-methylacetamide was dissolved in 24 mL anhydrous THF, 11 mL THF solution containing 5.3 mmol (1.1 equiv.) freshly made (3,4-dichlorobenzyl)magnesium bromide was added dropwise at −78° C. The reaction was allowed to warm up to room temperature stir at −78° C. for 1 h then at RT for 2 h. The reaction was quenched with saturated NH$_4$Cl solution, extracted with 20 mL ether three times. The combined organic layer was washed with 20 mL brine, dried with MgSO$_4$ and concentrated. Flash column chromatography on silica (150 mm fritted glass column, 150 mL SiO$_2$) using 3% EtOAc/hexanes→5% EtOAc/hexanes as eluent gave 672.8 mg (2.48 mmol) of pure product as a clear oil (52% yield).

$^1$H-NMR (500 MHz, CDCl$_3$) δ 7.39 (d, J=8.2 Hz, 1H), 7.29 (d, J=2.0 Hz, 1H), 7.02 (dd, J=8.2, 1.9 Hz, 1H), 3.64 (s, 2H), 2.49 (d, J=7.2 Hz, 2H), 2.23 (hept, J=7.3 Hz, 1H), 1.84-1.78 (m, 2H), 1.62-1.51 (m, 4H), 1.09-1.00 (m, 2H). $^{13}$C-NMR (126 MHz, CDCl$_3$) δ 207.0, 134.5, 132.7, 131.5, 131.3, 130.6, 129.0, 48.9, 48.9, 35.6, 32.7, 25.1.HRMS (TOF ESI+) m/z calculated for $C_{14}H_{17}OCl_2$ [M+H]$^+$: 271.0656, found 271.0666.

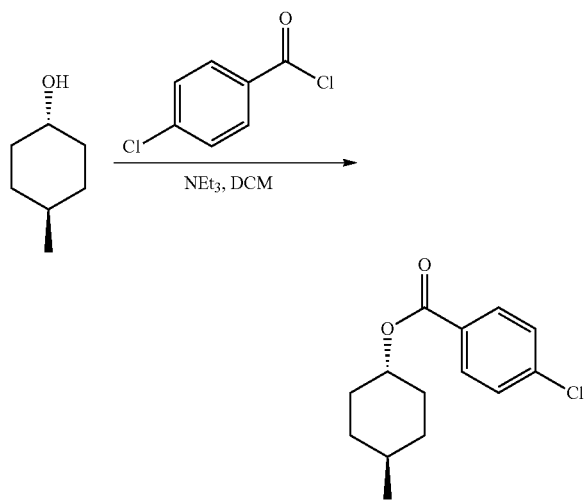

(±)-trans-4-Methylcyclohexyl 4-chlorobenzoate [S26]. In an oven dried 50 mL recovery flask was charged with trans-4-methylcyclohexanol 628.0 mg (5.5 mmol, 1.1 equiv.) in 10 mL anhydrous DCM. 0.64 mL (5 mmol, 1.0 equiv.) 4-chlorobenzoyl chloride and 1.05 mL (7.5 mmol, 1.5 equiv.) of triethylamine was sequentially added at 0° C. The reaction was warmed to room temperature and stirred overnight before quenched with 30 mL water. The aqueous layer was extracted with 30 mL DCM twice and the combined organic layer was washed with brine, dried with MgSO$_4$ and concentrated. Flash column chromatography on silica (150 mm fritted glass column, 250 mL SiO$_2$) using 1% EtOAc/hexanes→2% EtOAc/hexanes→5% EtOAc/hexanes as eluent gave 986.7 mg (3.90 mmol) of pure product as a white solid (78% yield).

$^1$H-NMR (500 MHz, CDCl$_3$) δ 7.98-7.95 (m, 2H), 7.41-7.38 (m, 2H), 4.90 (tt, J=11.1, 4.4 Hz, 1H), 2.09-2.05 (m, 2H), 1.80-1.76 (m, 2H), 1.50-1.44 (m, 3H), 1.12-1.09 (m, 2H), 0.92 (d, J=6.6 Hz, 3H). $^{13}$C-NMR (126 MHz, CDCl$_3$) δ 165.4, 139.2, 131.1, 129.5, 128.7, 74.5, 33.2, 31.9, 31.8, 22.0. HRMS (TOF ESI+) m/z calculated for $C_{14}H_{17}O_2NaCl$ [M+Na]$^+$: 275.0815, found 275.0805.

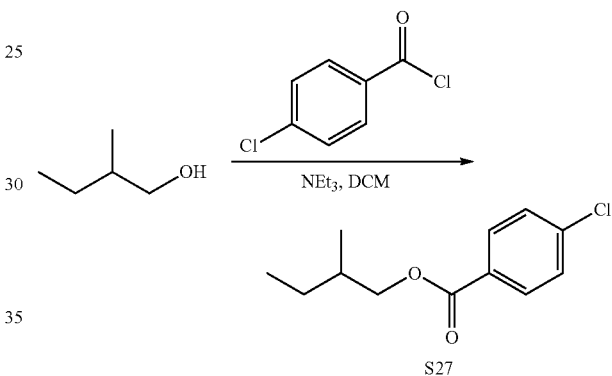

(±)-2-Methylbutyl 4-chlorobenzoate [S27]. In an oven dried 50 mL recovery flask was charged with 2-methylbutan-1-ol 1.08 mL (881.5 mg, 10.0 mmol, 1.0 equiv.) in 20 mL anhydrous DCM. 2.56 mL (20.0 mmol, 2.0 equiv.) 4-chlorobenzoyl chloride and 4.18 mL (30.0 mmol, 3.0 equiv.) of triethylamine was sequencially added at 0° C. The reaction was warmed to room temperature and stirred overnight before quenched with 30 mL water. The aqueous layer was extracted with 30 mL DCM twice and the combined organic layer was washed with brine, dried with MgSO$_4$ and concentrated. Flash column chromatography on silica (150 mm fritted glass column, 250 mL SiO$_2$) using 1% EtOAc/hexanes→2% EtOAc/hexanes→5% EtOAc/hexanes as eluent gave 2.094 g (9.24 mmol) of pure product as a clear oil (92% yield).

$^1$H-NMR (500 MHz, CDCl$_3$) δ 7.98 (d, J=8.6 Hz, 2H), 7.41 (d, J=8.6 Hz, 2H), 4.20 (dd, J=10.7, 6.0 Hz, 1H), 4.12 (dd, J=10.7, 6.7 Hz, 1H), 1.90-1.81 (m, 1H), 1.51 (dtd, J=13.3, 7.5, 5.7 Hz, 1H), 1.27 (dq, J=13.6, 7.5 Hz, 1H), 1.01 (d, J=6.8 Hz, 3H), 0.95 (t, J=7.5 Hz, 3H). $^{13}$C-NMR (126 MHz, CDCl$_3$) δ 165.9, 139.4, 131.1, 129.1, 128.8, 69.9, 34.4, 26.3, 16.7, 11.4. HRMS (TOF ESI+) m/z calculated for $C_{12}H_{15}O_2NaCl$ [M+Na]$^+$: 249.0658, found 249.0670.

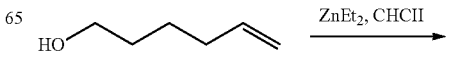

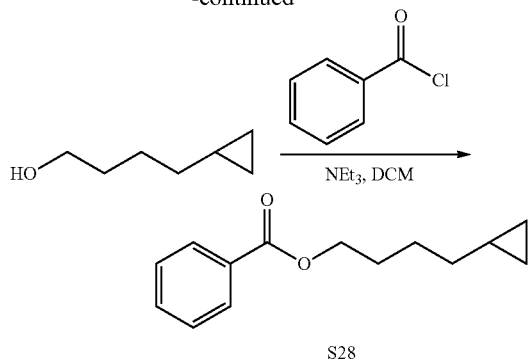

S28

4-Cyclopropylbutyl benzoate [S28]. In a flame dried 100 mL flask 14.2 mL of 1M diethyl zinc solution in toluene was added in 17 mL anhydrous 1,2-dichloroethane. 5.0 g (28.4 mmol) $CH_2ClI$ was added dropwise over 5 minutes at 0° C. The reaction was kept at 0° C. for 5 minutes before 801.3 mg (8.0 mmol) of 5-hexene-1-ol dissolved in 3 mL anhydrous 1,2-dichloroethane was added dropwise and the reaction was allowed to stir at RT overnight. 20 mL sat. $NH_4Cl$ solution was used to quench the reaction and the aqueous layer was extracted with 20 mL DCM 3 times. The combined organic layer was washed with 40 mL 1:1 brine:water and dried with $MgSO_4$. The crude mixture was dissovled in 40 mL anhydrous DCM, treated with benzoyl chloride (3.374 g, 24.0 mmol, 2.8 mL) and triethylamine (4.048 g, 40 mmol, 5.65 mL) at 0° C., stirred overnight at room temperature before diluted with 50 mL DCM and worked up with 50 mL 1 M HCl. The organic layer was washed by 50 mL sat. $NaHCO_3$, 50 mL brine, dried with $Na_2SO_4$ and concentrated. The crude mixture was treated with 2.34 g (9.5 mmol) 70% wt. mCPBA to convert the unreacted olefin impurity to the corresponding epoxide, which can be removed via column chromatography on silica (50 mm fitted glass column, 200 mL $SiO_2$) using 5% EtOAc/hexanes→10% EtOAc/hexanes as eluent to afford 389 mg (1.8 mmol) of pure product as a colorless oil (22% yield over 3 steps).

$^1$H-NMR (500 MHz, $CDCl_3$) δ 8.06-8.04 (m, 2H), 7.55 (td, J=7.3, 1.5 Hz, 1H), 7.44 (t, J=7.8 Hz, 2H), 4.32 (t, J=6.7 Hz, 2H), 1.83-1.77 (m, 2H), 1.55 (tt, J=7.6, 6.6 Hz, 2H), 1.27 (q, J=7.2 Hz, 2H), 0.72-0.64 (m, 1H), 0.43-0.40 (m, 2H), 0.03--0.00 (m, 2H). $^{13}$C-NMR (126 MHz, $CDCl_3$) δ 166.8, 132.9, 130.6, 129.7, 128.4, 65.3, 34.5, 28.7, 26.2, 10.9, 4.6. HRMS (TOF ESI+) m/z calculated for $C_{14}H_{18}O_2Na$ [M+Na]$^+$: 241.1204, found 241.1212.

General Oxidation Procedures (Table 4)

Method A: Single Catalyst Addition Protocol. A 40 mL vial was charged with substrate (0.3 mmol, 1.0 equiv.), catalyst (0.03 mmol, 10 mol %), $ClCH_2CO_2H$ (425 mg, 4.5 mmol, 15.0 equiv.) and a stir bar. MeCN (0.6 mL, 0.50 M) was added along the wall to ensure all compounds were washed beneath the solvent level and the vial was sealed with a screw cap fitted with a PTFE/Silicone septum. The vial was cooled to 0° C. with ice/water bath. A separate solution of $H_2O_2$ [(204 mg, 3.0 mmol, 10.0 equiv.), 50% wt. in $H_2O$, purchased from Sigma-Aldrich] in MeCN (3.75 mL) was loaded into a 10 mL syringe fitted with a 25 G needle and was added dropwise to the stirring reaction over 3 hours via a syringe pump (1.25 mL/h addition rate) while maintain the reaction at 0° C. Upon completion, the reaction mixture was concentrated to a minimum amount of solvent. The residue was dissolved in ~20 mL DCM and washed with 9 mL sat. $NaHCO_3$ solution (CAUTION: $CO_2$ was released) to remove $ClCH_2CO_2H$. The aqueous layer was extracted with ~15 mL DCM two times and the combined organic layer was dried with $Na_2SO_4$. The filtrate was concentrated and purified by flash chromatography on silica gel.

Method B: Iterative Catalyst Addition Protocol. This protocol was used when Method A gave low conversions. A 40 mL vial was charged with substrate (0.3 mmol, 1.0 equiv.), catalyst (0.015 mmol, 5 mol %), $ClCH_2CO_2H$ (425 mg, 4.5 mmol, 15.0 equiv.) and a stir bar. MeCN (0.6 mL, 0.50 M) was added along the wall to ensure all compounds were washed beneath the solvent level and the vial was sealed with a screw cap fitted with a PTFE/Silicone septum. The vial was cooled to −36° C. with 1,2-dichloroethane/dry ice bath or to 0° C. with ice/water bath. A separate solution of $H_2O_2$ [(204 mg, 3.0 mmol, 10.0 equiv.), 50% wt. in $H_2O$, purchased from Sigma-Aldrich] in MeCN (3.75 mL) was loaded into a 10 mL syringe fitted with a 25 G needle and was added dropwise to the stirring reaction over 3 hours via a syringe pump (1.25 mL/h addition rate) while maintain at the corresponding temperature.

The initial time is recorded as the time the first drop of $H_2O_2$ solution was added into the reaction. One hour after the initial time, another batch of catalyst (0.015 mmol, 5 mol %) was dissolved with 0.1 mL MeCN in a 0.5-dram vial and added dropwise into the reaction via syringe followed directly by another 0.1 mL MeCN that was used to rinse the vial. The addition of 5 mol % catalyst was repeated at two hours after the initial time using the same procedure. A total of 15 mol % of catalyst was used in this protocol. Upon completion, the reaction mixture was concentrated to a minimum amount of solvent. The residue was dissolved in 20 mL DCM and washed with 9 mL sat. $NaHCO_3$ solution (CAUTION: $CO_2$ was released) to remove $ClCH_2CO_2H$. The aqueous layer was extracted with ~15 mL DCM two times and the combined organic layer was dried with $Na_2SO_4$. The filtrate was concentrated and purified by flash chromatography on silica gel.

Method C: Slow Catalyst Addition Protocol. This protocol was used when Method A and Method B gave low conversions. A 40 mL vial was charged with substrate (0.3 mmol, 1.0 equiv.), $ClCH_2CO_2H$ (425 mg, 4.5 mmol, 15.0 equiv.) and a stir bar. MeCN (0.6 mL, 0.50 M) was added along the wall to ensure all compounds were washed beneath the solvent level and the vial was sealed with a screw cap fitted with a PTFE/Silicone septum. The vial was cooled to −36° C. with 1,2-dichloroethane/dry ice bath or to 0° C. with ice/water bath. A 1.0 mL syringe was filled with a solution of the catalyst (0.03 mmol, 10 mol %) in MeCN (0.375 mL, 0.083 M). A few drops of this solution were added to the reaction. A 10 mL syringe was filled with a solution of $H_2O_2$ (204 mg, 3.0 mmol, 10.0 equiv., 50% wt. in $H_2O$, purchased from Sigma-Aldrich) in MeCN (3.75 mL, 0.8 M). Both syringes were fitted with 25 G needles and loaded to a syringe pump resulting a slow simultaneous addition of catalyst and oxidant solutions over 3 hours while maintain at the corresponding temperature (1.25 mL/h addition rate set for the $H_2O_2$ syringe; 0.125 mL/h for the catalyst syringe). Upon completion, the reaction mixture was concentrated to a minimum amount of solvent. The residue was dissolved in ~20 mL DCM and washed with 9 mL sat. $NaHCO_3$ solution (CAUTION: $CO_2$ was released) to remove $ClCH_2CO_2H$. The aqueous layer was extracted with ~15 mL DCM two times and the combined organic layer was dried with $Na_2SO_4$. The filtrate was concentrated and purified by flash chromatography on silica gel.

C—H Oxidation of Substrates and Products Characterization (Table 4)

In all oxidations using Mn(CF$_3$-PDP) 1 with General Method A, B, C and D (vide infra), the yields of oxidation products are reported as isolated yields after column chromatography with >95% purity. Trace solvent residues are integrated out with quantitative $^1$H NMR characterization of the oxidation product.

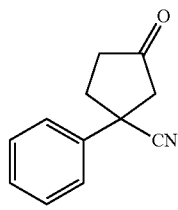 [SMILES: N#CC1(c2ccccc2)CCC(=O)C1]

3-Oxo-1-phenylcyclopentane-1-carbonitrile [7]. The reaction was run with General Method A: Single Catalyst Addition Protocol: 1-phenylcyclopentane-1-carbonitrile S3 (85.6 mg, 0.500 mmol, 1.0 equiv), (R,R)—Mn(CF$_3$-PDP) (67.8 mg, 0.050 mmol, 10 mol %), ClCH$_2$CO$_2$H (709 mg, 7.5 mmol, 15.0 equiv.), 50% wt. H$_2$O$_2$ (340 mg, 5.0 mmol, 10.0 equiv.), MeCN (1.0 mL in 40 mL vial, 6.25 mL with oxidant). The reaction was run at 0° C. with ice bath. The reaction was worked up with 15 mL saturated NaHCO$_3$ and DCM as described in General Method A. Flash column chromatography on silica (35 mm fritted glass column, 150 mL SiO$_2$) using 10% acetone/hexanes→20% acetone/hexanes as eluent. Fractions contain products were collected and the yield was obtained by $^1$H NMR analysis by adding nitrobenzene as internal standard. Run 1: (8.1 mg, 0.044 mmol, 8.7% yield), (17.7 mg, 0.103 mmol, 20.7% rsm). Run 2: (8.8 mg, 0.048 mmol, 9.5% yield), (20.4 mg, 0.120 mmol, 24.0% rsm). Run 3: (9.9 mg, 0.053 mmol, 10.7% yield), (19.8 mg, 0.116 mmol, 23.1% rsm). Average: 9.6% yield±1.0%, 22.6% rsm±1.7%.

$^1$H-NMR (500 MHz, CDCl$_3$) δ 7.46-7.37 (m, 5H), 3.06 (d, J=18.2 Hz, 1H), 2.86-2.79 (m, 2H), 2.70-2.63 (m, 1H), 2.56-2.43 (m, 2H). $^{13}$C-NMR (126 MHz, CDCl$_3$) δ 212.2, 137.6, 129.5, 128.9, 125.9, 122.6, 50.0, 44.2, 36.8, 36.5. HRMS (EI+) m/z calculated for C$_{12}$H$_{11}$ON [M]$^+$: 185.08407, found 185.08379.

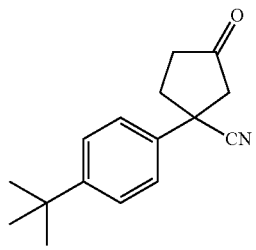 [SMILES: CC(C)(C)c1ccc(C2(C#N)CCC(=O)C2)cc1]

1-(4-(tert-Butyl)phenyl)-3-oxocyclopentane-1-carbonitrile [8]. The reaction was run with General Method A: Single Catalyst Addition Protocol: 1-(4-tert-butylphenyl)cyclopentane-1-carbonitrile S4 (113.7 mg, 0.500 mmol, 1.0 equiv), (R,R)—Mn(CF$_3$-PDP) (67.8 mg, 0.050 mmol, 10 mol %), ClCH$_2$CO$_2$H (709 mg, 7.5 mmol, 15.0 equiv.), 50% wt. H$_2$O$_2$ (340 mg, 5.0 mmol, 10.0 equiv.), MeCN (1.0 mL in 40 mL vial, 6.25 mL with oxidant). The reaction was run at 0° C. with ice bath. The reaction was worked up with 15 mL saturated NaHCO$_3$ and DCM as described in General Method A. Flash column chromatography on silica (35 mm fritted glass column, 150 mL SiO$_2$) using 10% acetone/hexanes→20% acetone/hexanes as eluent afforded product as a white solid. Run 1: (78.0 mg, 0.323 mmol, 64.6% yield), (11.8 mg, 0.052 mmol, 10.4% rsm). Run 2: (79.7 mg, 0.330 mmol, 66.0% yield), (10.8 mg, 0.048 mmol, 9.5% rsm). Run 3: (79.1 mg, 0.328 mmol, 65.6% yield), (13.1 mg, 0.058 mmol, 11.5% rsm). Average: 65.4% yield±0.7%, 10.5% rsm±1.0%.

$^1$H-NMR (500 MHz, CDCl$_3$) δ 7.46-7.44 (m, 2H), 7.39-7.36 (m, 2H), 3.03 (d, J=18.2 Hz, 1H), 2.84-2.78 (m, 2H), 2.69-2.61 (m, 1H), 2.54-2.42 (m, 2H), 1.33 (s, 9H). $^{13}$C-NMR (126 MHz, CDCl$_3$) δ 212.4, 152.0, 134.5, 126.4, 125.6, 122.8, 50.0, 43.8, 36.7, 36.4, 34.7, 31.3. HRMS (EI+) m/z calculated for C$_{16}$H$_{19}$ON [M]$^+$: 241.1467, found 241.1468.

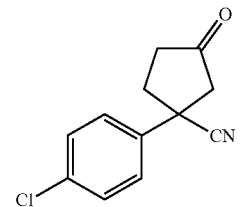 [SMILES: N#CC1(c2ccc(Cl)cc2)CCC(=O)C1]

1-(4-Chlorophenyl)-3-oxocyclopentane-1-carbonitrile [9]. The reaction was run with General Method A: Single Catalyst Addition Protocol: 1-(4-chlorophenyl)cyclopentane-1-carbonitrile S5 (102.8 mg, 0.500 mmol, 1.0 equiv), (R,R)—Mn(CF$_3$-PDP) (67.8 mg, 0.050 mmol, 10 mol %), ClCH$_2$CO$_2$H (709 mg, 7.5 mmol, 15.0 equiv.), 50% wt. H$_2$O$_2$ (340 mg, 5.0 mmol, 10.0 equiv.), MeCN (1.0 mL in 40 mL vial, 6.25 mL with oxidant). The reaction was run at 0° C. with ice bath. The reaction was worked up with 15 mL saturated NaHCO$_3$ and DCM as described in General Method A. Flash column chromatography on silica (35 mm fritted glass column, 150 mL SiO$_2$) using 10% acetone/hexanes→20% acetone/hexanes as eluent afforded product as a clear oil. Run 1: (86.8 mg, 0.395 mmol, 79.0% yield), (6.3 mg, 0.031 mmol, 6.2% rsm). Run 2: (90.6 mg, 0.413 mmol, 82.5% yield), (10.9 mg, 0.053 mmol, 10.6% rsm). Run 3: (89.1 mg, 0.406 mmol, 81.1% yield), (9.9 mg, 0.048 mmol, 9.6% rsm). Average: 80.9% yield±1.8%, 8.8% rsm 2.3%.

Gram-scale reaction: The reaction was run with reduced catalyst and chloroacetic acid loading according to a modified General Method A: Single Catalyst Addition Protocol with a scale up of appropriate apparatus. 1-(4-chlorophenyl)cyclopentane-1-carbonitrile S5 (1028 mg, 5.0 mmol, 1.0 equiv), (R,R)—Mn(CF$_3$-PDP) (339 mg, 0.25 mmol, 5 mol %), ClCH$_2$CO$_2$H (3.545 g, 37.5 mmol, 7.5 equiv.), 50% wt. H$_2$O$_2$ (3400 mg, 50.0 mmol, 10.0 equiv.), MeCN (10 mL in 100 mL recovery flask with a stir bar, 60 mL with oxidant in a 60 mL syringe). The reaction was run at 0° C. with ice bath. The reaction was worked up with 80 mL saturated NaHCO$_3$ and DCM as described in General Method A. Flash column chromatography on silica (50 mm fritted glass column, 200 mL SiO$_2$) using 10% acetone/hexanes→20% acetone/hexanes as eluent afforded product as a clear oil. Run 1: (791.2 mg, 0.3.60 mmol, 72.0% yield), (147.5 mg, 0.717 mmol, 14.3% rsm).

$^1$H-NMR (500 MHz, CDCl$_3$) δ 7.43-7.38 (m, 4H), 3.05 (d, J=18.1 Hz, 1H), 2.86-2.81 (m, 1H), 2.75 (d, J=18.1 Hz,

1H), 2.67 (dt, J=18.5, 9.2 Hz, 1H), 2.52 (ddd, J=19.0, 8.3, 3.9 Hz, 1H), 2.42 (ddd, J=13.0, 9.9, 8.1 Hz, 1H). $^{13}$C-NMR (126 MHz, CDCl$_3$) δ 211.6, 136.1, 134.9, 129.7, 127.3, 122.2, 49.8, 43.8, 36.7, 36.3. HRMS (TOF ESI+) m/z calculated for C$_{11}$H$_{10}$OCl [M−CN]$^+$: 193.0420, found 193.0423. Site of oxidation was confirmed based on a combination of $^1$H, gDQCOSY, gHSQC and gHMBC NMRs.

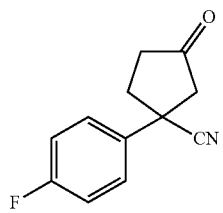 [SMILES: N#CC1(c2ccc(F)cc2)CCC(=O)C1]

1-(4-Fluorophenyl)-3-oxocyclopentane-1-carbonitrile [10]. The reaction was run with General Method B: Iterative Catalyst Addition Protocol: 1-(4-fluorophenyl)cyclopentane-1-carbonitrile S6 (94.6 mg, 0.500 mmol, 1.0 equiv), (R,R)—Mn(CF$_3$-PDP) (3 times addition of 33.9 mg, 0.025 mmol, 5 mol % batch; 15 mol % in total), ClCH$_2$CO$_2$H (709 mg, 7.5 mmol, 15.0 equiv.), 50% wt. H$_2$O$_2$ (340 mg, 5.0 mmol, 10.0 equiv.), MeCN (1.0 mL in 40 mL vial, 6.25 mL with oxidant). The reaction was run at 0° C. with ice bath. The reaction was worked up with 15 mL saturated NaHCO$_3$ and DCM as described in General Method A. Flash column chromatography on silica (35 mm fritted glass column, 150 mL SiO$_2$) using 20% acetone/hexanes→30% acetone/hexanes as eluent afforded product as a clear oil. Run 1: (57.9 mg, 0.285 mmol, 57.0% yield), (9.3 mg, 0.049 mmol, 9.8% rsm). Run 2: (58.4 mg, 0.287 mmol, 57.4% yield), (9.3 mg, 0.049 mmol, 9.8% rsm). Run 3: (55.6 mg, 0.273 mmol, 54.6% yield), (9.9 mg, 0.052 mmol, 10.5% rsm). Average: 56.3% yield±1.5%, 10.0% rsm±0.4%.

$^1$H-NMR (500 MHz, CDCl$_3$) δ 7.45-7.42 (m, 2H), 7.15-7.12 (m, 2H), 3.06 (d, J=18.1 Hz, 1H), 2.84 (dddd, J=12.7, 8.5, 3.9, 1.8 Hz, 1H), 2.75 (d, J=18.1 Hz, 1H), 2.67 (ddd, J=18.5, 9.7, 8.3 Hz, 1H), 2.52 (dddt, J=18.9, 8.2, 3.9, 1.1 Hz, 1H), 2.42 (ddd, J=13.0, 9.9, 8.1 Hz, 1H). $^{13}$C-NMR (126 MHz, CDCl$_3$) δ 211.8, 162.7 (d, J=249.0 Hz), 133.4 (d, J=3.3 Hz), 127.7 (d, J=8.4 Hz), 122.4, 116.5 (d, J=21.9 Hz), 50.0, 43.6, 36.7, 36.4. $^{19}$F-NMR (470 MHz, CDCl$_3$) δ −113.0. HRMS (TOF ESI+) m/z calculated for C$_{12}$H$_{11}$NOF [M+H]$^+$: 204.0825, found 204.0833.

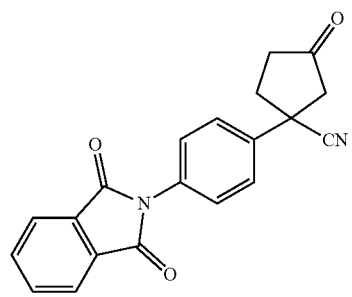 [SMILES: N#CC1(c2ccc(N3C(=O)c4ccccc4C3=O)cc2)CCC(=O)C1]

1-(4-(1,3-Dioxoisoindolin-2-yl)phenyl)-3-oxocyclopentane-1-carbonitrile [111]. The reaction was run with General Method A: Single Catalyst Addition Protocol: 1-(4-(1,3-dioxoisoindolin-2-yl)phenyl)cyclopentane-1-carbonitrile S7 (94.9 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), 4:1 MeCN:DCM (0.6 mL in 40 mL vial, 3.75 mL with oxidant). The reaction was run at 0° C. with ice bath. The reaction was worked up with 9 mL saturated NaHCO$_3$ and DCM as described in General Method A. Flash column chromatography on silica (35 mm fritted glass column, 150 mL SiO$_2$) using 20% acetone/hexanes→30% acetone/hexanes as eluent afforded product as a white solid. Run 1: (60.8 mg, 0.184 mmol, 61.3% yield), (17.4 mg, 0.055 mmol, 18.3% rsm). Run 2: (64.8 mg, 0.196 mmol, 65.3% yield), (20.1 mg, 0.064 mmol, 21.2% rsm). Run 3: (61.5 mg, 0.186 mmol, 62.1% yield), (18.8 mg, 0.060 mmol, 19.8% rsm). Average: 62.9% yield±2.1%, 19.8% rsm±1.5%.

$^1$H-NMR (500 MHz, acetone-d$_6$) δ 7.98-7.93 (m, 4H), 7.78 (d, J=8.6 Hz, 2H), 7.65 (d, J=8.6 Hz, 2H), 3.14 (d, J=17.9 Hz, 1H), 3.05 (d, J=17.8 Hz, 1H), 2.94 (dddd, J=12.9, 5.8, 4.2, 1.9 Hz, 1H), 2.72-2.55 (m, 3H). $^{13}$C-NMR (126 MHz, acetone-d$_6$) δ 212.4, 167.7, 138.8, 135.5, 133.5, 132.9, 128.5, 127.5, 124.2, 123.4, 50.5, 45.2, 37.2, 36.4. HRMS (TOF ESI+) m/z calculated for C$_{20}$H$_{15}$N$_2$O$_3$ [M+H]$^+$: 331.1083, found 331.1074.

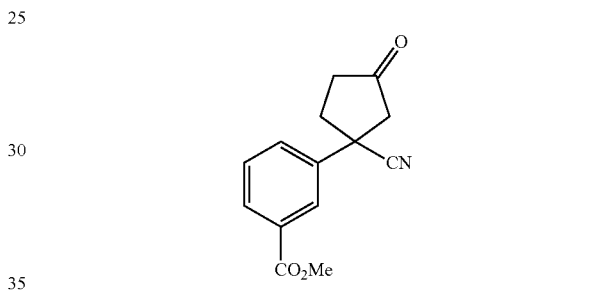

Methyl 3-(1-cyano-3-oxocyclopentyl)benzoate [12]. The reaction was run with General Method A: Single Catalyst Addition Protocol: methyl 3-(1-cyanocyclopentyl)benzoate S8 (114.6 mg, 0.500 mmol, 1.0 equiv), (R,R)—Mn(CF$_3$-PDP) (67.8 mg, 0.050 mmol, 10 mol %), ClCH$_2$CO$_2$H (709 mg, 7.5 mmol, 15.0 equiv.), 50% wt. H$_2$O$_2$ (340 mg, 5.0 mmol, 10.0 equiv.), MeCN (1.0 mL in 40 mL vial, 6.25 mL with oxidant). The reaction was run at 0° C. with ice bath. The reaction was worked up with 15 mL saturated NaHCO$_3$ and DCM as described in General Method A. Flash column chromatography on silica (35 mm fritted glass column, 150 mL SiO$_2$) using 15% acetone/hexanes→25% acetone/hexanes as eluent afforded product as a white solid. Run 1: (89.9 mg, 0.370 mmol, 73.9% yield), (15.5 mg, 0.068 mmol, 13.5% rsm). Run 2: (88.8 mg, 0.365 mmol, 73.0% yield), (21.2 mg, 0.092 mmol, 18.5% rsm). Run 3: (85.8 mg, 0.353 mmol, 70.6% yield), (20.6 mg, 0.090 mmol, 17.9% rsm). Average: 72.5% yield±1.7%, 16.6% rsm±2.7%. Selectivity=72.5/(100-16.6)=87%.

$^1$H-NMR (500 MHz, CDCl$_3$) δ 8.11 (s, 1H), 8.06 (d, J=7.7 Hz, 1H), 7.70-7.68 (m, 1H), 7.54 (t, J=7.8 Hz, 1H), 3.95 (s, 3H), 3.10 (d, J=18.2 Hz, 1H), 2.90-2.85 (m, 1H), 2.81 (d, J=18.0 Hz, 1H), 2.74-2.67 (m, 1H), 2.59-2.53 (m, 1H), 2.48 (ddd, J=12.9, 10.3, 8.1 Hz, 1H). $^{13}$C-NMR (126 MHz, CDCl$_3$) δ 211.5, 166.2, 138.0, 131.5, 130.5, 130.0, 129.7, 126.8, 122.1, 52.5, 49.9, 44.2, 36.8, 36.2. HRMS (TOF ESI+) m/z calculated for C$_{14}$H$_{14}$NO$_3$ [M+H]$^+$: 244.0974, found 244.0969.

Condition with Fe(CF$_3$-PDP): The reaction was conducted in slow addition protocok[10] same as Entry 10 of Table 3. In a 40 mL vial was charged with methyl 3-(1- cyanocyclopentyl)benzoate S8 (68.8 mg, 0.30 mmol, 1.0 equiv), AcOH (90.1 mg, 1.5 mmol, 5.0 equiv.), MeCN (0.60 mL) and a stir bar. A 1 mL syringe was charged with a solution of (R,R)—Fe(CF$_3$-PDP) catalyst (101.6 mg, 0.075 mmol, 0.25 equiv.) in MeCN (0.375 mL). A 10 mL syringe was charged with a solution of H$_2$O$_2$ (183.6 mg, 2.7 mmol, 9.0 equiv.) in MeCN (3.75 mL). Both syringes were fitted with 25 G needles and the solution was added dropwise via syringe pump over 1 hour. Upon completion of addition, the reaction was concentrated in vacuo to a minimum amount of MeCN and purified by column chromatography on silica (35 mm fritted glass column, 150 mL SiO$_2$) using 15% acetone/hexanes→25% acetone/hexanes as eluent to give both recovered starting material and product. Result: (8.0 mg, 0.033 mmol, 10.9% yield), 0% rsm. Selectivity=10.9/(100-0)=11%.

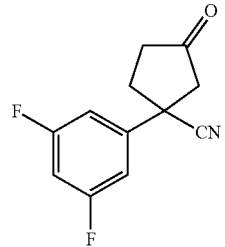 [SMILES: N#CC1(c2cc(F)cc(F)c2)CCC(=O)C1]

1-(3,5-Difluorophenyl)-3-oxocyclopentane-1-carbonitrile [13]. The reaction was run with General Method A: Single Catalyst Addition Protocol: 1-(3,5-difluorophenyl) cyclopentane-1-carbonitrile S9 (103.6 mg, 0.500 mmol, 1.0 equiv), (R,R)—Mn(CF$_3$-PDP) (67.8 mg, 0.050 mmol, 10 mol %), ClCH$_2$CO$_2$H (709 mg, 7.5 mmol, 15.0 equiv.), 50% wt. H$_2$O$_2$ (340 mg, 5.0 mmol, 10.0 equiv.), MeCN (1.0 mL in 40 mL vial, 6.25 mL with oxidant). The reaction was run at 0° C. with ice bath. The reaction was worked up with 15 mL saturated NaHCO$_3$ and DCM as described in General Method A. Flash column chromatography on silica (35 mm fritted glass column, 150 mL SiO$_2$) using 10% acetone/hexanes→20% acetone/hexanes as eluent afforded product as a white solid. Run 1: (73.1 mg, 0.331 mmol, 66.1% yield), (16.3 mg, 0.079 mmol, 15.7% rsm). Run 2: (73.5 mg, 0.332 mmol, 66.4% yield), (24.2 mg, 0.117 mmol, 23.4% rsm). Run 3: (71.3 mg, 0.322 mmol, 64.4% yield), (23.0 mg, 0.111 mmol, 22.2% rsm). Average: 65.6% yield±1.1%, 20.4% rsm±4.1%. Selectivity=65.6/(100-20.4)=82%.

$^1$H-NMR (500 MHz, CDCl$_3$) δ 7.03-6.98 (m, 2H), 6.87-6.83 (m, 1H), 3.05 (d, J=18.8 Hz, 1H), 2.83 (dddd, J=12.7, 8.4, 3.7, 1.9 Hz, 1H), 2.74-2.64 (m, 2H), 2.58-2.52 (m, 1H), 2.41 (ddd, J=13.0, 10.3, 8.2 Hz, 1H). $^{13}$C-NMR (126 MHz, CDCl$_3$) δ 210.8, 163.5 (dd, J=251.3, 12.9 Hz), 141.3 (t, J=9.0 Hz), 121.5, 109.6-109.4 (m), 104.6 (t, J=25.1 Hz), 49.7, 44.1 (t, J=2.2 Hz), 36.7, 36.2. $^{19}$F-NMR (470 MHz, CDCl$_3$) δ −107.0 (t, J=7.7 Hz). HRMS (TOF ESI+) m/z calculated for C$_{11}$H$_9$OF$_2$ [M−CN]$^P$: 195.0621, found 195.0622.

Condition with Fe(CF$_3$-PDP): The reaction was conducted in slow addition protocol, same as Entry 10 of Table 3. In a 40 mL vial was charged with 1-(3,5-difluorophenyl) cyclopentane-1-carbonitrile S9 (62.2 mg, 0.30 mmol, 1.0 equiv), AcOH (90.1 mg, 1.5 mmol, 5.0 equiv.), MeCN (0.60 mL) and a stir bar. A 1 mL syringe was charged with a solution of (R,R)—Fe(CF$_3$-PDP) catalyst (101.6 mg, 0.075 mmol, 0.25 equiv.) in MeCN (0.375 mL). A 10 mL syringe was charged with a solution of H$_2$O$_2$ (183.6 mg, 2.7 mmol, 9.0 equiv.) in MeCN (3.75 mL). Both syringes were fitted with 25 G needles and the solution was added dropwise via syringe pump over 1 hour. Upon completion of addition, the reaction was concentrated in vacuo to a minimum amount of MeCN and purified by column chromatography on silica (35 mm fritted glass column, 150 mL SiO$_2$) using 10% acetone/hexanes→20% acetone/hexanes as eluent to give both recovered starting material and product. Result: (7.6 mg, 0.034 mmol, 11.4% yield), (23.0 mg, 0.111 mmol, 37.0% rsm). Selectivity=11.4/(100-37.0)=18%.

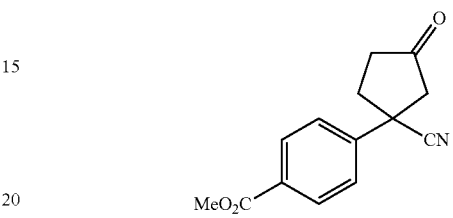

Methyl 4-(1-cyano-3-oxocyclopentyl)benzoate [14]. The reaction was run with General Method A: Single Catalyst Addition Protocol: methyl 4-(1-cyanocyclopentyl)benzoate S10 (68.8 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), MeCN (0.6 mL in 40 mL vial, 3.75 mL with oxidant). The reaction was run at 0° C. with ice bath. The reaction was worked up with 9 mL saturated NaHCO$_3$ and DCM as described in General Method A. Flash column chromatography on silica (35 mm fritted glass column, 150 mL SiO$_2$) using 20% acetone/hexanes→30% acetone/hexanes as eluent afforded product as a white solid. Run 1: (60.3 mg, 0.248 mmol, 82.6% yield), (9.1 mg, 0.040 mmol, 13.2% rsm). Run 2: (61.3 mg, 0.252 mmol, 83.9% yield), (8.6 mg, 0.038 mmol, 12.5% rsm). Run 3: (61.7 mg, 0.254 mmol, 84.6% yield), (6.9 mg, 0.030 mmol, 10.0% rsm). Average: 83.7% yield±1.0%, 11.9% rsm 1.7%. Selectivity=83.7/(100-11.9)=95%.

$^1$H-NMR (500 MHz, CDCl$_3$) δ 8.11-8.09 (m, 2H), 7.55-7.52 (m, 2H), 3.93 (s, 3H), 3.08 (d, J=18.2 Hz, 1H), 2.87-2.78 (m, 2H), 2.71-2.65 (m, 1H), 2.54 (dddt, J=18.8, 8.0, 3.6, 1.0 Hz, 1H), 2.46 (ddd, J=12.9, 10.0, 8.2 Hz, 1H). $^{13}$C-NMR (126 MHz, CDCl$_3$) δ 211.4, 166.2, 142.2, 130.8, 130.7, 126.0, 122.0, 52.5, 49.8, 44.4, 36.7, 36.4. HRMS (TOF ESI+) m/z calculated for C$_{14}$H$_{14}$NO$_3$ [M+H]$^+$: 244.0974, found 244.0971.

Condition with Fe(CF$_3$-PDP): The reaction was conducted in slow addition protocol, same as Entry 10 of Table 3. In a 40 mL vial was charged with methyl 4-(1-cyanocyclopentyl)benzoate S10 (68.8 mg, 0.30 mmol, 1.0 equiv), AcOH (90.1 mg, 1.5 mmol, 5.0 equiv.), MeCN (0.60 mL) and a stir bar. A 1 mL syringe was charged with a solution of (R,R)—Fe(CF$_3$-PDP) catalyst (101.6 mg, 0.075 mmol, 0.25 equiv.) in MeCN (0.375 mL). A 10 mL syringe was charged with a solution of H$_2$O$_2$ (183.6 mg, 2.7 mmol, 9.0 equiv.) in MeCN (3.75 mL). Both syringes were fitted with 25 G needles and the solution was added dropwise via syringe pump over 1 hour. Upon completion of addition, the reaction was concentrated in vacuo to a minimum amount of MeCN and purified by column chromatography on silica (35 mm fritted glass column, 150 mL SiO$_2$) using 20% acetone/hexanes→30% acetone/hexanes as eluent to give both recovered starting material and product. Result: (20.2 mg, 0.083 mmol, 27.6% yield), (4.8 mg, 0.021 mmol, 7.0% rsm). Selectivity=27.6/(100-7.0)=30%.

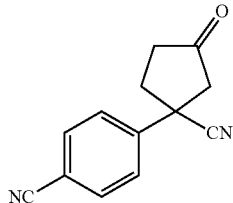 [SMILES: N#Cc1ccc(C2(C#N)CCC(=O)C2)cc1]

4-(1-Cyano-3-oxocyclopentyl)benzonitrile [15]. The reaction was run with General Method A: Single Catalyst Addition Protocol: 4-(1-cyanocyclopentyl)benzonitrile S11 (58.9 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), MeCN (0.6 mL in 40 mL vial, 3.75 mL with oxidant). The reaction was run at 0° C. with ice bath. The reaction was worked up with 9 mL saturated NaHCO$_3$ and DCM as described in General Method A. Flash column chromatography on silica (35 mm fritted glass column, 150 mL SiO$_2$) using 10% acetone/hexanes→20% acetone/hexanes as eluent afforded product as a white solid. Run 1: (46.3 mg, 0.220 mmol, 73.4% yield), (12.2 mg, 0.062 mmol, 20.7% rsm). Run 2: (45.6 mg, 0.217 mmol, 72.3% yield), (11.7 mg, 0.060 mmol, 19.9% rsm). Run 3: (43.8 mg, 0.208 mmol, 69.4% yield), (12.7 mg, 0.065 mmol, 21.6% rsm). Average: 71.7% yield±2.1%, 20.7% rsm±0.8%. Selectivity=71.7/(100-20.7)=90%.

$^1$H-NMR (500 MHz, CDCl$_3$) δ 7.73 (d, J=8.8 Hz, 2H), 7.60-7.58 (m, 2H), 3.05 (d, J=18.1 Hz, 1H), 2.87-2.81 (m, 1H), 2.76 (d, J=18.2 Hz, 1H), 2.71-2.63 (m, 1H), 2.57-2.50 (m, 1H), 2.43 (ddd, J=12.9, 10.3, 8.1 Hz, 1H). $^{13}$C-NMR (126 MHz, CDCl$_3$) δ 210.8, 142.5, 133.2, 126.8, 121.4, 117.9, 112.9, 49.5, 44.4, 36.6, 36.1. HRMS (EI+) m/z calculated for C$_{13}$H$_{10}$ON$_2$ [M]$^+$: 210.07932, found 210.07932.

Condition with Fe(CF$_3$-PDP): The reaction was conducted in slow addition protocol, same as Entry 10 of Table 3. In a 40 mL vial was charged with 4-(1-cyanocyclopentyl)benzonitrile S11 (58.9 mg, 0.30 mmol, 1.0 equiv), AcOH (90.1 mg, 1.5 mmol, 5.0 equiv.), MeCN (0.60 mL) and a stir bar. A 1 mL syringe was charged with a solution of (R,R)—Fe(CF$_3$-PDP) catalyst (101.6 mg, 0.075 mmol, 0.25 equiv.) in MeCN (0.375 mL). A 10 mL syringe was charged with a solution of H$_2$O$_2$ (183.6 mg, 2.7 mmol, 9.0 equiv.) in MeCN (3.75 mL). Both syringes were fitted with 25 G needles and the solution was added dropwise via syringe pump over 1 hour. Upon completion of addition, the reaction was concentrated in vacuo to a minimum amount of MeCN and purified by column chromatography on silica (35 mm fritted glass column, 150 mL SiO$_2$) using 10% acetone/hexanes→20% acetone/hexanes as eluent to give both recovered starting material and product. Result: (34.9 mg, 0.166 mmol, 55.3% yield), (4.5 mg, 0.023 mmol, 7.6% rsm). Selectivity=55.3/(100-7.6)=60%.

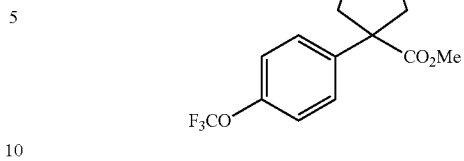

Methyl 3-oxo-1-(4-(trifluoromethoxy)phenyl)cyclopentane-1-carboxylate [16]. The reaction was run with General Method B: Iterative Catalyst Addition Protocol: methyl 1-(4-(trifluoromethoxy)phenyl)cyclopentane-1-carboxylate S12 (72.1 mg, 0.250 mmol, 1.0 equiv), (R,R)—Mn(CF$_3$-PDP) (3 times addition of 16.9 mg, 0.013 mmol, 5 mol % batch; 15 mol % in total), ClCH$_2$CO$_2$H (354 mg, 3.75 mmol, 15.0 equiv.), 50% wt. H$_2$O$_2$ (170 mg, 2.5 mmol, 10.0 equiv.), MeCN (0.5 mL in 40 mL vial, 3.13 mL with oxidant). The reaction was run at 0° C. with ice bath. The reaction was worked up with 9 mL saturated NaHCO$_3$ and DCM as described in General Method A. Flash column chromatography on silica (35 mm fritted glass column, 150 mL SiO$_2$) using 20% acetone/hexanes→30% acetone/hexanes as eluent afforded product as a clear oil. Run 1: (57.0 mg, 0.189 mmol, 75.4% yield), 0% rsm. Run 2: (58.4 mg, 0.193 mmol, 77.2% yield), 0% rsm. Run 3: (59.8 mg, 0.198 mmol, 79.1% yield), 0% rsm. Average: 77.2% yield±1.8%, 0% rsm.

$^1$H-NMR (500 MHz, CDCl$_3$) δ 7.39-7.36 (m, 2H), 7.22-7.20 (m, 2H), 3.67 (s, 3H), 3.26 (d, J=17.9 Hz, 1H), 3.01-2.96 (m, 1H), 2.58 (d, J=17.9 Hz, 1H), 2.38-2.28 (m, 3H). $^{13}$C-NMR (126 MHz, CDCl$_3$) δ 214.9, 174.5, 148.7, 139.8, 128.2, 121.2, 120.5 (q, J=257.4 Hz), 54.7, 53.2, 48.3, 37.1, 33.1. $^{19}$F-NMR (471 MHz, CDCl$_3$) δ −57.9. HRMS (TOF ESI+) m/z calculated for C$_{14}$H$_{14}$O$_4$F$_3$ [M+H]$^+$: 303.0844, found 303.0838.

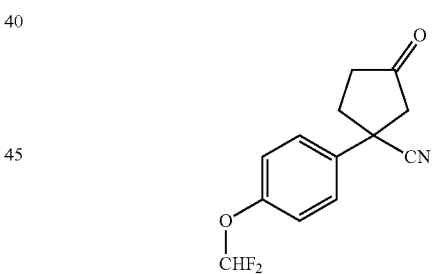

1-(4-(Difluoromethoxy)phenyl)-3-oxocyclopentane-1-carbonitrile [17]. The reaction was run with General Method B: Iterative Catalyst Addition Protocol: 1-(4-(difluoromethoxy)phenyl)cyclopentane-1-carbonitrile S13 (71.2 mg, 0.300 mmol, 1.0 equiv), (R,R)—Mn(CF$_3$-PDP) (3 times addition of 20.4 mg, 0.015 mmol, 5 mol % batch; 15 mol % in total), ClCH$_2$CO$_2$H (425 mg, 4.50 mmol, 15.0 equiv.), 50% wt. H$_2$O$_2$ 204 mg, 3.0 mmol, 10.0 equiv.), MeCN (0.6 mL in 40 mL vial, 3.75 mL with oxidant). The reaction was run at 0° C. with ice bath. The reaction was worked up with 9 mL saturated NaHCO$_3$ and DCM as described in General Method B. Flash column chromatography on silica (35 mm fritted glass column, 100 mL SiO$_2$) using 10% acetone/hexanes→20% acetone/hexanes→30% acetone/hexanes as eluent afforded product as a clear oil. Run 1: (40.7 mg, 0.162 mmol, 54.0% yield), 0% rsm. Run 2: (42.1 mg, 0.168 mmol, 55.9% yield), 0% rsm. Run 3: (40.4 mg, 0.161 mmol, 53.6% yield), 0% rsm. Average: 54.5% yield±1.2%, 0% rsm.

$^1$H-NMR (500 MHz, CDCl$_3$) δ 7.47-7.44 (m, 2H), 7.22-7.18 (m, 2H), 6.54 (t, J=73.2 Hz, 1H), 3.06 (d, J=18.1 Hz, 1H), 2.84 (dddd, J=12.7, 8.5, 3.9, 1.9 Hz, 1H), 2.78-2.74 (m, 1H), 2.69-2.64 (m, 1H), 2.52 (dddt, J=18.9, 8.2, 3.9, 1.0 Hz, 1H), 2.43 (ddd, J=12.9, 9.9, 8.1 Hz, 1H). $^{13}$C-NMR (126 MHz, CDCl$_3$) δ 211.6, 151.2 (t, J=2.9 Hz), 134.7, 127.5, 122.3, 120.6, 115.6 (t, J=261.6 Hz), 50.0, 43.7, 36.7, 36.5. $^{19}$F-NMR (471 MHz, CDCl$_3$) δ −81.4. HRMS (TOF ESI+) m/z calculated for C$_{13}$H$_{11}$NO$_2$F$_2$Na [M+Na]$^+$: 274.0656, found 274.0662.

Better selectivity can be obtained using General Method A: Single Catalyst Addition Protocol. 1-(4-(difluoromethoxy)phenyl)cyclopentane-1-carbonitrile S13 (71.2 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), MeCN (0.6 mL in 40 mL vial, 3.75 mL with oxidant). The reaction was run at 0° C. with ice bath. The reaction was worked up with 9 mL saturated NaHCO$_3$ and DCM as described in General Method A. Run 1: (32.5 mg, 0.129 mmol, 43.1% yield), (24.8 mg, 0.105 mmol, 34.8% rsm). Run 2: (34.9 mg, 0.139 mmol, 46.3% yield), (20.1 mg, 0.085 mmol, 28.2% rsm). Run 3: (36.4 mg, 0.145 mmol, 48.3% yield), (21.6 mg, 0.091 mmol, 30.3% rsm). Average: 45.9% yield±2.6%, 31.1% rsm±3.4%.

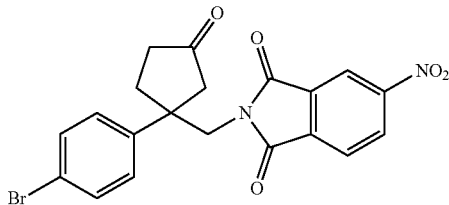 [SMILES: O=C1CCC(CN2C(=O)c3ccc([N+](=O)[O-])cc3C2=O)(c2ccc(Br)cc2)C1]

2-((1-(4-Bromophenyl)-3-oxocyclopentyl)methyl)-5-nitroisoindoline-1,3-dione [18]. The reaction was run with General Method A: Single Catalyst Addition Protocol: 2-((1-(4-bromophenyl)cyclopentyl)methyl)-5-nitroisoindoline-1,3-dione S14 (128.8 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), MeCN (0.6 mL in 40 mL vial, 3.75 mL with oxidant). The reaction was allowed to stir at 0° C. for ~30 min to facilitate the solubility of starting material before adding H$_2$O$_2$ and run at 0° C. with ice bath. The reaction was worked up with 9 mL saturated NaHCO$_3$ and DCM as described in General Method A. Flash column chromatography on silica (35 mm fritted glass column, 150 mL SiO$_2$) using 15% acetone/hexanes→25% acetone/hexanes as eluent afforded product as a white solid. Run 1: (76.1 mg, 0.172 mmol, 57.2% yield), <10% rsm. Run 2: (80.7 mg, 0.182 mmol, 60.7% yield), <10% rsm. Run 3: (83.8 mg, 0.189 mmol, 63.0% yield), <10% rsm. Average: 60.3% yield±2.9%, <10% rsm.

$^1$H-NMR (500 MHz, CDCl$_3$) δ 8.60-8.58 (m, 2H), 8.01-7.99 (m, 1H), 7.44 (dd, J=8.5, 1.9 Hz, 2H), 7.17-7.15 (m, 2H), 3.98 (d, J=14.0 Hz, 1H), 3.91 (d, J=14.1 Hz, 1H), 2.76 (d, J=17.8 Hz, 1H), 2.71 (d, J=18.2 Hz, 1H), 2.52-2.44 (m, 2H), 2.38-2.21 (m, 2H). $^{13}$C-NMR (126 MHz, CDCl$_3$) δ 215.8, 166.3, 166.0, 152.0, 142.0, 135.9, 133.0, 132.0, 129.6, 128.5, 124.9, 121.7, 119.1, 49.2, 49.2, 47.7, 36.3, 32.5. HRMS (TOF ESI+) m/z calculated for C$_{20}$H$_{16}$N$_2$O$_5$Br [M+H]$^+$: 443.0243, found 443.0237.

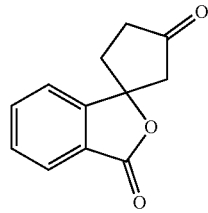 [SMILES: O=C1CCC2(C1)OC(=O)c1ccccc12]

3'H-Spiro[cyclopentane-1,1'-isobenzofuran]-3,3'-dione [19]. The reaction was run with a modified procedure according to General Method A: Single Catalyst Addition Protocol: 3'H-spiro[cyclopentane-1,1'-isobenzofuran]-3'-one S15 (94.1 mg, 0.500 mmol, 1.0 equiv), (R,R)—Mn (CF$_3$-PDP) (67.8 mg, 0.050 mmol, 10 mol %), ClCH$_2$CO$_2$H (709 mg, 7.5 mmol, 15.0 equiv.), 50% wt. H$_2$O$_2$ (340 mg, 5.0 mmol, 10.0 equiv.), MeCN (1.0 mL in 40 mL vial, 6.25 mL with oxidant). The reaction was run at 0° C. with ice bath. The reaction was concentrated to a minimal amount of solvent and directly load to column purification. Flash column chromatography on silica (35 mm fritted glass column, 150 mL SiO$_2$) using 30% acetone/hexanes→50% acetone/hexanes as eluent afforded product co-eluted with chloroacetic acid. The yield of product was determined by adding nitrobenzene as internal standard via quantitative $^1$H NMR. The chloroacetic acid can be later removed by NaHCO$_3$ wash with a slight loss of desired product. Run 1: (59.8 mg, 0.296 mmol, 59.1% yield), <10% rsm. Run 2: (63.3 mg, 0.313 mmol, 62.7% yield), <10% rsm. Run 3: (64.7 mg, 0.320 mmol, 64.1% yield), <10% rsm. Average: 62.0% yield±2.6%, <10% rsm.

$^1$H-NMR (500 MHz, methylene chloride-d$_2$) δ 7.89 (dt, J=7.6, 1.0 Hz, 1H), 7.76 (td, J=7.6, 1.1 Hz, 1H), 7.59 (td, J=7.5, 0.9 Hz, 1H), 7.52 (dt, J=7.7, 0.9 Hz, 1H), 2.80 (d, J=18.4 Hz, 1H), 2.82-2.72 (m, 1H), 2.67 (ddt, J=18.6, 2.9, 1.1 Hz, 1H), 2.63-2.50 (m, 2H), 2.39 (dddd, J=13.7, 9.4, 2.9, 1.4 Hz, 1H). $^{13}$C-NMR (126 MHz, methylene chloride-d$_2$) δ 213.4, 169.1, 150.8, 135.1, 130.3, 126.7, 126.2, 121.7, 90.8, 50.3, 38.0, 36.6. HRMS (TOF ESI+) m/z calculated for C$_{12}$H$_{11}$O$_3$ [M+H]$^+$: 203.0708, found 203.0710.

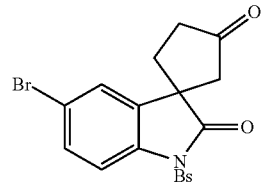

5'-Bromo-r-(phenylsulfonyl)spiro[cyclopentane-1,3'-indoline]-2',3-dione [20a]. The reaction was run with General Method A: Single Catalyst Addition Protocol: 5'-Bromo-1'-(phenylsulfonyl)spiro[cyclopentane-1,3'-indolin]-2'-one S16 (81.3 mg, 0.200 mmol, 1.0 equiv), (R,R)—Mn(CF$_3$-PDP) (27.1 mg, 0.020 mmol, 10 mol %), ClCH$_2$CO$_2$H (284 mg, 3.0 mmol, 15.0 equiv.), 50% wt. H$_2$O$_2$ (136 mg, 2.0 mmol, 10.0 equiv.), MeCN (0.4 mL in 40 mL vial, 2.50 mL with oxidant). The reaction was run at 0° C. with ice bath. The reaction was worked up with 6 mL saturated NaHCO$_3$ and DCM as described in General Method A. The crude mixture was dissolved with a small amount of DCM and concentrated onto silica (2 mL) for dry loading onto the column (35 mL silica) and then eluted with 10% EtOAc/hexane→20% EtOAc/hexane→40% EtOAc/hexane to afford 20a as a white solid and 20b alcohol diastereomers mixtures as a white solid. The recovered starting material was recycled 1× with same oxidation protocol.

Run 1: cycle 1: (20.1 mg, 0.0478 mmol, 23.9% yield of 20a), (10.4 mg, 0.0246 mmol, 12.3% yield of 20b), (38.7 mg, 0.0953 mmol, 47.6% rsm). cycle 2: (7.9 mg, 0.0188 mmol, 19.7% yield of 20a), (4.7 mg, 0.0111 mmol, 11.6% yield of 20b), (18.5 mg, 0.0455 mmol, 47.8% rsm). Overall: (28.0 mg, 0.066 mmol, 33.3% yield of 20a), (15.1 mg, 0.0358 mmol, 17.9% yield of 20b), (18.5 mg, 0.0455 mmol, 22.8% rsm). Run 2: cycle 1: (20.7 mg, 0.0493 mmol, 24.6% yield of 20a), (10.3 mg, 0.244 mmol, 12.2% yield of 20b), (37.4 mg, 0.0921 mmol, 46.0% rsm). cycle 2: (8.2 mg, 0.195 mmol, 21.2% yield of 20a), (4.5 mg, 0.0107 mmol, 11.6% yield of 20b), (17.8 mg, 0.0438 mmol, 47.6% rsm). Overall: (28.9 mg, 0.0688 mmol, 34.4% yield of 20a), (14.8 mg, 0.0350 mmol, 17.5% yield of 20b), (17.8 mg, 0.0438 mmol, 21.9% rsm). Run 3: cycle 1: (21.0 mg, 0.0500 mmol, 25.0% of 20a), (10.4 mg, 0.246 mmol, 12.3% yield of 20b), (39.6 mg, 0.0975 mmol, 48.7% rsm). cycle 2: (8.0 mg, 0.0190 mmol, 19.5% yield of 20a), (4.3 mg, 0.0102 mmol, 10.4% yield of 20b), (17.0 mg, 0.0418 mmol, 42.9% rsm). Overall: (29.0 mg, 0.0690 mmol, 34.5% yield of 20a), (14.7 mg, 0.0348 mmol, 17.4% yield of 20b), (17.0 mg, 0.0418 mmol, 20.9% rsm). Average: (34.1% yield of 20a±0.7%), (17.6% yield of 20b±0.3%), (21.9% rsm±1.0%).

$^1$H-NMR (500 MHz, CDCl$_3$) δ 8.06 (d, J=8.6 Hz, 2H), 7.85 (d, J=8.7 Hz, 1H), 7.69 (td, J=7.5, 1.2 Hz, 1H), 7.56 (t, J=8.0 Hz, 2H), 7.51 (dd, J=8.7, 2.1 Hz, 1H), 7.29 (d, J=1.8 Hz, 1H), 2.75 (ddd, J=18.8, 9.1 Hz, 1H), 2.57 (d, J=19.0 Hz, 1H), 2.55-2.48 (m, 1H), 2.38 (d, J=18.5 Hz, 1H), 2.40-2.34 (m, 1H), 2.15 (dd, J=13.5, 9.0 Hz, 1H). $^{13}$C-NMR (126 MHz, CDCl$_3$) δ 213.5, 177.5, 137.6, 137.4, 135.0, 133.4, 132.4, 129.5, 127.9, 126.0, 118.6, 115.7, 51.0, 47.2, 36.3, 34.5. HRMS (TOF ESI+) m/z calculated for C$_{18}$H$_{15}$BrNO$_4$S [M+H]$^+$: 419.9905, found 419.9897.

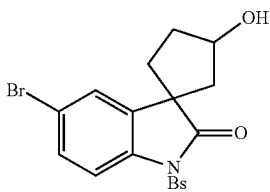

5'-Bromo-3-hydroxy-1'-(phenylsulfonyl)spiroicyclopentane-1,3'-indolin]-2'-one [20b]. The ratio of diastereomers is approximately 1.5:1 and could be separated by using preparative TLC. The reduction of 20a using NaBH$_4$ provided two diastereomers of alcohol and the spectroscopic data of them are consistent with those of both diastereomers of 20b.

Diastereomer 1: $^1$H-NMR (500 MHz, CDCl$_3$) δ 8.05 (d, J=7.7 Hz, 2H), 7.77 (d, J=8.7 Hz, 1H), 7.66 (t, J=7.5 Hz, 1H), 7.63 (d, J=2.1 Hz, 1H), 7.54 (t, J=7.9 Hz, 2H), 7.42 (dd, J=8.7, 2.1 Hz, 1H), 4.66-4.62 (m, 1H), 2.32 (dd, J=14.3, 4.9 Hz, 1H), 2.15-2.01 (m, 3H), 1.96-1.88 (m, 1H), 1.84 (dt, J=14.3, 2.2 Hz, 1H), 1.58 (br. H, 1H). $^{13}$C-NMR (126 MHz, CDCl$_3$) δ 180.2, 138.0, 137.3, 137.2, 134.7, 131.3, 129.4, 127.9, 127.7, 118.7, 115.0, 74.3, 53.5, 47.3, 38.7, 36.6. HRMS (TOF ESI+) m/z calculated for C$_{18}$H$_{17}$BrNO$_4$S [M+H]$^+$: 422.0062, found 422.0072.

Diastereomer 2: $^1$H-NMR (500 MHz, CDCl$_3$) δ 8.06 (d, J=8.1 Hz, 2H), 7.81 (d, J=8.7 Hz, 1H), 7.68 (t, J=7.5 Hz, 1H), 7.56 (t, J=7.9 Hz, 2H), 7.46 (dd, J=8.7, 2.0 Hz, 1H), 7.24 (d, J=2.1 Hz, 1H), 4.50 (dtt, J=10.2, 5.1, 2.3 Hz, 1H), 3.25 (dd, J=10.1, 3.0 Hz, 1H), 2.31 (dt, J=13.7, 8.1 Hz, 1H), 2.23-2.16 (m, 1H), 2.11-2.01 (m, 3H), 1.88 (ddd, J=13.9, 9.0, 5.3 Hz, 1H). $^{13}$C-NMR (126 MHz, CDCl$_3$) δ 181.6, 137.7, 137.5, 136.0, 135.0, 131.7, 129.5, 128.0, 125.9, 118.7, 115.5, 74.6, 54.3, 47.3, 38.2, 36.8. HRMS (TOF ESI+) m/z calculated for C$_{18}$H$_{17}$BrNO$_4$S [M+H]$^+$: 422.0062, found 422.0062.

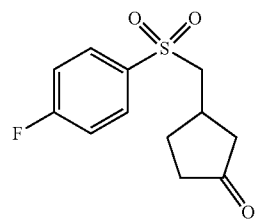 [SMILES: O=C1CCC(CS(=O)(=O)c2ccc(F)cc2)C1]

3-(((4-Fluorophenyl)sulfonyl)methyl)cyclopentan-1-one [21]. The reaction was run with General Method A: Single Catalyst Addition Protocol: 1-((cyclopentylmethyl)sulfonyl)-4-fluorobenzene S17 (121.2 mg, 0.500 mmol, 1.0 equiv), (R,R)—Mn(CF$_3$-PDP) (67.8 mg, 0.050 mmol, 10 mol %), ClCH$_2$CO$_2$H (709 mg, 7.5 mmol, 15.0 equiv.), 50% wt. H$_2$O$_2$ (340 mg, 5.0 mmol, 10.0 equiv.), MeCN (1.0 mL in 40 mL vial, 6.25 mL with oxidant). The reaction was run at 0° C. with ice bath. The reaction was worked up with 15 mL saturated NaHCO$_3$ and DCM as described in General Method A. Flash column chromatography on silica (35 mm fritted glass column, 150 mL SiO$_2$) using 15% acetone/hexanes→25% acetone/hexanes→40% acetone/hexanes as eluent afforded product as a clear oil. Run 1: (84.0 mg, 0.328 mmol, 65.6% yield), 0% rsm. Run 2: (84.6 mg, 0.330 mmol, 66.0% yield), 0% rsm. Run 3: (79.0 mg, 0.308 mmol, 61.6% yield), 0% rsm. Average: 64.4% yield±2.4%, 0% rsm.

$^1$H-NMR (500 MHz, CDCl$_3$) δ 7.97-7.93 (m, 2H), 7.29-7.25 (m, 2H), 3.27 (dd, J=14.0, 6.0 Hz, 1H), 3.20 (dd, J=14.0, 7.7 Hz, 1H), 2.76-2.66 (m, 1H), 2.55 (dd, J=18.6, 7.7 Hz, 1H), 2.38-2.30 (m, 2H), 2.22-2.14 (m, 1H), 1.96 (dd, J=18.4, 10.8 Hz, 1H), 1.69 (dtd, J=12.5, 10.8, 8.3 Hz, 1H). $^{13}$C-NMR (126 MHz, CDCl$_3$) δ 216.4, 166.0 (d, J=257.1 Hz), 135.6 (d, J=3.3 Hz), 130.9 (d, J=9.6 Hz), 117.0 (d, J=22.6 Hz), 61.4, 44.3, 37.9, 31.6, 29.5. $^{19}$F-NMR (470 MHz, CDCl$_3$) δ -103.2. HRMS (TOF ESI+) m/z calculated for C$_{12}$H$_{14}$O$_3$SF [M+H]$^+$: 257.0648, found 257.0646. Site of oxidation was assigned based on a combination of 41, gCOSY, gHSQC and gHMBC NMRs.

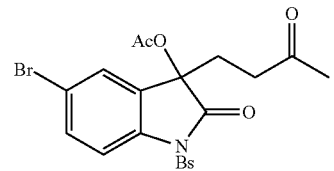

5-Bromo-2-oxo-3-(3-oxobutyl)-1-(phenylsulfonyl)indolin-3-yl acetate [22]. The reaction was run with General Method B: Iterative Catalyst Addition Protocol: 5-bromo-1-((4-bromophenyl)sulfonyl)-3-butyl-2-oxoindolin-3-yl acetate S18 (93.3 mg, 0.200 mmol, 1.0 equiv), (R,R)—Mn (CF₃-PDP) (3 times addition of 20.4 mg, 0.015 mmol, 5 mol % batch; 15 mol % in total), ClCH₂CO₂H (284 mg, 3.0 mmol, 15.0 equiv.), 50% wt. H₂O₂ (136 mg, 2.0 mmol, 10.0 equiv.), MeCN (0.4 mL in 40 mL vial, 2.50 mL with oxidant). The reaction was run at 0° C. with ice bath. The reaction was worked up with 6 mL saturated NaHCO₃ and DCM as described in General Method B. The crude mixture was dissolved with a small amount of DCM and concentrated onto silica (2 mL) for dry loading onto the column (silica, 30 mL) and then eluted with 15% EtOAc/hexane→30% EtOAc/hexane to afford 22 as a white solid. Run 1: (59.2 mg, 0.123 mmol, 61.6% yield), (13.2 mg, 0.0283 mmol, 14.2% rsm). Run 2: (59.1 mg, 0.123 mmol, 61.5% yield), (13.4 mg, 0.0288 mmol, 14.4% rsm). Run 3: (58.0 mg, 0.121 mmol, 60.4% yield), (15.0 mg, 0.0322 mmol, 16.1% rsm). Average: 61.2% yield±0.7%, 14.9% rsm±1.0%.

¹H-NMR (500 MHz, CDCl₃) δ 8.05 (d, J=7.7 Hz, 2H), 7.83 (d, J=8.7 Hz, 1H), 7.69-7.65 (m, 1H), 7.55-7.50 (m, 3H), 7.29 (d, J=2.1 Hz, 1H), 2.55 (ddd, J=18.0, 10.6, 5.1 Hz, 1H), 2.43 (ddd, J=18.0, 10.3, 5.0 Hz, 1H), 2.31-2.25 (m, 1H), 2.10 (s, 3H), 2.14-2.08 (m, 1H), 1.91 (s, 3H). ¹³C-NMR (125 MHz, CDCl₃) δ 206.0, 171.8, 168.7, 138.0, 137.1, 134.9, 133.5, 129.4, 129.2, 128.2, 126.0, 118.5, 115.4, 77.8, 35.7, 30.8, 30.1, 20.2. HRMS (TOF ESI+) m/z calculated for C₂₀H₁₈BrNNaO₆S [M+Na]⁺: 501.9936, found 501.9922.

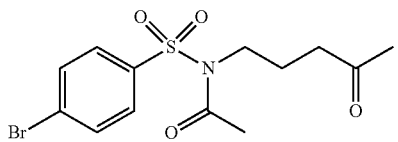 [SMILES: CC(=O)CCCN(C(C)=O)S(=O)(=O)c1ccc(Br)cc1]

N-((4-Bromophenyl)sulfonyl)-N-(4-oxopentyl)acetamide [23a]. The reaction was run with General Method A: Single Catalyst Addition Protocol: N-((4-bromophenyl)sulfonyl)-N-pentylacetamide S19 (104.5 mg, 0.300 mmol, 1.0 equiv), (R,R)—Mn(CF₃-PDP) (40.7 mg, 0.030 mmol, 10 mol %), ClCH₂CO₂H (425 mg, 4.5 mmol, 15.0 equiv.), 50% wt. H₂O₂ (204 mg, 3.0 mmol, 10.0 equiv.), MeCN (0.6 mL in 40 mL vial, 3.75 mL with oxidant). The reaction was run at 0° C. with ice bath. The reaction was worked up with saturated 9 mL NaHCO₃ and DCM as described in General Method A. Flash column chromatography on silica (35 mm fritted glass column, 150 mL SiO₂) using 20% acetone/hexanes→30% acetone/hexanes as eluent afforded N-((4-bromophenyl)sulfonyl)-N-(3-oxopentyl)acetamide (γ-ketone, 23b) product as a colorless oil and N-((4-bromophenyl)sulfonyl)-N-(4-oxopentyl)acetamide (δ-ketone, 23a) product as a colorless oil.

Run 1: (23.2 mg, 0.064 mmol, 21.3% yield of γ-ketone 22b), (64.7 mg, 0.179 mmol, 59.6% yield of δ-ketone 22a), (80.9% overall yield, 2.8:1 δ:γ ratio), <10% rsm. Run 2: (23.6 mg, 0.065 mmol, 21.7% yield of γ-ketone 22b), (67.1 mg, 0.185 mmol, 61.7% yield of δ-ketone 22a), (83.4% overall yield, 2.8:1 δ:γ ratio), <10% rsm. Run 3: (24.1 mg, 0.066 mmol, 22.1% yield of γ-ketone 22b), (63.2 mg, 0.175 mmol, 58.2% yield of δ-ketone 22a), (80.3% overall yield, 2.6:1 δ:γ ratio), <10% rsm. Average: 81.5% yield±1.6%, 2.8:1 δ:γ ratio, <10% rsm.

¹H-NMR (500 MHz, CDCl₃) 7.76 (d, J=8.2 Hz, 2H), 7.68 (d, J=8.8 Hz, 2H), 3.80-3.52 (m, 2H), 2.53 (m, 2H), 2.31 (s, 3H), 2.15 (s, 3H), 1.99-1.92 (m, 2H). ¹³C-NMR (126 MHz, CDCl₃) δ 207.6, 170.2, 138.5, 132.6, 129.3, 129.1, 46.5, 40.1, 30.0, 24.9, 23.7. HRMS (TOF ESI+) m/z calculated for C₁₃H₁₇NO₄SBr [M+H]⁺: 362.0062, found 362.0067.

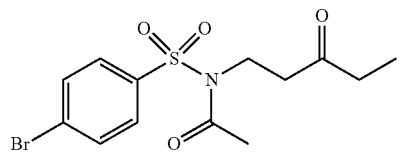 [SMILES: CCC(=O)CCN(C(C)=O)S(=O)(=O)c1ccc(Br)cc1]

N-((4-Bromophenyl)sulfonyl)-N-(3-oxopentyl)acetamide [23b]. ¹H-NMR (500 MHz, methylene Chloride-d₂) 7.78-7.75 (m, 2H), 7.73-7.71 (m, 2H), 3.98-3.95 (m, 2H), 2.88-2.85 (m, 2H), 2.43 (q, J=7.3 Hz, 2H), 2.32 (s, 3H), 1.02 (t, J=7.3 Hz, 3H). ¹³C-NMR (126 MHz, methylene Chloride-d₂) δ 209.2, 170.3, 138.8, 133.2, 129.6, 129.5, 42.9, 42.5, 36.5, 25.3, 7.9. HRMS (TOF ESI+) m/z calculated for for C₁₃H₁₇NO₄SBr [M+H]⁺: 362.0062, found 362.0053.

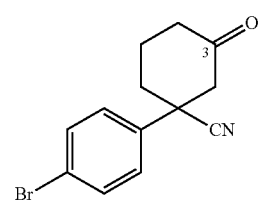

1-(4-Bromophenyl)-3-oxocyclohexane-1-carbonitrile [24a]. The reaction was run with General Method A: Single Catalyst Addition Protocol: 1-(4-bromophenyl)cyclohexane-1-carbonitrile S20 (79.3 mg, 0.300 mmol, 1.0 equiv), (R,R)—Mn(CF₃-PDP) (40.7 mg, 0.030 mmol, 10 mol %), ClCH₂CO₂H (425 mg, 4.5 mmol, 15.0 equiv.), 50% wt. H₂O₂ (204 mg, 3.0 mmol, 10.0 equiv.), MeCN (0.6 mL in 40 mL vial, 3.75 mL with oxidant). The reaction was run at 0° C. with ice bath. The reaction was worked up with 9 mL saturated NaHCO₃ and DCM as described in General Method A. Flash column chromatography on silica (35 mm fritted glass column, 150 mL SiO₂) using 20% acetone/hexanes→30% acetone/hexanes as eluent afforded 1-(4-bromophenyl)-3-oxocyclohexane-1-carbonitrile (3-ketone, 24a) product as a white solid and 1-(4-bromophenyl)-4-oxocyclohexane-1-carbonitrile (4-ketone, 24b) as a white solid. Run 1: (34.7 mg, 0.125 mmol, 41.5% yield of 3-ketone 24a), (18.7 mg, 0.067 mmol, 22.4% yield of 4-ketone 24b), (63.9% overall yield, 1.86:1 3-ketone:4-ketone ratio), (13.4 mg, 0.051 mmol, 16.9% rsm).

Run 2: (34.5 mg, 0.124 mmol, 41.3% yield of 3-ketone 24a), (18.5 mg, 0.067 mmol, 22.2% yield of 4-ketone 24b), (63.5% overall yield, 1.86:1 3-ketone:4-ketone ratio), (16.3 mg, 0.062 mmol, 20.6% rsm). Run 3: (34.2 mg, 0.123 mmol, 41.0% yield of 3-ketone 24a), (19.2 mg, 0.069 mmol, 23.0% yield of 4-ketone 24b), (64.0% overall yield, 1.78:1 3-ketone:4-ketone ratio), (12.8 mg, 0.049 mmol, 16.2% rsm). Average: 63.8% yield±0.3%, 1.83:1 3-ketone:4-ketone ratio, 17.9% rsm±2.4%.

¹H-NMR (500 MHz, CDCl₃) δ 7.58-7.55 (m, 2H), 7.36-7.33 (m, 2H), 2.88 (dt, J=14.6, 1.8 Hz, 1H), 2.82 (d, J=14.7, 1H), 2.57 (dddd, J=14.8, 5.8, 3.7, 1.6 Hz, 1H), 2.43-2.34 (m, 2H), 2.26-2.06 (m, 3H). ¹³C-NMR (126 MHz, CDCl₃) δ 205.1, 137.6, 132.6, 127.4, 122.9, 120.9, 50.6, 45.4, 40.2, 36.3, 22.4. HRMS (EI+) m/z calculated for C₁₃H₁₂ONBr [M]⁺: 277.0102, found 277.0103. Site of oxidation was assigned based on a combination of ¹H, gDQCOSY, gHSQC NMRs.

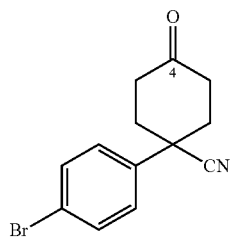 [SMILES: N#CC1(c2ccc(Br)cc2)CCC(=O)CC1]

1-(4-Bromophenyl)-4-oxocyclohexane-1-carbonitrile [24b]. $^1$H-NMR (500 MHz, CDCl$_3$) δ 7.59-7.55 (m, 2H), 7.41-7.38 (m, 2H), 2.91 (ddd, J=15.0, 13.8, 5.7 Hz, 2H), 2.58 (ddt, J=15.6, 4.4, 2.1 Hz, 2H), 2.47 (ddt, J=14.3, 5.9, 3.1 Hz, 2H), 2.25 (ddd, J=13.9, 13.9, 4.3 Hz, 2H). $^{13}$C-NMR (126 MHz, CDCl$_3$) δ 206.9, 137.8, 132.5, 127.3, 122.8, 120.9, 43.0, 38.6, 37.0. HRMS (EI+) m/z calculated for C$_{13}$H$_{12}$ONBr [M]+: 277.0102, found 277.0103.

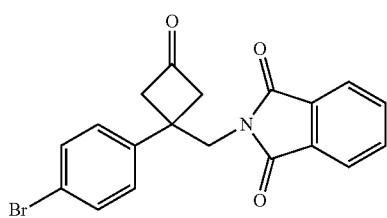 [SMILES: O=C1CC(CN2C(=O)c3ccccc3C2=O)(c2ccc(Br)cc2)C1]

2-((1-(4-Bromophenyl)-3-oxocyclobutyl)methyl)isoindoline-1,3-dione [25]. The reaction was run with General Method B: Iterative Catalyst Addition Protocol using 4:1 MeCN: DCM as solvent to improve the solubility of the starting material: 2-((1-(4-bromophenyl)cyclobutyl)methyl) isoindoline-1,3-dione S21 (111.1 mg, 0.300 mmol, 1.0 equiv), (R,R)—Mn(CF$_3$-PDP) (3 times addition of 20.4 mg, 0.015 mmol, 5 mol % batch; 15 mol % in total), ClCH$_2$CO$_2$H (425 mg, 4.5 mmol, 15.0 equiv.), 50% wt. H$_2$O$_2$ (204 mg, 3.0 mmol, 10.0 equiv.), 4:1 MeCN: DCM mixture (0.6 mL in 40 mL vial, 3.75 mL with oxidant). The reaction was allowed to stir at 0° C. for ~5 min to facilitate the solubility of starting material before adding H$_2$O$_2$ and run at 0° C. with ice bath. The reaction was worked up with 9 mL saturated NaHCO$_3$ and DCM as described in General Method A. Flash column chromatography on silica (35 mm fritted glass column, 150 mL SiO$_2$) using 20% acetone/hexanes→30% acetone/hexanes as eluent afforded product as a white solid. Run 1: (67.7 mg, 0.176 mmol, 58.7% yield), (14.9 mg, 0.040 mmol, 13.4% rsm). Run 2: (65.4 mg, 0.170 mmol, 56.7% yield), (23.2 mg, 0.063 mmol, 20.9% rsm). Run 3: (63.9 mg, 0.166 mmol, 55.4% yield), (20.9 mg, 0.056 mmol, 18.8% rsm). Average: 56.9% yield±1.7%, 17.7% rsm±3.9%.

$^1$H-NMR (500 MHz, CDCl$_3$) δ 7.80 (dd, J=5.4, 3.1 Hz, 2H), 7.72 (dd, J=5.5, 3.1 Hz, 2H), 7.45 (d, J=8.4 Hz, 2H), 7.17 (d, J=8.4 Hz, 2H), 4.04 (s, 2H), 3.68-3.63 (m, 2H), 3.45-3.39 (m, 2H). $^{13}$C-NMR (126 MHz, CDCl$_3$) δ 204.1, 168.5, 142.7, 134.5, 131.9, 131.6, 128.9, 123.7, 121.4, 56.6, 47.9, 39.2. HRMS (TOF ESI+) m/z calculated for C$_{19}$H$_{15}$NO$_3$Br [M+H]$^+$: 384.0235, found 384.0225.

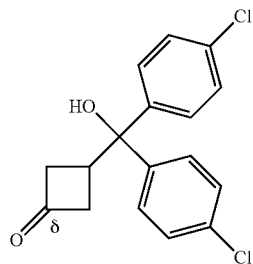 [SMILES: O=C1CC(C(O)(c2ccc(Cl)cc2)c2ccc(Cl)cc2)C1]

3-(Bis(4-chlorophenyl)(hydroxy)methyl)cyclobutan-1-one [26a]. The reaction was run with General Method A: Single Catalyst Addition Protocol: Bis(4-chlorophenyl) (cyclobutyl)methanol S22 (92.2 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), MeCN (0.6 mL in 40 mL vial, 3.75 mL with oxidant). The reaction was run at 0° C. with ice bath. The reaction was worked up with saturated 9 mL NaHCO$_3$ and DCM as described in General Method A. Flash column chromatography on silica (35 mm fritted glass column, 150 mL SiO$_2$) using 10% acetone/hexanes→20% acetone/hexanes as eluent afforded 2-(bis(4-chlorophenyl) (hydroxy)methyl)cyclobutan-1-one (γ-ketone, 26b) product as a white solid and 3-(bis(4-chlorophenyl)(hydroxy) methyl)cyclobutan-1-one (δ-ketone, 26a) product as a light yellow oil.

Run 1: (16.8 mg, 0.052 mmol, 17.4% yield of γ-ketone 26b), (32.2 mg, 0.100 mmol, 33.4% yield of δ-ketone 26a), (50.8% overall yield, 1.9:1 δ:γ ratio), 0% rsm. Run 2: (16.5 mg, 0.051 mmol, 17.1% yield of γ-ketone 26b), (33.0 mg, 0.103 mmol, 34.3% yield of δ-ketone 26a), (51.4% overall yield, 2.0:1 δ:γ ratio), 0% rsm. Run 3: (17.4 mg, 0.054 mmol, 18.1% yield of γ-ketone 26b), (34.8 mg, 0.108 mmol, 36.1% yield of δ-ketone 26a), (54.2% overall yield, 2.0:1 δ:γ ratio), 0% rsm. Average: 52.2% yield±1.8%, 2.0:1 δ:γ ratio, 0% rsm.

$^1$H-NMR (500 MHz, methylene chloride-d$_2$) δ 7.35-7.30 (m, 8H), 3.39 (tt, J=8.7, 6.6 Hz, 1H), 3.08-2.93 (m, 4H), 2.63 (br. s, 1H). $^{13}$C-NMR (126 MHz, methylene chloride-d$_2$) δ 206.3, 144.8, 133.8, 129.1, 128.1, 78.3, 48.5, 33.3. HRMS (EI+) m/z calculated for C$_{17}$H$_{14}$O$_2$Cl$_{12}$ [M]$^+$: 320.0371, found 320.0372.

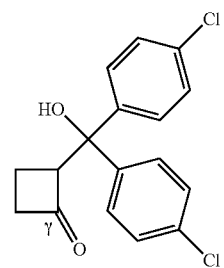 [SMILES: O=C1CCC1C(O)(c1ccc(Cl)cc1)c1ccc(Cl)cc1]

2-(Bis(4-chlorophenyl)(hydroxy)methyl)cyclobutan-1-one 126b1. $^1$H-NMR (500 MHz, methylene chloride-d$_2$) δ 7.33-7.27 (m, 8H), 4.43-4.38 (m, 1H), 3.02-2.94 (m, 1H), 2.80-2.72 (m, 2H), 2.02 (app. td, J=9.1, 7.4 Hz, 2H). $^{13}$C-NMR (126 MHz, methylene chloride-d$_2$) δ 208.4, 144.2, 144.1, 133.9, 133.5, 128.9, 128.85, 128.83, 128.0, 77.9, 68.8, 45.2, 14.0. HRMS (EI+) m/z calculated for C$_{17}$H$_{14}$O$_2$Cl$_2$ [M]$^+$: 320.0371, found 320.0374.

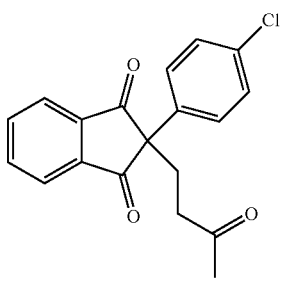 [SMILES: CC(=O)CCC1(c2ccc(Cl)cc2)C(=O)c2ccccc2C1=O]

2-(4-Chlorophenyl)-2-(3-oxobutyl)-1H-indene-1,3(2H)-dione [27]. The reaction was run with General Method A: Single Catalyst Addition Protocol: 2-butyl-2-(4-chlorophenyl)-1H-indene-1,3(2H)-dione S23 (93.8 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), MeCN (0.6 mL in 40 mL vial, 3.75 mL with oxidant). The reaction was run at 0° C. with ice bath. The reaction was worked up with saturated 9 mL NaHCO$_3$ and DCM as described in General Method A. Flash column chromatography on silica (35 mm fritted glass column, 150 mL SiO$_2$) using 20% acetone/hexanes→30% acetone/hexanes as eluent afforded product as a white solid. Run 1: (57.7 mg, 0.177 mmol, 58.9% yield), (13.0 mg, 0.042 mmol, 13.9% rsm). Run 2: (58.8 mg, 0.180 mmol, 60.0% yield), (13.0 mg, 0.042 mmol, 13.9% rsm). Run 3: (60.8 mg, 0.186 mmol, 62.0% yield), (13.4 mg, 0.043 mmol, 14.3% rsm). Average: 60.3% yield±1.6%, 14.0% rsm±0.2%.

$^1$H-NMR (500 MHz, CDCl$_3$) δ 8.04-8.00 (m, 2H), 7.91-7.87 (m, 2H), 7.38 (d, J=8.6 Hz, 2H), 7.29 (d, J=8.6 Hz, 2H), 2.44 (app. s, 4H), 2.05 (s, 3H). $^{13}$C-NMR (126 MHz, CDCl$_3$) δ 206.9, 200.9, 141.3, 136.4, 134.3, 134.1, 129.1, 128.6, 124.0, 59.8, 38.6, 30.0, 29.3. HRMS (TOF ESI+) m/z calculated for C$_{19}$H$_{16}$O$_3$Cl [M+H]$^+$: 327.0788, found 327.0795.

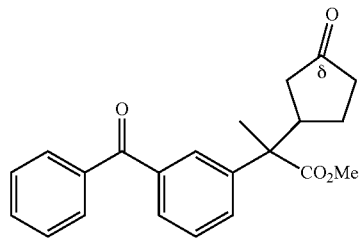 [SMILES: COC(=O)C(C)(c1cccc(C(=O)c2ccccc2)c1)C1CCC(=O)C1]

Methyl 2-(3-benzoylphenyl)-2-(3-oxocyclopentyl)propanoate [28a]. The reaction was run with General Method A: Single Catalyst Addition Protocol: methyl 2-(3-benzoylphenyl)-2-cyclopentylpropanoate S24 (110.6 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), MeCN (0.6 mL in 40 mL vial, 3.75 mL with oxidant). The reaction was run at 0° C. with ice bath. The reaction was worked up with 9 mL saturated NaHCO$_3$ and DCM as described in General Method A. Flash column chromatography on silica (35 mm fritted glass column, 150 mL SiO$_2$) using 20% acetone/hexanes→30% acetone/hexanes→40% acetone/hexanes as eluent afforded methyl 2-(3-benzoylphenyl)-2-(3-oxocyclopentyl)propanoate (δ-ketone, 28a) product as a yellow oil and methyl 2-(3-benzoylphenyl)-2-(2-oxocyclopentyl)propanoate (γ-ketone, 28b) as a yellow oil.

Run 1: (52.7 mg, 0.150 mmol, 50.1% yield of δ-ketone 28a), (6.3 mg, 0.018 mmol, 6.0% yield of γ-ketone 28b), (56.1% overall yield, 8.3:1 δ-ketone:γ-ketone ratio), 0% rsm. Run 2: (48.4 mg, 0.138 mmol, 46.1% yield of δ-ketone 28a), (5.3 mg, 0.015 mmol, 5.1% yield of γ-ketone 28b), (51.2% overall yield, 9.0:1 δ-ketone:γ-ketone ratio), 0% rsm. Run 3: (46.8 mg, 0.134 mmol, 44.6% yield of δ-ketone 28a), (4.7 mg, 0.013 mmol, 4.5% yield of γ-ketone 28b), (49.1% overall yield, 9.9:1 δ-ketone:γ-ketone ratio), 0% rsm. Average: 52.1% yield±3.6%, 9.1:1 δ-ketone:γ-ketone ratio, 0% rsm.

The δ-ketone product 28a is isolated as a mixture of ~1:1 ratio of diastereomers. Overlap of peaks are observed in both $^1$H and $^{13}$C NMR. $^1$H-NMR (500 MHz, CDCl$_3$) δ 7.80-7.74 (m, 3H), 7.70-7.67 (m, 1H), 7.62-7.59 (m, 1H), 7.54-7.44 (m, 4H), 3.71 & 3.70 (s, 3H), 3.09-2.99 (m, 1H), 2.43-2.04 (m, 4H), 1.89-1.68 (m, 1H), 1.65 & 1.63 (s, 3H), 1.57-1.47 (m, 1H). $^{13}$C-NMR (126 MHz, CDCl$_3$) δ 218.1, 217.8, 196.6, 196.5, 175.5, 175.4, 142.3, 142.1, 137.9, 137.5, 132.81, 132.79, 130.6, 130.5, 130.20, 130.19, 129.3, 129.2, 128.6, 128.54, 128.47, 127.9, 127.8, 52.57, 52.56, 52.3, 52.2, 44.9, 44.8, 41.4, 40.9, 38.8, 38.7, 25.1, 24.6, 18.94, 18.92. HRMS (TOF ESI+) m/z calculated for C$_{22}$H$_{23}$O$_4$ [M+H]$^+$: 351.1596, found 351.1599.

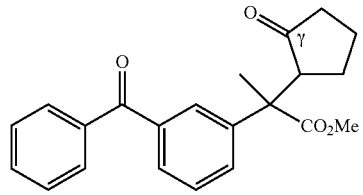 [SMILES: COC(=O)C(C)(c1cccc(C(=O)c2ccccc2)c1)C1CCCC1=O]

Methyl 2-(3-benzoylphenyl)-2-(2-oxocyclopentyl)propanoate [28b]. The γ-ketone product 28b is isolated as a single diastereomer. $^1$H-NMR (500 MHz, CDCl$_3$) δ 7.87 (t, J=1.9 Hz, 1H), 7.80-7.78 (m, 2H), 7.69-7.66 (m, 2H), 7.62-7.59 (m, 1H), 7.51-7.43 (m, 3H), 3.72 (s, 3H), 3.39 (dd, J=13.3, 7.8 Hz, 1H), 2.40-2.35 (m, 1H), 2.12-2.04 (m, 1H), 1.98-1.95 (m, 1H), 1.80-1.73 (m, 2H), 1.56 (s, 3H), 1.57-1.51 (m, 1H). $^{13}$C-NMR (126 MHz, CDCl$_3$) δ 217.3, 196.7, 175.0, 142.1, 137.8, 137.5, 132.8, 130.6, 130.2, 129.2, 128.6, 128.4, 128.0, 56.9, 52.8, 50.1, 39.0, 25.9, 20.2, 17.1. HRMS (TOF ESI+) m/z calculated for C$_{22}$H$_{23}$O$_4$ [M+H]$^+$: 351.1596, found 351.1599.

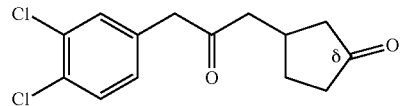 [SMILES: O=C1CCC(CC(=O)Cc2ccc(Cl)c(Cl)c2)C1]

3-(3-(3,4-Dichlorophenyl)-2-oxopropyl)cyclopentan-1-one [29a]. The reaction was run with General Method A: Single Catalyst Addition Protocol: 1-cyclopentyl-3-(3,4-dichlorophenyl)propan-2-one S25 (81.4 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), MeCN (0.6 mL in 40 mL vial, 3.75 mL with oxidant). The reaction was run at 0° C. with ice bath. The reaction was worked up with saturated 9 mL NaHCO$_3$ and DCM as described in General Method A. Flash column chromatography on silica (35 mm fitted glass column, 150 mL SiO$_2$) using 10% acetone/hexanes→20% acetone/hexanes as eluent afforded 2-(3-(3,4-dichlorophenyl)-2-oxopropyl)cyclopentan-1-one (γ-ketone, 29b) product as a white solid and 3-(3-(3,4-dichlorophenyl)-2-oxopropyl)cyclopentan-1-one (δ-ketone, 29a) product as a light yellow oil.

Run 1: (11.3 mg, 0.040 mmol, 13.2% yield of γ-ketone 29b), (35.0 mg, 0.123 mmol, 40.9% yield of δ-ketone 29a), (54.1% overall yield, 3.1:1 δ:γ ratio), 0% rsm. Run 2: (10.7 mg, 0.038 mmol, 12.5% yield of γ-ketone 29b), (32.3 mg, 0.113 mmol, 37.8% yield of δ-ketone 29a), (50.3% overall yield, 3.0:1 δ:γ ratio), 0% rsm. Run 3: (11.2 mg, 0.040 mmol, 13.1% yield of γ-ketone 29b), (35.2 mg, 0.124 mmol, 41.2% yield of δ-ketone 29a), (54.3% overall yield, 3.1:1 δ:γ ratio), 0% rsm. Average: 52.9% yield±2.3%, 3.1:1 δ:γ ratio, 0% rsm.

$^1$H-NMR (500 MHz, methylene chloride-d$_2$) δ 7.42 (d, J=8.2 Hz, 1H), 7.31 (d, J=2.0 Hz, 1H), 7.05 (dd, J=8.3, 2.1 Hz, 1H), 3.67 (s, 2H), 2.69-2.55 (m, 3H), 2.44-2.38 (m, 1H), 2.27-2.09 (m, 3H), 1.71 (ddd, J=18.2, 9.9, 1.2 Hz, 1H), 1.51-1.41 (m, 1H). $^{13}$C-NMR (126 MHz, methylene chloride-d$_2$) δ 218.4, 205.9, 135.0, 132.8, 132.0, 131.5, 131.0, 129.7, 49.2, 48.2, 45.0, 38.7, 32.7, 29.7. HRMS (TOF ESI+) m/z calculated for C$_{14}$H$_{15}$O$_2$Cl$_2$ [M+H]$^+$: 285.0449, found 285.0453. Site of oxidation was assigned based on a combination of $^1$H, gDQCOSY, gHSQC, gEIMBC NMRs.

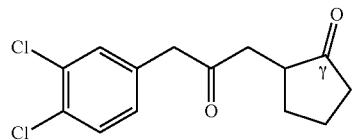 [SMILES: O=C(Cc1ccc(Cl)c(Cl)c1)CC1CCCC1=O]

2-(3-(3,4-Dichlorophenyl)-2-oxopropyl)cyclopentan-1-one [29b]. $^1$H-NMR (500 MHz, methylene chloride-d$_2$) δ 7.41 (d, J=8.2 Hz, 1H), 7.31 (d, J=2.1 Hz, 1H), 7.05 (dd, J=8.3, 2.1 Hz, 1H), 3.72 (d, J=16.4 Hz, 1H), 3.68 (d, J=16.4 Hz, 1H), 2.88 (dd, J=17.9, 4.4 Hz, 1H), 2.55 (dd, J=17.9, 7.2 Hz, 1H), 2.50-2.43 (m, 1H), 2.32-2.19 (m, 2H), 2.13 (ddd, J=18.7, 11.1, 8.9 Hz, 1H), 2.04-1.98 (m, 1H), 1.84-1.74 (m, 1H), 1.52-1.43 (m, 1H). $^{13}$C-NMR (126 MHz, methylene chloride-d$_2$) δ 220.0, 205.6, 135.1, 132.8, 132.1, 131.5, 130.9, 129.8, 49.1, 45.5, 42.6, 37.8, 29.9, 21.3. HRMS (TOF ESI+) m/z calculated for C$_{14}$H$_{15}$O$_2$Cl$_2$ [M+H]$^+$: 285.0449, found 285.0442. Site of oxidation was assigned based on a combination of $^1$H, COSY, gHSQC, gHMB C NMRs.

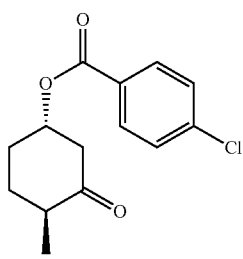 [SMILES: C[C@H]1CC[C@H](OC(=O)c2ccc(Cl)cc2)CC1=O]

(±)-trans-4-Methyl-3-oxocyclohexyl 4-chlorobenzoate [30a]. The reaction was run with General Method A: Single Catalyst Addition Protocol. (±)-trans-4-methylcyclohexyl 4-chlorobenzoate S26 (75.8 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv), 50% wt. H$_2$O$_2$ (204 mg, 3.0 mmol, 10.0 equiv.), 4:1 MeCN:DCM (0.6 mL in 40 mL vial, 3.75 mL with oxidant). The reaction was run at 0° C. with ice bath. The reaction was worked up with saturated 9 mL NaHCO$_3$ and DCM as described in General Method A. Flash column chromatography on silica (35 mm fritted glass column, 150 mL SiO$_2$) using 10% ethyl acetate/hexanes→20% ethyl acetate/hexanes→30% ethyl acetate/hexanes as eluent afforded (±)-trans-4-methyl-3-oxocyclohexyl 4-chlorobenzoate (γ-ketone, 30a) as a white solid and (±)-trans-4-hydroxy-4-methylcyclohexyl 4-chlorobenzoate (δ-alcohol, 30b) as a white solid. A trace amount (<5% yield) of (±)-trans-4-methyl-2-oxocyclohexyl 4-chlorobenzoate (β-ketone) can be observed.

Run 1: (24.9 mg, 0.093 mmol, 31.1% yield of γ-ketone 30a), (20.6 mg, 0.077 mmol, 25.6% yield of δ-alcohol 30b), (56.7% overall yield, 1.21:1 K:A ratio), (13.3 mg, 0.053 mmol, 17.5% rsm). Run 2: (26.8 mg, 0.101 mmol, 33.5% yield of γ-ketone 30a), (23.1 mg, 0.086 mmol, 28.7% yield of δ-alcohol 30b), (62.2% overall yield, 1.17:1 K:A ratio), (12.5 mg, 0.049 mmol, 16.4% rsm). Run 3: This reaction was performed at 0.5 mmol scale with the same procedure. (40.0 mg, 0.150 mmol, 30.0% yield of γ-ketone 30a), (35.1 mg, 0.131 mmol, 26.1% yield of δ-alcohol 30b), (56.1% overall yield, 1.15:1 K:A ratio), (21.8 mg, 0.086 mmol, 17.3% rsm). Average: 31.5% yield±1.8% of γ-ketone, 26.8% yield±1.7% of δ-alcohol, 58.3% overall yield with 1.2:1 K:A ratio, 17.1% rsm±0.6%.

$^1$H-NMR (500 MHz, CDCl$_3$) δ 7.96 (d, J=8.5 Hz, 2H), 7.42 (d, J=8.5 Hz, 2H), 5.21 (tt, J=10.2, 4.7 Hz, 1H), 2.92 (ddd, J=13.6, 5.0, 2.0 Hz, 1H), 2.57 (ddd, J=13.6, 10.7, 1.3 Hz, 1H), 2.42-2.33 (m, 2H), 2.15-2.11 (m, 1H), 1.91 (tdd, J=12.7, 10.2, 4.0 Hz, 1H), 1.42 (dtd, J=13.8, 12.0, 3.6 Hz, 1H), 1.10 (d, J=6.6 Hz, 3H). $^{13}$C-NMR (126 MHz, CDCl$_3$) δ 208.9, 164.7, 139.7, 131.2, 128.9, 128.6, 72.6, 47.0, 44.4, 30.4, 29.2, 14.5. HRMS (TOF ESI+) m/z calculated for C$_{14}$H$_{15}$O$_3$ClNa [M+Na]$^+$: 289.0607, found 289.0601.

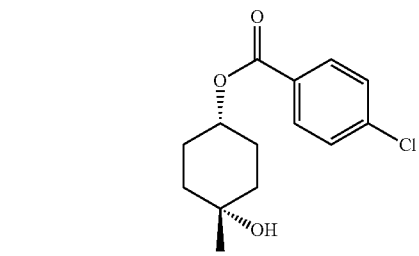 [SMILES: C[C@]1(O)CC[C@@H](OC(=O)c2ccc(Cl)cc2)CC1]

(±)-trans-4-Hydroxy-4-methylcyclohexyl 4-chlorobenzoate [30b]. $^1$H-NMR (500 MHz, CDCl$_3$) δ 7.97 (d, J=8.6 Hz, 2H), 7.40 (d, J=8.5 Hz, 2H), 4.97 (tt, J=9.4, 4.7 Hz, 1H), 1.95-1.85 (m, 4H), 1.79-1.74 (m, 2H), 1.57 (ddd, J=13.7, 11.4, 4.7 Hz, 2H), 1.28 (s, 3H), 1.25 (br. s, 1H). $^{13}$C-NMR (126 MHz, CDCl$_3$) δ 165.3, 139.3, 131.1, 129.3, 128.8, 73.0, 68.8, 36.7, 30.1, 27.4. HRMS (TOF ESI+) m/z calculated for C$_{14}$H$_{17}$O$_3$ClNa [M+Na]$^+$: 291.0764, found 291.0770.

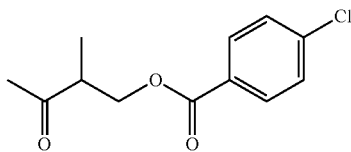 [SMILES: CC(=O)C(C)COC(=O)c1ccc(Cl)cc1]

(±)-2-Methyl-3-oxobutyl 4-chlorobenzoate [31a]. The reaction was run with General Method C: Slow Catalyst Addition Protocol: 2-methylbutyl 4-chlorobenzoate S27 (113.4 mg, 0.500 mmol, 1.0 equiv), ClCH$_2$CO$_2$H (709 mg, 7.5 mmol, 15.0 equiv.) were dissolved in MeCN (1.0 mL). (R,R)—Mn(CF$_3$-PDP) (67.8 mg, 0.050 mmol, 10 mol %) and MeCN (0.625 mL) added in a 1 mL syringe, 50% wt. H$_2$O$_2$ (340 mg, 5.0 mmol, 10.0 equiv.) and MeCN (6.25 mL) added in a 10 mL syringe. The reaction was run at −36° C. with 1,2-dichloroethane/dry ice bath. The reaction was worked up with 15 mL saturated NaHCO$_3$ and DCM as described in General Method C. Flash column chromatography on silica (35 mm fritted glass column, 150 mL SiO$_2$) using 10% ethyl acetate/hexanes→20% ethyl acetate/hexanes→35% ethyl acetate/hexanes as eluent afforded 2-(±)-methyl-3-oxobutyl 4-chlorobenzoate (γ-ketone, 31a) product as a yellow oil and (±)-2-hydroxy-2-methylbutyl 4-chlorobenzoate (β-alcohol, 31b) as a yellow oil.

Run 1: (45.7 mg, 0.190 mmol, 38.0% yield of γ-ketone 31a), (21.6 mg, 0.089 mmol, 17.8% yield of β-alcohol 31b), (55.8% overall yield, 2.13:1 K:A ratio), <10% rsm. Run 2: (47.7 mg, 0.198 mmol, 39.6% yield of γ-ketone 31a), (23.6 mg, 0.097 mmol, 19.4% yield of β-alcohol 31b), (59.0% overall yield, 2.04:1 K:A ratio), <10% rsm. Run 3: (47.7 mg, 0.198 mmol, 39.6% yield of γ-ketone 31a), (22.4 mg, 0.092 mmol, 18.5% yield of β-alcohol 31b), (58.1% overall yield, 2.14:1 K:A ratio), <10% rsm. Average: 39.1% yield±0.9% of γ-ketone, 18.5% yield±0.8% of β-alcohol, 57.6% overall yield with 2.1:1 K:A, <10% rsm.

$^1$H-NMR (500 MHz, CDCl$_3$) δ 7.91 (d, J=8.8 Hz, 2H), 7.39 (d, J=8.7 Hz, 2H), 4.47 (ddd, J=11.1, 7.3, 0.7 Hz, 1H), 4.39 (ddd, J=11.1, 5.5, 0.7 Hz, 1H), 3.04-2.97 (m, 1H), 2.23 (s, 3H), 1.21 (d, J=7.2 Hz, 3H). $^{13}$C-NMR (126 MHz, CDCl$_3$) δ 209.3, 165.5, 139.7, 131.1, 128.9, 128.4, 66.1, 46.2, 28.8, 13.5. HRMS (TOF ESI+) m/z calculated for C$_{12}$H$_{14}$O$_3$Cl [M+H]$^+$: 241.0631, found 241.0627. The NMR data matches with the literature.

Oxidation with TFDO: The reaction was performed using TFDO generated according to method described in Table 3. In a 1-dram vial charged with 2-methylbutyl 4-chlorobenzoate S27 (11.3 mg, 0.05 mmol, 1.0 equiv.) and a stir bar. 0.5 mL DCM freshly obtained from SDS was transferred into the vial via plastic syringe equipped with micropipette tip. The reaction was cooled to −20° C., and 0.38 mL 0.4M TFDO solution was added into the vial in 1-2 portions and the reaction was kept at −20° C. for 48 h. The reaction was concentrated on rotvap to remove all volatiles and the crude mixture was analyzed by $^1$H NMR with nitrobenzene added as internal standard.

Run 1: (2.8 mg, 0.012 mmol, 23.3% yield of γ-ketone 31a), (5.6 mg, 0.023 mmol, 46.1% yield of β-alcohol 31b), (69.4% overall yield, 1:2.0 K:A ratio), (1.2 mg, 0.005 mmol, 10.6% rsm). Run 2: (2.5 mg, 0.010 mmol, 20.8% yield of γ-ketone 31a), (5.1 mg, 0.021 mmol, 42.0% yield of β-alcohol 31b), (62.8% overall yield, 1:2.0 K:A ratio), (1.9 mg, 0.008 mmol, 16.8% rsm). Average: 22.1% yield of γ-ketone, 44.1% yield of β-alcohol, 66.2% overall yield with 1:2.0 K:A, 13.7% rsm.

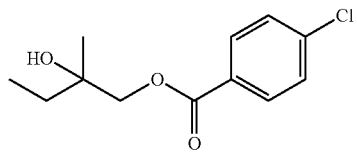 [SMILES: CCC(C)(O)COC(=O)c1ccc(Cl)cc1]

(±)-2-Hydroxy-2-methylbutyl 4-chlorobenzoate [31b]. $^1$H-NMR (500 MHz, CDCl$_3$) 7.99-7.97 (m, 2H), 7.43-7.41 (m, 2H), 4.25-4.20 (m, 2H), 1.90 (br. s, 1H), 1.64 (q, J=7.5 Hz, 2H), 1.28 (s, 3H), 0.98 (t, J=7.5 Hz, 3H). $^{13}$C-NMR (126 MHz, CDCl$_3$) 165.9, 139.8, 131.1, 128.9, 128.5, 72.3, 71.5, 31.9, 23.6, 8.1. HRMS (TOF ESI+) m/z calculated for C$_{12}$H$_{14}$ClO$_2$ [M−OH]$^+$: 225.0677, found 225.0687. The NMR data matches with the literature.

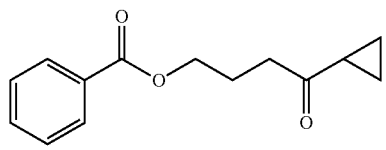 [SMILES: O=C(OCCCC(=O)C1CC1)c1ccccc1]

4-Cyclopropyl-4-oxobutyl benzoate [32a]. The reaction was run with General Method A: Single Catalyst Addition Protocol. 4-cyclopropylbutyl benzoate S28 (65.5 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), MeCN (0.6 mL in 40 mL vial, 3.75 mL with oxidant). The reaction was run at 0° C. with ice bath. The reaction was worked up with saturated 9 mL NaHCO$_3$ and DCM as described in General Method A. Flash column chromatography on silica (35 mm fritted glass column, 150 mL SiO$_2$) using 5% ethyl acetate/hexanes→15% ethyl acetate/hexanes→40% ethyl acetate/hexanes as eluent afforded 4-cyclopropyl-4-oxobutyl benzoate (ketone, 32a), 4-cyclopropyl-4-hydroxybutyl benzoate (alcohol, 32b) and 4-(2-chloroacetoxy)-4-cyclopropylbutyl benzoate (ester, 32c) products as colorless oils.

Run 1: (31.2 mg, 0.134 mmol, 44.8% yield of ketone 32a), (6.4 mg, 0.027 mmol, 9.1% yield of alcohol 32b), (6.3 mg, 0.020 mmol, 6.8% yield of ester 32c), (5.6 mg, 0.026 mmol, 8.6% rsm), (60.7% combined oxidation yield, 69.3% mass balance). Run 2: (28.5 mg, 0.123 mmol, 40.9% yield of ketone 32a), (7.3 mg, 0.031 mmol, 10.4% yield of alcohol 32b), (6.5 mg, 0.021 mmol, 7.0% yield of ester 32c), (5.0 mg, 0.023 mmol, 7.6% rsm), (58.3% combined oxidation yield, 65.9% mass balance). Run 3: (32.3 mg, 0.139 mmol, 46.4% yield of ketone 32a), (6.9 mg, 0.029 mmol, 9.8% yield of alcohol 32b), (6.0 mg, 0.019 mmol, 6.4% yield of ester 32c), (5.2 mg, 0.024 mmol, 7.9% rsm), (62.6% combined oxidation yield, 70.5% mass balance). Average: 44.0% yield±2.8% of ketone, 9.8% yield±0.7% of alcohol, 6.7% yield±0.3% of ester, 8.0% rsm±0.5%, 60.5% overall oxidation yield with 68.5% mass balance.

$^1$H-NMR (500 MHz, CDCl$_3$) δ 8.04 (dt, J=8.3, 1.2 Hz, 2H), 7.58-7.54 (m, 1H), 7.44 (td, J=7.7, 1.3 Hz, 2H), 4.34 (t, J=6.4 Hz, 2H), 2.74 (t, J=7.3 Hz, 2H), 2.09 (tt, J=7.5, 6.9 Hz, 2H), 1.94 (tdd, J=7.9, 5.1, 4.0 Hz, 1H), 1.05-1.02 (m, 2H), 0.87 (ddt, J=7.3, 4.0, 3.1 Hz, 2H). $^{13}$C-NMR (126 MHz, CDCl$_3$) δ 209.8, 166.6, 133.0, 130.3, 129.6, 128.4, 64.3, 39.8, 23.1, 20.6, 10.9. HRMS (TOF ESI+) m/z calculated for C$_{14}$H$_{16}$O$_3$Na [M+Na]$^+$: 255.0997, found 255.0991.

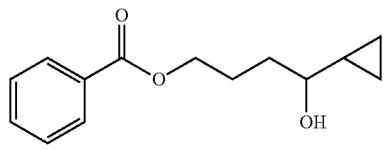 [SMILES: O=C(OCCCC(O)C1CC1)c1ccccc1]

4-Cyclopropyl-4-hydroxybutyl benzoate [32b]. $^1$H-NMR (500 MHz, CDCl$_3$) δ 8.05-8.03 (m, 2H), 7.55 (td, J=7.2, 1.4 Hz, 1H), 7.43 (t, J=7.8 Hz, 2H), 4.36 (t, J=6.6 Hz, 2H), 2.94-2.90 (m, 1H), 2.00-1.86 (m, 2H), 1.81-1.72 (m, 2H), 1.70 (br. s, 1H), 0.93 (qt, J=8.3, 4.9 Hz, 1H), 0.57-0.48 (m, 2H), 0.31-0.21 (m, 2H). $^{13}$C-NMR (126 MHz, CDCl$_3$) δ 166.8, 133.0, 130.5, 129.7, 128.5, 76.6, 65.2, 33.6, 25.3, 18.1, 3.0, 2.7. HRMS (TOF ESI+) m/z calculated for C$_{14}$H$_{18}$O$_3$Na [M+Na]$^+$: 257.1154, found 257.1147.

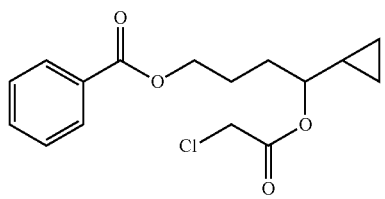 [SMILES: O=C(CCl)OC(CCCOC(=O)c1ccccc1)C1CC1]

4-(2-Chloroacetoxy)-4-cyclopropylbutyl benzoate [32c]. $^1$H-NMR (500 MHz, CDCl$_3$) δ 8.05-8.03 (m, 2H), 7.58-7.55 (m, 1H), 7.45 (t, J=7.8 Hz, 2H), 4.39 (dt, J=8.9, 5.5 Hz, 1H), 4.33 (t, J=5.8 Hz, 2H), 4.08 (s, 2H), 1.91-1.82 (m, 4H), 1.06-0.99 (m, 1H), 0.61 (tdd, J=8.5, 5.9, 4.6 Hz, 1H), 0.53 (tdd, J=8.9, 6.8, 5.2 Hz, 1H), 0.46 (ddt, J=9.5, 5.9, 4.8 Hz, 1H), 0.33-0.29 (m, 1H). $^{13}$C-NMR (126 MHz, CDCl$_3$) δ 167.3, 166.7, 133.1, 130.3, 129.7, 128.5, 80.9, 64.6, 41.3, 31.3, 24.9, 15.2, 3.6, 3.4. HRMS (TOF ESI+) m/z calculated for C$_{16}$H$_{19}$O$_4$ClNa [M+Na]$^+$: 333.0870, found 333.0864.

Example 5

Remote Methylene Oxidation of Aromatic Containing Compounds with Multiple Substitutions of Varied Electronic and Steric Properties (Table 5)

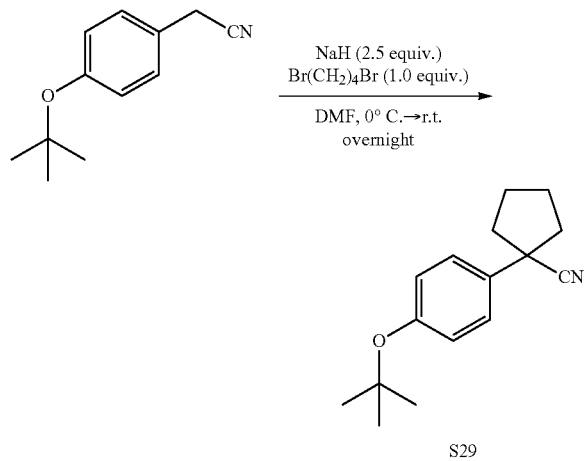

1-(4-(tert-Butoxy)phenyl)cyclopentane-1-carbonitrile [S29]. In a flamed dried 50 mL flask, 1.187 g (6.27 mmol) of 2-(4-(tert-butoxy)phenyl)acetonitrile was dissolved in 10 mL anhydrous DMF. 396 mg (95% purity, 15.68 mmol, 2.5 equiv.) of NaH was added in portions at 0° C. and the reaction was allowed to stir for 1 hour at 0° C. 1.354 g (0.75 mL, 6.27 mmol, 1.0 equiv.) of 1,4-dibromobutane was added dropwise at 0° C. and the reaction was allowed to stir overnight at room temperature. The reaction was quenched carefully with 10 mL water and extracted with 30 mL EtOAc three times. The combined organic layer was washed with 50 mL brine, dried with MgSO$_4$, filtered, and concentrated. Flash column chromatography on silica (50 mm fritted glass column, 300 mL SiO$_2$) using 10% EtOAc/hexanes→20% EtOAc/hexanes as eluent gave 1.057 g (4.34 mmol) of pure product as a white solid (69% yield).

$^1$H-NMR (500 MHz, CDCl$_3$) δ 7.34-7.31 (m, 2H), 6.99-6.96 (m, 2H), 2.48-2.44 (m, 2H), 2.08-1.99 (m, 4H), 1.99-1.89 (m, 2H), 1.35 (s, 9H). $^{13}$C-NMR (126 MHz, CDCl$_3$) δ 155.1, 134.5, 126.7, 124.8, 124.3, 78.9, 47.4, 40.6, 29.0, 24.3. HRMS (TOF ESI+) m/z calculated for C$_{16}$H$_{21}$NONa [M+Na]$^+$: 266.1521, found 266.1519.

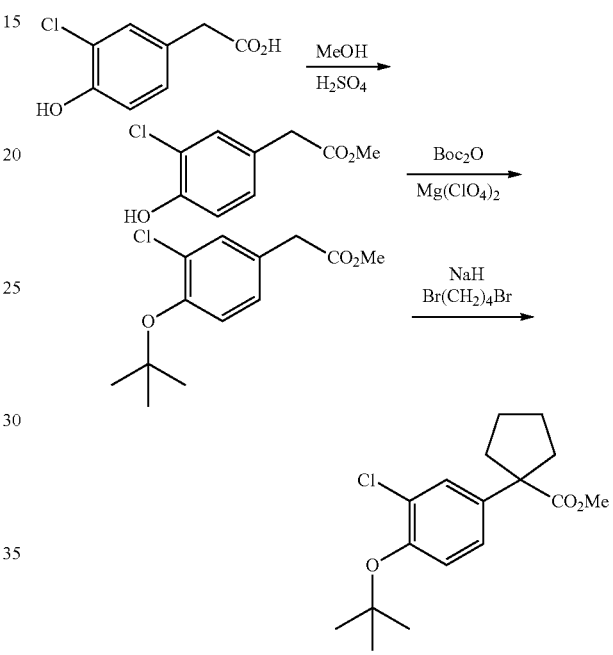

Methyl 1-(4-(tert-butoxy)-3-chlorophenyl)cyclopentane-1-carboxylate [S30]. In a 100 mL recovery flask was added 3-chloro-4-hydroxylphenylacetic acid 3.30 g (17.7 mmol), 35 mL methanol and 0.4 mL concentrated sulfuric acid. The reaction was allowed to reflux overnight. The reaction was concentrated, diluted with 50 mL ethyl acetate and neutralized with concentrated NaHCO$_3$. The organic layer was dried with MgSO$_4$ and plugged with 20% ethyl acetate/hexanes as eluent to get methyl 2-(3-chloro-4-hydroxyphenyl)acetate in quantitative yield. The resulted compound was dissolved in 27 mL anhydrous DCM, treated with Mg(ClO$_4$)$_2$ 396 mg (1.77 mmol, 10 mol %) and 8.9 g Boc$_2$O (40.8 mmol, 2.3 equiv.) sequentially. The reaction was heated to 40° C. for 24 hours and filtered through celite. The reaction was purified by CombiFlash (40 g column, hexanes→20% ethyl acetate/hexanes as eluent) to get methyl 2-(4-(tert-butoxy)-3-chlorophenyl)acetate 2.2624 g (8.81 mmol) in 50% yield. The product was dissolved in 18 mL anhydrous DMF in a flame dried 50 mL flask, 556 mg (95% purity, 22.0 mmol, 2.5 equiv.) of NaH was added in portions at 0° C. and the reaction was allowed to stir for 1 hour at 0° C. 1.05 mL (8.81 mmol, 1.0 equiv.) of 1,4-dibromobutane was added dropwise at 0° C. and the reaction was allowed to stir overnight at room temperature. The reaction was quenched carefully with ~15 mL water and extracted with 30 mL EtOAc three times, washed with 50 mL brine, dried with MgSO$_4$, filtered, and concentrated. Flash column chromatography on silica (50 mm fritted glass column, 200 mL SiO$_2$) using 2% EtOAc/hexanes→5% EtOAc/hexanes as eluent gave 1.3232 g (4.26 mmol) of S30 in 48% yield.

$^1$H-NMR (500 MHz, CDCl$_3$) δ 7.36 (d, J=2.3 Hz, 1H), 7.13 (dd, J=8.5, 2.4 Hz, 1H), 7.02 (d, J=8.5 Hz, 1H), 3.62 (s, 3H), 2.63-2.58 (m, 2H), 1.89-1.83 (m, 2H), 1.75-1.67 (m, 4H), 1.40 (s, 9H). $^{13}$C-NMR (126 MHz, CDCl$_3$) δ 176.2, 150.8, 139.2, 128.8, 128.8, 125.7, 124.2, 81.3, 58.5, 52.6, 36.4, 29.0, 23.7. HRMS (TOF ESI+) m/z calculated for C$_{17}$H$_{23}$ClO$_3$Na [M+Na]$^+$: 337.1233, found 337.1227.

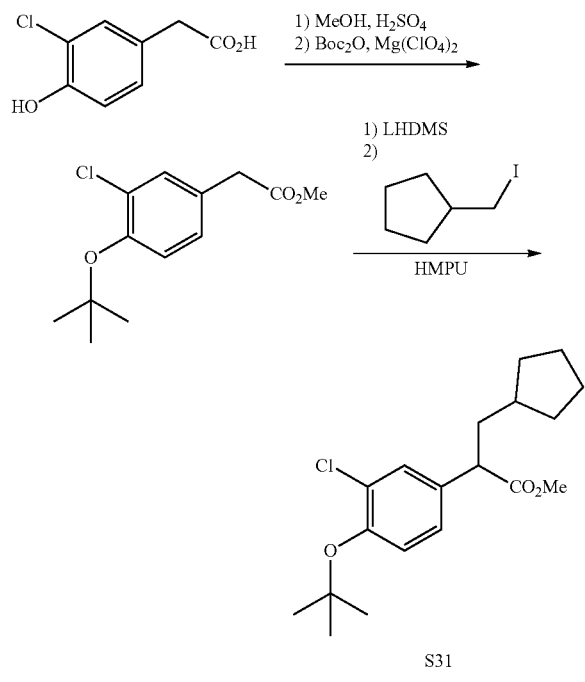

S31

(±)-Methyl 2-(4-(tert-butoxy)-3-chlorophenyl)-3-cyclopentylpropanoate [S31]. 2-(3-chloro-4-hydroxyphenyl)acetic acid (3.3 g, 17.7 mmol) was dissolved in 35 mL MeOH and added concentrated H$_2$SO$_4$ (0.4 mL). The reaction was refluxed overnight and concentrated. The residue oil was diluted with ether, washed with sat. NaHCO$_3$ twice, water 3 times and brine. The organic layer was dried over MgSO$_4$ and concentrated. The crude methyl ester was dissolved in DCM (27 mL), added Mg(ClO$_4$)$_2$ (396 mg, 1.77 mmol) and Boc$_2$O (8.9 g, 40.8 mmol, 2.3 equiv.). The reaction was heated at 40° C. for 24 hours. The reaction was concentrated and purified by CombiFlash (40 g column) eluting with pure hexanes→80% ethyl acetate/hexanes. Methyl 2-(4-(tert-butoxy)-3-chlorophenyl)acetate was isolated as clear oil (1.4917 g, 5.81 mmol) in 33% yield. $^1$H-NMR (500 MHz, CDCl$_3$) δ 7.30 (d, J=1.9 Hz, 1H), 7.09-7.04 (m, 2H), 3.71 (s, 3H), 3.55 (s, 2H), 1.41 (s, 9H). In a flame dried 100 mL flask charged with HN(TMS)$_2$ (2.11 g, 13.07 mmol, 2.25 equiv.), 13 mL anhydrous THF and a stir bar. The flask was cooled to −78° C. and n-BuLi solution (1.6 M in hexanes, 7.6 mL, 12.2 mmol, 2.1 equiv.) was added dropwise and the reaction was stirred at −78° C. for 15 min. A solution of ethyl 2-(4-(tert-butoxy)-3-chlorophenyl)acetate (1.4917 g, 5.81 mmol) in 12 mL THF was added and the reaction was stirred at −78° C. for 30 minutes then at room temperature for 20 min. The reaction was cooled back to −78° C. and charged with (iodomethyl)cyclopentane (1.83 g, 8.72 mmol, 1.5 equiv.) and DIVIPU (1.5 mL, 12.2 mmol, 2.1 equiv.). The reaction was allowed to gradually warmed up to room temperature and stirred overnight. The reaction was quenched with sat. NH$_4$Cl and extracted with ethyl acetate 3 times. The combined organic layer was combined, washed with brine, dried with MgSO$_4$ and concentrated.

The crude material was plugged through silica using 5% ethyl acetate/hexanes to obtain a mixture of desired (±)-methyl 2-(4-(tert-butoxy)-3-chlorophenyl)-3-cyclopentylpropanoate and dialkylated methyl 2-(4-(tert-butoxy)-3-chlorophenyl)-3-cyclopentyl-2-(cyclopentylmethyl)propanoate. The mixture was purified by hydrolyzing in a mixture of MeOH (6 mL) and 3M NaOH (6 mL) at 60° C. for 16 h, cooled to room temperature and extracted with DCM 3 times to remove the unhydrolyzed methyl 2-(4-(tert-butoxy)-3-chlorophenyl)-3-cyclopentyl-2-(cyclopentylmethyl)propanoate. The aqueous layer was acidified with 3M HCl and the aqueous layer was extracted with DCM 3 times. The combined organic layer was plugged through silica using 5% ethyl acetate/hexanes→20% acetone/hexanes doped with 1% acetic acid to obtain the pure 2-(4-(tert-butoxy)-3-chlorophenyl)-3-cyclopentylpropanoic acid. The resulted compound was dissolved in 9 mL benzene and 2 mL MeOH, and treated with trimethylsilyldiazomethane (2M solution, 3.5 mL, 7.0 mmol, 2.0 equiv.) for 1 hour. The reaction was concentrated and purified by flash column chromatography on silica (50 mm fritted glass column, 150 mL SiO$_2$) using 2% EtOAc/hexanes→5% EtOAc/hexanes as eluent gave 546.2 mg (1.61 mmol) of (±)-methyl 2-(4-(tert-butoxy)-3-chlorophenyl)-3-cyclopentylpropanoate in 28% yield.

$^1$H-NMR (500 MHz, CDCl$_3$) δ 7.33 (d, J=2.2 Hz, 1H), 7.10 (dd, J=8.4, 2.2 Hz, 1H), 7.04 (d, J=8.4 Hz, 1H), 3.67 (s, 3H), 3.52 (t, J=7.8 Hz, 1H), 2.05 (dt, J=13.4, 7.7 Hz, 1H), 1.78-1.69 (m, 3H), 1.64-1.57 (m, 3H), 1.50-1.46 (m, 2H), 1.40 (s, 9H), 1.14-1.04 (m, 2H). $^{13}$C-NMR (126 MHz, CDCl$_3$) δ 174.6, 151.2, 135.2, 129.8, 129.2, 126.7, 124.6, 81.4, 52.2, 50.1, 40.1, 38.0, 32.8, 32.5, 29.0, 25.2 (2 carbons). HRMS (TOF ESI+) m/z calculated for C$_{19}$H$_{27}$O$_3$NaCl [M+Na]$^+$: 361.1546, found 361.1540.

Scheme 6. General procedure for the synthesis of substrate S32-S33.

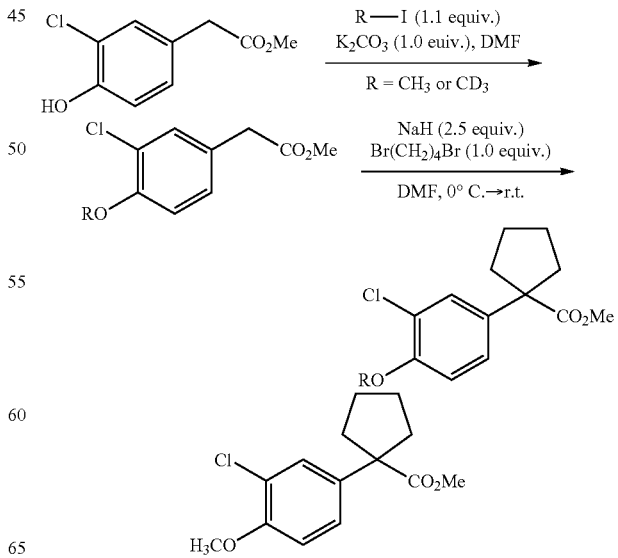

Methyl 1-(3-chloro-4-methoxyphenyl)cyclopentane-1-carboxylate [S32]. In a 50 mL flask charged methyl 2-(3-chloro-4-hydroxyphenyl)acetate (2.00 g, 10 mmol, 1.0 equiv.), $K_2CO_3$ (1.38 g, 1.0 equiv.) and anhydrous DMF (20 mL). MeI (0.65 mL, 1.1 equiv.) was added dropwise and the reaction was stirred overnight. The reaction was quenched with water and extracted with DCM and the crude compound was plugged through silica with 5% ethyl acetate/hexanes to get methyl 2-(3-chloro-4-methoxyphenyl)acetate (2.305 g, 9.48 mmol) in 95% yield. The resulted compound was dissolved in 15 mL anhydrous DMF, treated with NaH (95%, 599 mg, 23.7 mmol, 2.5 equiv.) at 0° C. After stirring at 0° C. for 1 h, 1,4-dibromobutane (1.13 mL, 9.48 mmol, 1.0 equiv,) was added and the reaction was allowed to warm up to room temperature overnight. The reaction was quenched with water and extracted with ether (30 mL) 3 times. The combined organic layer was washed with brine and dried over $Na_2SO_4$. Flash column chromatography on silica (50 mm fritted glass column, 200 mL $SiO_2$) using 2% EtOAc/hexanes→5% EtOAc/hexanes→10% EtOAc/hexanes as eluent gave 967 mg (3.60 mmol) of pure product as a white solid (38% yield).

$^1$H-NMR (500 MHz, $CDCl_3$) δ 7.37 (d, J=2.4 Hz, 1H), 7.21 (dd, J=8.6, 2.4 Hz, 1H), 6.86 (d, J=8.6 Hz, 1H), 3.88 (s, 3H), 3.61 (s, 3H), 2.63-2.58 (m, 2H), 1.89-1.83 (m, 2H), 1.74-1.69 (m, 4H). $^{13}$C-NMR (126 MHz, $CDCl_3$) δ 176.3, 153.9, 136.6, 129.0, 126.3, 122.2, 111.9, 58.3, 56.3, 52.6, 36.4, 23.6. HRMS (TOF ESI+) m/z calculated for $C_{14}H_{18}O_3Cl$ [M+H]$^+$: 269.0944, found 269.0945.

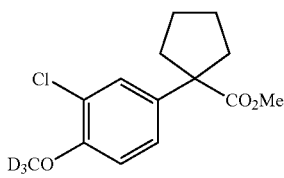

Methyl 1-(3-chloro-4-(methoxy-$d_3$)phenyl)cyclopentane-1-carboxylate [S33]. The compound was prepared in the same procedure as S32 using $CD_3I$ from methyl 2-(3-chloro-4-hydroxyphenyl)acetate (1.00 g, 5 mmol.). Product was isolated as a white solid (515 mg, 1.90 mmol) in 38% yield over 2 steps.

$^1$H-NMR (500 MHz, $CDCl_3$) δ 7.37 (d, J=2.4 Hz, 1H), 7.21 (dd, J=8.6, 2.4 Hz, 1H), 6.85 (d, J=8.6 Hz, 1H), 3.61 (s, 3H), 2.62-2.57 (m, 2H), 1.89-1.83 (m, 2H), 1.74-1.68 (m, 4H). $^{13}$C-NMR (126 MHz, $CDCl_3$) δ 176.3, 153.8, 136.6, 129.0, 126.3, 122.2, 111.8, 58.3, 56.0-54.9 (m, 1C), 52.5, 36.3, 23.6. HRMS (TOF ESI+) m/z calculated for $C_{14}H_{15}D_3O_3Cl$ [M+H]$^+$: 272.1133, found 272.1142.

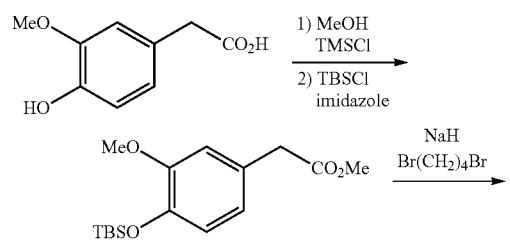

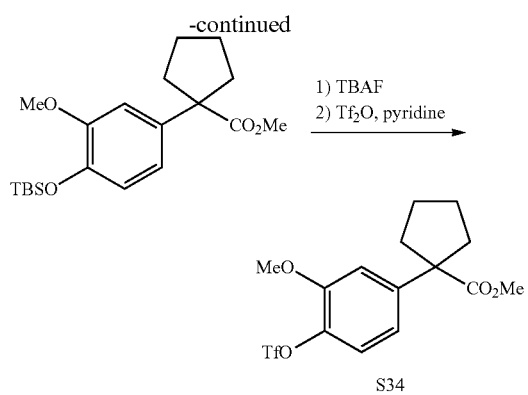

Methyl 1-(3-methoxy-4-(((trifluoromethyl)sulfonyl)oxy)phenyl)cyclopentane-1-carboxylate [S34]. To a 300 mL flask added 2-(4-hydroxy-3-methoxyphenyl)acetic acid 1.8218 g (10 mmol, 1.0 equiv.), 2.54 mL TMSCl (20 mmol, 2.0 equiv.) and 100 mL MeOH. The reaction was sitrred under room temperature for 24 hours before diluted with 100 mL DCM and extracted with 100 mL brine. The organic layer was dried with $Na_2SO_4$ and concentrated. The crude compound was redissolved in 50 mL anhydrous DCM, and treated with 1.809 g (12 mmol, 1.2 equiv.) TB SCl, 1.020 g (15 mmol, 1.5 equiv.) imidazole and 122 mg (1 mmol, 0.1 equiv.) DMAP. The reaction was stirred overnight, worked up with water and extracted with DCM. The combined organic layer was washed with brine and dried with $Na_2SO_4$. The crude product was dissolved in 15 mL anhydrous DMF and transferred to a 50 mL flamed dried flask. 632 mg (95% purity, 25 mmol, 2.5 equiv.) of NaH was added in portions at 0° C. and the reaction was allowed to stir for 1 hour at 0° C. 1.18 mL (10.0 mmol, 1.0 equiv.) of 1,4-dibromobutane was added dropwise at 0° C. and the reaction was allowed to stir overnight at room temperature. The reaction was quenched carefully with ~10 mL water and extracted with 30 mL EtOAc three times, washed with 50 mL brine, dried with $MgSO_4$, filtered, and concentrated. The product was dissolved in 2 mL THF and added 1.5 mL 1M TBAF solution and stirred overnight then concentrated. The previous aqueous layer was acidified with 3M HCl then extract with 30 mL EtOAc three times. The combined organic layer was washed with 50 mL brine, dried with $MgSO_4$, filtered, and concentrated to get 378 mg of crude phenol compound. The crude was dissolved in 5 mL anhydrous DCM, cooled to 0° C. and treated with 0.31 mL (1.8 mmol, 1.2 equiv.) of triflate anhydride and 0.18 mL (2.27 mmol, 1.5 equiv.) of pyridine. The reaction was then stirred for 5 hours at room temperature before quenched with ~10 mL water. 15 mL DCM was used to extract the reaction 3 times and the combined organic layer was dried with $Na_2SO_4$ and concentrated. Flash column chromatography on silica (50 mm fritted glass column, 200 mL $SiO_2$) using 5% EtOAc/hexanes→10% EtOAc/hexanes as eluent gave 542.2 mg (1.42 mmol) of pure product as a colorless oil (14% yield over 5 steps).

$^1$H-NMR (500 MHz, $CDCl_3$) δ 7.13 (d, J=8.4 Hz, 1H), 7.01 (d, J=2.1 Hz, 1H), 6.96 (dd, J=8.5, 2.2 Hz, 1H), 3.91 (s, 3H), 3.64 (s, 3H), 2.68-2.63 (m, 2H), 1.90-1.85 (m, 2H), 1.77-1.71 (m, 4H). $^{13}$C-NMR (126 MHz, $CDCl_3$) δ 175.8, 151.1, 145.0, 137.6, 122.1, 119.5, 118.87 (d, J=321.2 Hz), 112.2, 59.3, 56.3, 52.7, 36.4, 23.7. $^{19}$F-NMR (470 MHz, $CDCl_3$) δ -73.9. HRMS (TOF ESI+) m/z calculated for $C_{15}H_{18}F_3O_6S$ [M]$^+$: 383.0771, found 383.0773.

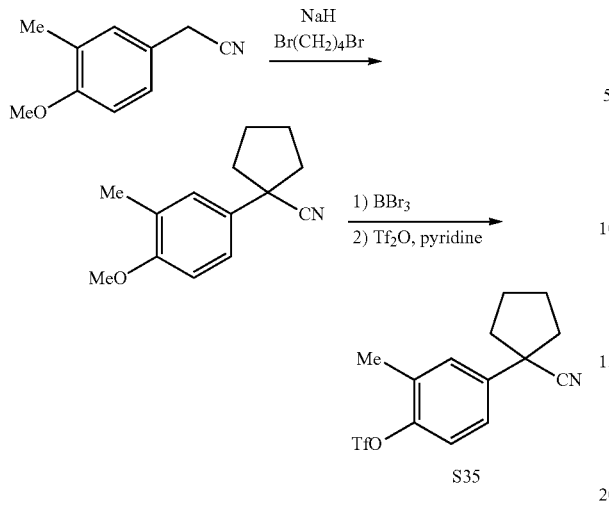

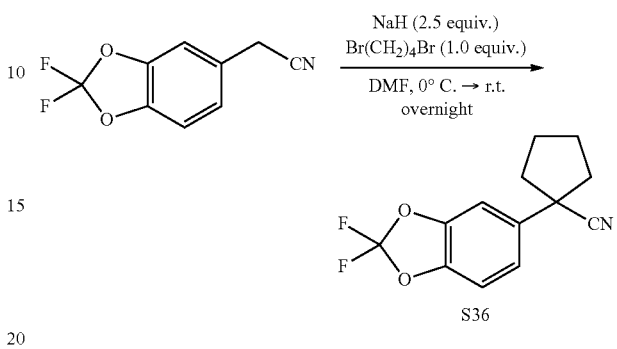

NMR (126 MHz, CDCl₃) δ 147.8, 140.2, 131.6, 130.2, 125.4, 123.9, 121.8, 118.7 (q, J=320.1 Hz), 47.5, 40.7, 24.4, 16.7. ¹⁹F-NMR (470 MHz, CDCl₃) δ −74.1. HRMS (TOF ESI+) m/z calculated for $C_{14}H_{15}NF_3O_3S$ [M+H]⁺: 334.0725, found 334.0721.

4-(1-Cyanocyclopentyl)-2-methylphenyl trifluoromethanesulfonate [S35]. To a 50 mL flask added 2-(4-methoxy-3-methylphenyl)acetonitrile 1.0 g (6.2 mmol, 1.0 equiv.), dissolved in 10 mL anhydrous DMF. 392 mg (95% purity, 15.5 mmol, 2.5 equiv.) of NaH was added in portions at 0° C. and the reaction was allowed to stir for 1 hour at 0° C. 0.74 mL (6.2 mmol, 1.0 equiv.) of 1,4-dibromobutane was added dropwise at 0° C. and the reaction was allowed to stir overnight at room temperature. The reaction was quenched carefully with ~10 mL water and extracted with 30 mL EtOAc three times, washed with 50 mL brine, dried with MgSO₄, filtered, and concentrated. Flash column chromatography on silica (50 mm fritted glass column, 200 mL SiO₂) using 5% EtOAc/hexanes→10% EtOAc/hexanes as eluent gave 1.2217 g (5.67 mmol) of 1-(4-methoxy-3-methylphenyl)cyclopentane-1-carbonitrile in 91% yield. ¹H-NMR (500 MHz, CDCl₃) δ 7.23 (dd, J=8.4, 2.6 Hz, 1H), 7.20-7.19 (m, 1H), 6.80 (d, J=8.4 Hz, 1H), 3.83 (s, 3H), 2.46-2.41 (m, 2H), 2.23 (s, 3H), 2.07-1.90 (m, 6H).

The product was dissolved in 20 mL dry DCM, followed by 28.4 mL BBr3 solution (1M in DCM, 5 equiv.) at −78° C. The reaction was stirred at −78° C. for 30 minutes then allowed to stir at room temperature for overnight. The reaction was quenched with NaHCO₃, separated, the organic layer washed with brine and dried with Na₂SO₄. Flash column chromatography on silica (50 mm fritted glass column, 200 mL SiO₂) using 10% EtOAc/hexanes→20% EtOAc/hexanes as eluent gave 890.7 mg (4.43 mmol) of the free phenol in 78% yield. ¹H-NMR (500 MHz, CDCl₃) δ 7.20 (d, J=2.5 Hz, 1H), 7.14 (dd, J=8.3, 2.5 Hz, 1H), 6.76 (d, J=8.3 Hz, 1H), 4.68 (br. s, 1H), 2.44 (dq, J=10.0, 5.8, 5.0 Hz, 2H), 2.26 (s, 3H), 2.08-1.87 (m, 6H).

The free phenol was dissolved in 25 mL anhydrous DCM, treated with 0.89 mL (5.32 mmol, 1.2 equiv.) Tf₂O and 0.54 mL (6.65 mmol, 1.5 equiv.) pyridine at 0° C. then stirred at room temperature overnight. The reaction was quenched with ~10 mL water. 15 mL DCM was used to extract the reaction 3 times and the combined organic layer was dried with Na₂SO₄ and concentrated. Flash column chromatography on silica (50 mm fritted glass column, 200 mL SiO₂) using 5% EtOAc/hexanes→10% EtOAc/hexanes as eluent gave 1.294 g (3.88 mmol) of pure product as a colorless oil (88% yield).

¹H-NMR (500 MHz, CDCl₃) δ 7.41 (d, J=2.5 Hz, 1H), 7.33 (dd, J=8.7, 2.5 Hz, 1H), 7.24 (d, J=8.6 Hz, 1H), 2.51-2.46 (m, 2H), 2.40 (s, 3H), 2.09-1.92 (m, 6H). ¹³C-

1-(2,2-Difluorobenzo[d][1,3]dioxol-5-yl)cyclopentane-1-carbonitrile [S36]. In a flamed dried 50 mL flask, 591.4 mg (3.0 mmol) of 2-(2,2-difluorobenzo[d][1,3]dioxol-5-yl)acetonitrile was dissolved in 6 mL anhydrous DMF. 344.8 mg (95% purity, 13.7 mmol, 2.5 equiv.) of NaH was added in portions at 0° C. and the reaction was allowed to stir for 1 hour at 0° C. 647.7 mg (0.36 mL, 3.0 mmol, 1.0 equiv.) of 1,4-dibromobutane was added dropwise at 0° C. and the reaction was allowed to stir overnight at room temperature. The reaction was quenched carefully with ~10 mL water and extracted with 30 mL EtOAc three times. The combined organic layer was washed with 50 mL brine, dried with MgSO₄, filtered, and concentrated. Flash column chromatography on silica (50 mm fritted glass column, 200 mL SiO₂) using 5% EtOAc/hexanes→10% EtOAc/hexanes as eluent gave 396.9 mg (1.58 mmol) of pure product as a colorless oil (53% yield).

¹H-NMR (500 MHz, CDCl₃) δ 7.20 (dd, J=8.4, 2.0 Hz, 1H), 7.16 (d, J=1.9 Hz, 1H), 7.05 (d, J=8.4 Hz, 1H), 2.54-2.48 (m, 2H), 2.09-1.91 (m, 6H). ¹³C-NMR (126 MHz, CDCl₃) δ 144.3, 143.3, 136.2, 131.8 (t, J=256.1 Hz), 123.9, 121.6, 109.6, 107.8, 47.7, 40.7, 24.2. ¹⁹F-NMR (470 MHz, CDCl₃) δ −49.9. HRMS (TOF ESI+) m/z calculated for $C_{13}H_{11}NO_2F_2$ [M]⁺: 251.0758, found 251.0758.

C—H Oxidation of Substrates and Products Characterization (Table 5)

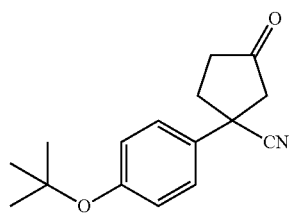 [SMILES: CC(C)(C)Oc1ccc(C2(C#N)CCC(=O)C2)cc1]

1-(4-(tert-Butoxy)phenyl)-3-oxocyclopentane-1-carbonitrile [33]. The reaction was run with General Method A: Single Catalyst Addition Protocol: 1-(4-(tert-butoxy)phenyl)cyclopentane-1-carbonitrile S29 (73.0 mg, 0.300 mmol, 1.0 equiv), (R,R)—Mn(CF₃-PDP) (40.7 mg, 0.030 mmol, 10 mol %), ClCH₂CO₂H (425 mg, 4.5 mmol, 15.0 equiv.), 50% wt. H₂O₂ (204 mg, 3.0 mmol, 10.0 equiv.), 4:1 MeCN:DCM (0.6 mL in 40 mL vial, 3.75 mL with oxidant). The reaction was run at 0° C. with ice bath. The reaction was worked up with 9 mL saturated NaHCO₃ and DCM as described in General method A. Flash column chromatography on silica (35 mm fritted glass column, 150 mL SiO$_2$) using 20% acetone/hexanes→30% acetone/hexanes as eluent. All fractions are collected and analyzed by ¹H NMR with nitrobenzene as internal standard.

Result: (10.6 mg, 0.043 mmol, 14.5% rsm).

TABLE 5

Remote methylene oxidation of aromatic containing compounds with multiple substitutions of varied electronic and steric properties.

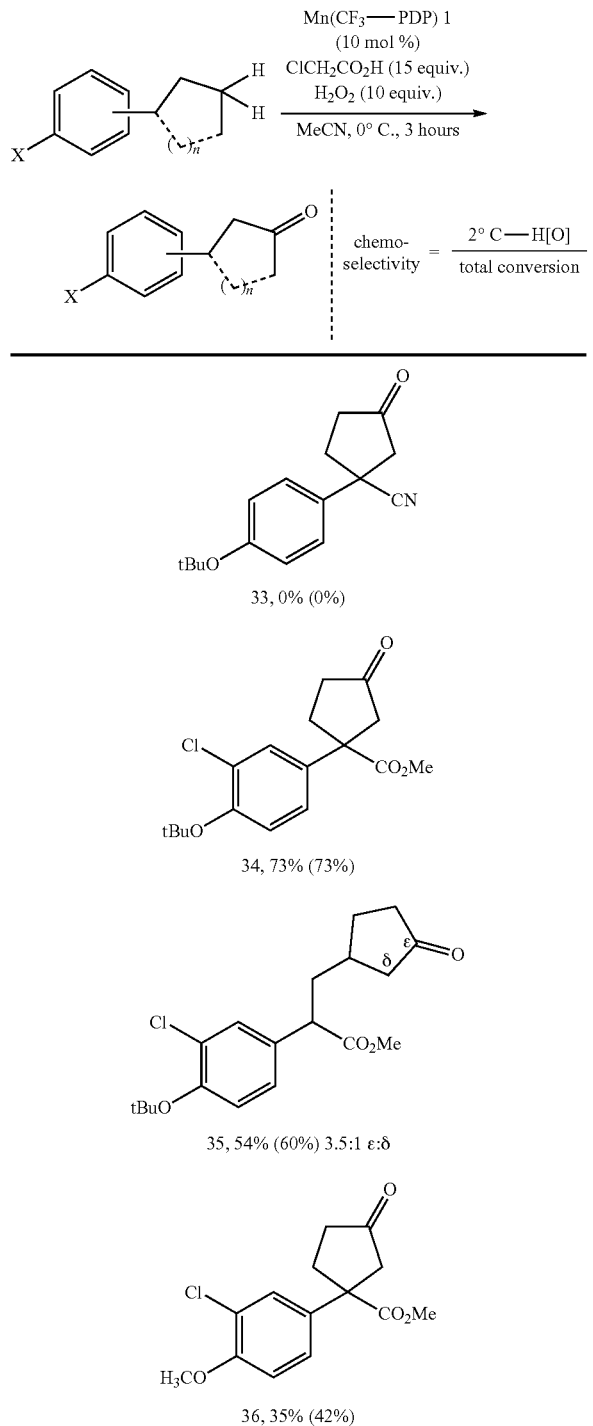

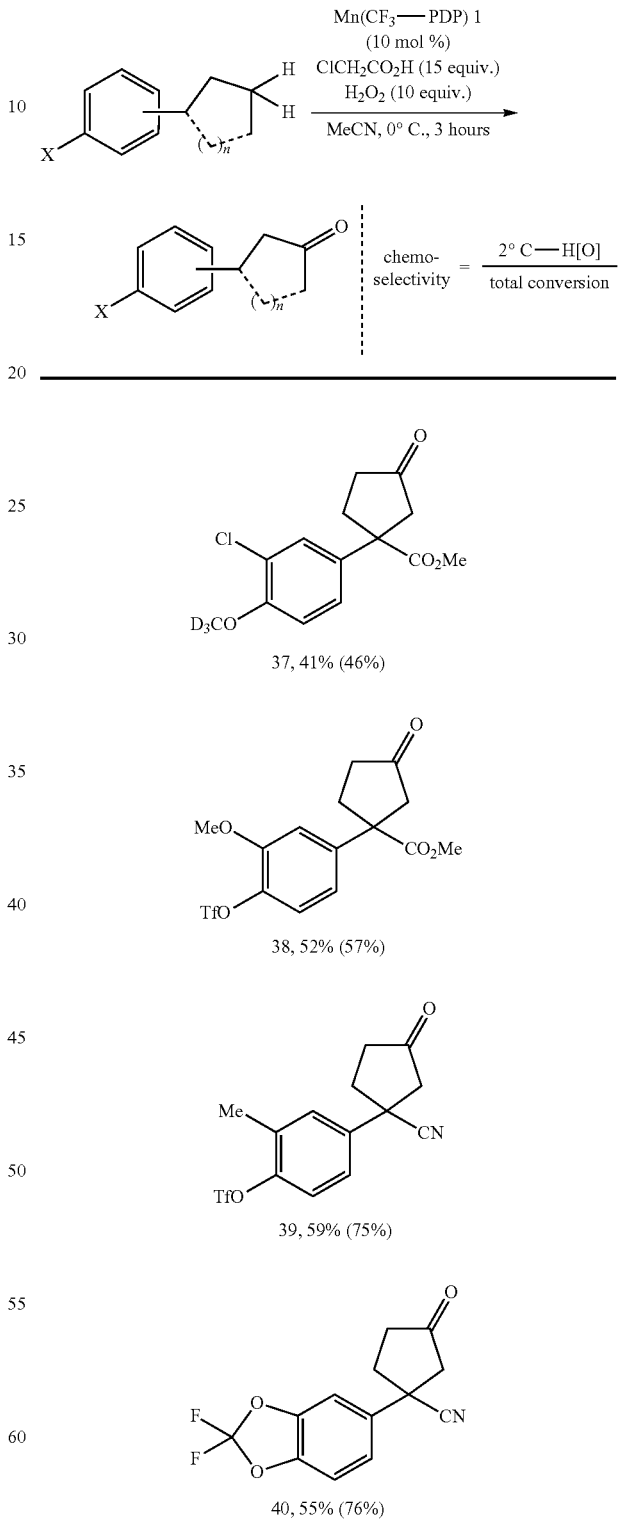

Method A: single catalyst addition protocol is used. Isolated yields are average of three runs.

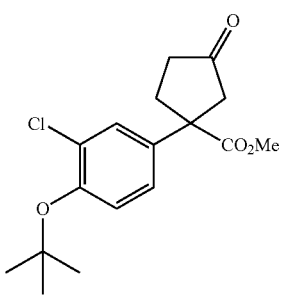 [SMILES: COC(=O)C1(c2ccc(OC(C)(C)C)c(Cl)c2)CCC(=O)C1]

Methyl 1-(4-(tert-butoxy)-3-chlorophenyl)-3-oxocyclopentane-1-carboxylate [34]. The reaction was run with General Method A: Single Catalyst Addition Protocol. Methyl 1-(4-(tert-butoxy)-3-chlorophenyl)cyclopentane-1-carboxylate S30 (93.2 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), MeCN (0.6 mL in 40 mL vial, 3.75 mL with oxidant). The reaction was run at 0° C. with ice bath. The reaction was worked up with 9 mL saturated NaHCO$_3$ and DCM as described in the general method A. Flash column chromatography on silica (35 mm fritted glass column, 150 mL SiO$_2$) using 10% acetone/hexanes→20% acetone/hexanes→30% acetone/hexanes as eluent afforded product as a clear oil. Run 1: (71.9 mg, 0.221 mmol, 73.8% yield), 0% rsm. Run 2: (69.0 mg, 0.212 mmol, 70.8% yield), 0% rsm. Run 3: (71.7 mg, 0.221 mmol, 73.6% yield), 0% rsm. Average: 72.7% yield±1.7%, 0% rsm.

$^1$H-NMR (500 MHz, CDCl$_3$) δ 7.34 (d, J=2.3 Hz, 1H), 7.11 (dd, J=8.5, 2.4 Hz, 1H), 7.07 (d, J=8.5 Hz, 1H), 3.66 (s, 3H), 3.21 (d, J=17.9 Hz, 1H), 2.93 (dddd, J=11.4, 7.7, 4.1, 1.9 Hz, 1H), 2.56 (d, J=18.0 Hz, 1H), 2.36-2.27 (m, 3H), 1.40 (s, 9H). $^{13}$C-NMR (126 MHz, CDCl$_3$) 215.1, 174.5, 151.7, 136.7, 129.4, 128.6, 125.4, 124.3, 81.6, 54.4, 53.1, 48.3, 37.1, 33.0, 29.0. HRMS (TOF ESI+) m/z calculated for C$_{17}$H$_{22}$ClO$_4$ [M+H]$^+$: 325.1207, found 325.1204.

hexanes→15% ethyl acetate/hexanes→25% ethyl acetate/hexanes as eluent afforded clean ε-ketone (35a) and δ-ketone (35b) with small impurity as clear oil.

The position of oxidation was assigned by analogy with all other compounds examined where oxidation is preferred at the sites most remote from electron-withdrawing groups (ester in this case). The assignment can be further supported by the relative $^1$H chemical shift of the benzylic proton where the proton in δ-ketone (35b) is more downfield than the proton in ε-ketone (35a).

Run 1: (44.1 mg, 0.125 mmol, 41.7% yield of ε-ketone 35a), (13.1 mg, 0.037 mmol, 12.4% yield of δ-ketone 35b), (54.1% overall yield, 3.36:1 ε:δ ratio), <10% rsm. Run 2: (43.7 mg, 0.124 mmol, 41.3% yield of ε-ketone 35a), (12.1 mg, 0.034 mmol, 11.4% yield of δ-ketone 35b), (52.7% overall yield, 3.62:1 ε:δ ratio), <10% rsm. Run 3: (45.2 mg, 0.128 mmol, 42.7% yield of ε-ketone 35a), (13.1 mg, 0.037 mmol, 12.4% yield of δ-ketone 35b), (55.1% overall yield, 3.44:1 ε:δ ratio), <10% rsm. Average: 41.9% yield±0.7% of ε-ketone, 12.1% yield±0.6% of δ-ketone, 54.0% overall yield with 3.5:1 ε:δ ratio, <10% rsm. ε-ketone (35a) was isolated as a mixture of diastereomers with ~1:1 ratio.

$^1$H-NMR (500 MHz, CDCl$_3$) δ 7.33 (t, J=2.3 Hz, 1H), 7.09 (app. ddd, J=8.1, 4.4, 2.1 Hz, 1H), 7.05 (d, J=8.3 Hz, 1H), 3.68 (s, 3H), 3.54 (app. td, J=7.7, 4.2 Hz, 1H), 2.39-1.99 (m, 6H), 1.96-1.75 (m, 2H), 1.57-1.48 (m, 1H), 1.41 (s, 9H). $^{13}$C-NMR (126 MHz, CDCl$_3$) 218.6 & 218.5, 174.0 & 173.9, 151.6, 134.33 & 134.25, 129.7 & 129.6, 129.5 & 129.4, 126.63 & 126.57, 124.7 & 124.6, 81.5, 52.42 & 52.40, 49.3 & 49.2, 45.1 & 44.8, 39.5 & 39.4, 38.6 & 38.5, 35.3 & 35.2, 29.7 & 29.5, 29.1. HRMS (TOF ESI+) m/z calculated for C$_{19}$H$_{25}$ClO$_4$Na [M+Na]$^+$: 375.1339, found 375.1330.

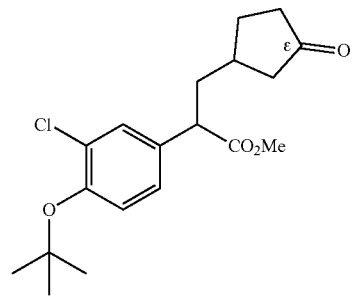 [SMILES: COC(=O)C(CC1CCC(=O)C1)c1ccc(OC(C)(C)C)c(Cl)c1]

Methyl 2-(4-(tert-butoxy)-3-chlorophenyl)-3-(3-oxocyclopentyl)propanoate [35a]. The reaction was run with General Method A: Single Catalyst Addition Protocol. Methyl 2-(4-(tert-butoxy)-3-chlorophenyl)-3-cyclopentylpropanoate S31 (101.6 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), MeCN (0.6 mL in 40 mL vial, 3.75 mL with oxidant). The reaction was run at 0° C. with ice bath. The reaction was worked up with 9 mL saturated NaHCO$_3$ and DCM as described in the general method A. Flash column chromatography on silica (35 mm fritted glass column, 100 mL SiO$_2$) using 5% ethyl acetate/

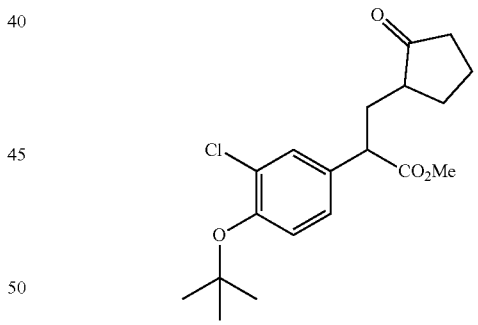

Methyl 2-(4-(tert-butoxy)-3-chlorophenyl)-3-(2-oxocyclopentyl)propanoate [35b]. δ-ketone (35b) was isolated as a mixture of diastereomers with ~1:1 ratio and contain a minor impurity. $^1$H-NMR (500 MHz, CDCl$_3$) δ 7.33 (app. dd, J=9.8, 2.2 Hz, 1H), 7.12-7.09 (m, 1H), 7.05-7.03 (m, 1H), 3.66 (s, 3H), 3.71-3.65 (m, 1H), 2.32-1.85 (m, 6H), 1.76-1.66 (m, 2H), 1.54-1.44 (m, 1H), 1.40 (s, 9H). $^{13}$C-NMR (126 MHz, CDCl$_3$) 220.3 & 220.2, 173.8 & 173.7, 151.44 & 151.36, 134.4 & 133.9, 129.79 & 129.76, 129.2, 126.8 & 126.5, 124.51 & 124.48, 81.3, 52.19 & 52.16, 48.6 & 48.3, 46.9 & 46.6, 37.89 & 37.87, 33.7 & 33.5, 30.2 & 29.8, 28.9, 20.64 & 20.61. HRMS (TOF ESI+) m/z calculated for C$_{19}$H$_{25}$ClO$_4$Na [M+Na]$^+$: 375.1339, found 375.1337.

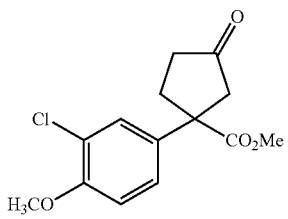

Methyl 1-(3-chloro-4-methoxyphenyl)-3-oxocyclopentane-1-carboxylate [36]. The reaction was run with General Method A: Single Catalyst Addition Protocol: methyl 1-(3-chloro-4-methoxyphenyl)cyclopentane-1-carboxylate S32 (80.6 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), MeCN (0.6 mL in 40 mL vial, 3.75 mL with oxidant). The reaction was run at 0° C. with ice bath. The reaction was worked up with 9 mL saturated NaHCO$_3$ and DCM as described in General Method A. Flash column chromatography on silica (35 mm fritted glass column, 150 mL SiO$_2$) using 20% acetone/hexanes→40% acetone/hexanes as eluent to obtain pure product as a white solid. Run 1: (32.8 mg, 0.116 mmol, 38.7% yield), (11.5 mg, 0.043 mmol, 14.3% rsm). Run 2: (27.0 mg, 0.096 mmol, 31.8% yield), (14.6 mg, 0.054 mmol, 18.1% rsm). Run 3: (29.4 mg, 0.104 mmol, 34.7% yield), (13.8 mg, 0.051 mmol, 17.1% rsm). Average: 35.1% yield±3.5%, 16.5% rsm±2.0%.

$^1$H-NMR (500 MHz, CDCl$_3$) δ 7.36 (d, J=2.4 Hz, 1H), 7.19 (dd, J=8.6, 2.4 Hz, 1H), 6.90 (d, J=8.6 Hz, 1H), 3.89 (s, 3H), 3.66 (s, 3H), 3.21 (dd, J=17.9, 2.0 Hz, 1H), 2.96-2.91 (m, 1H), 2.57 (d, J=17.9 Hz, 1H), 2.36-2.26 (m, 3H). $^{13}$C-NMR (126 MHz, CDCl$_3$) δ 215.1, 174.6, 154.6, 134.2, 128.7, 126.0, 122.9, 112.1, 56.3, 54.2, 53.1, 48.3, 37.1, 33.0. HRMS (TOF ESI+) m/z calculated for C$_{14}$H$_{16}$O$_4$Cl [M+H]$^+$: 283.0737, found 283.0733.

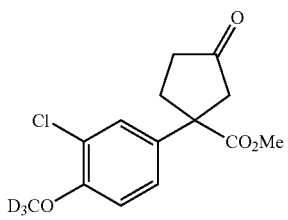 [SMILES: COC(=O)C1(c2ccc(OC)c(Cl)c2)CCC(=O)C1]

Methyl 1-(3-chloro-4-(methoxy-d$_3$)phenyl)-3-oxocyclopentane-1-carboxylate [37]. The reaction was run with General Method A: Single Catalyst Addition Protocol: methyl 1-(3-chloro-4-(methoxy-d$_3$)phenyl)cyclopentane-1-carboxylate S33 (81.5 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), MeCN (0.6 mL in 40 mL vial, 3.75 mL with oxidant). The reaction was run at 0° C. with ice bath. The reaction was worked up with 9 mL saturated NaHCO$_3$ and DCM as described in General Method A. Flash column chromatography on silica (35 mm fritted glass column, 150 mL SiO$_2$) using 20% acetone/hexanes→40% acetone/hexanes as eluent to obtain pure product as a white solid. Run 1: (33.4 mg, 0.117 mmol, 39.0% yield), (10.1 mg, 0.037 mmol, 12.4% rsm). Run 2: (34.6 mg, 0.121 mmol, 40.4% yield), (9.5 mg, 0.035 mmol, 11.7% rsm). Run 3: (36.3 mg, 0.127 mmol, 42.3% yield), (9.9 mg, 0.036 mmol, 12.1% rsm). Average: 40.6% yield±1.7%, 12.1% rsm±0.4%.

$^1$H-NMR (500 MHz, CDCl$_3$) δ 7.35 (d, J=2.4 Hz, 1H), 7.18 (dd, J=8.6, 2.4 Hz, 1H), 6.89 (d, J=8.6 Hz, 1H), 3.65 (s, 3H), 3.20 (dd, J=17.9, 2.0 Hz, 1H), 2.95-2.90 (m, 1H), 2.56 (d, J=17.9 Hz, 1H), 2.35-2.27 (m, 3H). $^{13}$C-NMR (126 MHz, CDCl$_3$) δ 215.0, 174.61, 154.5, 134.2, 128.6, 126.0, 122.8, 112.1, 55.84-55.18 (m, 1 carbon), 54.18, 53.11, 48.28, 37.04, 32.99. HRMS (TOF ESI+) m/z calculated for C$_{14}$H$_{13}$D$_3$O$_4$Cl [M+H]$^+$: 286.0925, found 286.0924.

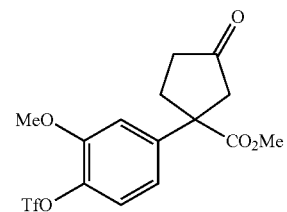 [SMILES: COC(=O)C1(c2ccc(OS(=O)(=O)C(F)(F)F)c(OC)c2)CCC(=O)C1]

Methyl 1-(3-methoxy-4-(((trifluoromethyl)sulfonyl)oxy)phenyl)-3-oxocyclopentane-1-carboxylate [38]. The reaction was run with General Method A: Single Catalyst Addition Protocol. Methyl 1-(3-methoxy-4-(((trifluoromethyl)sulfonyl)oxy)phenyl)cyclopentane-1-carboxylate S34 (114.7 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), MeCN (0.6 mL in 40 mL vial, 3.75 mL with oxidant). The reaction was run at 0° C. with ice bath. The reaction was worked up with 9 mL saturated NaHCO$_3$ and DCM as described in General Method A. Flash column chromatography on silica (35 mm fritted glass column, 150 mL SiO$_2$) using 15% ethyl acetate/hexanes→35% ethyl acetate/hexanes→60% ethyl acetate/hexanes as eluent afforded product as a white solid. Run 1: (64.6 mg, 0.163 mmol, 54.3% yield), (9.3 mg, 0.024 mmol, 8.1% rsm). Run 2: (59.6 mg, 0.150 mmol, 50.1% yield), (13.3 mg, 0.035 mmol, 11.6% rsm). Run 3: (61.8 mg, 0.156 mmol, 52.0% yield), (8.6 mg, 0.022 mmol, 7.5% rsm). Average: 52.1% yield±2.1%, 9.1% rsm±2.1%.

$^1$H-NMR (500 MHz, methylene chloride-d$_2$) δ 7.22 (d, J=8.5 Hz, 1H), 7.02 (d, J=2.2 Hz, 1H), 6.98 (dd, J=8.5, 2.2 Hz, 1H), 3.93 (s, 3H), 3.66 (s, 3H), 3.23 (dd, J=17.7, 2.1 Hz, 1H), 3.02-2.93 (m, 1H), 2.57 (d, J=17.8 Hz, 1H), 2.39-2.30 (m, 3H). $^{13}$C-NMR (126 MHz, methylene chloride-d$_2$) 214.6, 174.6, 151.9, 143.7, 138.5, 122.9, 119.7, 119.3 (q, J=320.4 Hz), 112.4, 56.9, 55.5, 53.6, 48.7, 37.4, 33.5. $^{19}$F-NMR (471 MHz, methylene chloride-d$_2$) δ −74.3. HRMS (TOF ESI+) m/z calculated for C$_{15}$H$_{15}$O$_7$F$_3$SNa [M+Na]$^+$: 419.0388, found 419.0386.

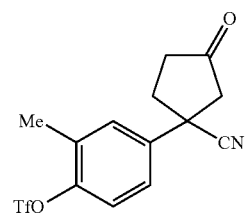 [SMILES: Cc1cc(C2(C#N)CCC(=O)C2)ccc1OS(=O)(=O)C(F)(F)F]

4-(1-Cyano-3-oxocyclopentyl)-2-methylphenyl trifluoromethanesulfonate [39]. The reaction was run with General Method A: Single Catalyst Addition Protocol. 4-(1-cyanocyclopentyl)-2-methylphenyl trifluoromethanesulfonate S35 (100.0 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), H$_2$O$_2$ (204 mg, 3.0 mmol, 10.0 equiv.), MeCN (0.6 mL in 40 mL vial, 3.75 mL with oxidant). The reaction was run at 0° C. with ice bath. The reaction was worked up with 9 mL saturated NaHCO$_3$ and DCM as described in General Method A. Flash column chromatography on silica (35 mm fritted glass column, 150 mL SiO$_2$) using 10% acetone/hexanes→20% acetone/hexanes→40% acetone/hexanes as eluent afforded product as a clear oil. Run 1: (61.3 mg, 0.176 mmol, 58.8% yield), (21.9 mg, 0.066 mmol, 21.9% rsm). Run 2: (61.4 mg, 0.177 mmol, 59.0% yield), (23.1 mg, 0.069 mmol, 23.1% rsm). Run 3: (60.2 mg, 0.173 mmol, 57.8% yield), (21.9 mg, 0.066 mmol, 21.9% rsm). Average: 58.5% yield±0.6%, 22.3% rsm±0.7%.

$^1$H-NMR (500 MHz, CDCl$_3$) δ 7.42 (d, J=2.3 Hz, 1H), 7.34 (dd, J=8.7, 2.4 Hz, 1H), 7.32 (d, J=8.7 Hz, 1H), 3.07 (d, J=18.1 Hz, 1H), 2.85 (dddd, J=12.9, 8.5, 3.8, 1.9 Hz, 1H), 2.76 (d, J=18.2 Hz, 1H), 2.73-2.66 (m, 1H), 2.55 (dddt, J=18.9, 8.2, 3.8, 1.1 Hz, 1H), 2.43 (s, 3H), 2.46-2.40 (m, 1H). $^{13}$C-NMR (126 MHz, CDCl$_3$) 211.3, 148.4, 137.7, 132.5, 130.0, 125.2, 122.4, 122.0, 118.66 (q, J=320.1 Hz), 49.9, 43.9, 36.8, 36.4, 16.8. $^{19}$F-NMR (471 MHz, CDCl$_3$) δ −73.66. HRMS (TOF ESI+) m/z calculated for C$_{14}$H$_{12}$NO$_4$F$_3$SNa [M+Na]$^+$: 370.0337, found 370.0350.

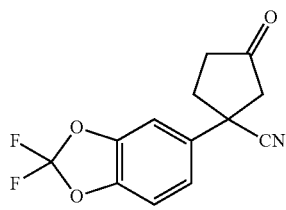 [SMILES: N#CC1(c2ccc3c(c2)OC(F)(F)O3)CCC(=O)C1]

1-(2,2-Difluorobenzo[d][1,3]dioxol-5-yl)-3-oxocyclopentane-1-carbonitrile [40]. The reaction was run with General Method A: Single Catalyst Addition Protocol. 1-(2,2-difluorobenzo[d][1,3]dioxol-5-yl)cyclopentane-1-carbonitrile S36 (75.4 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), MeCN (0.6 mL in 40 mL vial, 3.75 mL with oxidant). The reaction was run at 0° C. with ice bath. The reaction was worked up with 9 mL saturated NaHCO$_3$ and DCM as described in General Method A. Flash column chromatography on silica (35 mm fritted glass column, 150 mL SiO$_2$) using 10% ethyl acetate/hexanes→25% ethyl acetate/hexanes→50% ethyl acetate/hexanes as eluent afforded product as a clear oil. Run 1: (43.6 mg, 0.164 mmol, 54.8% yield), (19.1 mg, 0.076 mmol, 25.3% rsm). Run 2: (45.8 mg, 0.173 mmol, 57.6% yield), (19.0 mg, 0.076 mmol, 25.2% rsm). Run 3: (42.2 mg, 0.159 mmol, 53.0% yield), (23.5 mg, 0.094 mmol, 31.2% rsm). Average: 55.1% yield±2.3%, 27.2% rsm±3.4%.

$^1$H-NMR (500 MHz, CDCl$_3$) δ 7.19-7.17 (m, 2H), 7.13-7.12 (m, 1H), 3.07 (d, J=18.0 Hz, 1H), 2.85 (dddd, J=12.5, 8.5, 3.9, 1.9 Hz, 1H), 2.73 (d, J=18.1 Hz, 1H), 2.73-2.65 (m, 1H), 2.54 (ddd, J=19.0, 8.2, 3.9 Hz, 1H), 2.41 (ddd, J=13.0, 10.1, 8.2 Hz, 1H). $^{13}$C-NMR (126 MHz, CDCl$_3$) 211.1, 144.7, 144.0, 133.8, 131.8 (t, J=257.4 Hz), 122.1, 121.5, 110.2, 107.7, 50.1, 44.1, 36.7, 36.5. $^{19}$F-NMR (471 MHz, CDCl$_3$) δ −49.8. HRMS (TOF ESI+) m/z calculated for C$_{13}$H$_9$NO$_3$F$_2$ [M]$^+$: 265.0550, found 265.0553.

Example 6

Remote Methylene Oxidation of Aromatic Substrates with Heteroaromatic or 3° Amine Substituents Preparation of Substrates and Compounds Characterization (Table 6)

General Procedure for Reductive Amination: To a round bottom flask equipped with a magnetic stir bar was added the corresponding amine (1.0 equiv.), 1,2-dichloroethane (0.1 M), the corresponding aldehyde (1.5 equiv.), and AcOH (1% v/v). After 30 minutes, NaBH(OAc)$_3$ (1.5 equiv.) was added in one portion and reaction solution was stirred overnight at room temperature. The reaction was quenched with saturated aqueous NaHCO$_3$ solution and extracted with CH$_2$Cl$_2$ 3 times. Combined organic layer was washed with saturated aqueous NaHCO$_3$ solution once and brine once, dried over anhydrous MgSO$_4$, filtered and concentrated under reduced pressure. The crude mixture was purified by flash column chromatography.

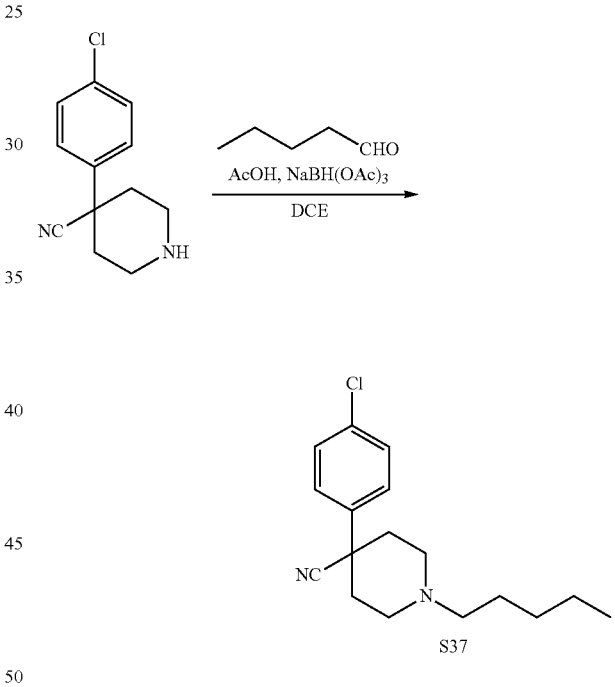

4-(4-Chlorophenyl)-1-pentylpiperidine-4-carbonitrile [S37]. According to general procedure for reductive amination, 4-(4-chlorophenyl)piperidine-4-carbonitrile (2.21 g, 10.0 mmol, 1.0 equiv.), valeraldehyde (1.6 mL, 15.0 mmol, 1.5 equiv.), acetic acid (1.0 mL, 1% v/v), and NaBH(OAc)$_3$ (3.18 g, 15.0 mmol, 1.5 equiv.) in DCE (100 mL, 0.1 M) were reacted. Flash column chromatography on silica eluting with 2% MeOH in CHCl$_3$ yielded S37 (1.57 g, 5.40 mmol, 54%) as a pale yellow oil.

$^1$H-NMR (500 MHz, CDCl$_3$) δ 7.44-7.41 (m, 2H), 7.37-7.34 (m, 2H), 3.04-3.00 (m, 2H), 2.47-2.40 (m, 4H), 2.11-2.02 (m, 4H), 1.54-1.48 (m, 2H), 1.37-1.25 (m, 4H), 0.90 (t, J=7.1 Hz, 3H). $^{13}$C-NMR (126 MHz, CDCl$_3$) δ 139.0, 134.1, 129.2, 127.2, 121.8, 58.7, 50.8, 42.6, 36.7, 29.9, 26.8, 22.7, 14.2. HRMS (TOF ESI+) m/z calculated for C$_{17}$H$_{24}$N$_2$Cl [M+H]$^+$: 291.1628, found 291.1624.

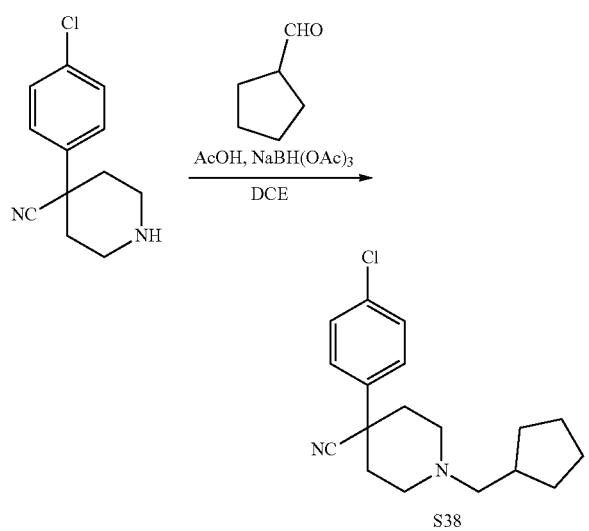

S38

4-(4-Chlorophenyl)-1-(cyclopentylmethyl)piperidine-4-carbonitrile [S38]. According to general procedure for reductive amination, 4-(4-chlorophenyl)piperidine-4-carbonitrile (1.10 g, 5.00 mmol, 1.0 equiv.), cyclopentanecarbaldehyde (540 mg, 5.50 mmol, 1.1 equiv.), acetic acid (0.5 mL, 1% v/v), and NaBH(OAc)$_3$ (1.17 g, 5.50 mmol, 1.1 equiv.) in DCE (100 mL, 0.1 M) were reacted. Flash column chromatography on silica eluting with 3% MeOH in CHCl$_3$ yielded compound S38 (615 mg, 2.03 mmol, 41%) as a pale-yellow solid.

$^1$H-NMR (500 MHz, CDCl$_3$) δ 7.47-7.41 (m, 2H), 7.40-7.33 (m, 2H), 3.08-2.95 (m, 2H), 2.53-2.39 (m, 2H), 2.36 (d, J=7.3 Hz, 2H), 2.14-2.00 (m, 5H), 1.82-1.70 (m, 2H), 1.67-1.47 (m, 4H), 1.25-1.15 (m, 2H). $^{13}$C-NMR (126 MHz, CDCl$_3$) δ 139.2, 134.1, 129.3, 127.2, 122.0, 64.5, 51.1, 42.7, 37.5, 36.8, 31.6, 25.3. HRMS (TOF ESI+) m/z calcd for C$_{18}$H$_{24}$N$_2$Cl [M+H]$^+$: 303.1628, found 303.1624.

TABLE 6

Remote methylene oxidation of aromatic substrates with heteroaromatic or 3° amine substituents.

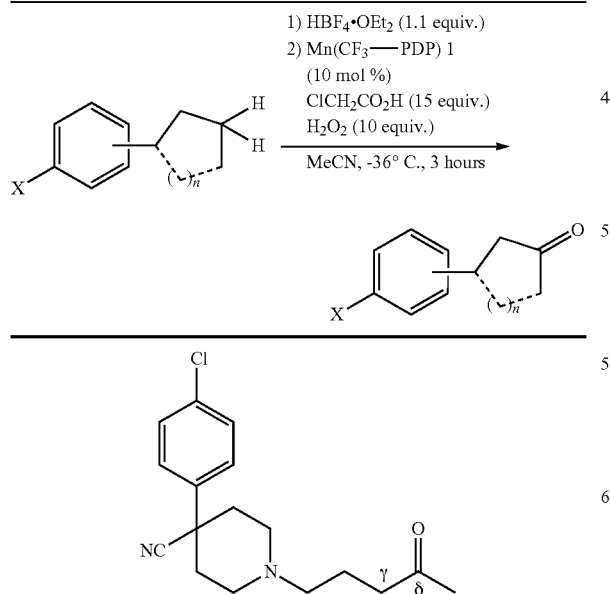

41, 67%$^a$ 13:1 δ:γ
No HBF$_4$: 0%

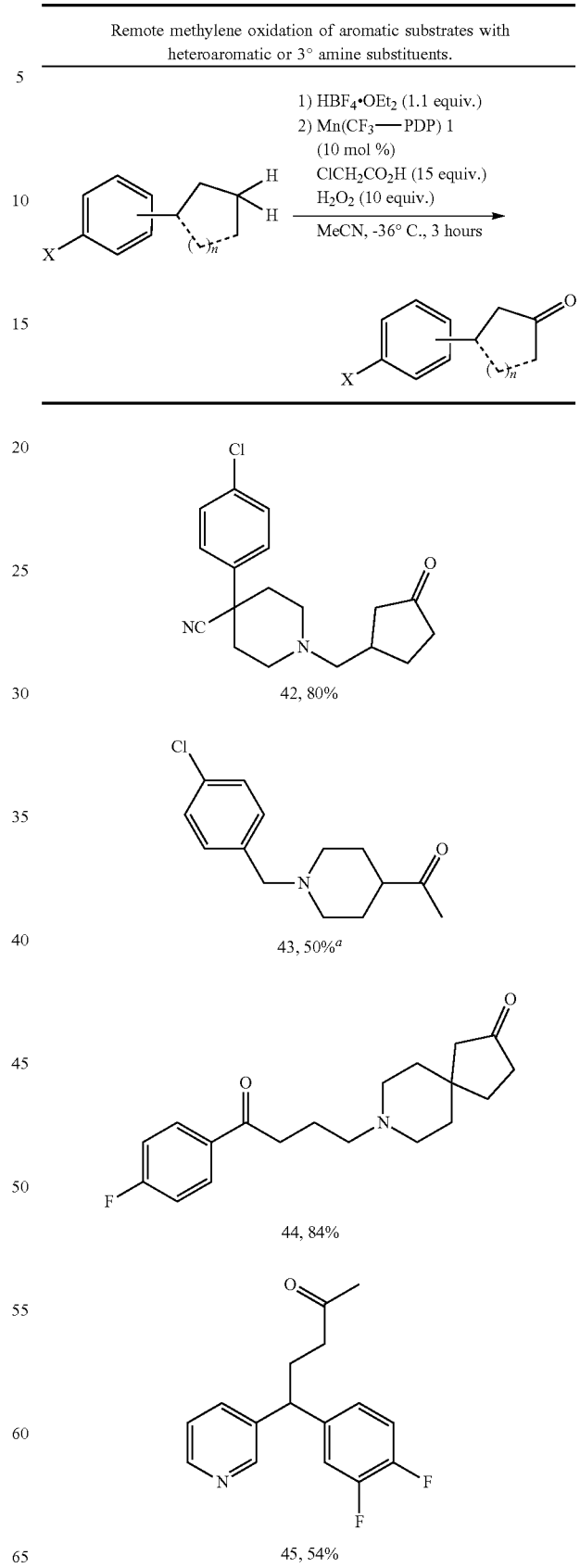

TABLE 6-continued

Remote methylene oxidation of aromatic substrates with heteroaromatic or 3° amine substituents.

42, 80%

43, 50%$^a$ 44, 84%

45, 54%

TABLE 6-continued

Remote methylene oxidation of aromatic substrates with heteroaromatic or 3° amine substituents.

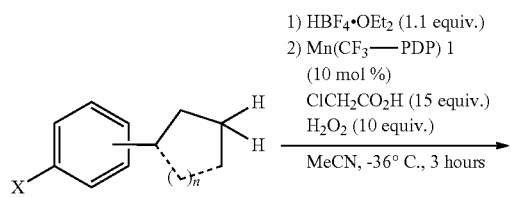

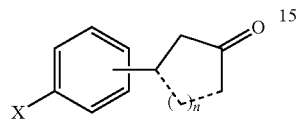

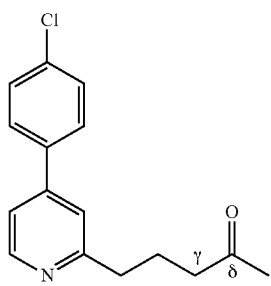

46, 78% 5:1 δ:γ

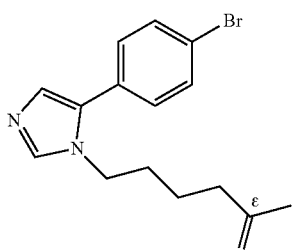

47, 50%[b] 2:1 ε:mixture
cat. 6[d]: <5%

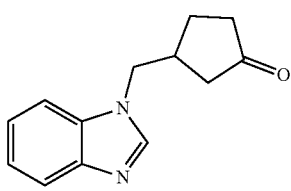

48, 55%[b,c] 10:1 δ:γ
cat. 6[d]: <5%

TABLE 6-continued

Remote methylene oxidation of aromatic substrates with heteroaromatic or 3° amine substituents.

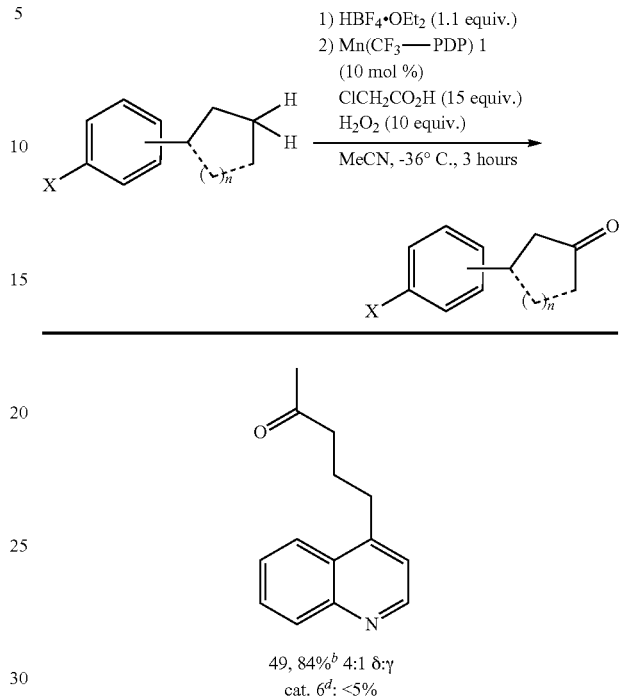

49, 84%[b] 4:1 δ:γ
cat. 6[d]: <5%

Unless otherwise noted, HBF$_4$.OEt$_2$ protection followed by slow catalyst addition protocol (method C) is used: substrate (0.3 mmol) and ClCH$_2$CO$_2$H (4.5 mmol) dissolved in MeCN (0.6 mL) maintained –36° C., a solution of H$_2$O$_2$ (50% wt., 3.0 mmol) in MeCN (3.75 mL, 0.8 M) and a solution of Mn(CF$_3$-PDP) 1 (0.030 mmol) in MeCN (0.375 mL, 0.08M) were simultaneously added via syringe pump over 3 hours. Isolated yields are average of three runs. [a]Method C used at 0° C. [b]Without HBF$_4$.OEt$_2$ resulted <5% oxidation product. Method B (iterative catalyst addition protocol) used. [d]25 mol % Fe(CF$_3$-PDP) 6 with slow addition protocol.

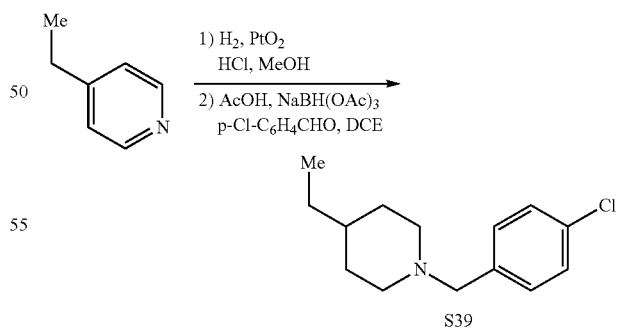

1-(4-Chlorobenzyl)-4-ethylpiperidine [S39]. A mixture of 4-ethylpyridine (1.14 mL, 10.0 mmol, 1.0 equiv.), platinum (IV) oxide (114 mg, 0.50 mmol, 0.05 equiv.) and HCl solution (2.75 ml, 11.0 mmol, 4 M in dioxane, 1.1 equiv.) in methanol (50 ml, 0.2 M) was hydrogenated at 100 psi overnight. The catalyst was removed by filtration through celite and the filtrate evaporated under reduced pressure. The residue was treated with saturated aqueous NaHCO$_3$ solution and extracted with CH$_2$Cl$_2$ twice. The combined organic extracts were washed with water and brine. Dried over anhydrous MgSO$_4$, filtered and concentrated under reduced pressure. The crude mixture was used in the next step without further purification. According to general procedure for reductive amination, the corresponding piperidine (10.0 mmol, 1.0 equiv.), p-chlorobenzaldehyde (2.11 g, 15.0 mmol, 1.5 equiv.), acetic acid (1.0 mL, 1% v/v), and NaBH(OAc)$_3$ (3.18 g, 15.0 mmol, 1.5 equiv.) were reacted. Flash column chromatography on silica eluting with 10% EtOAc/CHCl$_3$ yielded compound S39 (876 mg, 3.68 mmol, 37% over 2 steps) as a pale-yellow oil.

$^1$H-NMR (500 MHz, CDCl$_3$) δ 7.31-7.22 (m, 4H), 3.45 (s, 2H), 2.84 (dt, J=12.1, 3.2 Hz, 2H), 1.95-1.90 (m, 2H), 1.67-1.63 (m, 2H), 1.29-1.09 (m, 5H), 0.87 (t, J=7.4 Hz, 3H). $^{13}$C-NMR (126 MHz, CDCl$_3$) δ 137.5, 132.6, 130.6, 128.4, 62.9, 54.2, 37.6, 32.2, 29.4, 11.5. HRMS (TOF ESI+) m/z calcd for C$_{14}$H$_{21}$NCl [M+H]$^+$: 238.1363, found 238.1358.

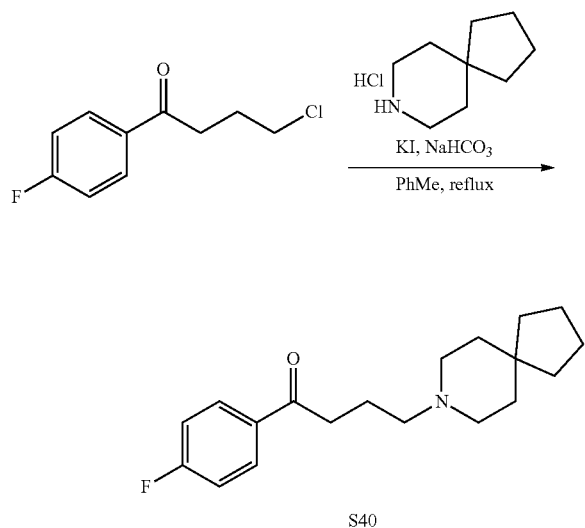

S40

1-(4-Fluorophenyl)-4-(8-azaspiro[4.5]decan-8-yl)butan-1-one [S40]. A stirring mixture of the 4-chloro-1-(4-fluorophenyl)butan-1-one (1.25 mL, 7.67 mmol, 1.0 equiv.), KI (128 mg, 0.77 mmol, 0.1 equiv.), NaHCO$_3$ (1.93 g, 23.0 mmol, 3.0 equiv.), and 8-azaspiro[4.5]decane hydrochloride (1.35 g, 7.67 mmol, 1.0 equiv.) in toluene (15 mL, 0.5 M) was heated to reflux for 30 h under N$_2$. After this period, the reaction mixture was cooled down, filtered through a celite plug, and the solvent was removed under reduced pressure. Flash column chromatography on silica eluting with 5% MeOH/CHCl$_3$ yielded compound S40 (1.44 g, 4.75 mmol, 62%) as a pale-yellow solid.

$^1$H-NMR (500 MHz, CDCl$_3$) δ 8.01-7.98 (m, 2H), 7.11 (t, J=8.6 Hz, 2H), 2.95 (t, J=7.2 Hz, 2H), 2.38-2.35 (m, 6H), 1.92 (p, J=7.2 Hz, 2H), 1.57-1.55 (m, 4H), 1.43-1.41 (m, 4H), 1.37-1.34 (m, 4H). $^{13}$C-NMR (126 MHz, CDCl$_3$) δ 198.7, 165.7 (d, J=254.2 Hz), 133.7 (d, J=2.9 Hz), 130.8 (d, J=9.4 Hz), 115.7 (d, J=21.9 Hz), 58.3, 51.5, 40.9, 37.7 (overlapped, 4 carbons), 36.5, 24.4, 22.0. $^{19}$F-NMR (470 MHz, CDCl$_3$) δ -106.2. HRMS (TOF ESI+) m/z calcd for C$_{19}$H$_{27}$NOF [M+H]$^+$: 304.2077, found 304.2082.

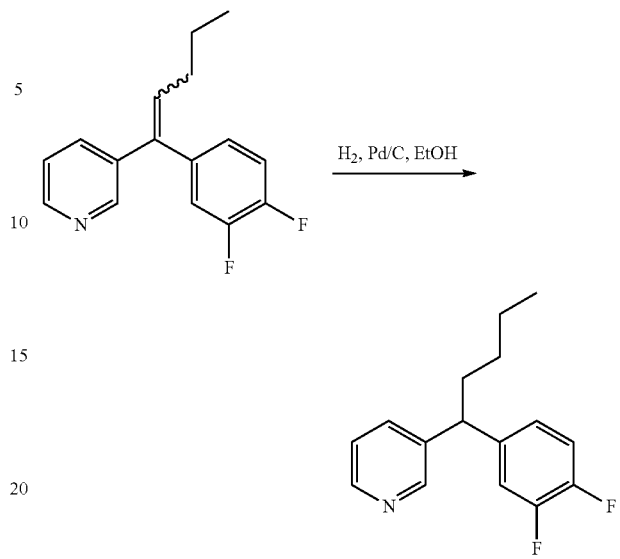

S41

3-(1-(3,4-Difluorophenyl)pentyl)pyridine [S41]. A suspension of (E/Z)-3-(1-(3,4-difluorophenyl)pent-1-en-1-yl)pyridine (857 mg, 3.31 mmol, 1.0 equiv.), 10% Pd/C (359 mg, 0.337 mmol, 0.1 equiv.) in EtOH (50 mL, 0.07 M) was stirred under a balloon pressure of hydrogen for 14 hours. The reaction mixture was filtered through Celite with ethyl acetate. The solvent was removed under reduced pressure and the residue was purified by flash column chromatography on silica eluting 20% ethyl acetate/hexanes as eluent to yield the desired product (560 mg, 2.14 mmol, 65%) as a colorless oil.

$^1$H-NMR (500 MHz, CDCl$_3$) δ 8.48 (d, J=2.3 Hz, 1H), 8.44 (dd, J=4.8, 1.6 Hz, 1H), 7.47 (dt, J=7.9, 2.0 Hz, 1H), 7.21 (dd, J=7.9, 4.8 Hz, 1H), 7.06 (dt, J=10.1, 8.3 Hz, 1H), 7.01 (ddd, J=11.5, 7.6, 2.3 Hz, 1H), 6.93 (ddt, J=8.1, 3.8, 1.7 Hz, 1H), 3.85 (t, J=7.8 Hz, 1H), 2.02-1.97 (m, 2H), 1.36-1.29 (m, 2H), 1.24-1.17 (m, 2H), 0.85 (t, J=7.3 Hz, 3H). $^{13}$C-NMR (126 MHz, CDCl$_3$) δ 150.7 (dd, J=170.5, 12.7 Hz), 149.6, 149.2 (dd, J=169.0, 13.4 Hz), 148.0, 141.2 (t, J=4.4 Hz), 139.8, 135.0, 123.8 (dd, J=6.1, 3.5 Hz), 123.7, 117.4 (d, J=17.0 Hz), 116.6 (d, J=17.2 Hz), 48.2, 35.2, 30.0, 22.6, 14.0. $^{19}$F-NMR (470 MHz, CDCl$_3$) δ -137.8 (m), -141.4 (m). HRMS (TOF ESI+) m/z calcd for C$_{16}$H$_{18}$NF$_2$ [M+H]$^+$: 262.1407, found 262.1409.

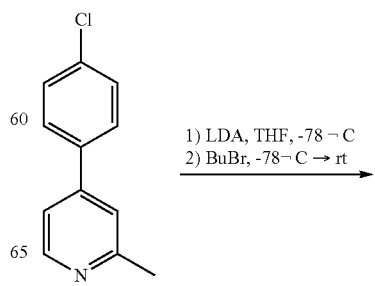

1) LDA, THF, -78 → C
2) BuBr, -78 → C → rt

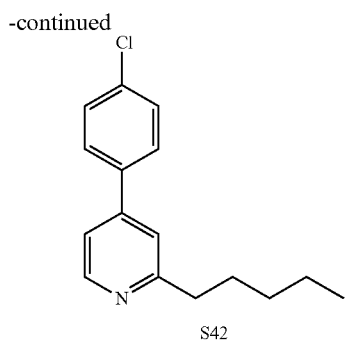

S42

4-(4-Chlorophenyl)-2-pentylpyridine [S42]. To a solution of diisopropylamine (298 mg, 2.95 mmol, 1.2 equiv.) in THF (1.5 mL, 2.0 M) at −78° C. was added n-butyllithium (1.8 mL, 2.88 mmol, 1.6 M in hexanes, 1.15 equiv.) dropwise. The reaction was stirred at −78° C. for 15 minutes, then warmed to room temperature for 5 minutes, then cooled back down to −78° C. To the LDA solution was added 4-(4-chlorophenyl)-2-methylpyridine (509 mg, 2.5 mmol, 1 equiv.) in THF (5 mL, 0.5 M) dropwise, and this mixture was allowed to react for 1 hour at −78° C. After this period, 1-bromobutane (383 mg, 2.8 mmol, 1.1 equiv.) was added dropwise at −78° C. and the reaction was allowed to warm to room temperature and stirred overnight. The reaction was quenched with water, and the aqueous layer was extracted with $CH_2Cl_2$ (3 times). The combined organics were dried over $Na_2SO_4$ and concentrated under reduced pressure. The residue was purified by flash column chromatography on silica eluting 5%→7.5%→15%→25% EtOAc:hexanes to yield the desired product (409 mg, 1.57 mmol, 63% yield) as a yellow oil.

$^1$H-NMR (500 MHz, CDCl$_3$) δ 8.57 (dd, J=5.2, 0.8 Hz, 1H), 7.60-7.52 (m, 2H), 7.50-7.40 (m, 2H), 7.33-7.30 (m, 1H), 7.27 (dd, J=5.2, 1.8 Hz, 1H), 2.84 (dd, J=9.7, 6.2 Hz, 2H), 1.82-1.76 (m, 2H), 1.40-1.37 (m, 4H), 0.91 (t, J=7.5 Hz, 3H). $^{13}$C-NMR (126 MHz, CDCl$_3$) δ 163.4, 149.8, 147.6, 137.1, 135.2, 129.4, 128.4, 120.6, 118.9, 38.7, 31.8, 29.8, 22.7, 14.2. HRMS (TOF ESI+) m/z calculated for C$_{16}$H$_{19}$NCl [M+H]$^+$: 260.1206, found 260.1206.

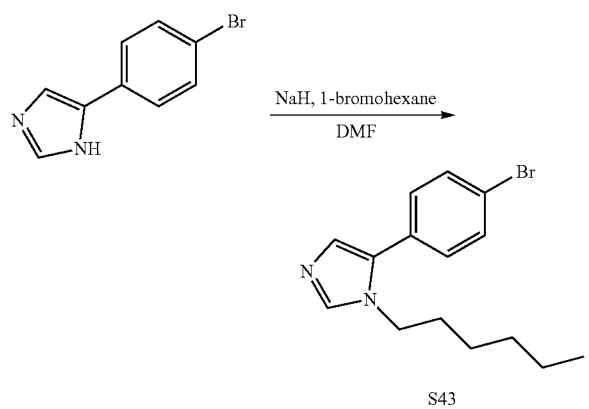

S43

5-(4-bromophenyl)-1-hexyl-1H-imidazole [S43]. In a flame dried 50 mL recovery flask was charged 5-(4-bromophenyl)-1H-imidazole (1.115 g, 5.0 mmol, 1.0 equiv.) and anhydrous DMF (10 mL, 0.5 M). NaH (95%, 158 mg, 6.25 mmol, 1.25 equiv.) was added portionwise at 0° C. followed by 1-bromohexane (772 µL, 5.5 mmol, 1.1 equiv.). The reaction was allowed to warm up to room temperature and stirred overnight. The reaction was quenched with sat. NH$_4$Cl, extracted with ethyl acetate 3 times. The combined organic layer was washed with water 3 times, brine and dried with Na$_2$SO$_4$. Flash column chromatography on silica (50 mm fritted glass column, 200 mL SiO$_2$) using 30% ethyl acetate/hexanes→50% ethyl acetate/hexanes→80% ethyl acetate/hexanes as eluent twice to get product co-eluded with a yellow impurity. The resulted compound was dissolved in a minimum amount of DCM, crashed out with pentane, and the solid was washed with pentane until no yellow color was observed in the eluent. The product was obtained as white fluffy solid (939 mg, 3.06 mmol, 61% yield). The purity of the compound is crucial to the oxidation.

$^1$H-NMR (500 MHz, CDCl$_3$) δ 7.65-7.62 (m, 2H), 7.50-7.47 (m, 3H), 7.19 (d, J=1.3 Hz, 1H), 3.94 (t, J=7.1 Hz, 2H), 1.81 (p, J=7.2 Hz, 2H), 1.35-1.28 (m, 6H), 0.89 (t, J=6.9 Hz, 3H). $^{13}$C-NMR (126 MHz, CDCl$_3$) δ 141.3, 137.6, 133.4, 131.8, 126.4, 120.4, 115.0, 47.5, 31.4, 31.1, 26.4, 22.6, 14.1. HRMS (TOF ESI+) m/z calcd for C$_{15}$H$_{20}$N$_2$Br [M+H]$^+$: 307.0810, found 307.0804.

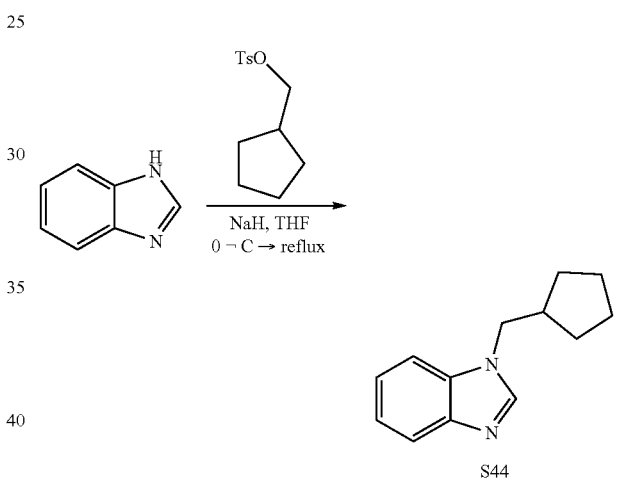

S44

1-(Cyclopentylmethyl)-1H-benzoldhmidazole [S44]. To a stirring solution of benzimidazole (1.0 g, 8.46 mmol, 1.0 equiv.) in THF (6 mL, 1.4 M) at 0° C. was added NaH 95% (214 mg, 8.46 mmol, 1.0 equiv.). After 30 min, the cyclopentylmethyl 4-methylbenzenesulfonate (2.59 g, 10.2 mmol, 1.2 equiv.) in THF (2 mL, 5.1 M) was added dropwise and the reaction mixture was warmed and stirred under reflux overnight. The reaction was quenched with the addition of H$_2$O. The layers were separated, and the aqueous layer was extracted with EtOAc (3 times). The combined organic layers were washed with brine (once), dried over MgSO$_4$, filtered, and concentrated under reduced pressure. The crude mixture was purified by flash column chromatography on silica eluting 30% EtOAc:CHCl$_3$ as eluent to yield the desired product (1.51 g, 7.54 mmol, 89%) as a white solid.

$^1$H-NMR (500 MHz, CDCl$_3$) δ 7.86 (s, 1H), 7.83-7.74 (m, 1H), 7.43-7.35 (m, 1H), 7.33-7.20 (m, 2H), 4.04 (d, J=7.5 Hz, 2H), 2.43 (hept, J=7.5 Hz, 1H), 1.74-1.60 (m, 4H), 1.60-1.49 (m, 2H), 1.30-1.19 (m, 2H). $^{13}$C-NMR (126 MHz, CDCl$_3$) δ 143.9, 143.1, 134.0, 122.8, 122.0, 120.4, 109.8, 49.9, 40.3, 30.6, 25.0. HRMS (TOF ESI+) m/z calcd for C$_{13}$H$_{17}$N$_2$ [M+H]$^+$: 201.1392, found 201.1397.

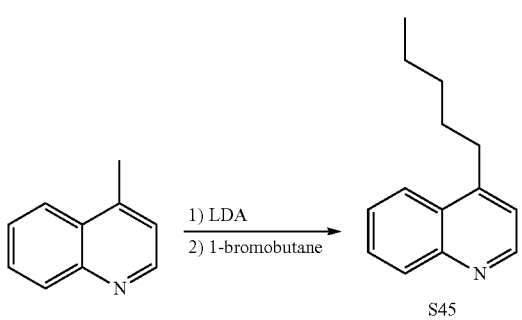

4-Pentylquinoline [S45]. In a 50 mL flame dried flask was added DIPEA (1.84 mL, 13.1 mmol) and 12 mL anhydrous THF. n-BuLi (1.6M, 7.8 mL, 12.5 mmol) was added dropwise at −78° C. and kept at −78° C. for 10 min. After stirred for another 30 min at room temperature, the LDA solution was cooled back to −78° C. and added dropwise into a solution of 4-methylquinoline (1.45 mL, 11 mmol) in 40 mL anhydrous THF at −78° C. After 2.5 h, 1-bromobutane (1.55 mL, 14.3 mmol, 1.3 equiv.) was added at −78° C. The reaction was allowed to stir at −78° C. for another 3 h before warmed up to room temperature and stirred overnight. The reaction was worked up with $NH_4Cl$ and extracted with ether 3 time. The combined organic layer was washed with brine and dried with $Na_2SO_4$. Flash column chromatography on silica (50 mm fritted glass column, 200 mL $SiO_2$) using 20% ethyl acetate/hexanes→30% ethyl acetate/hexanes as eluent twice to get product as yellowish oil (1.823 g, 9.15 mmol, 83% yield).

$^1$H-NMR (500 MHz, $CDCl_3$) δ 8.80 (d, J=4.4 Hz, 1H), 8.11 (d, J=8.4 Hz, 1H), 8.03 (d, J=8.5 Hz, 1H), 7.68 (dd, J=8.3, 6.8 Hz, 1H), 7.54 (dd, J=7.5, 6.9 Hz, 1H), 7.22 (d, J=4.4 Hz, 1H), 3.07-3.03 (m, 2H), 1.76 (p, J=7.5 Hz, 2H), 1.45-1.34 (m, 4H), 0.91 (t, J=7.0 Hz, 3H). $^{13}$C-NMR (126 MHz, $CDCl_3$) δ 150.3, 148.8, 148.5, 130.4, 129.0, 127.7, 126.3, 123.7, 120.9, 32.2, 32.0, 29.9, 22.6, 14.1. HRMS (TOF ESI+) m/z calcd for $C_{14}H_{18}N$ [M+H]$^+$: 200.1439, found 200.1447.

General procedure for the $HBF_4.OEt_2$ protection (Table 6). In a flamed dried 40 mL vial were charged with substrate (0.3 mmol, 1.0 equiv.) and a stir bar. 1.2 mL anhydrous DCM was added to dissolve the substrate and the vial was flushed with an argon stream and then cooled to 0° C. $HBF_4.OEt_2$ (45.5 μL, 1.1 equiv.) was added via syringe and the reaction was allowed to stir at 0° C. for 30 minutes then 1 h at room temperature. The reaction was concentrated in vacuo and left on high vacuum overnight (12-24 h). Resultant $HBF_4$ salt were used as substrates following the corresponding oxidation protocol described in Section IV.

C—H Oxidation of Substrates and Products Characterization (Table 6)

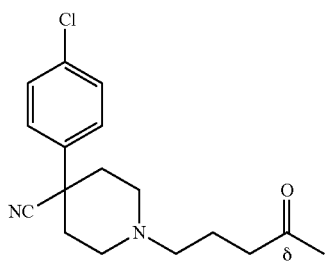 [SMILES: CC(=O)CCCN1CCC(C#N)(c2ccc(Cl)cc2)CC1]

4-(4-Chlorophenyl)-1-(4-oxopentyl)piperidine-4-carbonitrile [41a]. Substrate 4-(4-chlorophenyl)-1-pentylpiperidine-4-carbonitrile S37 (87.2 mg, 0.300 mmol, 1.0 equiv), was protected with $HBF_4.OEt_2$ (45.5 μL, 0.330 mmol, 54 wt. %, 1.1 equiv.) in $CH_2Cl_2$ (1.2 mL, 0.25 M) according to the general procedure for the $HBF_4.OEt_2$ protection in Table 6. The reaction was run with General Method C: Slow Catalyst Addition Protocol at 0° C.: the resultant S37.$HBF_4$ (0.300 mmol, 1.0 equiv.), $ClCH_2CO_2H$ (425 mg, 4.5 mmol, 15.0 equiv.), (R,R)—Mn($CF_3$-PDP) (40.7 mg, 0.030 mmol, 10 mol %), 50% wt. $H_2O_2$ (204 mg, 3.0 mmol, 10.0 equiv.), MeCN (0.6 mL in 40 mL vial, 0.38 mL with catalyst, 3.75 mL with oxidant). The reaction was run at 0° C. with ice/water bath. The reaction was worked up with 9 mL saturated $NaHCO_3$ and DCM as described in General Method C. Flash column chromatography on silica using 2% $MeOH/CHCl_3$ as eluent afforded 4-(4-chlorophenyl)-1-(4-oxopentyl)piperidine-4-carbonitrile (δ-ketone, 41a) product as a yellow oil. 4-(4-chlorophenyl)-1-(3-oxopentyl)piperidine-4-carbonitrile (γ-ketone, 41b) was produced in very low amount and was not characterized.

Run 1: (56.1 mg, 0.184 mmol, 61.3% yield of δ-ketone 41a), (4.3 mg, 0.014 mmol, 4.7% yield of γ-ketone 41b), (66.0% overall yield, 13.0:1 δ-ketone:γ-ketone ratio), (2.4 mg. 0.008 mmol, 2.8% rsm). Run 2: (58.2 mg, 0.191 mmol, 63.6% yield of δ-ketone 41a), (4.0 mg, 0.013 mmol, 4.4% yield of γ-ketone 41b), (68.0% overall yield, 14.4:1 δ-ketone:γ-ketone ratio), (2.3 mg. 0.008 mmol, 2.6% rsm). Run 3: (56.0 mg, 0.184 mmol, 61.3% yield of δ-ketone 41a), (5.2 mg, 0.017 mmol, 5.7% yield of γ-ketone 41b), (67.0% overall yield, 10.8:1 δ-ketone:γ-ketone ratio), (3.7 mg. 0.013 mmol, 4.3% rsm). Average: 67.0% yield±1.0%, 12.6:1 δ-ketone:γ-ketone ratio, 3.2% rsm±0.9%.

$^1$H-NMR (400 MHz, $CDCl_3$) δ 7.44-7.41 (m, 2H), 7.38-7.35 (m, 2H), 3.01-2.97 (m, 2H), 2.48-2.41 (m, 6H), 2.16 (s, 3H), 2.10-1.99 (m, 4H), 1.80 (p, J=7.2 Hz, 2H). $^{13}$C-NMR (126 MHz, $CDCl_3$) δ 208.5, 138.8, 134.1, 129.2, 127.1, 121.7, 57.5, 50.6, 42.5, 41.4, 36.6, 30.3, 21.2. HRMS (TOF ESI+) m/z calculated for $C_{17}H_{22}N_2OCl$ [M+H]$^+$: 305.1421, found 305.1427.

Other Oxidation Conditions for Substrate S37:

Oxidizing the S37.$HBF_4$ using General Method A: Single Catalyst Addition Protocol: the resultant S37.$HBF_4$ (0.300 mmol, 1.0 equiv.), $ClCH_2CO_2H$ (425 mg, 4.5 mmol, 15.0 equiv.), (R,R)—Mn($CF_3$-PDP) (40.7 mg, 0.030 mmol, 10 mol %), 50% wt. $H_2O_2$ (204 mg, 3.0 mmol, 10.0 equiv.), MeCN (0.6 mL in 40 mL vial, 3.75 mL with oxidant). The reaction was run at 0° C. with ice bath. The reaction was worked up with 9 mL saturated $NaHCO_3$ and DCM as described in the general method A and columned with same column conditions. Drop in conversion and maintained selectivity was observed under this condition. Run 1: (23.5 mg, 0.077 mmol, 25.7% yield of δ-ketone 41a), (1.8 mg, 0.006 mmol, 2.0% yield of γ-ketone 41b), (27.7% overall yield, 12.9:1 δ-ketone:γ-ketone ratio), (52.9 mg. 0.182 mmol, 60.7% rsm). Run 2: (21.3 mg, 0.070 mmol, 23.3% yield of δ-ketone 41a), (1.6 mg, 0.005 mmol, 1.7% yield of γ-ketone 41b), (25.0% overall yield, 13.7:1 δ-ketone:γ-ketone ratio), (53.8 mg. 0.185 mmol, 61.7% rsm). Average: 26.4% yield, 13.3:1 δ-ketone:γ-ketone ratio, 61.2% rsm.

Oxidizing the S37.$HBF_4$ using modified procedure of General Method C: Slow Catalyst Addition Protocol at −36° C.: the resultant S37.$HBF_4$ (0.300 mmol, 1.0 equiv.), $ClCH_2CO_2H$ (425 mg, 4.5 mmol, 15.0 equiv.), (R,R)—Mn ($CF_3$-PDP) (40.7 mg, 0.030 mmol, 10 mol %), 50% wt. $H_2O_2$ (204 mg, 3.0 mmol, 10.0 equiv.), MeCN (0.6 mL in 40 mL vial, 0.38 mL with catalyst, 3.75 mL with oxidant). The reaction was run at −36° C. with dry ice/1,2-dichloroethane bath. The reaction was worked up with 9 mL saturated NaHCO$_3$ and DCM as described in the general method C and columned with same column conditions. A decrease in conversion and yield of ketone products was observed at this low temperature. Run 1: (44.5 mg, 0.146 mmol, 48.7% yield of δ-ketone 41a), (3.0 mg, 0.010 mmol, 3.3% yield of γ-ketone 41b), (52.0% overall yield, 14.8:1 δ-ketone:γ-ketone ratio), (29.0 mg. 0.100 mmol, 33.2% rsm).

Oxidizing the S37 using General Method C: Slow Catalyst Addition Protocol without protection with HBF$_4$.OEt$_2$: Substrate 4-(4-chlorophenyl)-1-pentylpiperidine-4-carbonitrile S37 (87.2 mg, 0.300 mmol, 1.0 equiv), ClCH$_2$CO$_2$H (425 mg, 4.5 mmol, 15.0 equiv.), (R,R)—Mn(CF$_3$-PDP) (40.7 mg, 0.030 mmol, 10 mol %), 50% wt. H$_2$O$_2$ (204 mg, 3.0 mmol, 10.0 equiv.), MeCN (0.6 mL in 40 mL vial, 0.38 mL with catalyst, 3.75 mL with oxidant). The reaction was run at −36° C. with 1,2-dichloroethane/dry ice bath. The reaction was worked up with 9 mL saturated NaHCO$_3$ and DCM as described in the general method C. No product formed without the HBF$_4$.OEt$_2$ protection indicating it is still necessary even with ClCH$_2$COOH used in reaction media. Run 1: (79.6 mg, 0.274 mmol, 91.2% rsm). Run 2: (79.2 mg, 0.272 mmol, 90.8% rsm). Run 3: (79.7 mg, 0.274 mmol, 91.3% rsm). Average: 91.1% rsm±0.2%.

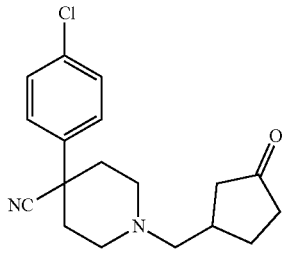 [SMILES: N#CC1(c2ccc(Cl)cc2)CCN(CC2CCC(=O)C2)CC1]

4-(4-Chlorophenyl)-1-(3-oxocyclopentyl)methyl)piperidine-4-carbonitrile [42]. Substrate 4-(4-chlorophenyl)-1-(cyclopentylmethyl)piperidine-4-carbonitrile S38 (90.9 mg, 0.300 mmol, 1.0 equiv), was protected with HBF$_4$.OEt$_2$ (45.5 μL, 0.330 mmol, 54 wt. %, 1.1 equiv.) in CH$_2$Cl$_2$ (1.2 mL, 0.25M) according to the general procedure for the HBF$_4$.OEt$_2$ protection in Table 6. The reaction was run with General Method C: Slow Catalyst Addition Protocol: the resultant S38.HBF$_4$ (0.300 mmol, 1.0 equiv.), ClCH$_2$CO$_2$H (425 mg, 4.5 mmol, 15.0 equiv.), (R,R)—Mn(CF$_3$-PDP) (40.7 mg, 0.030 mmol, 10 mol %), 50% wt. H$_2$O$_2$ (204 mg, 3.0 mmol, 10.0 equiv.), MeCN (0.6 mL in 40 mL vial, 0.38 mL with catalyst, 3.75 mL with oxidant). The reaction was run at −36° C. with 1,2-dichloroethane/dry ice bath. The reaction was worked up with 9 mL saturated NaHCO$_3$ and DCM as described in General Method C. Flash column chromatography on silica using 3% MeOH/CHCl$_3$ as eluent afforded product as a pale yellow solid. Site of oxidation was confirmed based on a combination of gHSQC and gHMBC NMRs. Run 1: (76.1 mg, 0.240 mmol, 80.1% yield), 0% rsm. Run 2: (76.2 mg, 0.240 mmol, 80.2% yield), 0% rsm. Run 3: (74.9 mg, 0.236 mmol, 78.8% yield), 0% rsm. Average: 79.7% yield±0.8%, 0% rsm.

$^1$H-NMR (500 MHz, CDCl$_3$) δ 7.44-7.42 (m, 2H), 7.39-7.36 (m, 2H), 3.01-2.96 (m, 2H), 2.55-2.27 (m, 7H), 2.22-2.12 (m, 2H), 2.11-2.01 (m, 4H), 2.00-1.91 (m, 1H), 1.74-1.56 (m, 1H). $^{13}$C-NMR (126 MHz, CDCl$_3$) δ 219.3, 138.8, 134.2, 129.3, 127.2, 121.7, 63.2, 51.4, 50.9, 43.9, 42.5, 37.9, 36.7, 36.7, 34.7, 27.7. HRMS (TOF ESI+) m/z calculated for C$_{18}$H$_{22}$N$_2$OCl [M+H]$^+$: 317.1421, found 317.1424.

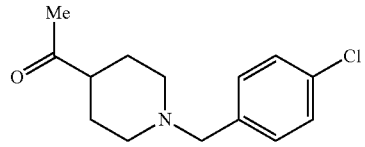 [SMILES: CC(=O)C1CCN(Cc2ccc(Cl)cc2)CC1]

1-(1-(4-Chlorobenzyl)piperidin-4-yl)ethan-1-one [43]. Substrate 1-(4-chlorobenzyl)-4-ethylpiperidine S39 (71.3 mg, 0.300 mmol, 1.0 equiv), was protected with HBF$_4$.OEt$_2$ (45.5 μL, 0.330 mmol, 54 wt. %, 1.1 equiv.) in CH$_2$Cl$_2$ (1.2 mL, 0.25M) according to the general procedure for the HBF$_4$.OEt$_2$ protection in Table 6. The reaction was run with General Method C: Slow Catalyst Addition Protocol at 0° C.: the resultant S39HBF$_4$ (0.300 mmol, 1.0 equiv.), ClCH$_2$CO$_2$H (425 mg, 4.5 mmol, 15.0 equiv.), (R,R)—Mn(CF$_3$-PDP) (40.7 mg, 0.030 mmol, 10 mol %), 50% wt. H$_2$O$_2$ (204 mg, 3.0 mmol, 10.0 equiv.), MeCN (0.6 mL in 40 mL vial, 0.38 mL with catalyst, 3.75 mL with oxidant). The reaction was run at 0° C. with ice bath. The reaction was worked up with 9 mL saturated NaHCO$_3$ and DCM as described in General Method C. Flash column chromatography on silica using 2% MeOH/CHCl$_3$ as eluent afforded product as a pale yellow solid. Run 1: (38.5 mg, 0.153 mmol, 51.0% yield), (11.6 mg, 0.049 mmol, 16.3% rsm). Run 2: (37.5 mg, 0.149 mmol, 49.7% yield), (13.8 mg, 0.058 mmol, 19.3% rsm). Run 3: (38.2 mg, 0.152 mmol, 50.6% yield), (14.1 mg, 0.059 mmol, 19.8% rsm). Average: 50.4% yield±0.7%, 18.5% rsm±1.9%.

$^1$H-NMR (500 MHz, CDCl$_3$) δ 7.28-7.23 (m, 4H), 3.45 (s, 2H), 2.86 (dt, J=11.9, 3.6 Hz, 2H), 2.28 (tt, J=11.5, 3.8 Hz, 1H), 2.13 (s, 3H), 2.00 (td, J=11.6, 2.5 Hz, 2H), 1.82 (dt, J=13.3, 2.9 Hz, 2H), 1.65 (dtd, J=13.2, 11.6, 3.8 Hz, 2H). $^{13}$C-NMR (126 MHz, CDCl$_3$) δ 211.1, 137.0, 132.8, 130.4, 128.5, 62.5, 53.1, 49.4, 27.9, 27.8. HRMS (TOF ESI+) m/z calculated for C$_{14}$H$_{19}$NOCl [M+H]$^+$: 252.1155, found 252.1161.

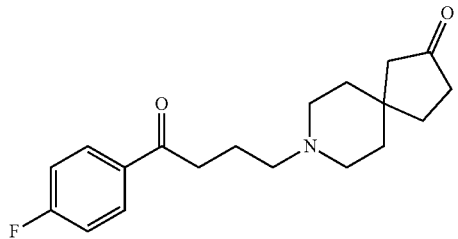

8-(4-(4-Fluorophenyl)-4-oxobutyl)-8-azaspiro[4.5]decan-2-one [44]. Substrate 1-(4-fluorophenyl)-4-(8-azaspiro[4.5]decan-8-yl)butan-1-one S40 (91.0 mg, 0.300 mmol, 1.0 equiv), was protected with HBF$_4$.OEt$_2$ (45.5 μL, 0.330 mmol, 54 wt. %, 1.1 equiv.) in CH$_2$Cl$_2$ (1.2 mL, 0.25M) according to the general procedure for the HBF$_4$.OEt$_2$ protection in Table 6. The reaction was run with General Method C: Slow Catalyst Addition Protocol: the resultant S40HBF$_4$ (0.300 mmol, 1.0 equiv.), ClCH$_2$CO$_2$H (425 mg, 4.5 mmol, 15.0 equiv.), (R,R)—Mn(CF$_3$-PDP) (40.7 mg, 0.030 mmol, 10 mol %), 50% wt. H$_2$O$_2$ (204 mg, 3.0 mmol, 10.0 equiv.), MeCN (0.6 mL in 40 mL vial, 0.38 mL with catalyst, 3.75 mL with oxidant). The reaction was run at −36° C. with 1,2-dichloroethane/dry ice bath. The reaction was worked up with 9 mL saturated NaHCO₃ and DCM as described in General Method C. Flash column chromatography on silica using 5% MeOH/CHCl₃ as eluent afforded product as a pale yellow solid. Run 1: (82.8 mg, 0.261 mmol, 87.0% yield), 0% rsm. Run 2: (79.7 mg, 0.251 mmol, 83.7% yield), 0% rsm. Run 3: (78.1 mg, 0.246 mmol, 82.0% yield), 0% rsm. Average: 84.2% yield±2.5%, 0% rsm.

¹H-NMR (500 MHz, CDCl₃) δ 8.01-7.98 (m, 2H), 7.13-7.10 (m, 2H), 2.96 (t, J=7.1 Hz, 2H), 2.58-2.54 (m, 2H), 2.40 (t, J=7.2 Hz, 2H), 2.26-2.20 (m, 4H), 2.10 (s, 2H), 1.94 (p, J=7.1 Hz, 2H), 1.80 (t, J=7.9 Hz, 2H), 1.58-1.49 (m, 4H). ¹³C-NMR (126 MHz, CDCl₃) δ 219.3, 198.5, 165.7 (d, J=254.4 Hz), 133.7 (d, J=3.0 Hz), 130.8 (d, J=9.2 Hz), 115.7 (d, J=22.1 Hz), 58.0, 50.6 (2 carbons), 50.1 (broad), 38.5, 36.6 (2 carbons), 36.4, 36.3, 34.5 (broad), 21.9. ¹⁹F-NMR (470 MHz, CDCl₃) δ −106.1. HRMS (TOF ESI+) m/z calculated for $C_{19}H_{25}NO_2F$ [M+H]⁺: 318.1869, found 318.1858.

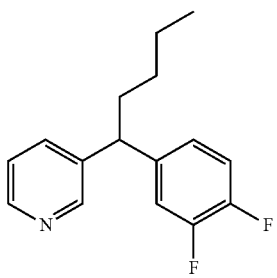 [SMILES: CCCCC(c1cccnc1)c1ccc(F)c(F)c1]

5-(3,4-Difluorophenyl)-5-(pyridin-3-yl)pentan-2-one [45]. Substrate 3-(1-(3,4-difluorophenyl)pentyl)pyridine S41 (78.4 mg, 0.300 mmol, 1.0 equiv), was protected with HBF₄.OEt₂ (45.5 μL, 0.330 mmol, 54 wt. %, 1.1 equiv.) in CH₂Cl₂ (1.2 mL, 0.25M) according to the general procedure for the HBF₄.OEt₂ protection in Table 6. The reaction was run with General Method C: Slow Catalyst Addition Protocol: the resultant S41.HBF₄ (0.300 mmol, 1.0 equiv.), ClCH₂CO₂H (425 mg, 4.5 mmol, 15.0 equiv.), (R,R)—Mn(CF₃-PDP) (40.7 mg, 0.030 mmol, 10 mol %), 50% wt. H₂O₂ (204 mg, 3.0 mmol, 10.0 equiv.), MeCN (0.6 mL in 40 mL vial, 0.38 mL with catalyst, 3.75 mL with oxidant). The reaction was run at −36° C. with 1,2-dichloroethane/dry ice bath. The reaction was worked up with 9 mL saturated NaHCO₃ and DCM as described in General Method C. Flash column chromatography on silica using 2% MeOH/CHCl₃ as eluent afforded product as a pale yellow oil. Run 1: (44.9 mg, 0.163 mmol, 54.4% yield), (10.2 mg, 0.039 mmol, 13.0% rsm). Run 2: (44.5 mg, 0.162 mmol, 53.9% yield), (9.7 mg, 0.037 mmol, 12.4% rsm). Run 3: (44.2 mg, 0.161 mmol, 53.5% yield), (8.4 mg, 0.032 mmol, 10.7% rsm). Average: 53.9% yield±0.5%, 12.0% rsm±1.2%.

¹H-NMR (500 MHz, CDCl₃) 8.47-8.45 (m, 2H), 7.48 (dt, J=8.0, 1.9 Hz, 1H), 7.22 (dd, J=7.9, 4.7 Hz, 1H), 7.08 (dt, J=10.1, 8.3 Hz, 1H), 7.00 (ddd, J=11.4, 7.5, 2.2 Hz, 1H), 6.94-6.91 (m, 1H), 3.91 (t, J=7.9 Hz, 1H), 2.38 (t, J=6.7 Hz, 2H), 2.30-2.25 (m, 2H), 2.07 (s, 3H). ¹³C-NMR (126 MHz, CDCl₃) δ 207.8, 151.0 (dd, J=155.9, 12.6 Hz), 149.7, 149.1 (dd, J=155.0, 12.7 Hz), 148.6, 140.4 (t, J=4.4 Hz), 139.1, 135.1, 123.9, 123.9 (q, J=3.4 Hz), 117.7 (d, J=17.1 Hz), 116.8 (d, J=17.4 Hz), 47.1, 41.5, 30.3, 29.0. ¹⁹F NMR (470 MHz, CDCl₃) δ −137.30 (dt, J=20.8, 10.1 Hz), −140.79 (dt, J=20.3, 9.9 Hz). HRMS (TOF ESI+) m/z calculated for $C_{16}H_{16}NOF_2$ [M+H]⁺: 276.1200, found 276.1196.

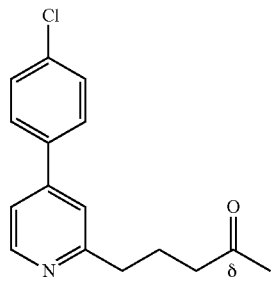 [SMILES: CC(=O)CCCc1cc(-c2ccc(Cl)cc2)ccn1]

5-(4-(4-Chlorophenyl)pyridin-2-yl)pentan-2-one [46a]. Substrate 4-(4-chlorophenyl)-2-pentylpyridine S42 (77.9 mg, 0.300 mmol, 1.0 equiv), was protected with HBF₄.OEt₂ (45.5 μL, 0.330 mmol, 54 wt. %, 1.1 equiv.) in CH₂Cl₂ (1.2 mL, 0.25M) according to the general procedure for the HBF₄.OEt₂ protection in Table 6. The reaction was run with General Method C: Slow Catalyst Addition Protocol: the resultant S42.HBF₄ (0.300 mmol, 1.0 equiv.), ClCH₂CO₂H (425 mg, 4.5 mmol, 15.0 equiv.), (R,R)—Mn(CF₃-PDP) (40.7 mg, 0.030 mmol, 10 mol %), 50% wt. H₂O₂ (204 mg, 3.0 mmol, 10.0 equiv.), MeCN (0.6 mL in 40 mL vial, 0.38 mL with catalyst, 3.75 mL with oxidant). The reaction was run at −36° C. with 1,2-dichloroethane/dry ice bath. The reaction was worked up with 9 mL saturated NaHCO₃ and DCM as described in General Method C. Flash column chromatography on silica using 20% ethyl acetate/hexanes as eluent afforded 5-(4-(4-chlorophenyl)pyridin-2-yl)pentan-2-one (δ-ketone, 46a) product as a yellow oil and 1-(4-(4-chlorophenyl)pyridin-2-yl)pentan-3-one (γ-ketone, 46b) as a yellow oil.

Run 1: (56.0 mg, 0.205 mmol, 68.2% yield of δ-ketone 46a), (11.8 mg, 0.043 mmol, 14.4% yield of γ-ketone 46b), (82.6% overall yield, 4.7:1 δ-ketone:γ-ketone ratio), (7.0 mg. 0.027 mmol, 9.0% rsm). Run 2: (52.1 mg, 0.190 mmol, 63.4% yield of δ-ketone 46a), (11.4 mg, 0.042 mmol, 13.9% yield of γ-ketone 46b), (77.3% overall yield, 4.6:1 δ-ketone:γ-ketone ratio), (12.1 mg. 0.047 mmol, 15.5% rsm). Run 3: (51.2 mg, 0.187 mmol, 62.4% yield of δ-ketone 46a), (10.3 mg, 0.038 mmol, 12.5% yield of γ-ketone 46b), (74.9% overall yield, 5.0:1 δ-ketone:γ-ketone ratio), (12.1 mg. 0.049 mmol, 16.3% rsm). Average: 78.3% yield±3.9%, 4.8:1 δ-ketone:γ-ketone ratio, 13.6% rsm±4.0%.

¹H-NMR (500 MHz, CDCl₃) δ 8.56 (d, J=5.2 Hz, 1H), 7.57-7.55 (m, 2H), 7.46-7.44 (m, 2H), 7.33 (d, J=1.5 Hz, 1H), 7.29 (dd, J=5.2, 1.8 Hz, 1H), 2.85 (dd, J=8.4, 6.9 Hz, 2H), 2.52 (t, J=7.3 Hz, 2H), 2.14 (s, 3H), 2.06 (app. p, J=7.5 Hz, 2H). ¹³C-NMR (126 MHz, CDCl₃) δ 208.8, 162.2, 149.9, 147.8, 136.9, 135.4, 129.4, 128.4, 120.7, 119.2, 43.1, 37.6, 30.1, 23.9. HRMS (TOF ESI+) m/z calculated for $C_{16}H_{17}NOCl$ [M+H]⁺: 274.0999, found 274.0990.

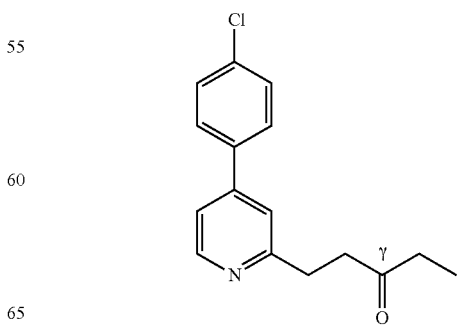

1-(4-(4-Chlorophenyl)pyridin-2-yl)pentan-3-one [46b]. $^1$H-NMR (500 MHz, CDCl$_3$) δ 8.54 (d, J=5.2 Hz, 1H), 7.57-7.54 (m, 2H), 7.46-7.43 (m, 2H), 7.37 (d, J=1.7 Hz, 1H), 7.28 (dd, J=5.2, 1.8 Hz, 1H), 3.13 (t, J=7.2 Hz, 2H), 2.97 (t, J=7.3 Hz, 2H), 2.48 (q, J=7.3 Hz, 2H), 1.06 (t, J=7.3 Hz, 3H). $^{13}$C-NMR (126 MHz, CDCl$_3$) δ 210.8, 161.5, 149.9, 147.7, 136.9, 135.3, 129.4, 128.4, 121.1, 119.2, 41.3, 36.2, 32.0, 8.0. HRMS (TOF ESI+) m/z calculated for C$_{16}$H$_{17}$NOCl [M+H]$^+$: 274.0999, found 274.0992.

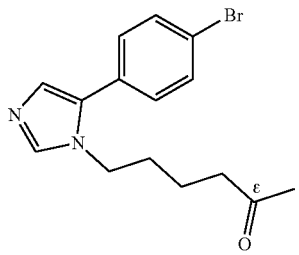 [SMILES: CC(=O)CCCCn1cncc1-c1ccc(Br)cc1]

6-(5-(4-Bromophenyl)-1H-imidazol-1-yl)hexan-2-one [47]. Substrate 5-(4-bromophenyl)-1-hexyl-1H-imidazole S43 (92.2 mg, 0.300 mmol, 1.0 equiv), was protected with HBF$_4$.OEt$_2$ (45.5 µL, 0.330 mmol, 54 wt. %, 1.1 equiv.) in CH$_2$Cl$_2$ (1.2 mL, 0.25M) according to the general procedure for the HBF$_4$.OEt$_2$ protection in Table 6. The reaction was run with General Method C: Slow Catalyst Addition Protocol: the resultant S43.HBF$_4$ (0.300 mmol, 1.0 equiv.), ClCH$_2$CO$_2$H (425 mg, 4.5 mmol, 15.0 equiv.), (R,R)—Mn (CF$_3$-PDP) (40.7 mg, 0.030 mmol, 10 mol %), 50% wt. H$_2$O$_2$ (204 mg, 3.0 mmol, 10.0 equiv.), MeCN (0.6 mL in 40 mL vial, 0.38 mL with catalyst, 3.75 mL with oxidant). The reaction was run at −36° C. with 1,2-dichloroethane/dry ice bath. The reaction was concentrated to a minimum amount of solvent and dissolved in ~15 mL DCM. 15 mL 1M NaOH solution was added and the mixture was stirred vigorously at RT for 30 minutes before layers was separated. The aqueous layer was extracted with 30 mL DCM twice and the combined organic layer was dried with Na$_2$SO$_4$. Flash column chromatography on silica (35 mm fritted glass column, 100 mL SiO$_2$) using 2% MeOH/CH$_2$Cl$_2$→5% MeOH/CH$_2$Cl$_2$→10% MeOH/CH$_2$Cl$_2$ as eluent afforded 6-(5-(4-bromophenyl)-1H-imidazol-1-yl)hexan-2-one (ε-ketone 47) and a mixture of ketones in other positions as a pale yellow oil.

Run 1: (30.1 mg, 0.094 mmol, 31.2% yield of ε-ketone 47), (17.4 mg, 0.054 mmol, 18.1% yield of ketone mixtures in other positions), (49.3% overall yield, 1.7:1 ε-ketone:other ketones ratio), <10% rsm. Run 2: (32.3 mg, 0.101 mmol, 33.5% yield of ε-ketone 47), (17.4 mg, 0.054 mmol, 18.1% yield of ketone mixtures in other positions), (51.6% overall yield, 1.9:1 ε-ketone:other ketones ratio), <10% rsm. Run 3: (29.8 mg, 0.093 mmol, 30.9% yield of ε-ketone 47), (16.1 mg, 0.050 mmol, 16.7% yield of ketone mixtures in other positions), (47.6% overall yield, 1.9:1 ε-ketone:other ketones ratio), <10% rsm. Average: 49.5% yield±2.0%, 1.8:1 ε-ketone:other ketones ratio, <10% rsm.

$^1$H-NMR (500 MHz, CDCl$_3$) δ 7.63 (d, J=8.2 Hz, 2H), 7.49-7.47 (m, 3H), 7.19 (s, 1H), 3.95 (t, J=7.1 Hz, 2H), 2.47 (t, J=7.0 Hz, 2H), 2.13 (s, 3H), 1.84-1.78 (m, 2H), 1.64-1.58 (m, 2H). $^{13}$C-NMR (126 MHz, CDCl$_3$) δ 207.9, 141.5, 137.5, 133.3, 131.8, 126.4, 120.5, 114.9, 47.3, 42.8, 30.6, 30.1, 20.7. HRMS (TOF ESI+) m/z calculated for C$_{15}$H$_{18}$N$_2$OBr [M+H]$^+$: 321.0602, found 321.0616.

Other Oxidation Conditions for Substrate S43:

Oxidizing S43 using General Method C: Slow Catalyst Addition Protocol without protection with HBF$_4$.OEt$_2$: Substrate 5-(4-bromophenyl)-1-hexyl-1H-imidazole S43 (92.2 mg, 0.300 mmol, 1.0 equiv.), ClCH$_2$CO$_2$H (425 mg, 4.5 mmol, 15.0 equiv.), (R,R)—Mn(CF$_3$-PDP) (40.7 mg, 0.030 mmol, 10 mol %), 50% wt. H$_2$O$_2$ (204 mg, 3.0 mmol, 10.0 equiv.), MeCN (0.6 mL in 40 mL vial, 0.38 mL with catalyst, 3.75 mL with oxidant). The reaction was run at −36° C. with 1,2-dichloroethane/dry ice bath. The reaction was concentrated to a minimum amount of solvent and dissolved in ~15 mL DCM. 15 mL 1M NaOH solution was added and the mixture was stirred vigorously at RT for 30 minutes before layers was separated. The aqueous layer was extracted with 30 mL DCM twice and the combined organic layer was dried with Na$_2$SO$_4$. Flash column chromatography with the same condition and eluents was generously collected and concentrated via rotvap. The residue was analyzed by quantitative $^1$H-NMR using nitrobenzene as internal standard. No product formed without the HBF$_4$.OEt$_2$ protection indicating it is still necessary even with ClCH$_2$COOH was used for the less basic imidazole substrate.

Oxidizing S43.HBF$_4$ using Fe(CF$_3$-PDP): Substrate 5-(4-bromophenyl)-1-hexyl-1H-imidazole S43 (92.2 mg, 0.300 mmol, 1.0 equiv), was protected with HBF$_4$.OEt$_2$ (45.5 µL, 0.330 mmol, 54 wt. %, 1.1 equiv.) in CH$_2$Cl$_2$ (1.2 mL, 0.25M) according to the general procedure for the HBF$_4$.OEt$_2$ protection in Table 6. The reaction was conducted in slow addition protocol, same as Entry 10 of Table 3. In a 40 mL vial was charged with S43.HBF$_4$ (0.30 mmol, 1.0 equiv), AcOH (90.1 mg, 1.5 mmol, 5.0 equiv.), MeCN (0.60 mL) and a stir bar. A 1 mL syringe was charged with a solution of (S,S)—Fe(CF$_3$-PDP) catalyst (101.6 mg, 0.075 mmol, 0.25 equiv.) in MeCN (0.38 mL). A 10 mL syringe was charged with a solution of H$_2$O$_2$ (183.6 mg, 2.7 mmol, 9.0 equiv.) in MeCN (3.75 mL). Both syringes were fitted with 25 G needles and the solution was added dropwise via syringe pump over 1 hour. Upon completion of addition, the reaction was concentrated in vacuo to a minimum amount of MeCN and dissolved in ~15 mL DCM. 15 mL 1M NaOH solution was added and the mixture was stirred vigorously at RT for 30 minutes before layers was separated. The aqueous layer was extracted with 30 mL DCM twice and the combined organic layer was dried with Na$_2$SO$_4$. Flash column chromatography with the same condition and eluents was generously collected and concentrated via rotvap. The residue was analyzed by quantitative $^1$H-NMR using nitrobenzene as internal standard. No product formed with the Fe(CF$_3$-PDP) catalyst indicating the protonated imidazole substituted with an aromatic ring is still prone to aromatic oxidation with Fe catalyst. Run 1: <10% rsm+ketone products combined.

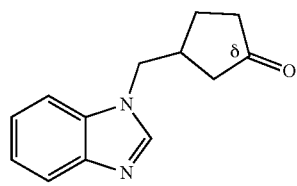 [SMILES: O=C1CCC(Cn2cnc3ccccc32)C1]

3((1H-Benzo[d]imidazol-1-yl)methyl)cyclopentan-1-one [48a]. Substrate 1-(cyclopentylmethyl)-1H-benzo[d]imidazole S44 (60.1 mg, 0.300 mmol, 1.0 equiv) was protected with HBF$_4$.OEt$_2$ (45.5 µL, 0.330 mmol, 54 wt. %, 1.1 equiv.) in CH$_2$Cl$_2$ (1.2 mL, 0.25M) according to the general procedure for the HBF$_4$.OEt$_2$ protection in Table 6. The reaction was run with General Method B: Iterative Catalyst Addition Protocol: the resultant S44.HBF$_4$ (0.300 mmol, 1.0 equiv.), ClCH$_2$CO$_2$H (425 mg, 4.5 mmol, 15.0 equiv.), (R,R)—Mn (CF$_3$-PDP) (3 time addition of 20.4 mg, 0.015 mmol, 5 mol %; 15 mol % used in total), 50% wt. H$_2$O$_2$ (204 mg, 3.0 mmol, 10.0 equiv.), MeCN (0.6 mL in 40 mL vial, 0.38 mL with catalyst, 3.75 mL with oxidant). The reaction was run at −36° C. with 1,2-dichloroethane/dry ice bath. The reaction was worked up with 9 mL saturated NaHCO$_3$ and DCM as described in General Method B. Flash column chromatography on silica using 5% MeOH/CHCl$_3$ as eluent afforded 3-((1H-benzo[d]imidazol-1-yl)methyl)cyclopentan-1-one (δ-ketone, 48a) and 2-((1H-benzo[d]imidazol-1-yl)methyl) cyclopentan-1-one (γ-ketone, 48b) as brown solid.

Run 1: (31.9 mg, 0.149 mmol, 49.6% yield of δ-ketone 48a), (3.1 mg, 0.014 mmol, 4.8% yield of γ-ketone 48b), (54.4% overall yield, 10.3:1 δ-ketone:γ-ketone ratio), 0% rsm. Run 2: (33.4 mg, 0.156 mmol, 52.0% yield of δ-ketone 48a), (3.5 mg, 0.016 mmol, 5.4% yield of γ-ketone 48b), (57.4% overall yield, 9.6:1 δ-ketone:γ-ketone ratio), 0% rsm. Run 3: (32.1 mg, 0.150 mmol, 49.9% yield of δ-ketone 48a), (2.9 mg, 0.014 mmol, 4.5% yield of γ-ketone 48b), (54.4% overall yield, 11.1:1 δ-ketone:γ-ketone ratio), 0% rsm. Average: 55.4% yield±1.7%, 10.3:1 δ-ketone:γ-ketone ratio, 0% rsm.

$^1$H-NMR (500 MHz, CDCl$_3$) δ 7.88 (s, 1H), 7.82-7.80 (m, 1H), 7.40-7.38 (m, 1H), 7.33-7.27 (m, 2H), 4.27 (dd, J=14.4, 6.8 Hz, 1H), 4.20 (dd, J=14.4, 7.5 Hz, 1H), 2.85-2.75 (m, 1H), 2.41-2.31 (m, 2H), 2.22-2.14 (m, 1H), 2.14-2.06 (m, 1H), 1.97 (ddd, J=18.3, 10.2, 1.4 Hz, 1H), 1.71-1.63 (m, 1H). $^{13}$C-NMR (126 MHz, CDCl$_3$) δ 216.3, 143.9, 142.9, 133.9, 123.3, 122.5, 120.7, 109.5, 49.1, 42.8, 38.0, 37.7, 27.4. HRMS (TOF ESI+) m/z calculated for C$_{13}$H$_{15}$N$_2$O [M+H]$^+$: 215.1184, found 215.1181.

Oxidizing S44 using General Method B: Iterative Catalyst Addition Protocol without protection with HBF$_4$.OEt$_2$: Substrate 1-(cyclopentylmethyl)-1H-benzo[d]imidazole S44 (60.1 mg, 0.300 mmol, 1.0 equiv), ClCH$_2$CO$_2$H (425 mg, 4.5 mmol, 15.0 equiv.), (R,R)—Mn(CF$_3$-PDP) (3 time addition of 20.4 mg, 0.015 mmol, 5 mol %; 15 mol % used in total), 50% wt. H$_2$O$_2$ (204 mg, 3.0 mmol, 10.0 equiv.), MeCN (0.6 mL in 40 mL vial, 0.38 mL with catalyst, 3.75 mL with oxidant). The reaction was run at −36° C. with 1,2-dichloroethane/dry ice bath. The reaction was worked up with 9 mL saturated NaHCO$_3$ and DCM as described in General Method B. Flash column chromatography with the same condition and eluents was generously collected and concentrated via rotvap. The residue was analyzed by quantitative $^1$H-NMR using nitrobenzene as internal standard. No product formed without the HBF$_4$.OEt$_2$ protection indicating it is still necessary even with ClCH$_2$COOH was used for the less basic benzimidazole substrate. Run 1: <5% product, <5% rsm.

Oxidizing S44.HBF$_4$ using Fe(CF$_3$-PDP): Substrate 1-(cyclopentylmethyl)-1H-benzo[d]imidazole S44 (60.1 mg, 0.300 mmol, 1.0 equiv), was protected with HBF$_4$.OEt$_2$ (45.5 μL, 0.330 mmol, 54 wt. %, 1.1 equiv.) in CH$_2$Cl$_2$ (1.2 mL, 0.25M) according to the general procedure for the HBF$_4$.OEt$_2$ protection in Table 6. The reaction was conducted in slow addition protocol, same as Entry 10 of Table 3. In a 40 mL vial was charged with S44.HBF$_4$ (0.30 mmol, 1.0 equiv), AcOH (90.1 mg, 1.5 mmol, 5.0 equiv.), MeCN (0.60 mL) and a stir bar. A 1 mL syringe was charged with a solution of (S,S)—Fe(CF$_3$-PDP) catalyst (101.6 mg, 0.075 mmol, 0.25 equiv.) in MeCN (0.38 mL). A 10 mL syringe was charged with a solution of H$_2$O$_2$ (183.6 mg, 2.7 mmol, 9.0 equiv.) in MeCN (3.75 mL). Both syringes were fitted with 25 G needles and the solution was added dropwise via syringe pump over 1 hour. Upon completion of addition, the reaction was concentrated in vacuo to a minimum amount of MeCN and dissolved in ~15 mL DCM. 15 mL 1M NaOH solution was added and the mixture was stirred vigorously at RT for 30 minutes before layers was separated. The aqueous layer was extracted with 30 mL DCM twice and the combined organic layer was dried with Na$_2$SO$_4$. Flash column chromatography with the same condition and eluents was generously collected and concentrated via rotvap. The residue was analyzed by quantitative $^1$H-NMR using nitrobenzene as internal standard. No product formed with the Fe(CF$_3$-PDP) catalyst indicating the protonated benzimidazole is still prone to aromatic oxidation with Fe catalyst. Run 1: <5% product, <5% rsm.

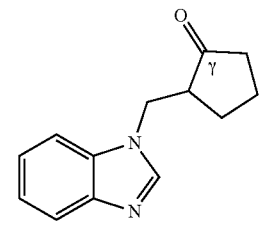 [SMILES: O=C1CCCC1Cn1cnc2ccccc21]

2((1H-Benzo[d]imidazol-1-yl)methyl)cyclopentan-1-one [48b]. $^1$H-NMR (500 MHz, CDCl$_3$) δ 7.88 (s, 1H), 7.82-7.80 (m, 1H), 7.41-7.39 (m, 1H), 7.33-7.27 (m, 2H), 4.52 (dd, J=14.8, 4.6 Hz, 1H), 4.34 (dd, J=14.8, 6.8 Hz, 1H), 2.64-2.58 (m, 1H), 2.39 (ddq, J=18.7, 8.1, 1.7 Hz, 1H), 2.17 (dddt, J=12.2, 8.2, 6.2, 1.9 Hz, 1H), 2.07 (ddd, J=19.2, 10.9, 8.9 Hz, 1H), 1.97 (dddt, J=13.1, 8.9, 6.7, 2.0 Hz, 1H), 1.81-1.72 (m, 1H), 1.53 (qd, J=11.9, 6.6 Hz, 1H). $^{13}$C-NMR (126 MHz, CDCl$_3$) δ 217.8, 143.9, 143.5, 134.1, 123.3, 122.4, 120.7, 109.7, 50.3, 43.9, 38.0, 28.1, 20.4. HRMS (TOF ESI+) m/z calculated for C$_{13}$H$_{15}$N$_2$O [M+H]$^+$: 215.1184, found 215.1188.

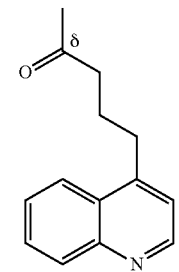 [SMILES: CC(=O)CCCc1ccnc2ccccc12]

5-(Quinolin-4-yl)pentan-2-one [49a]. Substrate 4-pentylquinoline S45 (59.8 mg, 0.300 mmol, 1.0 equiv), was protected with HBF$_4$.OEt$_2$ (45.5 μL, 0.330 mmol, 54 wt. %, 1.1 equiv.) in CH$_2$Cl$_2$ (1.2 mL, 0.25M) according to the general procedure for the HBF$_4$.OEt$_2$ protection in Table 6. The reaction was run with General Method C: Slow Catalyst Addition Protocol: the resultant S45.HBF$_4$ (0.300 mmol, 1.0 equiv.), ClCH$_2$CO$_2$H (425 mg, 4.5 mmol, 15.0 equiv.), (R,R)—Mn(CF$_3$-PDP) (40.7 mg, 0.030 mmol, 10 mol %), 50% wt. H$_2$O$_2$ (204 mg, 3.0 mmol, 10.0 equiv.), MeCN (0.6 mL in 40 mL vial, 0.38 mL with catalyst, 3.75 mL with oxidant). The reaction was run at −36° C. with 1,2-dichloroethane/dry ice bath. The reaction was concentrated to a minimum amount of solvent and dissolved in ~15 mL DCM. 15 mL 1M NaOH solution was added and the mixture was stirred vigorously at RT for 30 minutes before layers were separated. The aqueous layer was extracted with 30 mL DCM twice and the combined organic layer was dried with Na$_2$SO$_4$. Flash column chromatography on silica (35 mm fritted glass column, 100 mL SiO$_2$) using 15% acetone/hexanes→30% acetone/hexanes→50% acetone/hexanes as eluent afforded 5-(quinolin-4-yl)pentan-2-one (δ-ketone, 49a) and 1-(quinolin-4-yl)pentan-3-one (γ-ketone, 49b) as pale yellow oil.

Run 1: (42.6 mg, 0.200 mmol, 66.6% yield of δ-ketone 49a), (11.3 mg, 0.053 mmol, 17.7% yield of γ-ketone 49b), (84.3% overall yield, 3.8:1 δ-ketone:γ-ketone ratio), <5% rsm. Run 2: (42.7 mg, 0.200 mmol, 66.7% yield of δ-ketone 49a), (11.7 mg, 0.055 mmol, 18.3% yield of γ-ketone 49b), (85.0% overall yield, 3.6:1 δ-ketone:γ-ketone ratio), <5% rsm. Run 3: (41.3 mg, 0.194 mmol, 64.5% yield of δ-ketone 49a), (11.5 mg, 0.054 mmol, 18.0% yield of γ-ketone 49b), (82.5% overall yield, 3.6:1 δ-ketone:γ-ketone ratio), <5% rsm. Average: 83.9% yield±1.3%, 3.7:1 δ-ketone:γ-ketone ratio, <5% rsm.

$^1$H-NMR (500 MHz, CDCl$_3$) δ 8.79 (d, J=4.3 Hz, 1H), 8.11-8.07 (m, 2H), 7.69 (dd, J=8.4, 6.8 Hz, 1H), 7.56 (dd, J=8.3, 6.8 Hz, 1H), 7.22-7.19 (m, 1H), 3.07 (dd, J=9.6, 6.8 Hz, 2H), 2.54-2.51 (m, 2H), 2.13 (s, 3H), 2.03 (p, J=7.1 Hz, 2H). $^{13}$C-NMR (126 MHz, CDCl$_3$) δ 208.2, 150.3, 148.5, 147.8, 130.4, 129.2, 127.6, 126.6, 123.7, 121.0, 42.9, 31.4, 30.2, 23.9. HRMS (TOF ESI+) m/z calculated for C$_{14}$H$_{16}$NO [M+H]$^+$: 214.1232, found 214.1232.

Oxidizing S45 using General Method C: Slow Catalyst Addition Protocol without protection with HBF$_4$.OEt$_2$: Substrate 4-pentylquinoline S45 (59.8 mg, 0.300 mmol, 1.0 equiv), ClCH$_2$CO$_2$H (425 mg, 4.5 mmol, 15.0 equiv.), (R,R)—Mn(CF$_3$-PDP) (40.7 mg, 0.030 mmol, 10 mol %), 50% wt. H$_2$O$_2$ (204 mg, 3.0 mmol, 10.0 equiv.), MeCN (0.6 mL in 40 mL vial, 0.38 mL with catalyst, 3.75 mL with oxidant). The reaction was run at −36° C. with 1,2-dichloroethane/dry ice bath. The reaction was concentrated to a minimum amount of solvent and dissolved in ~15 mL DCM. 15 mL 1M NaOH solution was added and the mixture was stirred vigorously at RT for 30 minutes before layers was separated. The aqueous layer was extracted with 30 mL DCM twice and the combined organic layer was dried with Na$_2$SO$_4$. Flash column chromatography with the same condition and eluents was generously collected and concentrated via rotvap. The residue was analyzed by quantitative $^1$H-NMR using nitrobenzene as internal standard. No product formed without the HBF$_4$.OEt$_2$ protection indicating quinoline substrate deactivate the catalyst in reaction conditions. Run 1: <5% product, (45.7 mg, 0.229 mmol, 76.5% rsm).

Oxidizing S45.HBF$_4$ using Fe(CF$_3$-PDP): Substrate 4-pentylquinoline S45 (59.8 mg, 0.300 mmol, 1.0 equiv), was protected with HBF$_4$.OEt$_2$ (45.5 μL, 0.330 mmol, 54 wt. %, 1.1 equiv.) in CH$_2$Cl$_2$ (1.2 mL, 0.25M) according to the general procedure for the HBF$_4$.OEt$_2$ protection in Table 6. The reaction was conducted in slow addition protocol, same as Entry 10 of Table 3. In a 40 mL vial was charged with S45.HBF$_4$ (0.30 mmol, 1.0 equiv), AcOH (90.1 mg, 1.5 mmol, 5.0 equiv.), MeCN (0.60 mL) and a stir bar. A 1 mL syringe was charged with a solution of (S,S)—Fe(CF$_3$-PDP) catalyst (101.6 mg, 0.075 mmol, 0.25 equiv.) in MeCN (0.38 mL). A 10 mL syringe was charged with a solution of H$_2$O$_2$ (183.6 mg, 2.7 mmol, 9.0 equiv.) in MeCN (3.75 mL). Both syringes were fitted with 25 G needles and the solution was added dropwise via syringe pump over 1 hour. Upon completion of addition, the reaction was concentrated in vacuo to a minimum amount of MeCN and dissolved in ~15 mL DCM. 15 mL 1M NaOH solution was added and the mixture was stirred vigorously at RT for 30 minutes before layers was separated. The aqueous layer was extracted with 30 mL DCM twice and the combined organic layer was dried with Na$_2$SO$_4$. Flash column chromatography with the same condition and eluents was generously collected and concentrated via rotvap. The residue was analyzed by quantitative $^1$H-NMR using nitrobenzene as internal standard. No product formed with the Fe(CF$_3$-PDP) catalyst indicating the protonated quinoline is still prone to aromatic oxidation with Fe catalyst. Run 1: <5% product, <5% rsm.

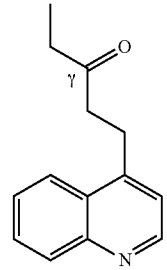 [SMILES: CCC(=O)CCc1ccnc2ccccc12]

1-(Quinolin-4-yl)pentan-3-one [49b]. $^1$H-NMR (500 MHz, CDCl$_3$) δ 8.80-8.79 (m, 1H), 8.12 (d, J=8.3 Hz, 1H), 8.01 (d, J=8.5 Hz, 1H), 7.71 (t, J=6.9 Hz, 1H), 7.57 (t, J=6.9 Hz, 1H), 7.24-7.21 (m, 1H), 3.37 (t, J=7.7 Hz, 2H), 2.88 (t, J=7.7 Hz, 2H), 2.44 (q, J=7.3 Hz, 2H), 1.07 (t, J=7.3 Hz, 3H). $^{13}$C-NMR (126 MHz, CDCl$_3$) δ 209.7, 150.4, 148.5, 147.2, 130.5, 129.3, 127.4, 126.7, 123.4, 120.9, 42.2, 36.3, 25.9, 7.9. HRMS (TOF ESI+) m/z calculated for C$_{14}$H$_{16}$NO [M+H]$^+$: 214.1232, found 214.1222.

Example 7

Preparation of Substrates and Compounds Characterization (Table 7)

Scheme 7. General procedure for the synthesis of substrate S46-S48.

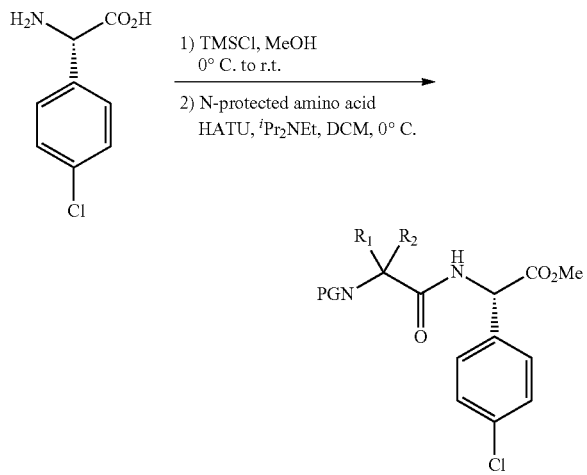

-continued

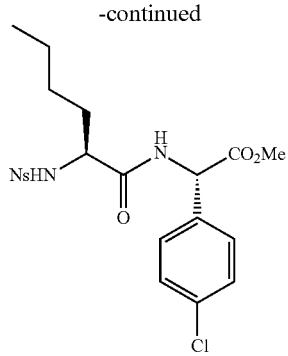

(+)-Methyl (S)-2-(4-chlorophenyl)-2-((S)-2-((4-nitrophenyl)sulfonamido) hexanamido)acetate [(+)-S46]. A 50 mL round bottom flask was charged with a stir bar, (S)-4-chlorophenyl glycine (H—ClPhg-OH, 371 mg, 2.0 mmol, 1.0 equiv.), and MeOH and cooled to 0° C. To the stirred mixture was added TMSCl (1.04 mL, 8.2 mmol, 4.1 equiv.) dropwise at 0° C. and the reaction was stirred at room temperature. After stirring for 24 h, the reaction was concentrated under reduced pressure to afford (S)-4-chlorophenylglycine methyl ester hydrochloride (H—ClPhg-OMe.HCl) as a white solid in quantitative yield. Longer reaction time causes racemization of the amino acid and smaller amount of TMSCl gives lower conversion of the reaction. A 50 mL round bottom flask was charged with a stir bar, H—ClPhg-OMe.HCl, N-nitrobenzenesulfonyl norleucine (Ns-Nle-OH, 633 mg, 2.0 mmol, 1.0 equiv.), O-(7-azabenzotriazol-1-yl)-N,N,N',N'-tetramethyluronium hexafluorophosphate (HATU, 761 mg, 2.0 mmol, 1.0 equiv.) and DCM (10 mL) and cooled to 0° C. To this suspension was added $^i$Pr$_2$NEt (1 mL) dropwise and the reaction was stirred at 0° C. After stirring for 6 h, saturated aqueous NaHCO$_3$ (20 mL) was added then the mixture was separated, and the aqueous layer was extracted with DCM (2×10 mL). The combined organic layers were washed with 10 wt % of aqueous citric acid (20 mL) and the aqueous layer was extracted with DCM (2×10 mL). The combined organic layers were washed with brine (20 mL), dried over Na$_2$SO$_4$, filtered, and concentrated under reduced pressure. The crude mixture was dissolved with a small amount of DCM and concentrated onto silica gel (10 mL) for dry loading onto the column (SiO$_2$, 75 mL) and then eluted with 10%→30% ethyl acetate/hexanes to give a coupling product with a small impurity. The additional column chromatography (SiO2, 75 mL) eluted by CHCl$_3$→5% ethyl acetate/CHCl$_3$ gave 801 mg (1.61 mmol) of Ns-Nle-ClPhg-OMe (+)-S46 as a white solid in 80% yield.

$^1$H-NMR (500 MHz, CDCl$_3$) δ 8.13 (d, J=8.8 Hz, 2H), 7.91 (d, J=8.8 Hz, 2H), 7.27 (d, J=8.5 Hz, 2H), 7.12 (d, J=8.4 Hz, 2H), 6.97 (d, J=7.1 Hz, 1H), 5.84 (br. s, 1H), 5.33 (d, J=7.0 Hz, 1H), 3.88 (t, J=6.7 Hz, 1H), 3.69 (s, 3H), 1.76-1.69 (m, 1H), 1.61-1.55 (m, 1H), 1.31-1.20 (m, 4H), 0.82 (t, J=6.8 Hz, 3H). $^{13}$C-NMR (126 MHz, CDCl$_3$) δ 170.6, 170.1, 150.1, 145.8, 135.1, 134.3, 129.3, 128.5, 128.4, 124.3, 57.0, 55.8, 53.4, 33.5, 27.3, 22.2, 13.9. $[\alpha]_D^{24}$=+124 (c=1.02, CHCl$_3$). HRMS (TOF ESI+) m/z calculated for C$_{21}$H$_{25}$N$_3$O$_7$SCl [M+H]$^+$: 498.1102, found 498.1109.

TABLE 7

Oxidation of aromatic dipeptides.

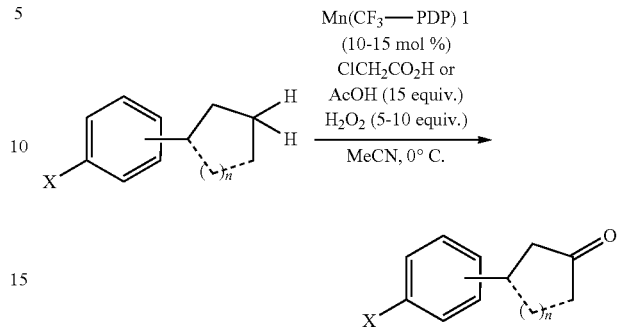

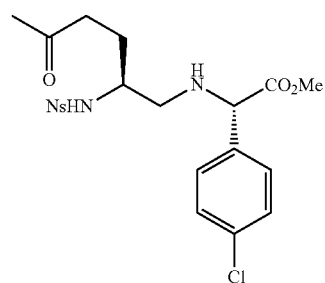

(+)-50, 55%$^a$
with 6$^b$: <5%

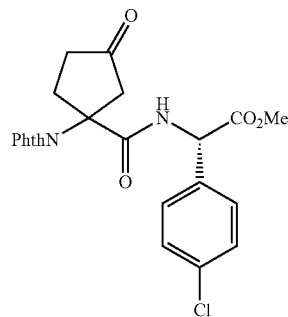

51, 59%

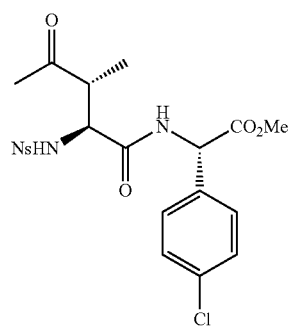

(+)-52, 44%$^{a,c}$
2°:3° = 9:1

TABLE 7-continued

Oxidation of aromatic dipeptides.

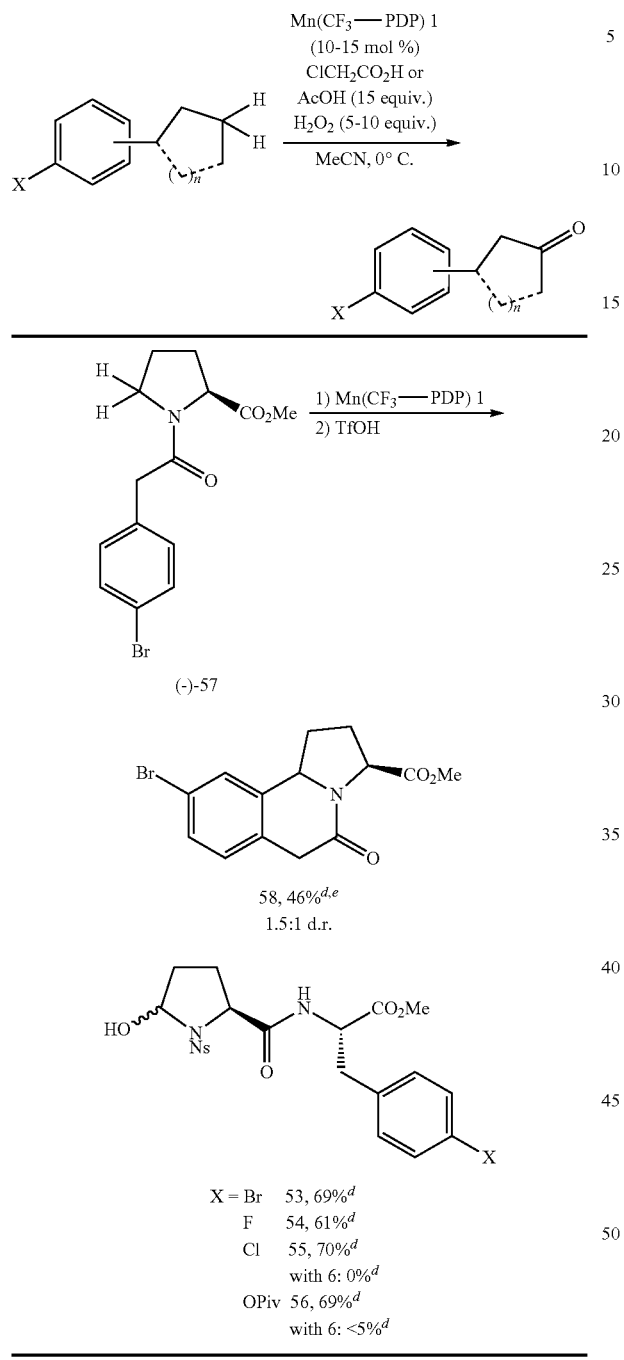

X = Br  53, 69%[d]
F  54, 61%[d]
Cl  55, 70%[d]
  with 6: 0%[d]
OPiv  56, 69%[d]
  with 6: <5%[d]

Method A: single catalyst addition protocol is used unless otherwise noted. Isolated yields are average of three runs with 1. [a]Iterative catalyst addition protocol (method B): substrate (0.3 mmol) with Mn(CF$_3$-PDP) 1 (0.015 mmol) and ClCH$_2$CO$_2$H (4.5 mmol) dissolved in MeCN (0.6 mL) maintained 0° C., a solution of H$_2$O$_2$ (50% wt., 3.0 mmol) in MeCN (3.75 mL, 0.8 M) was added via syringe pump over 3 hours; two additional portions of Mn(CF$_3$-PDP) 1 (0.015 mmol each) in MeCN (0.2 mL each) were added to the reaction after one and two hours. [b]25 mol % Fe(CF$_3$-PDP) 6, slow addition protocol. [c]Starting material recycled 1×. [d]Method A used with AcOH (15 equiv.) and H$_2$O$_2$ (5.0 or 7.5 equiv.) at 0° C. [e]Crude hemiaminal, TfOH (2.0 equiv.), 90° C., 2 hours.

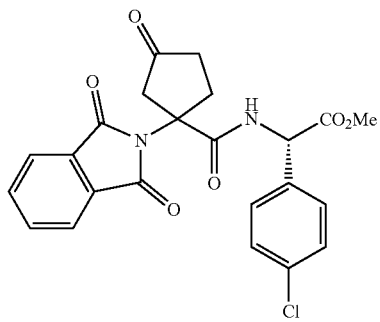 [SMILES: COC(=O)[C@@H](NC(=O)C1(N2C(=O)c3ccccc3C2=O)CCC(=O)C1)c1ccc(Cl)cc1]

(+)-Methyl (S)-2-(4-chlorophenyl)-2-(1-(1,3-dioxoisoindolin-2-yl)cyclopentane-1-carboxamido)-acetate [(+)-S47]. The preparation was performed according to the procedure for (+)-S46. Fleshly prepared H—ClPhg-OMe.HCl (3.0 mmol, 1.0 equiv.) reacted with N-phthaloyl cycloleucine (Phth-CyLeu-OH, 778 mg, 3.0 mmol, 1.0 equiv.), HATU (1.14 g, 3.0 mmol, 1.0 equiv.), and $^i$Pr$_2$NEt (1.5 mL) in DCM (15 mL). The crude mixture was dissolved with a small amount of DCM and concentrated onto SiO$_2$ (10 mL) for dry loading onto the column (SiO$_2$, 150 mL) and then eluted with 20% ethyl acetate/hexane to afford 978 mg (2.22 mmol) of Phth-CyLeu-ClPhg-OMe (+)-S47 as a white solid in 74% yield.

$^1$H-NMR (500 MHz, CDCl$_3$) 7.83-7.79 (m, 2H), 7.73-7.69 (m, 2H), 7.30-7.24 (m, 4H), 6.97 (d, J=6.6 Hz, 1H), 5.48 (d, J=6.5 Hz, 1H), 3.67 (s, 3H), 2.69-2.64 (m, 1H), 2.59-2.56 (m, 2H), 2.50-2.46 (m, 1H), 1.84-1.75 (m, 4H). $^{13}$C-NMR (126 MHz, CDCl$_3$) δ 171.6, 171.0, 169.0, 135.0, 134.5, 134.3, 131.8, 129.2, 128.6, 123.4, 70.9, 56.3, 53.1, 35.8, 35.7, 23.7, 23.7. $[α]_D^{24}$=+98.0 (c=1.01, CHCl$_3$). HRMS (TOF ESI+) m/z calculated for C$_{23}$H$_{22}$N$_2$O$_5$Cl [M+H]$^+$: 411.1217, found 411.1230.

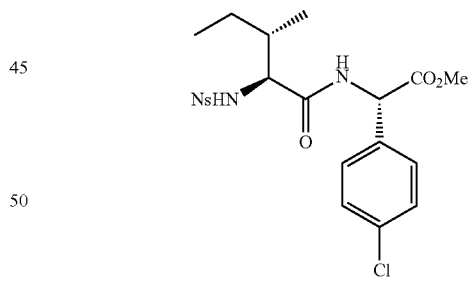

(+)-Methyl methyl (S)-2-(4-chlorophenyl)-2-((2S,3S)-3-methyl-2-((4-nitrophenyl) sulfonamido)pentanamido)acetate [(+)-S48]. The preparation was performed according to the procedure for (+)-S46. Fleshly prepared H-ClPhg-OMe.HCl (3.0 mmol, 1.0 equiv.) reacted with N-nitrobenzenesulfonyl norleucine (Ns-Ile-OH, 949 mg, 3.0 mmol, 1.0 equiv.), HATU (1.14 g, 3.0 mmol, 1.0 equiv.), and $^i$Pr$_2$NEt (1.5 mL) in DCM (15 mL). The crude mixture was dissolved with a small amount of DCM and concentrated onto silica gel (10 mL) for dry loading onto the column (SiO$_2$, 75 mL) and then eluted with 10%→30% ethyl acetate/hexanes to give a coupling product with a small impurity. The additional column chromatography (SiO$_2$, 75 mL) eluted by CHCl$_3$→5% ethyl acetate/CHCl$_3$ gave 1.03 g (2.07 mmol) of Ns-Ile-ClPhg-OMe (+)-S48 as a white solid in 69% yield.

$^1$H-NMR (500 MHz, CDCl$_3$) 8.13-8.10 (m, 2H), 7.91-7.88 (m, 2H), 7.28 (d, J=8.4 Hz, 2H), 7.08 (d, J=8.5 Hz, 2H), 6.66 (br. s, 1H), 5.53 (br. s, 1H), 5.29 (d, J=6.9 Hz, 1H), 3.72-3.69 (m, 1H), 3.69 (s, 3H), 1.79 (dtd, J=9.8, 6.4, 3.6 Hz, 1H), 1.44 (ddp, J=14.9, 7.4, 3.8 Hz, 1H), 1.12 (ddt, J=14.1, 9.4, 7.2 Hz, 1H), 0.94 (d, J=6.8 Hz, 3H), 0.87 (t, J=7.4 Hz, 3H). $^{13}$C-NMR (126 MHz, CDCl$_3$) δ 170.6, 169.5, 150.0, 145.7, 135.1, 134.2, 129.3, 128.5, 128.4, 124.2, 61.6, 55.8, 53.3, 38.6, 24.5, 15.5, 11.3. [α]$_D^{24}$=+136 (c=1.04, CHCl$_3$). HRMS (TOF ESI+) m/z calculated for C$_{21}$H$_{25}$N$_3$O$_7$SCl [M+H]$^+$: 498.1102, found 498.1095.

then eluted with 5% ethyl acetate/CHCl$_3$ to afford 1.74 g (3.22 mmol) of Ns-Pro-BrPhe-OMe (−)-S49 as a white solid in 79% yield.

$^1$H-NMR (500 MHz, CDCl$_3$) 8.38 (d, J=8.8 Hz, 2H), 8.03 (d, J=8.8 Hz, 2H), 7.41 (d, J=8.4 Hz, 2H), 7.05-7.01 (m, 3H), 4.88-4.80 (m, 1H), 4.15-4.13 (m, 1H), 3.78 (s, 3H), 3.40 (ddd, J=10.0, 6.9, 3.3 Hz, 1H), 3.24-3.14 (m, 2H), 3.02 (dd, J=14.0, 7.1 Hz, 1H), 2.09 (dt, J=8.3, 3.2 Hz, 1H), 1.70-1.59 (m, 3H). $^{13}$C-NMR (126 MHz, CDCl$_3$) δ 171.3, 170.2, 150.6, 142.3, 135.0, 131.8, 131.2, 129.2, 124.7, 121.3, 62.4, 53.2, 52.8, 49.7, 37.5, 30.2, 24.5. [α]$_D^{24}$=−48.6 (c=1.03, CHCl$_3$). HRMS (TOF ESI+) m/z calculated for C$_{21}$H$_{23}$N$_3$O$_7$SBr [M+H]$^+$: 540.0440, found 540.0445.

Scheme 8. General procedure for the synthesis of substrate S49-S52.

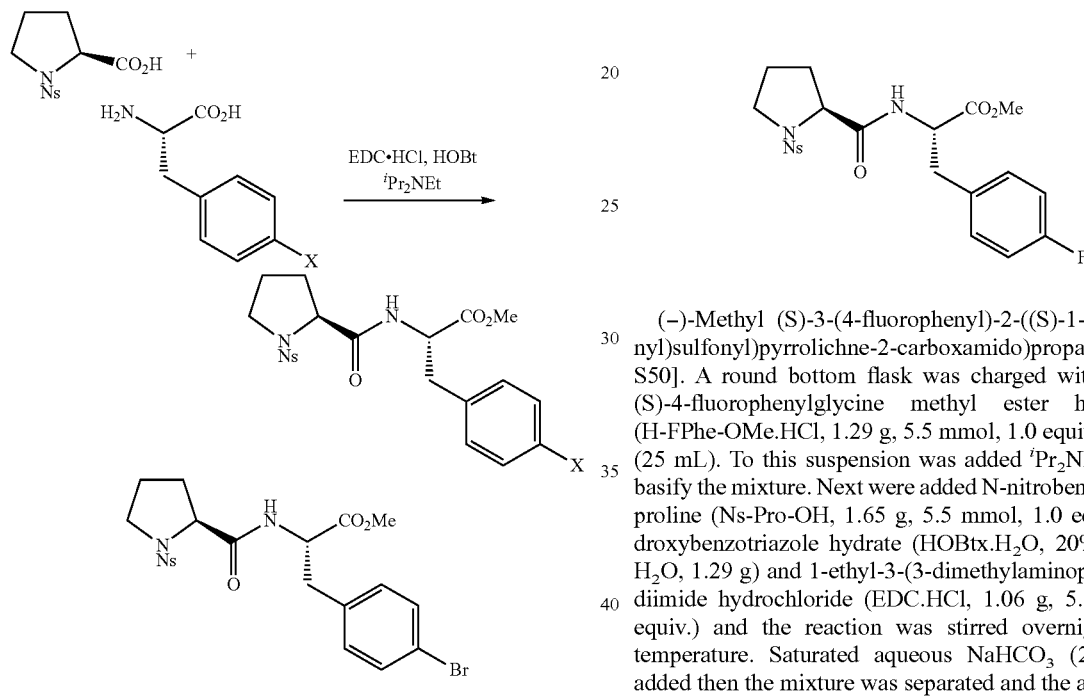

(−)-Methyl (S)-3-(4-bromophenyl)-2-((S)-1-((4-nitrophenyl)sulfonyl)pyrrolichne-2-carboxamido)propanoate [(−)-S49]. A round bottom flask was charged with a stir bar, (S)-4-bromophenylglycine methyl ester hydrochloride (H-BrPhe-OMe.HCl, 1.24 g, 4.1 mmol, 1.0 equiv.) and DCM (25 mL). To this suspension was added $^i$Pr$_2$NEt (2 mL) to basify the mixture. Next were added N-nitrobenzenesulfonyl proline (Ns-Pro-OH, 1.24 g, 4.1 mmol, 1.0 equiv.), N-hydroxybenzotriazole hydrate (HOBt.xH$_2$O, 20% by weight H$_2$O, 944 mg) and 1-ethyl-3-(3-dimethylaminopropyl)carbodiimide hydrochloride (EDC.HCl, 788 mg, 5.0 mmol, 1.0 equiv.) and the reaction was stirred overnight at room temperature. Saturated aqueous NaHCO$_3$ (20 mL) was added then the mixture was separated, and the aqueous layer was extracted with DCM (2×10 mL). The combined organic layers were washed with 10 wt % of aqueous citric acid (20 mL) and the aqueous layer was extracted with DCM (2×10 mL). The combined organic layers were washed with brine (20 mL), dried over Na$_2$SO$_4$, filtered, and concentrated under reduced pressure. The residue was diluted with DCM and concentrated under reduced pressure onto silica gel (~8 mL) for dry loading onto the column (SiO$_2$, 125 mL) and (−)-Methyl (S)-3-(4-fluorophenyl)-2-((S)-1-((4-nitrophenyl)sulfonyl)pyrrolichne-2-carboxamido)propanoate [(−)-S50]. A round bottom flask was charged with a stir bar, (S)-4-fluorophenylglycine methyl ester hydrochloride (H-FPhe-OMe.HCl, 1.29 g, 5.5 mmol, 1.0 equiv.) and DCM (25 mL). To this suspension was added $^i$Pr$_2$NEt (2 mL) to basify the mixture. Next were added N-nitrobenzenesulfonyl proline (Ns-Pro-OH, 1.65 g, 5.5 mmol, 1.0 equiv.), N-hydroxybenzotriazole hydrate (HOBtx.H$_2$O, 20% by weight H$_2$O, 1.29 g) and 1-ethyl-3-(3-dimethylaminopropyl)carbodiimide hydrochloride (EDC.HCl, 1.06 g, 5.5 mmol, 1.0 equiv.) and the reaction was stirred overnight at room temperature. Saturated aqueous NaHCO$_3$ (20 mL) was added then the mixture was separated and the aqueous layer was extracted with DCM (2×10 mL). The combined organic layers were washed with 10 wt % of aqueous citric acid (20 mL) and the aqueous layer was extracted with DCM (2×10 mL). The combined organic layers were washed with brine (20 mL), dried over Na$_2$SO$_4$, filtered, and concentrated under reduced pressure. The residue was diluted with DCM and concentrated under reduced pressure onto silica gel (~8 mL) for dry loading onto the column (SiO$_2$, 125 mL) and then eluted with 5% ethyl acetate/CHCl$_3$ to afford 1.87 g (3.90 mmol) of Ns-Pro-FPhe-OMe (−)-S50 as a white solid in 71% yield.

$^1$H-NMR (500 MHz, CDCl$_3$) 8.38-8.36 (m, 2H), 8.04-8.02 (m, 2H), 7.12-7.09 (m, 2H), 7.04 (d, J=7.9 Hz, 1H), 6.98-6.95 (m, 2H), 4.84-4.80 (m, 1H), 4.15-4.13 (m, 1H), 3.77 (s, 3H), 3.40 (ddt, J=9.9, 6.8, 3.1 Hz, 1H), 3.24-3.15 (m, 2H), 3.04 (dd, J=14.1, 7.1 Hz, 1H), 2.10-2.08 (m, 1H), 1.70-1.59 (m, 3H). $^{13}$C-NMR (126 MHz, CDCl$_3$) δ 171.4, 170.2, 162.1 (d, J=245.6 Hz), 150.6, 142.3, 131.7 (d, J=3.3 Hz), 130.9 (d, J=7.9 Hz), 129.1, 124.7, 115.5 (d, J=21.2 Hz), 62.4, 53.4, 52.7, 49.7, 37.2, 30.2, 24.5. $^{19}$F-NMR (470 MHz, CDCl$_3$) δ −115.8. [α]$_D^{25}$=−69.1 (c=1.02, CHCl$_3$). HRMS (TOF ESI+) m/z calculated for C$_{21}$H$_{23}$N$_3$O$_7$FCl [M+H]$^+$: 480.1241, found 480.1234.

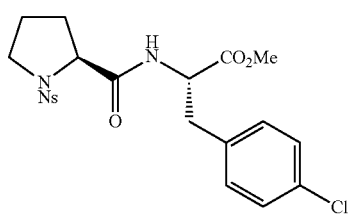

(−)-methyl (S)-3-(4-chlorophenyl)-2((S)-1-((4-nitrophenyl)sulfonyl)pyrrolidine-2-carboxamido)propanoate [(−)-S51]. A round bottom flask was charged with a stir bar, (S)-4-chlorophenylglycine methyl ester hydrochloride (H—ClPhe-OMe.HCl, 1.25 g, 5.0 mmol, 1.0 equiv.) and DCM (25 mL). To this suspension was added $^{i}$Pr$_2$NEt (2 mL) to basify the mixture. Next were added N-nitrobenzenesulfonyl proline (Ns-Pro-OH, 1.50 g, 5.0 mmol, 1.0 equiv.), N-hydroxybenzotriazole hydrate (HOBt.xH$_2$O, 20% by weight H$_2$O, 1.15 g) and 1-ethyl-3-(3-dimethylaminopropyl)carbodiimide hydrochloride (EDC.HCl, 959 mg, 5.0 mmol, 1.0 equiv.) and the reaction was stirred overnight at room temperature. Saturated aqueous NaHCO$_3$ (20 mL) was added then the mixture was separated, and the aqueous layer was extracted with DCM (2×10 mL). The combined organic layers were washed with 10 wt % of aqueous citric acid (20 mL) and the aqueous layer was extracted with DCM (2×10 mL). The combined organic layers were washed with brine (20 mL), dried over Na$_2$SO$_4$, filtered, and concentrated under reduced pressure. The residue was diluted with DCM and concentrated under reduced pressure onto silica gel (~8 mL) for dry loading onto the column (SiO$_2$, 125 mL) and then eluted with 5% ethyl acetate/CHCl$_3$ to afford 2.04 g (4.11 mmol) of Ns-Pro-ClPhe-OMe (−)-S51 as a white solid in 82% yield.

$^1$H-NMR (500 MHz, CDCl$_3$) 8.39-8.36 (m, 2H), 8.04-8.01 (m, 2H), 7.26-7.23 (m, 2H), 7.08-7.04 (m, 3H), 4.85-4.81 (m, 1H), 4.15-4.13 (m, 1H), 3.77 (s, 3H), 3.40 (ddd, J=9.9, 6.8, 3.1 Hz, 1H), 3.25-3.15 (m, 2H), 3.04 (dd, J=14.0, 7.1 Hz, 1H), 2.11-2.07 (m, 1H), 1.70-1.58 (m, 3H). $^{13}$C-NMR (126 MHz, CDCl$_3$) δ 171.4, 170.3, 150.8, 142.8, 134.6, 133.3, 130.8, 129.2, 128.9, 124.6, 62.5, 53.4, 52.7, 49.7, 37.5, 30.2, 24.6. [α]$_D^{25}$=−56.2 (c=0.87, CHCl$_3$). HRMS (TOF ESI+) m/z calculated for C$_{21}$H$_{23}$N$_3$O$_7$SCl [M+H]$^+$: 496.0945, found 496.0941.

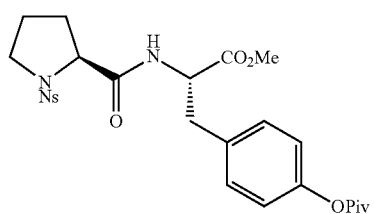

(−)-4-((S)-3-Methoxy-2-((S)-1-((4-nitrophenyl)sulfonyl)pyrrolidine-2-carboxamido)-3-oxopropyl)phenyl pivalate [(−)-S52]. A round bottom flask was charged with a stir bar, (S)-4-(2-amino-3-methoxy-3-oxopropyl)phenyl pivalate trifluoroacetic acid complex (H-OPivPhe-OMe.TFA, 1.18 g, 3.0 mmol, 1.0 equiv.) and DCM (15 mL). To this suspension was added $^{i}$Pr$_2$NEt (0.6 mL) to basify the mixture. Next were added N-nitrobenzenesulfonyl proline (Ns-Pro-OH, 901 mg, 3.0 mmol, 1.0 equiv.), N-hydroxybenzotriazole hydrate (HOBt.xH$_2$O, 20% by weight H$_2$O, 557 mg) and 1-ethyl-3-(3-dimethylaminopropyl)carbodiimide hydrochloride (EDC.HCl, 581 mg, 3.0 mmol, 1.0 equiv.) and the reaction was stirred overnight at room temperature. Saturated aqueous NaHCO$_3$ (20 mL) was added then the mixture was separated, and the aqueous layer was extracted with DCM (2×10 mL). The combined organic layers were washed with 10 wt % of aqueous citric acid (20 mL) and the aqueous layer was extracted with DCM (2×10 mL). The combined organic layers were washed with brine (20 mL), dried over Na$_2$SO$_4$, filtered, and concentrated under reduced pressure. The residue was purified by flash column chromatagraphy (SiO$_2$, 200 mL) and then eluted with 40% ethyl acetate/hexanes→80% ethyl acetate/hexanes, and the collected product was rotvaped with pentane 3 times to remove trace solvent residue to afford 1.01 g (1.80 mmol) of Ns-Pro-OPivPhe-OMe (−)-S52 as a white solid in 60% yield.

$^1$H-NMR (500 MHz, CDCl$_3$) 8.37 (d, J=8.8 Hz, 2H), 8.03 (d, J=8.8 Hz, 2H), 7.14 (d, J=8.4 Hz, 2H), 6.99-6.96 (m, 3H), 4.85 (td, J=7.5, 5.6 Hz, 1H), 4.16-4.14 (m, 1H), 3.78 (s, 3H), 3.38 (ddd, J=10.3, 7.2, 3.3 Hz, 1H), 3.26 (dd, J=14.1, 5.6 Hz, 1H), 3.21-3.18 (m, 1H), 3.06 (dd, J=14.1, 7.2 Hz, 1H), 2.09-2.06 (m, 1H), 1.68-1.56 (m, 3H), 1.33 (s, 9H). $^{13}$C-NMR (126 MHz, CDCl$_3$) δ 177.1, 171.5, 170.2, 150.6, 150.4, 142.6, 133.3, 130.3, 129.2, 124.7, 121.8, 62.4, 53.3, 52.7, 49.8, 39.2, 37.4, 30.3, 27.3, 24.5. [α]$_D^{25}$=−51.0 (c=0.96, CHCl$_3$). HRMS (TOF ESI+) m/z calculated for C$_{26}$H$_{32}$N$_3$O$_9$S [M+H]$^+$: 562.1859, found 562.1861.

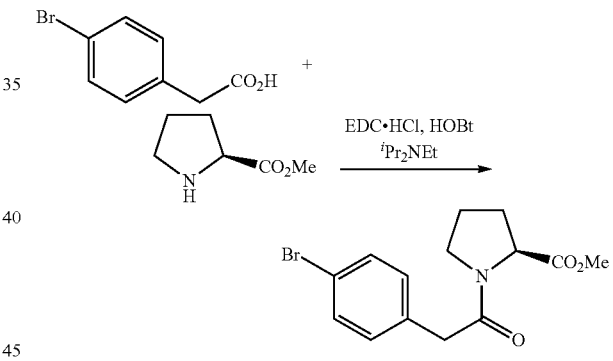

(−)-Methyl (2-(4-bromophenyl)acetyl)-L-prolinate [(−)-57]. The preparation was performed according to the procedure for (+)-S46. 4-Bromophenylacetic acid (1.08 g, 5.0 mmol, 1.0 equiv.) reacted with H-Pro-OMe.HCl (828 mg, 5.0 mmol, 1.0 equiv.), EDC.HCl (959 g, 5.0 mmol, 1.0 equiv.), HOBt.xH$_2$O (1.15 g), and $^{i}$Pr$_2$NEt (2 mL) in DCM (25 mL). The crude mixture was purified by flash column chromatography by using 5% ethyl acetate/CHCl$_3$ as eluent to afford 1.65 g (5.06 mmol) product as a colorless oil in quantitative yield.

A pair of rotamers are observed by NMR. $^1$H-NMR (500 MHz, CDCl$_3$) 7.45-7.42 (m, 2H), 7.17-7.11 (m, 2H), 4.50 (dd, J=8.5, 3.9 Hz) & 4.42 (dd, J=8.5, 2.6 Hz, 1H combined), 3.72 (s) & 3.69 (s, 3H combined), 3.72-3.45 (m, 4H), 2.23-1.89 (m, 4H). $^{13}$C-NMR (126 MHz, CDCl$_3$) δ 172.8, 169.3, 133.5, 131.8 & 131.7, 131.0 & 130.9, 120.9, 59.7 & 59.0, 52.7 & 52.4, 47.4 & 46.8, 41.3 & 41.1, 31.6 & 29.3, 25.0 & 22.6. [α]$_D^{25}$=−53.8 (c=1.02, CHCl$_3$). HRMS (TOF ESI+) m/z calculated for C$_{14}$H$_{17}$NO$_3$Br [M+H]$^+$: 326.0392, found 326.0392.

General Oxidation Procedure for Proline-Containing Peptides (Table 7)

General Method D: Oxidation of Proline-Containing Peptides. A 40 mL vial was charged with substrate (0.2 mmol, 1.0 equiv.), catalyst (0.02 mmol, 10 mol %), AcOH (172 µL, 3.0 mmol, 15.0 equiv.), MeCN (0.4 mL, 0.50 M), a stir bar and sealed with a screw cap incorporated with PTFE/Silicone septa. The vial was cooled to □36° C. with 1,2-dichloroethane/dry ice bath. A separate solution of $H_2O_2$ [(56.7 µL, 1.0 mmol, 5.0 equiv.), 50 wt % in $H_2O$, purchased from Sigma-Aldrich] in MeCN (2.5 mL) was loaded into a 3 mL syringe fitted with a 25 G needle and was added dropwise to the stirring reaction over 1 hour via a syringe pump (2.5 mL/h addition rate). Upon completion, the reaction mixture was allowed to warm to room temperature and concentrated in vacuo. The residue was dissolved with DCM (20 mL) and saturated aqueous $NaHCO_3$ (20 mL). The mixture was separated, and the aqueous layer was extracted with DCM (2×10 mL). The combined organic layers were washed with 0.1 M ethylenediaminetetraacetic acid (EDTA) disodium salt solution (30 mL) and the aqueous layer was extracted with DCM (2×10 mL). The combined organic layers were dried over $Na_2SO_4$, filtered and concentrated in vacuo. The crude mixture was dissolved with small amount of DCM and concentrated onto silica gel (~2 mL) for dry loading onto the column ($SiO_2$, 25 mL) and then eluted with ethyl acetate/$CHCl_3$ to give a desired hemiaminal. Recovered starting material was determined as $^1H$ NMR yield with nitrobenzene as an internal standard after the column chromatography.

C–H Oxidation of Substrates and Products Characterization (Table 7)

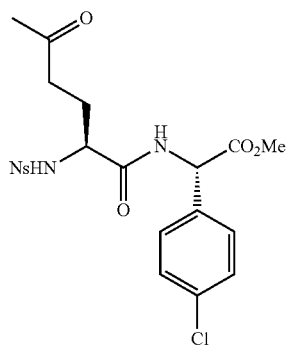

(+)-Methyl (S)-2-(4-chlorophenyl)-2-((S)-2-((4-nitrophenyl)sulfonamido)-5-oxohexanamido)acetate [(+)-50]. The reaction was run with General Method B: Iterative Catalyst Addition Protocol: Ns-Nle-ClPhg-OMe (+)-S46 (99.6 mg, 0.200 mmol, 1.0 equiv), (R,R)—Mn($CF_3$-PDP) (3 times addition of 13.6 mg, 0.010 mmol, 5 mol % batch; 15 mol % in total), $ClCH_2CO_2H$ (284 mg, 3.00 mmol, 15.0 equiv.), 50% wt. $H_2O_2$ (136 mg, 2.0 mmol, 10.0 equiv.), MeCN (0.4 mL in 40 mL vial, 2.5 mL with oxidant). The reaction was run at 0° C. with ice bath. The reaction was worked up with 9 mL saturated $NaHCO_3$ and DCM as described in General Method B. The combined organic layer was additionally washed with 30 mL 0.1M $Na_2EDTA$ solution and dried with $Na_2SO_4$. The crude mixture was concentrated and redissolved with small amount of DCM and concentrated onto silica gel (2 mL) for dry loading onto the column ($SiO_2$, 30 mL) and then eluted with 10%→20% ethyl acetate/$CHCl_3$ to afford a product as a white solid. Run 1: (56.2 mg, 0.110 mmol, 54.9% yield), (13.6 mg, 0.027 mmol, 13.7% rsm). Run 2: (56.4 mg, 0.110 mmol, 55.1% yield), (14.7 mg, 0.030 mmol, 14.8% rsm). Run 3: (57.1 mg, 0.112 mmol, 55.8% yield), (15.4 mg, 0.031 mmol, 15.5% rsm). Average: 55.3% yield±0.5%, 14.7% rsm±0.9%.

$^1$H-NMR (500 MHz, $CDCl_3$) δ 8.13 (d, J=8.8 Hz, 2H), 7.89 (d, J=8.8 Hz, 2H), 7.38 (d, J=7.2 Hz, 1H), 7.27 (d, J=7.7 Hz, 2H), 7.09 (d, J=8.1 Hz, 2H), 6.11 (d, J=8.4 Hz, 1H), 5.27 (d, J=7.1 Hz, 1H), 3.88 (td, J=8.8, 3.8 Hz, 1H), 3.68 (s, 3H), 2.84 (ddd, J=19.0, 9.6, 4.0 Hz, 1H), 2.60 (ddd, J=18.9, 6.3, 4.1 Hz, 1H), 2.19 (s, 3H), 2.06 (ddt, J=13.9, 9.4, 4.0 Hz, 1H), 1.75 (dddd, J=13.9, 9.8, 6.2, 4.1 Hz, 1H). $^{13}$C-NMR (126 MHz, $CDCl_3$) δ 210.0, 170.4, 169.7, 150.1, 145.2, 135.1, 134.2, 129.3, 128.5, 128.5, 124.3, 56.0, 55.6, 53.3, 38.9, 30.3, 28.2. $[α]_D^{24}$=+146 (c=1.07, $CHCl_3$). HRMS (TOF ESI+) m/z calculated for $C_{21}H_{22}N_3O_8SClNa$ $[M+Na]^+$: 534.0714, found 534.0729.

Condition with Fe($CF_3$-PDP): The reaction was conducted in slow addition protocol, same as Entry 10 of Table 3. In a 40 mL vial was charged with Ns-Nle-ClPhg-OMe (+)-S46 (99.6 mg, 0.200 mmol, 1.0 equiv), AcOH (60.1 mg, 1.0 mmol, 5.0 equiv.), MeCN (0.40 mL) and a stir bar. A 1 mL syringe was charged with a solution of (R,R)—Fe($CF_3$-PDP) catalyst (67.8 mg, 0.050 mmol, 0.25 equiv.) in MeCN (0.25 mL). A 10 mL syringe was charged with a solution of $H_2O_2$ (122.4 mg, 1.8 mmol, 9.0 equiv.) in MeCN (2.5 mL). Both syringes were fitted with 25 G needles and the solution was added dropwise via syringe pump over 1 hour. Upon completion of addition, the reaction was concentrated in vacuo to a minimum amount of MeCN. The crude mixture was concentrated and redissolved with small amount of DCM and concentrated onto silica gel (2 mL) for dry loading onto the column ($SiO_2$, 30 mL) and then eluted with 10%→20% ethyl acetate/$CHCl_3$ and the result was analyzed by quantitative $^1$H NMR with nitrobenzene as internal standard. Result: <5% yield, <5% rsm.

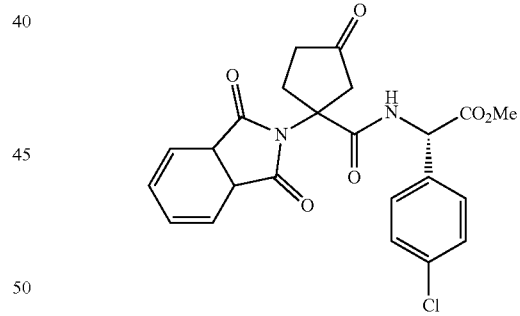

Methyl (2S)-2-(4-chlorophenyl)-2-(1-(1,3-dioxoisoindolin-2-yl)-3-oxocyclopentane-1-carboxamido)acetate [51]. The reaction was run with General Method A: Single Catalyst Addition Protocol: Phth-CyLeu-ClPhg-OMe (+)-S47 (88.2 mg, 0.200 mmol, 1.0 equiv), (R,R)—Mn($CF_3$-PDP) (27.1 mg, 0.020 mmol, 10 mol %), $ClCH_2CO_2H$ (284 mg, 3.00 mmol, 15.0 equiv.), 50% wt. $H_2O_2$ (136 mg, 2.0 mmol, 10.0 equiv.), MeCN (0.4 mL in 40 mL vial, 2.5 mL with oxidant). The reaction was run at 0° C. with ice bath. The reaction was worked up with 9 mL saturated $NaHCO_3$ and DCM as described in General Method A. The combined organic layer was additionally washed with 30 mL 0.1M $Na_2EDTA$ solution and dried with $Na_2SO_4$. The crude mixture was concentrated and redissolved with small amount of DCM and concentrated onto silica gel (2 mL) for dry loading onto the column (SiO$_2$, 30 mL) and then eluted with 10%→20% ethyl acetate/CHCl$_3$ to afford a product as a white solid. Run 1: (52.8 mg, 0.116 mmol, 58.0% yield), <10% rsm. Run 2: (54.3 mg, 0.119 mmol, 59.7% yield), <10% rsm. Run 3: (54.1 mg, 0.119 mmol, 59.5% yield), <10% rsm. Average: 59.1% yield±0.9%, <10% rsm.

The product is a mixture of diastereomers with ~1:1 diastereomeric ratio. $^1$H-NMR (500 MHz, CDCl$_3$) δ 7.88-7.85 (m, 2H), 7.80-7.77 (m, 2H), 7.32-7.23 (m, 3H), 7.20 (d, J=8.5 Hz, 1H), 7.10 (d, J=6.6 Hz) & 7.05 (d, J=6.5 Hz, 1H combined), 5.47-5.44 (m, 1H), 3.68 (s) & 3.65 (s, 3H combined), 3.48-3.36 (m, 1H), 3.14-3.09 (m) & 2.96-2.87 (m, 3H combined), 2.47-2.33 (m, 2H). $^{13}$C-NMR (126 MHz, CDCl$_3$) δ 212.9 & 212.9, 170.7 & 170.7, 170.3 & 170.1, 168.6, 135.0, 134.8 & 134.8, 134.7 & 134.3, 131.4, 129.4 & 129.3, 128.6 & 128.6, 123.9, 66.6, 56.5 & 56.3, 53.3 & 53.3, 47.8 & 47.7, 36.0 & 36.0, 32.1 & 32.1. HRMS (TOF ESI+) m/z calculated for C$_{23}$H$_{20}$N$_2$O$_6$Cl [M+H]$^+$: 455.1010, found 455.1028.

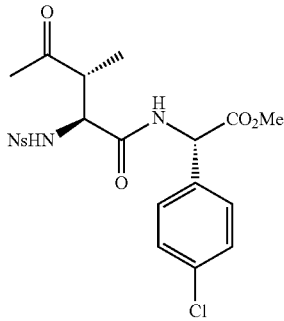

(+)-Methyl (S)-2-(4-chlorophenyl)-2-((2S,3R)-3-methyl-2-((4-nitrophenyl) sulfonamido)-4-oxopentanamido)acetate [(+)-52]. The reaction was run with General Method B: Iterative Catalyst Addition Protocol with recycle the recovered starting material once: Ns-Ile-CPhg-OMe (+)-S48 (99.6 mg, 0.200 mmol, 1.0 equiv), (R,R)—Mn(CF$_3$-PDP) (3 times addition of 13.6 mg, 0.010 mmol, 5 mol % batch; 15 mol % in total), ClCH$_2$CO$_2$H (284 mg, 3.00 mmol, 15.0 equiv.), 50% wt. H$_2$O$_2$ (136 mg, 2.0 mmol, 10.0 equiv.), MeCN (0.4 mL in 40 mL vial, 2.5 mL with oxidant). The reaction was run at 0° C. with ice bath. The reaction was worked up with 9 mL saturated NaHCO$_3$ and DCM as described in General Method B. The combined organic layer was additionally washed with 30 mL 0.1M Na$_2$EDTA solution and dried with Na$_2$SO$_4$. The crude mixture was concentrated and redissolved with small amount of DCM and concentrated onto silica gel (2 mL) for dry loading onto the column (SiO$_2$, 30 mL) and then eluted with 10% ethyl acetate/CHCl$_3$ to afford a product as a white solid and recovered starting material. The recovered starting material was recycled to the oxidation with the same protocol and the products from both cycles are combined.

Run 1: cycle 1: (35.0 mg, 0.068 mmol, 34.2% yield), (<5% yield of 3° alcohol was also observed), (34.2 mg, 0.069 mmol, 34.3% rsm); cycle 2: (9.5 mg, 0.019 mmol, 27.0% yield), (13.0 mg, 0.026 mmol, 38.0% rsm); overall: (44.5 mg, 0.087 mmol, 43.5% yield), (<5% yield of 3° alcohol), (13.0 mg, 0.026 mmol, 13.1% rsm). Run 2: (35.5 mg, 0.069 mmol, 34.7% yield), (<5% yield of 3° alcohol was also observed), (34.8 mg, 0.070 mmol, 34.9% rsm); cycle 2: (9.6 mg, 0.019 mmol, 26.8% yield), (14.1 mg, 0.028 mmol, 40.5% rsm); overall: (45.1 mg, 0.088 mmol, 44.0% yield), (<5% yield of 3° alcohol), (14.1 mg, 0.028 mmol, 14.2% rsm). Run 3: (35.4 mg, 0.069 mmol, 34.6% yield), (<5% yield of 3° alcohol was also observed), (34.9 mg, 0.070 mmol, 35.0% rsm); cycle 2: (10.4 mg, 0.020 mmol, 29.1% yield), (13.6 mg, 0.027 mmol, 39.2% rsm); overall: (45.8 mg, 0.089 mmol, 44.7% yield), (<5% yield of 3° alcohol), (13.6 mg, 0.027 mmol, 13.7% rsm). Average: 44.1% yield±0.6%, <5% 3° alcohol, 9:1 K:A ratio, 13.7% rsm±0.6%.

$^1$H-NMR (500 MHz, DMSO-d$_6$) δ 9.06 (d, J=7.1 Hz, 1H), 8.69 (d, J=9.5 Hz, 1H), 8.13 (d, J=8.9 Hz, 2H), 7.83 (d, J=8.8 Hz, 2H), 7.43 (d, J=8.5 Hz, 2H), 7.24 (d, J=8.5 Hz, 2H), 5.00 (d, J=7.0 Hz, 1H), 4.19 (t, J=10.0 Hz, 1H), 3.54 (s, 3H), 2.80-2.74 (m, 1H), 2.14 (s, 3H), 1.01 (d, J=7.1 Hz, 3H). $^{13}$C-NMR (126 MHz, DMSO-d$_6$) δ 208.8, 170.2, 168.5, 149.2, 146.2, 134.1, 133.2, 129.5, 128.6, 128.0, 123.9, 57.4, 55.3, 52.4, 48.6, 28.8, 13.1. [α]$_D^{24}$=+164 (c=0.97, CHCl$_3$). HRMS (TOF ESI+) m/z calculated for C$_{21}$H$_{23}$N$_3$O$_8$SCl [M+H]$^+$: 512.0894, found 512.0912.

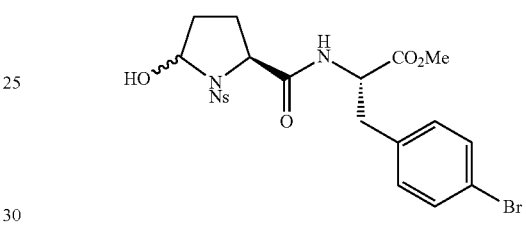

Methyl (2S)-3-(4-bromophenyl)-2-((2S)-5-hydroxy-1-((4-nitrophenyl)sulfonyl) pyrrolidine-2-carboxamido)propanoate [53]. The reaction was run with General Method D: Oxidation of Proline-Containing Peptides: Ns-Pro-BrPhe-OMe (−)-S49 (108 mg, 0.200 mmol, 1.0 equiv), (S,S)—Mn(CF$_3$-PDP) (27.1 mg, 0.020 mmol, 10 mol %), AcOH (172 µL, 3.00 mmol, 15.0 equiv.), 50% wt. H$_2$O$_2$ (68 mg, 1.0 mmol, 5.0 equiv.), MeCN (0.4 mL in 40 mL vial, 2.5 mL with oxidant). The reaction was run at −36° C. with dry ice/1,2-dichloroethane bath. The reaction was worked up with 9 mL saturated NaHCO$_3$ and DCM. The combined organic layer was additionally washed with 30 mL 0.1M Na$_2$EDTA solution and dried with Na$_2$SO$_4$. The crude mixture was concentrated and redissolved with small amount of DCM and concentrated onto silica gel (2 mL) for dry loading onto the column (SiO$_2$, 30 mL) and then eluted with 10% ethyl acetate/CHCl$_3$ to afford a product as a colorless oil and recovered starting material.

Run 1: (78.7 mg, 0.141 mmol, 70.7% yield), (9.2 mg, 0.017 mmol, 8.5% rsm). Run 2: (76.2 mg, 0.137 mmol, 68.5% yield), (9.5 mg, 0.018 mmol, 8.8% rsm). Run 3: (75.4 mg, 0.136 mmol, 67.8% yield), (8.2 mg, 0.015 mmol, 7.6% rsm). Average: 69.0% yield±1.5%, 8.3% rsm 0.6%.

The product is isolated as a mixture of diastereomers approximately 5:1 ratio. $^1$H-NMR (500 MHz, CDCl$_3$) δ 8.32-8.28 (m, 2H), 8.06-8.00 (m, 2H), 7.45-7.38 (m, 2H), 7.19-7.10 (m, 1H), 7.08-7.02 (m, 2H), 5.63 (dt, J=8.8, 4.2 Hz) & 5.54 (d, J=3.8 Hz, 1H combined), 4.91-4.72 (m, 1H), 4.26-4.19 (m, 2H), 3.76-3.71 (m, 3H), 3.14-3.10 (m, 1H), 3.01-2.96 (m, 1H), 2.07-1.76 (m, 4H). $^{13}$C-NMR (126 MHz, CDCl$_3$) δ 171.4, 171.3, 171.1, 170.4, 150.5, 150.3, 144.9, 144.0, 134.9, 134.9, 131.9, 131.8, 131.2, 131.2, 129.3, 128.8, 124.6, 124.2, 123.8, 121.3, 86.2, 85.1, 62.5, 61.6, 53.4, 53.3, 52.8, 52.7, 37.4, 37.3, 33.3, 32.9, 29.2, 28.7. HRMS (TOF ESI−) m/z calculated for C$_{21}$H$_{21}$N$_3$O$_8$SBr [M−H]$^-$: 554.0233, found 554.0225.

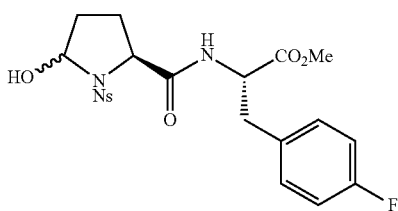

Methyl (2S)-3-(4-fluorophenyl)-2-((2S)-5-hydroxy-1-((4-nitrophenyl)sulfonyl) pyrrolidine-2-carboxamido)propanoate [54]. The reaction was run with General Method D: Oxidation of Proline-Containing Peptides: Ns-Pro-FPhe-OMe (−)-S50 (95.9 mg, 0.200 mmol, 1.0 equiv), (S,S)—Mn(CF$_3$-PDP) (27.1 mg, 0.020 mmol, 10 mol %), AcOH (172 μL, 3.00 mmol, 15.0 equiv.), 50% wt. H$_2$O$_2$ (68 mg, 1.0 mmol, 5.0 equiv.), MeCN (0.4 mL in 40 mL vial, 2.5 mL with oxidant). The reaction was run at −36° C. with dry ice/1,2-dichloroethane bath. The reaction was worked up with 9 mL saturated NaHCO$_3$ and DCM. The combined organic layer was additionally washed with 30 mL 0.1M Na$_2$EDTA solution and dried with Na$_2$SO$_4$. The crude mixture was concentrated and redissolved with small amount of DCM and concentrated onto silica gel (2 mL) for dry loading onto the column (SiO$_2$, 30 mL) and then eluted with 10% ethyl acetate/CHCl$_3$ to afford a product as a colorless oil and recovered starting material.

Run 1: (61.5 mg, 0.124 mmol, 62.1% yield), (5.8 mg, 0.012 mmol, 6.0% rsm). Run 2: (59.9 mg, 0.121 mmol, 60.4% yield), (3.7 mg, 0.007 mmol, 3.9% rsm). Run 3: (60.7 mg, 0.123 mmol, 61.3% yield), (6.2 mg, 0.013 mmol, 6.5% rsm). Average: 61.3% yield±0.9%, 5.5% rsm 1.4%.

The product is isolated as a mixture of diastereomers approximately 5:1 ratio. $^1$H-NMR (500 MHz, CDCl$_3$) δ 8.32-8.28 (m, 2H), 8.08-8.00 (m, 2H), 7.22-7.07 (m, 3H), 6.99-6.96 (m, 2H), 5.62 (m) & 5.54 (m, 1H combined), 4.74 (q, J=6.9 Hz, 1H), 4.27-4.18 (m, 1H), 3.94 (br. s) & 3.77 (br. s, 1H combined), 3.74 (s) & 3.72 (s, 3H combined), 3.14 (dd, J=14.2, 5.4 Hz, 1H), 3.01 (dd, J=14.1, 6.9 Hz, 1H), 2.09-1.74 (m, 4H). $^{13}$C-NMR (126 MHz, CDCl$_3$) δ 171.4, 170.9, 162.3 (d, J=245.8 Hz), 150.7, 144.4, 131.64-131.62 (m, 1C), 131.1 (d, J=8.0 Hz), 129.3 & 128.9, 124.7 & 124.3, 115.71 (d, J=21.0 Hz), 86.4 & 85.2, 62.7 & 61.9, 53.7, 52.7, 37.4, 33.4 & 32.9, 29.3 & 28.8. $^{19}$F-NMR (470 MHz, CDCl$_3$) δ −115.6. HRMS (TOF ESI+) m/z calculated for C$_{21}$H$_{22}$N$_3$O$_8$SNaF [M+H]$^+$: 518.1009, found 518.0995.

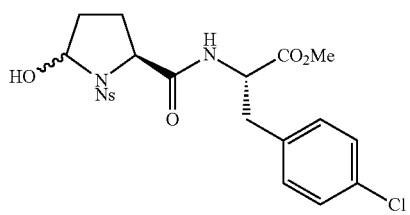

Methyl (2S)-3-(4-chlorophenyl)-2-((2S)-5-hydroxy-1-((4-nitrophenyl)sulfonyl) pyrrolidine-2-carboxamido)propanoate [55]. The reaction was run with General Method D: Oxidation of Proline-Containing Peptides: Ns-Pro-ClPhe-OMe (−)-S51 (99.2 mg, 0.200 mmol, 1.0 equiv), (S,S)—Mn(CF$_3$-PDP) (27.1 mg, 0.020 mmol, 10 mol %), AcOH (172 μL, 3.00 mmol, 15.0 equiv.), 50% wt. H$_2$O$_2$ (68 mg, 1.0 mmol, 5.0 equiv.), MeCN (0.4 mL in 40 mL vial, 2.5 mL with oxidant). The reaction was run at −36° C. with dry ice/1,2-dichloroethane bath. The reaction was worked up with 9 mL saturated NaHCO$_3$ and DCM. The combined organic layer was additionally washed with 30 mL 0.1M Na$_2$EDTA solution and dried with Na$_2$SO$_4$. The crude mixture was concentrated and redissolved with small amount of DCM and concentrated onto silica gel (2 mL) for dry loading onto the column (SiO$_2$, 30 mL) and then eluted with 10% ethyl acetate/CHCl$_3$ to afford a product as a colorless oil and recovered starting material.

Run 1: (69.3 mg, 0.135 mmol, 67.7% yield), (11.0 mg, 0.022 mmol, 11.1% rsm). Run 2: (73.9 mg, 0.144 mmol, 72.2% yield), (9.8 mg, 0.020 mmol, 9.9% rsm). Run 3: (71.5 mg, 0.140 mmol, 69.8% yield), (9.7 mg, 0.020 mmol, 9.8% rsm). Average: 69.9% yield±2.3%, 10.3% rsm±0.7%.

The product is isolated as a mixture of diastereomers approximately 5:1 ratio. $^1$H-NMR (500 MHz, CDCl$_3$) δ 8.33-8.29 (m, 2H), 8.06-7.99 (m, 2H), 7.27-7.25 (m, 2H), 7.18-7.06 (m, 3H), 5.64-5.61 (m) & 5.54-5.52 (m, 1H combined), 4.78-4.73 (m, 1H), 4.27-4.18 (m, 1H), 4.01 (d, J=5.4 Hz, 1H), 3.77-3.72 (m, 3H), 3.15 (ddd, J=14.0, 11.6, 5.4 Hz, 1H), 3.01 (dd, J=14.1, 7.0 Hz, 1H), 2.08-1.76 (m, 4H). $^{13}$C-NMR (126 MHz, CDCl$_3$) δ 171.4, 171.3, 171.0, 170.3, 150.5, 150.4, 144.9, 144.1, 134.4, 134.3, 133.3, 133.3, 130.9, 130.8, 129.3, 129.1, 128.9, 128.8, 124.6, 124.3, 86.3, 85.1, 62.6, 61.7, 53.5, 53.4, 52.8, 52.7, 37.4, 37.3, 33.3, 32.8, 29.2, 28.7. HRMS (TOF ESI−) m/z calculated for C$_{21}$H$_{21}$N$_3$O$_8$SCl [M−H]$^-$: 510.0738, found 510.0729.

Other Oxidation Conditions for Substrate S51:

Condition with Fe(CF$_3$-PDP): The reaction was proceeded with the same procedure by replacing (S,S)—Mn(CF$_3$-PDP) (27.1 mg, 0.020 mmol, 10 mol %) with (S,S)—Fe(CF$_3$-PDP) (27.1 mg, 0.020 mmol, 10 mol %). Run 1: 0% yield, (20.0 mg, 0.040 mmol, 20.2% rsm). Condition with Fe(PDP): The reaction was proceeded with the standard iterative addition protocol with (S,S)—Fe(PDP). Run 1: trace yield, (18.5 mg, 0.037 mmol, 18.7% rsm).

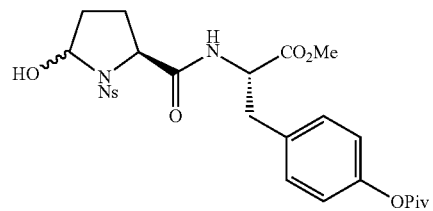

4-((2S)-2-((2S)-5-Hydroxy-1-((4-nitrophenyl)sulfonyl) pyrrolidine-2-carboxamido)-3-methoxy-3-oxopropyl)phenyl pivalate [56]. The reaction was run with General Method D: Oxidation of Proline-Containing Peptides with slightly modifications: Ns-Pro-OPivPhe-OMe (−)-S52 (112.3 mg, 0.200 mmol, 1.0 equiv), (S,S)—Mn(CF$_3$-PDP) (27.1 mg, 0.020 mmol, 10 mol %), AcOH (172 μL, 3.00 mmol, 15.0 equiv.), 50% wt. H$_2$O$_2$ (102 mg, 1.5 mmol, 7.5 equiv.), MeCN (0.4 mL in 40 mL vial, 2.5 mL with oxidant). The hydrogen peroxide solution was added over 3 hours at −36° C. with dry ice/1,2-dichloroethane bath. The reaction was worked up with 9 mL saturated NaHCO$_3$ and DCM. The combined organic layer was additionally washed with 30 mL 0.1M Na$_2$EDTA solution and dried with Na$_2$SO$_4$. The crude mixture was concentrated and purified with column chromatography (SiO$_2$, 100 mL) and then eluted with 20% ethyl acetate/CHCl₃→40% ethyl acetate/CHCl₃ to afford a product as a white solid and recovered starting material.

Run 1: (82.6 mg, 0.143 mmol, 71.5% yield), (31.6 mg, 0.056 mmol, 28.1% rsm). Run 2: (78.5 mg, 0.136 mmol, 68.0% yield), (32.8 mg, 0.058 mmol, 29.2% rsm). Run 3: (79.1 mg, 0.137 mmol, 68.5% yield), (31.2 mg, 0.056 mmol, 27.8% rsm). Average: 69.3% yield±1.9%, 28.4% rsm±0.7%.

The product is isolated as a mixture of diastereomers approximately 5:1 ratio. $^1$H-NMR (500 MHz, CDCl₃) δ 8.32-8.28 (m, 2H), 8.07-7.98 (m, 2H), 7.18-7.12 (m, 2H), 7.04-6.92 (m, 3H), 5.61-5.53 (m, 1H), 4.92-4.71 (m, 1H), 4.22 (br. s, 1H), 3.90-3.72 (m, 4H), 3.22-3.15 (m, 1H), 3.08-3.00 (m, 1H), 2.08-1.66 (m, 4H), 1.34 (s, 9H). $^{13}$C-NMR (126 MHz, CDCl₃) δ 177.7, 171.4, 171.1, 150.3, 150.2, 144.4, 133.2, 130.4 & 130.2, 129.3 & 128.8, 124.5 & 124.2, 121.9 & 121.8, 86.1, 62.4, 53.2, 52.6, 39.1, 37.1, 33.5, 29.2, 27.1. HRMS (TOF ESI−) m/z calculated for C₂₆H₃₀N₃O₁₀S [M−H]⁻: 576.1657, found 576.1652.

Condition with Fe(CF₃-PDP): The reaction was proceeded with the same procedure by replacing (S,S)—Mn(CF₃-PDP) (27.1 mg, 0.020 mmol, 10 mol %) with (S,S)—Fe(CF₃-PDP) (27.1 mg, 0.020 mmol, 10 mol %). Run 1: <5% yield, (30.2 mg, 0.054 mmol, 26.9% rsm).

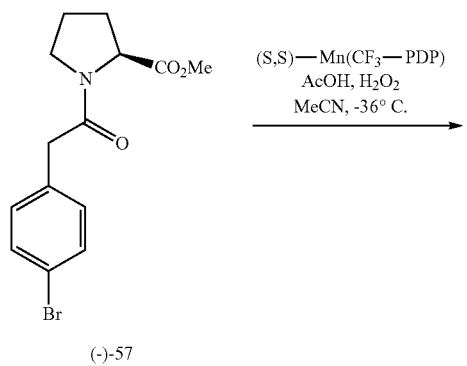

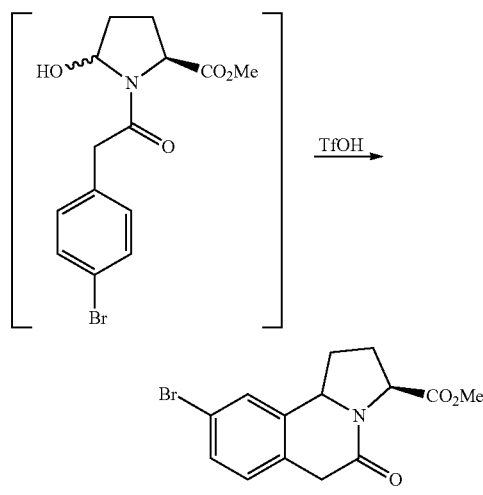

Methyl (3S)-9-bromo-5-oxo-1,2,3,5,6,10b-hexahydropyrrolo[2,1-a]isoquinoline-3-carboxylate [58]. The reaction was run with General Method D: Oxidation of Proline-Containing Peptides: methyl (2-(4-bromophenyl)acetyl)-L-prolinate (−)-57 (65.2 mg, 0.200 mmol, 1.0 equiv), (S,S)—Mn(CF₃-PDP) (27.1 mg, 0.020 mmol, 10 mol %), AcOH (172 μL, 3.00 mmol, 15.0 equiv.), 50% wt. H₂O₂ (68 mg, 1.0 mmol, 5.0 equiv.), MeCN (0.4 mL in 40 mL vial, 2.5 mL with oxidant). The reaction was run at −36° C. with 1,2-dichloroethane/dry ice bath. After the completion of oxidation, the mixture was filer through a silica plug (SiO₂, 15 mL) with ethyl acetate (150 mL) and the resulting solution was concentrated in vacuo. The crude compound was transferred into a new 40 mL vial with DCM and dried on high vacuum for 2 hours. In a sealed tube charged with a stir bar and 1 mL anhydrous 1,2-dichloroethane and TfOH (177 μL, 2.0 equiv.) was added under Ar. The crude hemiaminal was dissolved in 2 mL anhydrous 1,2-dichloroethane under Ar and transferred into the sealed tube dropwise. The hemiaminal vial was rinsed with another 2 mL anhydrous 1,2-dichloroethane and transferred into the sealed tube. The reaction was heated at 90° C. for 2 hours. After the reaction completed the mixture was diluted with water and basified with sat. NaHCO₃. The aqueous layer was extracted with DCM×3. The combined organic layer dried with Na₂SO₄, filtered and concentrated. The crude mixture was purified by column chromatography (SiO₂, 25 mL) and elueted with pure CHCl₃→20% ethyl acetate/CHCl₃ to give product as a colorless oil.

Run 1: 30.1 mg, 0.093 mmol, 46.4% yield. Run 2: 28.7 mg, 0.089 mmol, 44.3% yield. Run 3: 30.8 mg, 0.095 mmol, 47.5% yield. Average: 46.1% yield±1.6%.

The product is isolated as a mixture of diastereomers approximately 1.5:1 ratio. $^1$H-NMR (500 MHz, CDCl₃) δ 7.37 (dd, J=8.1, 1.6 Hz, 1H), 7.30-7.27 (m, 1H), 7.06-7.03 (m, 1H), 4.88-4.84 (m) & 4.70 (dd, J=11.0, 5.9 Hz, 1H combined), 4.57 (d, J=9.3 Hz) & 4.51 (t, J=8.4 Hz, 1H combined), 3.76 (s) & 3.64 (s, 3H combined), 3.66-3.48 (m, 2H), 2.65-2.31 (m, 2H), 2.22-1.88 (m, 2H). $^{13}$C-NMR (126 MHz, CDCl₃) δ 172.6 & 171.8, 167.5 & 166.9, 138.3 & 137.5, 132.0 & 131.4, 130.9 & 130.8, 129.14 & 129.06, 127.5 & 127.1, 120.9, 60.1, 59.9, 58.2, 57.8, 52.7, 52.6, 38.7, 38.0, 31.5, 29.5, 28.9, 28.3. HRMS (TOF ESI+) m/z calculated for C₁₄H₁₅NO₃Br [M+H]⁺: 324.0235, found 324.0231.

Example 8

Late-Stage Oxidation of Aromatic Drug Derivatives

Oxidation of HIV-1 Drug Efavirenz Derivative

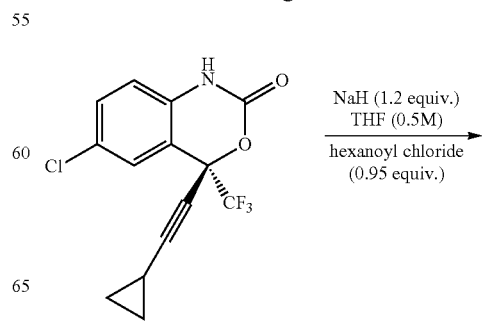

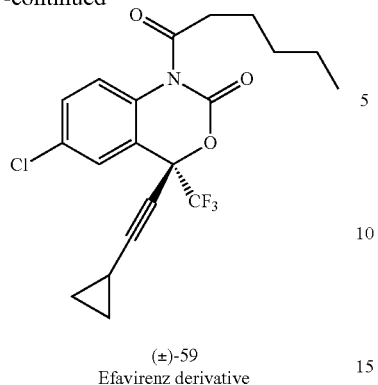

(±)-59
Efavirenz derivative (±)-6-Chloro-4-(cyclopropylethynyl)-1-hexanoyl-4-(trifluoromethyl)-1,4-dihydro-2H-benzo[d][1,3]oxazin-2-one

[59] In a flame dried 50 mL recovery flask charged with (±)-efavirenz (1.263 g, 4.0 mmol, 1.0 equiv.) in anhydrous THF (8 mL, 0.5 M), NaH (95%, 121 mg. 4.8 mmol, 1.2 equiv.) was added at 0° C. and the reaction was kept at 0° C. for 10 min. Hexanoyl chloride (531 μL, 3.8 mmol, 0.95 equiv.) was added and the reaction was stirred at room temperature overnight. The reaction was diluted with water and extracted with ethyl acetate. The organic layer was washed with 30 mL 1 M acetic acid solution, 30 mL sat. NaHCO$_3$ then brine. The combined organic layer was dried over Na$_2$SO$_4$ and concentrated. Purified by CombiFlash (40 g column) flushing with hexanes→100% ethyl acetate/hexanes yield product as a white solid (567 mg, 1.37 mmol) in 34% yield.

$^1$H-NMR (500 MHz, methylene chloride-d$_2$) 7.65 (d, J=8.9 Hz, 1H), 7.61 (d, J=2.4 Hz, 1H), 7.48 (dd, J=8.9, 2.4 Hz, 1H), 3.04-2.98 (m, 1H), 2.90 (dt, J=17.4, 7.4 Hz, 1H), 1.72-1.69 (m, 2H), 1.42-1.30 (m, 5H), 0.94-0.89 (m, 5H), 0.86-0.79 (m, 2H). $^{13}$C-NMR (126 MHz, methylene chloride-d$_2$) δ 173.8, 148.4, 133.0, 132.3, 131.2, 126.9, 125.1, 123.4, 122.5 (q, J=286.5 Hz), 97.4, 78.3 (q, J=35.1 Hz), 65.6, 38.6, 31.7, 25.0, 23.0, 14.2, 9.3, 9.2, −0.3. $^{19}$F-NMR (471 MHz, methylene chloride-d$_2$) δ −78.5. HRMS (TOF ESI+) m/z calculated for C$_{20}$H$_{19}$NO$_3$F$_3$NaCl [M+Na]$^+$: 436.0903, found 436.0893.

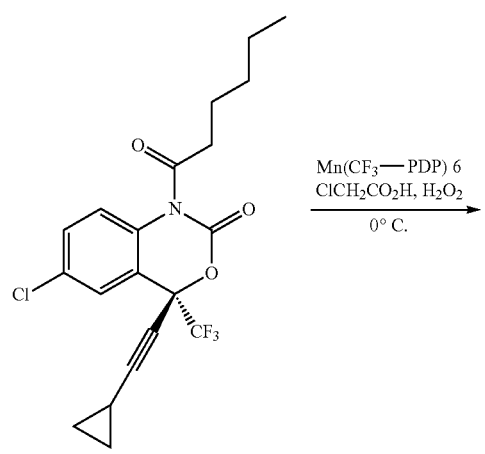

(±)-59
Efavirenz derivative

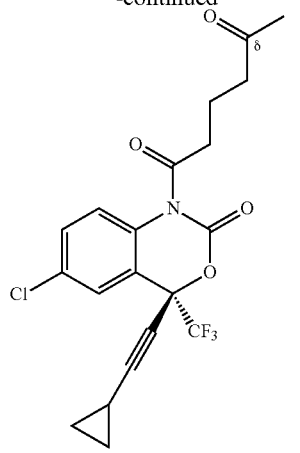

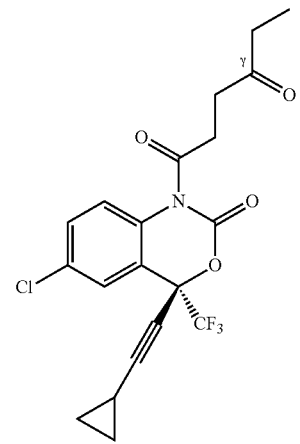 [SMILES: CCC(=O)CCC(=O)N1C(=O)O[C@](C#CC2CC2)(C(F)(F)F)c2cc(Cl)ccc21]

(±)-1-(6-Chloro-4-(cyclopropylethynyl)-2-oxo-4-(trifluoromethyl)-2H-benzo[d][1,3]oxazin-1(4H)-yl)hexane-1,5-dione [60a]. The reaction was run with General Method A: Single Catalyst Addition Protocol. 6-chloro-4-(cyclopropylethynyl)-1-hexanoyl-4-(trifluoromethyl)-1,4-dihydro-2H-benzo[d][1,3]oxazin-2-one 59 (82.8 mg, 0.200 mmol, 1.0 equiv), (R,R)—Mn(CF$_3$-PDP) 1 (27.1 mg, 0.020 mmol, 10 mol %), ClCH$_2$CO$_2$H (284 mg, 3.0 mmol, 15.0 equiv.), 50% wt. H$_2$O$_2$ (136 mg, 2.0 mmol, 10.0 equiv.), MeCN (0.4 mL in 40 mL vial, 2.5 mL with oxidant). The reaction was run at 0° C. with ice bath. The reaction was worked up with 9 mL saturated NaHCO$_3$ and DCM as described in the General Method A. Flash column chromatography on silica (35 mm fritted glass column, 150 mL SiO$_2$) using 10% ethyl acetate/hexanes→25% ethyl acetate/hexanes→50% ethyl acetate/hexanes as eluent afforded δ-ketone (60a) and γ-ketone (60b) products as white solid.

Run 1: (11.3 mg, 0.026 mmol, 13.2% yield of γ-ketone 60b), (36.5 mg, 0.085 mmol, 42.7% yield of δ-ketone 60a), (55.9% overall yield, 3.2:1 δ:γ ratio), (18.3 mg, 0.044 mmol, 22.1% rsm). Run 2: (13.0 mg, 0.030 mmol, 15.2% yield of γ-ketone 60b), (36.9 mg, 0.086 mmol, 43.1% yield of δ-ketone 60a), (58.3% overall yield, 2.8:1 δ:γ ratio), (17.9 mg, 0.043 mmol, 21.6% rsm). Run 3: (12.0 mg, 0.028 mmol, 14.0% yield of γ-ketone 60b), (37.9 mg, 0.089 mmol, 44.3% yield of δ-ketone 60a), (58.3% overall yield, 3.2:1 δ:γ ratio), (21.1 mg, 0.051 mmol, 25.5% rsm). Average: 57.5% yield±1.4%, 3.1:1 δ:γ ratio, 23.1% rsm±2.1%.

$^1$H-NMR (500 MHz, methylene chloride-d$_2$) 7.66 (d, J=8.9 Hz, 1H), 7.62 (d, J=2.4 Hz, 1H), 7.48 (dd, J=8.9, 2.4 Hz, 1H), 3.05 (ddd, J=17.8, 7.7, 6.7 Hz, 1H), 2.91 (dt, J=17.7, 7.3 Hz, 1H), 2.53 (t, J=7.2 Hz, 2H), 2.11 (s, 3H), 1.95 (p, J=7.2 Hz, 2H), 1.41 (tt, J=8.3, 5.0 Hz, 1H), 0.95-0.92 (m, 2H), 0.83 (tdd, J=6.2, 5.5, 3.2 Hz, 2H). $^{13}$C-NMR (126 MHz, methylene chloride-d$_2$) δ 208.0, 173.2, 148.4, 132.8, 132.5, 131.2, 127.0, 125.2, 123.5, 122.5 (q, J=286.7 Hz), 97.6, 78.4 (q, J=35.1 Hz), 65.5, 42.6, 37.6, 30.2, 19.3, 9.3, 9.2, −0.3. $^{19}$F-NMR (471 MHz, methylene chloride-d$_2$) δ −78.5. HRMS (TOF ESI+) m/z calculated for $C_{20}H_{17}NO_4F_3NaCl$ [M+Na]$^+$: 450.0696, found 450.0706.

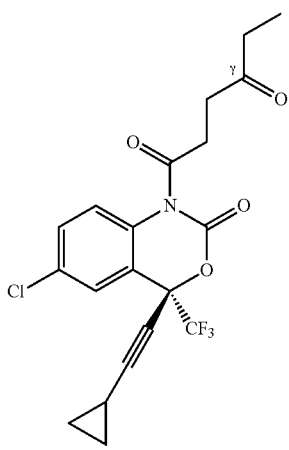

(±)-1-(6-Chloro-4-(cyclopropylethynyl)-2-oxo-4-(trifluoromethyl)-2H-benzo[d][1,3]oxazin-1(4H)-yl)hexane-1,4-dione [60b]. $^1$H-NMR (500 MHz, methylene chloride-d$_2$) 7.61 (d, J=2.5 Hz, 1H), 7.59 (d, J=8.9 Hz, 1H), 7.46 (dd, J=8.9, 2.4 Hz, 1H), 3.28 (ddd, J=18.4, 7.5, 5.0 Hz, 1H), 3.14 (ddd, J=18.4, 7.0, 4.7 Hz, 1H), 2.90-2.78 (m, 2H), 2.49 (q, J=7.4 Hz, 2H), 1.43 (tt, J=8.3, 5.0 Hz, 1H), 1.04 (t, J=7.3 Hz, 3H), 0.95-0.92 (m, 2H), 0.86-0.83 (m, 2H). $^{13}$C-NMR (126 MHz, methylene chloride-d$_2$) δ 209.5, 173.6, 148.1, 133.0, 132.3, 131.3, 127.1, 125.0, 123.1, 122.50 (q, J=286.8 Hz), 97.6, 78.5 (q, J=35.2 Hz), 65.5, 37.2, 36.2, 33.2, 9.24, 9.22, 8.1, −0.2. $^{19}$F-NMR (471 MHz, methylene chloride-d$_2$) δ −78.7. HRMS (TOF ESI+) m/z calculated for $C_{20}H_{17}NO_4F_3NaCl$ [M+Na]$^+$: 450.0696, found 450.0689.

Oxidation of a γ-Secretase Modulator Analogue

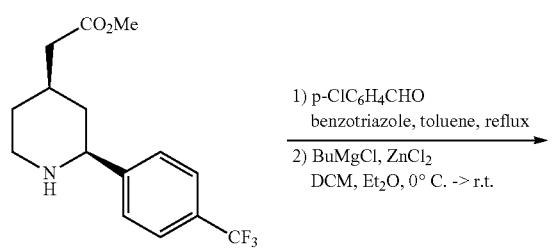

1) p-ClC$_6$H$_4$CHO benzotriazole, toluene, reflux
2) BuMgCl, ZnCl$_2$ DCM, Et$_2$O, 0° C. -> r.t.

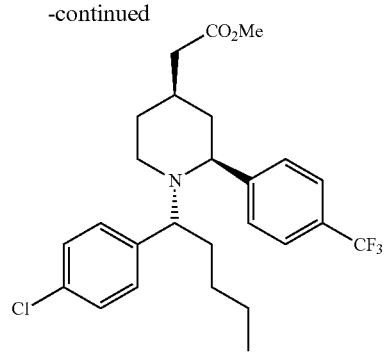

(±)-61

(±)-Methyl 2-((2SR,4RS)-1-((RS)-1-(4-chlorophenyl)pentyl)-2-(4-(trifluoromethyl) phenyl)piperidin-4-yl)acetate [61]. A mixture of methyl (±)-2-((2SR,4RS)-2-(4-(trifluoromethyl)phenyl)piperidin-4-yl)acetate (557 mg, 1.85 mmol, 1.0 equiv.), 4-chlorobenzaldehyde (268 mg, 1.91 mmol, 1.03 equiv.), and benzotriazole (228 mg, 1.91 mmol, 1.03 equiv.) in toluene (10 ml, 0.18 M) was refluxed with a Dean-Stark apparatus for 18 hours. After cooling to room temperature, the solvent was evaporated, and the residual gum was dissolved in CH$_2$Cl$_2$ (17 ml, 0.11 M). In another flask, a solution of ZnCl$_2$.OEt$_2$ (5.8 mL, 5.4 mmol, 1M in Et$_2$O, 3.1 equiv.) was added dropwise to a solution of butylmagnesium chloride (2.8 mL, 5.55 mmol, 2M in Et2O, 3.1 equiv.) in Et$_2$O (3 mL, final concentration=0.48 M) at 0° C. The cooling bath was removed, and the mixture was stirred at room temperature for 1 hour, then recooled in an ice bath. The portion of the solution of the benzotriazole adduct in CH$_2$Cl$_2$ was added over 5 minutes, the cooling bath was removed, and the reaction was stirred at room temperature for 20 hours. After this period, the reaction was quenched with saturated aqueous solution of NH$_4$Cl. The mixture was partitioned with CH$_2$Cl$_2$ and H$_2$O. The aqueous layer was extracted with CH$_2$Cl$_2$ (twice) and the combined extracts were washed with water (once), dried over MgSO$_4$, filtered, and concentrated under reduced pressure. The crude mixture was purified by flash column chromatography on silica eluting 5% EtOAc/hexanes as eluent to yield the desired product (691 mg, 1.43 mmol, 77%) as a colorless oil.

$^1$H-NMR (500 MHz, CDCl$_3$) δ 7.63 (d, J=8.0 Hz, 2H), 7.56 (d, J=7.8 Hz, 2H), 7.29-7.21 (m, 2H), 7.21-7.15 (m, 2H), 3.70 (dd, J=11.0, 2.8 Hz, 1H), 3.62 (s, 3H), 3.41 (dd, J=7.8, 6.2 Hz, 1H), 2.67 (dt, J=11.6, 3.5 Hz, 1H), 2.32 (td, J=11.8, 2.5 Hz, 1H), 2.23 (dd, J=15.3, 6.7 Hz, 1H), 2.16 (dd, J=15.3, 7.5 Hz, 1H), 1.99-1.86 (m, 1H), 1.80 (dq, J=13.0, 3.0 Hz, 1H), 1.77-1.69 (m, 2H), 1.63 (dt, J=13.0, 3.1 Hz, 1H), 1.36-1.27 (m, 1H), 1.21-1.15 (m, 2H), 1.12 (dd, J=12.4, 4.1 Hz, 1H), 1.07-0.98 (m, 1H), 0.80 (t, J=7.3 Hz, 3H), 0.85-0.71 (m, 1H). $^{13}$C-NMR (126 MHz, CDCl$_3$) δ 173.1, 148.8 (q, J=1.0 Hz), 140.5, 132.3, 130.1, 129.7 (q, J=32.3 Hz), 128.2 (2 carbons), 125.8 (q, J=3.4 Hz), 124.3 (q, J=271.8 Hz), 64.6, 60.9, 51.6, 44.6, 42.9, 41.0, 33.9, 32.5, 29.6, 23.0, 22.3, 14.1. $^{19}$F-NMR (470 MHz, CDCl$_3$) δ −62.7. HRMS (TOF ESI+) m/z calcd for $C_{26}H_{32}NO_2F_3Cl$ [M+H]$^+$: 482.2074, found: 482.2068.

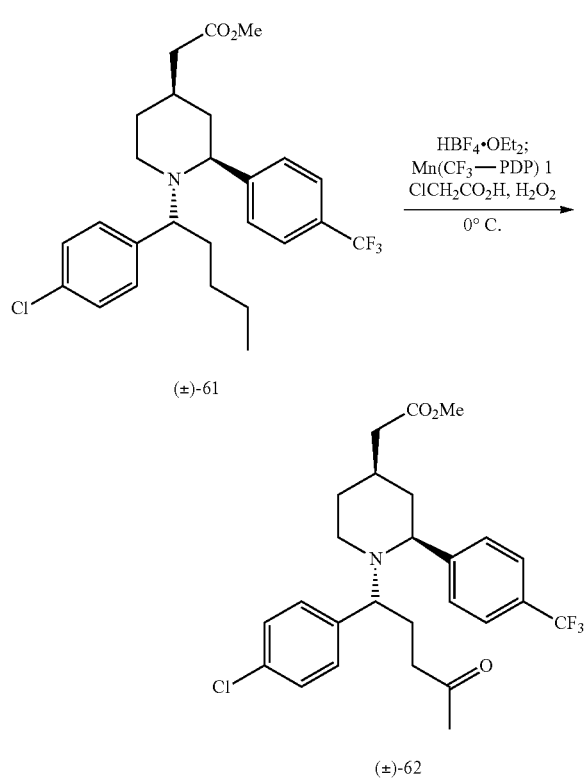

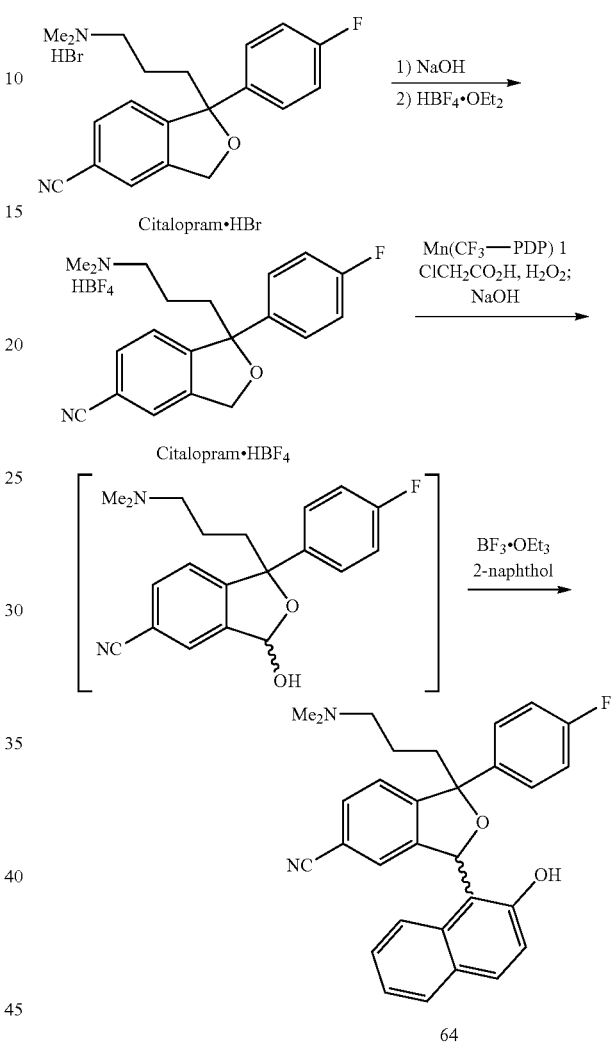

(±)-Methyl 2-((2SR,4RS)-1-((RS)-1-(4-chlorophenyl)-4-oxopentyl)-2-(4-(trifluoro methyl)phenyl)piperidin-4-yl)acetate [62]. Substrate (±)-Methyl 2-((2SR,4RS)-1-((RS)-1-(4-chlorophenyl)pentyl)-2-(4-(trifluoromethyl)phenyl) piperidin-4-yl)acetate 61 (154.0 mg, 0.300 mmol, 1.0 equiv), was protected with $HBF_4 \cdot OEt_2$ (45.5 µL, 0.330 mmol, 54 wt. %, 1.1 equiv.) in $CH_2Cl_2$ (1.2 mL, 0.25M) according to the general procedure for the $HBF_4 \cdot OEt_2$ protection in Table 6. The reaction was run with General Method C: Slow Catalyst Addition Protocol at 0° C.: the resultant $61 \cdot HBF_4$ (0.300 mmol, 1.0 equiv.), $ClCH_2CO_2H$ (425 mg, 4.5 mmol, 15.0 equiv.), (R,R)—Mn(CF$_3$-PDP) (40.7 mg, 0.030 mmol, 10 mol %), 50% wt. $H_2O_2$ (204 mg, 3.0 mmol, 10.0 equiv.), MeCN (0.6 mL in 40 mL vial, 0.38 mL with catalyst, 3.75 mL with oxidant). The reaction was run at 0° C. with ice bath. The reaction was worked up with 9 mL saturated $NaHCO_3$ and DCM as described in General Method C. Flash column chromatography on silica using 15% MeOH/CHCl$_3$ as eluent afforded product as a pale yellow oil.

Run 1: (76.6 mg, 0.154 mmol, 51.5% yield), (23.0 mg, 0.048 mmol, 15.9% rsm). Run 2: (85.3 mg, 0.172 mmol, 57.3% yield), (13.2 mg, 0.027 mmol, 9.1% rsm). Run 3: (84.4 mg, 0.170 mmol, 56.7% yield), (13.8 mg, 0.029 mmol, 9.5% rsm). Average: 55.2% yield±3.2%, 11.5% rsm±3.8%.

$^1$H-NMR (500 MHz, CDCl$_3$) δ7.63 (d, J=8.0 Hz, 2H), 7.57 (d, J=7.9 Hz, 2H), 7.29-7.23 (m, 2H), 7.16-7.09 (m, 2H), 3.72 (dd, J=11.0, 2.8 Hz, 1H), 3.61 (s, 3H), 3.39 (dd, J=10.6, 3.7 Hz, 1H), 2.69 (dt, J=11.4, 3.4 Hz, 1H), 2.38 (td, J=11.8, 2.5 Hz, 1H), 2.27-2.01 (m, 5H), 1.98 (s, 3H), 1.96-1.85 (m, 2H), 1.81 (dq, J=12.9, 2.9 Hz, 1H), 1.64 (dt, J=13.5, 2.5 Hz, 1H), 1.35-1.27 (m, 1H), 1.11 (qd, J=12.2, 3.8 Hz, 1H). $^{13}$C-NMR (126 MHz, CDCl$_3$) δ 207.8, 172.9, 148.5, 139.3, 132.8, 130.0, 129.7 (q, J=32.0 Hz), 128.4, 128.2, 125.8 (q, J=3.8 Hz), 124.2 (q, J=272.1 Hz), 64.4, 60.6, 51.6, 44.4, 42.8, 41.3, 41.0, 33.7, 32.3, 30.1, 16.1. $^{19}$F-NMR (470 MHz, CDCl$_3$) δ -62.7. HRMS (TOF ESI+) m/z calculated for $C_{26}H_{30}NO_3F_3Cl$ [M+H]$^+$: 496.1866, found 496.1858.

Oxidative Derivatization of Antidepressant Citalopram 1-(3-(Dimethylamino)propyl)-1-(4-fluorophenyl)-3-(2-hydroxynaphthalen-1-yl)-1,3-dihydroisobenzofuran-5-carbonitrile [64]. In a 20 mL vial charge with (±)-citalopram-.HBr (commercially available from Sigma-Aldrich, 121.6 mg, 0.30 mmol, 1.0 equiv.) in 3 mL DCM. 3 mL 3M NaOH solution was added and the reaction was stirred for 30 min. The reaction was extracted with 20 mL DCM 3 times and the combined organic layer was dried over $Na_2SO_4$ and concentrated. The residue was transferred into a 40 mL vial and the free amine citalopram was protected with $HBF_4 \cdot OEt_2$ (45.5 µL, 0.330 mmol, 54 wt. %, 1.1 equiv.) in $CH_2Cl_2$ (1.2 mL, 0.25M) according to the general procedure for the $HBF_4 \cdot OEt_2$ protection in Table 6.

The reaction was run with General Method A: Single Catalyst Addition Protocol with slightly modification: the resultant citalopram.HBF$_4$ (0.300 mmol, 1.0 equiv.), $ClCH_2CO_2H$ (425 mg, 4.5 mmol, 15.0 equiv.), (R,R)—Mn (CF$_3$-PDP) (40.7 mg, 0.030 mmol, 10 mol %), 50% wt. $H_2O_2$ (40.8 mg, 0.6 mmol, 2.0 equiv.), MeCN (0.6 mL in 40 mL vial, 0.38 mL with catalyst, 3.75 mL with oxidant). The reaction was run at −36° C. with dry ice/1,2-dichloroethane bath. The reaction was concentrated, redissolved in 15 mL DCM and quenched with 10 mL 1M NaOH solution for 30 min. The aqueous layer was extracted with 20 mL DCM 3 times and the combined organic layer was dried over Na₂SO₄ and concentrated. Flash column chromatography on silica (35 mm fritted glass column, 50 mL SiO₂) using 5% methanol/DCM→10% methanol/DCM→20% methanol/DCM as eluent afforded crude hemiacetal in about 50% yield. The crude hemiacetal was transferred into an oven-dried 40 mL vial and dried on high vacuum overnight. The crude hemiacetal was charged with 2-naphthol (43.3 mg, 0.3 mmol, 1.0 equiv.) and anhydrous DCM (1.6 mL), cooled to −78° C. and BF₃·OEt₂ (73.8 μL, 0.6 mmol, 2.0 equiv.) was added dropwise. The reaction was allowed to react at −78° C. for 1 h and 0° C. for 2 h before diluted with DCM (10 mL) and quenched with 1M NaOH (15 mL) for 20 min. The aqueous layer was extracted with 20 mL DCM 3 times and the combined organic layer was dried over Na₂SO₄ and concentrated. Flash column chromatography on silica (35 mm fritted glass column, 50 mL SiO₂) using 2% methanol/DCM→5% methanol/DCM→10% methanol/DCM→20% methanol/DCM as eluent afforded arylated product as a mixture of diastereomers.

Run 1: 62.9 mg, 0.135 mmol, 3.0:1 d.r., 44.9% yield over 2 steps. Run 2: 59.0 mg, 0.126 mmol, 3.4:1 d.r., 42.2% yield over 2 steps. Run 3: 56.3 mg, 0.121 mmol, 3.2:1 d.r., 40.2% yield over 2 steps. Average: 42.4% yield±2.4%, 3.2:1 d.r.

The site of arylation was assigned based on a combination of ¹H, gHSQC and gHMBC NMRs. The assigned site of reaction matches the arylation of proline-hemiaminal with 2-naphthanol. Major diastereomer: ¹H-NMR (500 MHz, CDCl₃) δ 7.85-7.79 (m, 3H), 7.67-7.63 (m, 2H), 7.55-7.48 (m, 3H), 7.38 (dd, J=7.8, 6.8 Hz, 1H), 7.26-7.25 (m, 1H), 7.12 (s, 1H), 7.07 (t, J=8.6 Hz, 2H), 6.94 (s, 1H), 2.86 (dt, J=12.9, 7.3 Hz, 1H), 2.54 (ddd, J=11.9, 8.3, 6.1 Hz, 1H), 2.41 (s, 6H), 2.46-2.38 (m, 2H), 1.81-1.70 (m, 2H). ¹³C-NMR (126 MHz, CDCl₃) δ 162.4 (d, J=247.2 Hz), 154.9, 148.3, 143.4, 137.3 (d, J=3.0 Hz), 132.9, 132.3, 131.4, 129.3, 129.0, 127.6, 127.2 (d, J=8.1 Hz), 126.2, 123.4, 122.6, 121.0, 120.0, 118.6, 115.9 (d, J=21.4 Hz), 113.0, 112.5, 90.7, 78.7, 58.9, 44.4, 38.7, 21.1. ¹⁹F-NMR (470 MHz, CDCl₃) δ −114.4. HRMS (TOF ESI+) m/z calcd for C₃₀H₂₈N₂O₂F [M+H]⁺: 467.2135, found: 467.2135. Minor diastereomer is mixed with the major diastereomer and cannot be cleanly characterized.

Rapid Access of Drug Lead Metabolite Lead to Piragliatin

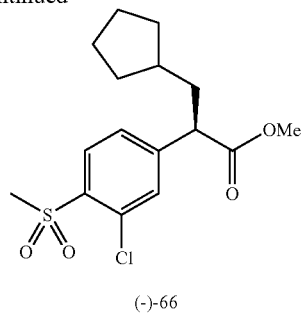

(−)-66

(−)-Methyl (R)-2-(3-chloro-4-(methylsulfonyl)phenyl)-3-cyclopentylpropanoate [(−)-66]. In a flame dried 50 mL recovery flask, (R)-2-(3-chloro-4-(methylsulfonyl)phenyl)-3-cyclopentylpropanoic acid (814 mg, 2.46 mmol, 1.0 equiv.) was dissolved in MeOH (24.6 mL) and cooled to −30° C. SOCl₂ (1.25 mL, 17.2 mmol, 7.0 equiv.) was added dropwise and the reaction was warmed up to room temperature then refluxed at 70° C. for 8 h. The reaction was concentrated and plugged through a silica plug eluting with 40% ethyl acetate/hexanes to afford product as a colorless oil (777.0 mg, 2.25 mmol) in 92% yield. The enantiomeric excess (ee) was determined by chiral HPLC (AD-RH, 55:45 MeCN:H₂O, 0.5 mL/min flow rate, 254 nm): 93%.

¹H-NMR (500 MHz, CDCl₃) δ 8.09 (d, J=8.2 Hz, 1H), 7.53 (d, J=1.6 Hz, 1H), 7.41 (dd, J=8.2, 1.7 Hz, 1H), 3.69 (s, 3H), 3.69-3.65 (m, 1H), 3.26 (s, 3H), 2.09 (ddd, J=13.4, 8.3, 7.2 Hz, 1H), 1.84-1.79 (m, 1H), 1.77-1.71 (m, 2H), 1.63-1.58 (m, 3H), 1.53-1.43 (m, 2H), 1.16-1.05 (m, 2H). ¹³C-NMR (126 MHz, CDCl₃) δ 173.3, 147.2, 136.9, 132.8, 131.5, 131.1, 127.4, 52.6, 50.6, 42.9, 39.9, 37.9, 32.9, 32.3, 25.2 (2 carbons). [α]_D²⁵=−44.8° (c=0.87, CHCl₃). HRMS (TOF ESI+) m/z calcd for C₁₆H₂₂O₄SCl [M+H]⁺: 345.0927, found: 345.0928.

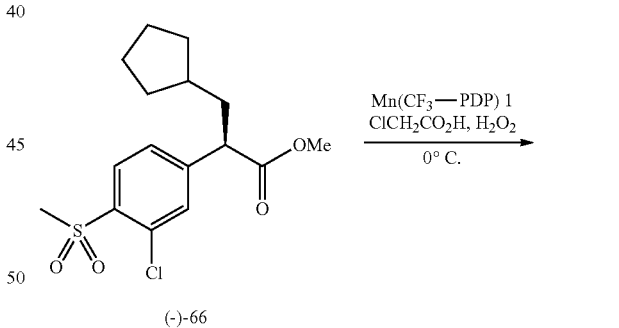

(−)-66

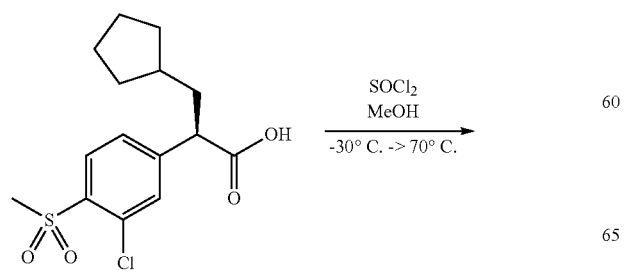

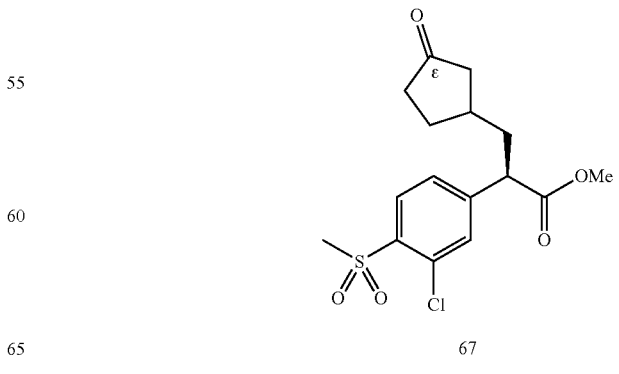

67

Methyl (2R)-2-(3-chloro-4-(methylsulfonyl)phenyl)-3-(3-oxocyclopentyl)propanoate [67]. The reaction was run with General Method A: Single Catalyst Addition Protocol. methyl (R)-2-(3-chloro-4-(methylsulfonyl)phenyl)-3-cyclopentylpropanoate (−)-66 (103.5 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.5 mmol, 15.0 equiv.), 50% wt. H$_2$O$_2$ (204 mg, 3.0 mmol, 10.0 equiv.), MeCN (0.6 mL in 40 mL vial, 3.75 mL with oxidant). The reaction was run at 0° C. with ice bath. The reaction was worked up with 9 mL saturated NaHCO$_3$ and DCM as described in General Method A. Flash column chromatography on silica (35 mm fritted glass column, 100 mL SiO$_2$) using 30% ethyl acetate/hexanes→50% ethyl acetate/as eluent afforded clean ε-ketone (67) as a colorless oil and a fraction of δ-ketone with small impurities.

Run 1: (57.6 mg, 0.161 mmol, 53.5% yield of ε-ketone, 1:1 d.r.), (~14% yield of δ-ketone), <5% rsm. Run 2: (59.2 mg, 0.165 mmol, 55.0% yield of ε-ketone, 1:1 d.r.), (~12% yield of δ-ketone), <5% rsm. Run 3: (58.5 mg, 0.163 mmol, 54.3% yield of ε-ketone, 1:1 d.r.), (~14% yield of δ-ketone), <5% rsm. Average: 54.3% yield±0.8% of ε-ketone, 1:1 d.r., <5% rsm.

ε-ketone 67 was isolated as a mixture of diastereomers with ~1:1 ratio. $^1$H-NMR (500 MHz, methylene chloride-d$_2$) δ 8.08 (dd, J=8.3, 0.9 Hz, 1H), 7.57-7.55 (m, 1H), 7.45-7.42 (m, 1H), 3.74-3.71 (m, 1H), 3.67 (s, 3H), 3.24 (s, 3H), 2.34-1.91 (m, 7H), 1.84-1.75 (m, 1H), 1.58-1.50 (m, 1H). $^{13}$C-NMR (126 MHz, methylene chloride-d$_2$) 217.42 & 217.41, 172.54 & 172.49, 146.42 & 146.37, 137.1, 132.7, 131.35 & 131.32, 131.0, 127.25 & 127.22, 52.4, 49.6 & 49.5, 44.7 & 44.3, 42.7, 38.97 & 38.94, 38.30 & 38.25, 34.98 & 34.92, 29.5 & 29.1. HRMS (TOF ESI+) m/z calculated for C$_{16}$H$_{20}$O$_5$SCl [M+H]$^+$: 359.0720, found 359.0720.

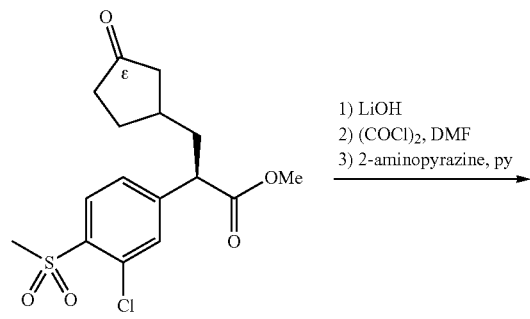

67

(2R)-2-(3-Chloro-4-(methylsulfonyl)phenyl)-3-(3-oxocyclopentyl)-N-(pyrazin-2-yl)propanamide [S53]. In a 20 mL vial charged with methyl (2R)-2-(3-chloro-4-(methylsulfonyl)phenyl)-3-(3-oxocyclopentyl)propanoate 67 (95.9 mg, 0.267 mmol) and 3:1 THF/H$_2$O solution (0.8 mL). LiOHH$_2$O (56.0 mg, 1.335 mmol, 5 equiv,) was added in 1 portion at 0° C. and the reaction was stirred at room temp for 24 hours. The reaction was cooled back to 0° C. and quenched with 1M KHSO$_4$ solution until pH=2. The resulting mixture was extracted with 15 mL ethyl acetate, and the aqueous layer was extracted with 15 mL ethyl acetate twice. Combined organic layer was washed with brine and dried over MgSO$_4$ to obtain the crude acid. After drying under high vacuum overnight, the acid was dissolved in anhydrous DCM (2.7 mL) in an oven dried 20 mL vial, added oxalyl chloride (35 μL, 0.294 mmol, 1.1 equiv.) and 1 drop of DMF at 0° C. The reaction was kept at 0° C. for 10 min then room temp for 25 min to get a soluble solution of acid chloride. A solution of 2-aminopyrazine (55.9 mg, 0.59 mmol, 2.2 equiv.), pyridine (47 μL, 0.59 mmol, 2.2 equiv.) in anhydrous THF (2.2 mL) was added to the reaction and solid was crushed out immediately. The reaction was left at room temp for 24 h, concentrated and purified by flash column chromatography on silica (35 mm fitted glass column, 50 mL SiO$_2$) using 70% ethyl acetate/hexanes→90% ethyl acetate/ as eluent afforded product as a white solid. Result: 60.9 mg, 0.144 mmol, 54% Yield Over 2 Steps Product is a diastereomeric mixture with ~1:1 d.r. $^1$H-NMR (500 MHz, methanol-d$_4$) δ 9.40 (s, 1H), 8.38-8.32 (m, 2H), 8.12 (d, J=8.3 Hz, 1H), 7.82-7.80 (m, 1H), 7.70-7.68 (m, 1H), 4.10-4.04 (m, 1H), 3.34 (s, 3H), 2.44-1.90 (m, 8H), 1.69-1.60 (m, 1H). This NMR matches the reported spectra. The δ-ketone isomer has a benzylic peak at 4.21-4.41 ppm. Better NMR was be obtained by using the more soluble chloroform solvent: $^1$H-NMR (500 MHz, CDCl$_3$) δ 9.51 (s, 1H), 8.43 (t, J=17.1 Hz, 1H), 8.35 (d, J=2.5 Hz, 1H), 8.19 (s, 1H), 8.11 (ddd, J=7.3, 4.6, 2.5 Hz, 1H), 7.63-7.61 (m, 1H), 7.51 (ddd, J=8.4, 3.9, 1.7 Hz, 1H), 3.78-3.77 (m, 1H), 3.28 (s, 3H), 2.47-2.29 (m, 3H), 2.25-1.82 (m, 5H), 1.63-1.55 (m, 1H). $^{13}$C-NMR (126 MHz, CDCl$_3$) 217.9, 169.9, 147.8, 146.6, 146.4, 142.2, 141.0, 137.2, 133.4, 131.7, 131.4 & 131.3, 127.1 & 127.1, 45.0 & 44.7, 43.0, 39.6, 39.68 & 39.53, 39.64 & 39.49, 35.3 & 35.1, 29.8 & 29.6. HRMS (TOF ESI+) m/z calculated for C$_{19}$H$_{21}$N$_3$O$_4$SCl [M+H]$^+$: 422.0941, found 422.0929.

Example 9

Sequential 2° Benzylic/2° Aliphatic Oxidation of Ethinylestradiol Derivative (Scheme 9)

Synthesis of Ethinylestradiol Derivative (−)-69

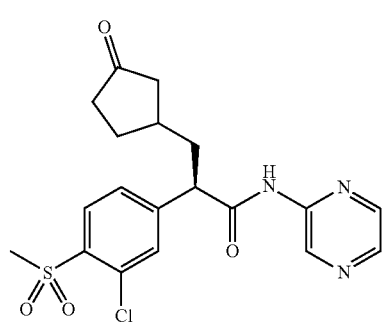

S53

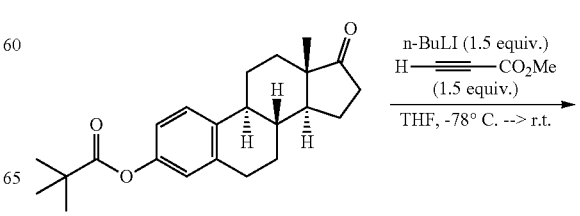

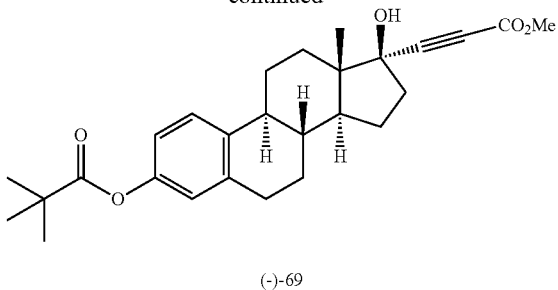

(-)-69

(-)-Methyl 3-((8R,9S,13S,14S,17S)-17-hydroxy-13-methyl-3-(pivaloyloxy)-7,8,9,11,12,13,14,15,16,17-decahydro-6H-cyclopenta[a]phenanthren-17-yl)propiolate [(-)-69]. In a flamed dried 100 mL flask, 2.4 mL (27.0 mmol, 1.5 equiv.) methyl propinolate was dissolved in 36 mL anhydrous THF. 16.9 mL 1.6 M n-BuLi (27.0 mmol, 1.5 equiv.) solution was added slowly at −78° C. and the mixture was stirred at −78° C. for 10 min after which the organolithium reagent solution was cannulated into a 100 mL flame dried flask containing 6.38 g (18.0 mmol, 1.0 equiv.) pivalated estrone in 36 mL anhydrous THF at −78° C. The reaction was stirred at −78° C. for 30 min then at room temperature for 10 min. Saturated NH$_4$Cl was added to quench the reaction and the aqueous layer was extracted with 3×30 mL ether. The combined organic layer was washed with 20 mL brine, dried with MgSO$_4$ and concentrated. The crude mixture was purified by CombiFlash (40 g silica column) using hexanes→30% EtOAc/hexanes gradient eluent to provide 4.60 g (10.48 mmol) of pure product as a slightly yellow solid (58% yield).

$^1$H-NMR (500 MHz, CDCl$_3$) δ 7.27 (d, J=7.3 Hz, 1H), 6.81 (dd, J=8.4, 2.6 Hz, 1H), 6.76 (d, J=2.4 Hz, 1H), 3.79 (s, 3H), 2.87-2.85 (m, 2H), 2.42-2.36 (m, 2H), 2.28 (td, J=11.1, 4.3 Hz, 1H), 2.09-2.02 (m, 2H), 1.90-1.77 (m, 4H), 1.67 (ddd, J=12.0, 10.6, 7.4 Hz, 1H), 1.58-1.37 (m, 4H), 1.34 (s, 9H), 0.90 (s, 3H). $^{13}$C-NMR (126 MHz, CDCl$_3$) δ 177.5, 154.1, 149.0, 138.2, 137.5, 126.4, 121.5, 118.7, 90.9, 80.1, 78.0, 52.9, 50.0, 48.0, 43.7, 39.2, 39.2, 38.8, 33.1, 29.6, 27.3, 27.1, 26.3, 23.1, 12.8. [α]$_D^{23}$=−14.6 (c=0.96, CHCl$_3$). HRMS (TOF ESI+) m/z calculated for C$_{27}$H$_{35}$O$_5$ [M+H]$^+$: 439.2484, found 439.2476.

Scheme 9. Sequential 2° benzylic/2° aliphatic oxidation of ethinylestradiol derivative.

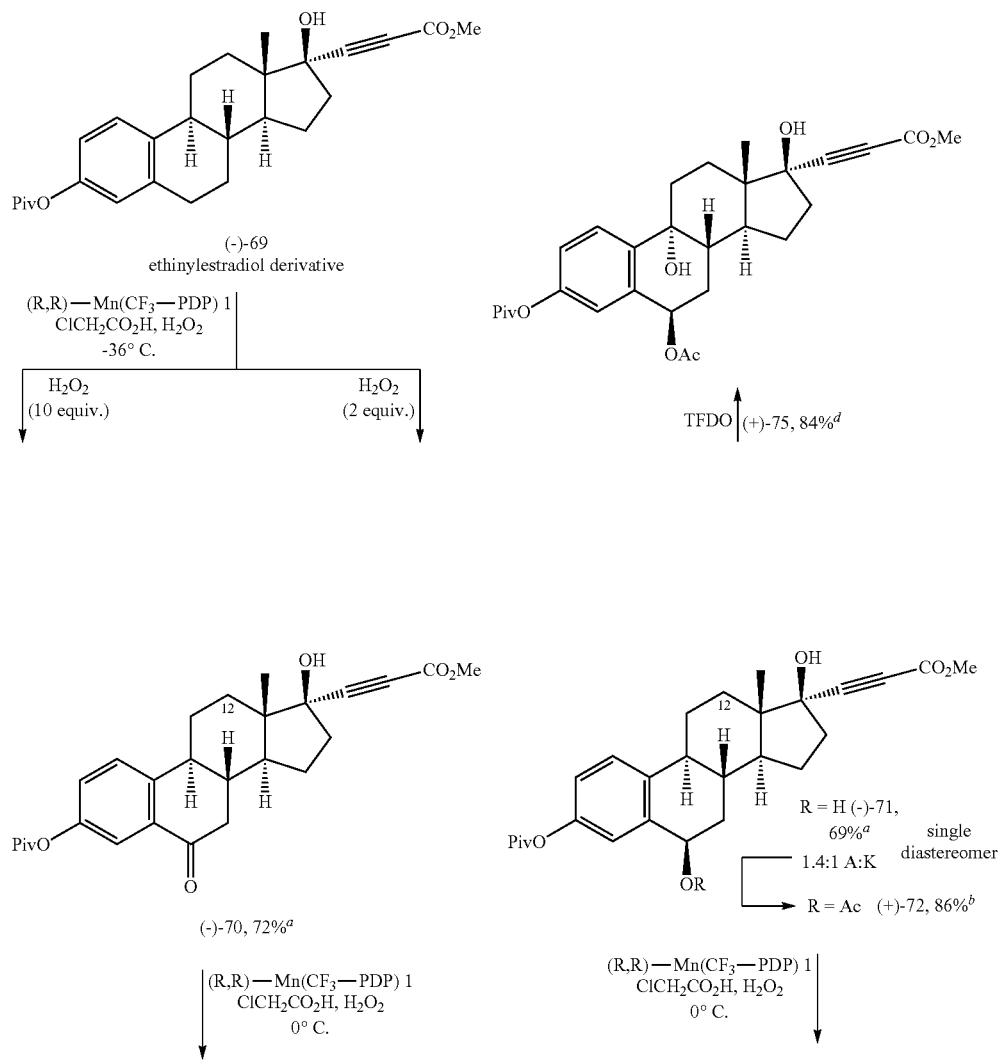

-continued

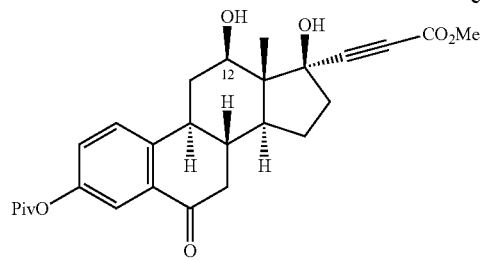

(−)-73, 47%[c]

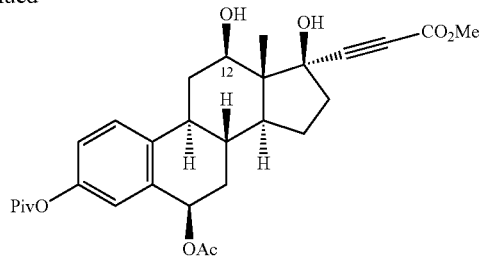

(+)-74, 32%[c]

[a]Method A used with these modifications: 1 (5 mol %), ClCH$_2$CO$_2$H (7.5 equiv.), H$_2$O$_2$ (10 equiv. for 70 or 2 equiv. for 71), 4:1 MeCN:CH$_2$Cl$_2$ at -36° C. [b] Ac$_2$O (2.4 equiv.), NEt$_3$ (2.4 equiv.), CH$_2$Cl$_2$, 86%. [c] Method A used with 4:1 MeCN:CH$_2$Cl$_2$ at 0° C. Crystal structures of 73 and 74 show 12β configuration. [d] Oxidation with TFDO: 72 (0.05 mmol) in CH$_2$Cl$_2$ (0.5 mL) at -20° C. TFDO (0.4M solution, 0.25 mL, 2 equiv.) added at -20° C. and stirred for 40 minutes in dark.

Benzylic Oxidation of Ethinylestradiol Derivative (−)-69

Condition I: The reaction was run with General Method A: Single Catalyst Addition Protocol: methyl 3-((8R,9S,13S,14S,17S)-17-hydroxy-13-methyl-3-(pivaloyloxy)-7,8,9,11,12,13,14,15,16,17-decahydro-6H-cyclopenta[α]phenanthren-17-yl)propiolate (−)-69 (131.6 mg, 0.300 mmol, 1.0 equiv), (R,R)—Mn(CF$_3$-PDP) (20.3 mg, 0.015 mmol, 5 mol %), ClCH$_2$CO$_2$H (213 mg, 2.25 mmol, 7.5 equiv.), 50% wt. H$_2$O$_2$ (204 mg, 3.0 mmol, 10.0 equiv.), 4:1 MeCN:DCM mixture (0.6 mL in 40 mL vial, 3.75 mL with oxidant). The reaction was run at −36° C. with 1,2-dichloroethane/dry ice bath and worked up with 9 mL saturated NaHCO$_3$ and DCM as described in General Method A. Flash column chromatography on silica (35 mm fritted glass column, 150 mm SiO$_2$) using 20% EtOAc/hexanes→25% EtOAc/hexanes→50% EtOAc/hexanes as eluent afforded benzylic ketone oxidation product (−)-70 as a white solid. Run 1: (100.6 mg, 0.222 mmol, 74.1% yield of benzylic ketone (−)-70), 0% rsm. Run 2: (95.9 mg, 0.212 mmol, 70.6% yield of benzylic ketone (−)-70), 0% rsm. Average: 72.4% yield of benzylic ketone (−)-70, 0% rsm.

This oxidation can be scaled up with further reduction of catalyst loading to 2 mol % without loss of reactivity. The reaction was run with General Method A: Single Catalyst Addition Protocol: methyl 3-((8R,9S,13S,14S,17S)-17-hydroxy-13-methyl-3-(pivaloyloxy)-7,8,9,11,12,13,14,15,16,17-decahydro-6H-cyclopenta[a]phenanthren-17-yl)propiolate (−)-69 (1316 mg, 3.0 mmol, 1.0 equiv), (R,R)—Mn(CF$_3$-PDP) (81.3 mg, 0.060 mmol, 2 mol %), ClCH$_2$CO$_2$H (2.126 g, 22.5 mmol, 7.5 equiv.), 50% wt. H$_2$O$_2$ (2040 mg, 30.0 mmol, 10.0 equiv.), 4:1 MeCN:DCM mixture (6 mL in 100 mL recovery flask with a stir bar, 37.5 mL with oxidant in a 60 mL syringe). The reaction was run at −36° C. with 1,2-dichloroethane/dry ice bath and worked up with 40 mL saturated NaHCO$_3$ and DCM as described in General Method A. Run 1: (998.9 mg, 2.207 mmol, 73.6% yield of benzylic ketone (−)-70), 0% rsm.

Condition II: The reaction was run with General Method A: Single Catalyst Addition Protocol: methyl 3-((8R,9S,13S,14S,17S)-17-hydroxy-13-methyl-3-(pivaloyloxy)-7,8,9,11,12,13,14,15,16,17-decahydro-6H-cyclopenta[α]phenanthren-17-yl)propiolate (−)-69 (877.1 mg, 2.000 mmol, 1.0 equiv), (R,R)—Mn(CF$_3$-PDP) (135.5 mg, 0.100 mmol, 5 mol %), ClCH$_2$CO$_2$H (1.418 g, 15.0 mmol, 7.5 equiv.), 50% wt. H$_2$O$_2$ (272 mg, 4.0 mmol, 2.0 equiv.), 4:1 MeCN:DCM mixture (4.0 mL in 50 mL recovery flask, 25.0 mL with oxidant). The reaction was run at −36° C. with 1,2-dichloroethane/dry ice bath and worked up with 30 mL saturated NaHCO$_3$ and DCM as described in General Method A. Flash column chromatography on silica (50 mm fritted glass column, 200 mm SiO$_2$) using 20% EtOAc/hexanes→30% EtOAc/hexanes→40% EtOAc/hexanes→60% EtOAc/hexanes as eluent afforded benzylic ketone oxidation product (−)-70 and benzylic alcohol oxidation product (−)-71 separately as white solids.

Run 1: (359.2 mg, 0.790 mmol, 39.5% yield of benzylic alcohol (−)-71), (262.5 mg, 0.580 mmol, 29.0% yield of benzylic ketone (−)-70), (159.3 mg, 0.363 mmol, 18.2% rsm). Run 2: (386.0 mg, 0.849 mmol, 42.5% yield of benzylic alcohol (−)-71), (248.6 mg, 0.549 mmol, 27.5% yield of benzylic ketone (−)-70), (153.4 mg, 0.350 mmol, 17.5% rsm). Average: 41.0% yield of benzylic alcohol (−)-71, 28.3% yield of benzylic ketone (−)-70, 17.9% rsm.

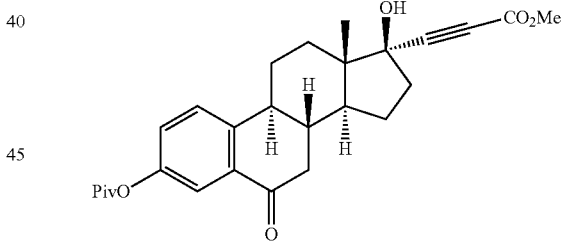

(−)-Methyl 3-((8R,9S,13S,14S,17S)-17-hydroxy-13-methyl-6-oxo-3-(pivaloyloxy)-7,8,9,11,12,13,14,15,16,17-decahydro-6H-cyclopentaialphenanthren-17-yl)propiolate [(−)-70]. $^1$H-NMR (749 MHz, methylene chloride-d$_2$) δ 7.67 (d, J=2.7 Hz, 1H), 7.48 (d, J=8.6 Hz, 1H), 7.24 (dd, J=8.5, 2.7 Hz, 1H), 3.77 (s, 3H), 2.73 (dd, J=16.8, 3.4 Hz, 1H), 2.61 (td, J=10.9, 4.7 Hz, 1H), 2.49 (dtd, J=13.3, 4.4, 2.8 Hz, 1H), 2.39 (ddd, J=14.0, 9.3, 5.8 Hz, 1H), 2.35 (br. s, 1H), 2.31 (dd, J=16.8, 13.4 Hz, 1H), 2.06 (ddd, J=13.9, 12.0, 3.6 Hz, 1H), 2.03-1.99 (m, 1H), 1.92-1.80 (m, 4H), 1.66 (qd, J=12.5, 4.5 Hz, 1H), 1.48-1.41 (m, 1H), 1.35 (s, 9H), 0.91 (s, 3H). $^{13}$C-NMR (126 MHz, methylene chloride-d$_2$) δ 197.2, 177.6, 154.3, 150.3, 144.6, 134.1, 127.4, 127.3, 120.2, 90.7, 80.1, 78.5, 53.3, 50.2, 48.1, 44.2, 43.1, 40.7, 39.5, 39.1, 33.1, 27.4, 26.0, 23.2, 12.8. $[α]_D^{24}$=−40.8 (c=1.00, CHCl$_3$). HRMS (TOF ESI+) m/z calculated for C$_{27}$H$_{33}$O$_6$ [M+H]$^+$: 453.2277, found 453.2274.

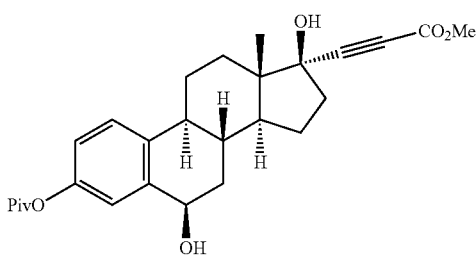

(−)-Methyl 3-((6R,8R,9S,13S,14S,17S)-6,17-dihydroxy-13-methyl-3-(pivaloyloxy)-7,8,9,11,12,13,14,15,16,17-decahydro-6H-cyclopenta[α]phenanthren-17-yl)propiolate [(−)-71]. $^1$H-NMR (749 MHz, methylene chloride-d$_2$) δ 7.35 (d, J=8.6 Hz, 1H), 7.05 (d, J=2.6 Hz, 1H), 6.94 (dd, J=8.5, 2.6 Hz, 1H), 4.76 (br. s, 1H), 3.76 (s, 3H), 2.43-2.40 (m, 1H), 2.37 (ddd, J=13.9, 9.7, 5.7 Hz, 1H), 2.31 (s, 1H), 2.21 (td, J=11.4, 4.4 Hz, 1H), 2.05 (ddd, J=13.9, 11.9, 3.9 Hz, 1H), 2.01-1.98 (m, 2H), 1.85-1.78 (m, 4H), 1.71 (td, J=11.6, 7.5 Hz, 1H), 1.65-1.54 (m, 2H), 1.51-1.45 (m, 1H), 1.34 (s, 9H), 0.92 (s, 3H). $^{13}$C-NMR (126 MHz, methylene chloride-d$_2$) δ 177.8, 154.4, 150.0, 140.0, 138.1, 126.9, 123.0, 121.6, 91.1, 80.3, 78.3, 67.6, 53.2, 50.0, 48.5, 44.1, 39.5, 39.2, 36.6, 33.9, 33.5, 27.4, 26.3, 23.3, 13.0. $[α]_D^{24}$=−34.4 (c=0.98, CHCl$_3$). HRMS (TOF ESI+) m/z calculated for C$_{27}$H$_{34}$O$_6$Na [M+Na]$^+$: 477.2253, found 477.2252. The stereochemistry of the benzylic alcohol was assigned based on the NMR of the following acetate protected compound.

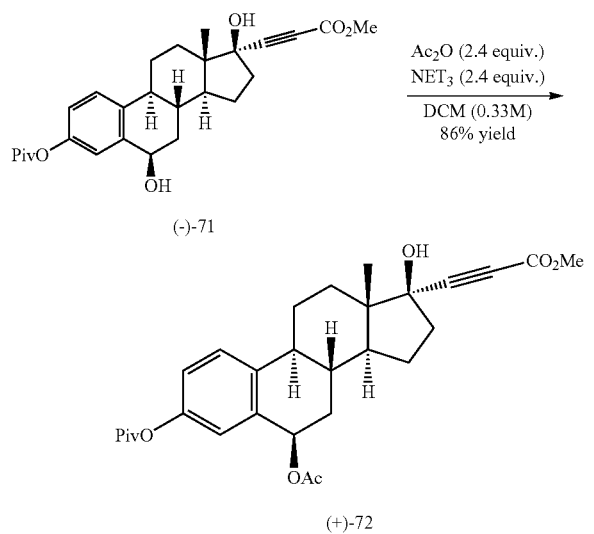

(+)-Methyl 3-((6R,8R,9S,13S,14S,17S)-6-acetoxy-17-hydroxy-13-methyl-3-(pivaloyloxy)-7,8,9,11,12,13,14,15,16,17-decahydro-6H-cyclopenta[α]phenanthren-17-yl)propiolate [(+)-72]. In a 20 mL vial, 444.9 mg (0.98 mmol, 1.0 equiv.) methyl 3-((6R,8R,9S,13S,14S,17S)-6,17-dihydroxy-13-methyl-3-(pivaloyloxy)-7,8,9,11,12,13,14,15,16,17-decahydro-6H-cyclopenta[α]phenanthren-17-yl)propiolate (−)-71 was dissolved in 3 mL anhydrous DCM. 111 μL (1.18 mmol, 1.2 equiv.) acetic anhydride and 164 μL (1.18 mmol, 1.2 equiv.) triethylamine were added sequentially at 0° C. and the reaction was warmed to room temperature. Another batch of both 0.6 equiv. acetic anhydride and 0.6 equiv. triethylamine were added after 24 and 48 hours at room temperature. The crude mixture was loaded directly on silica (50 mm fritted glass column, 200 mm SiO$_2$) using 20% EtOAc/hexanes→50% EtOAc/hexanes gradient eluent gave 419.0 mg (0.84 mmol) of pure product as a white solid (86% yield).

$^1$H-NMR (749 MHz, methylene chloride-d$_2$) δ 7.38 (d, J=8.6 Hz, 1H), 6.98 (dd, J=8.5, 2.6 Hz, 1H), 6.95 (d, J=2.5 Hz, 1H), 5.97 (dd, J=4.4, 2.1 Hz, 1H), 3.76 (s, 3H), 2.44 (dt, J=13.3, 3.8 Hz, 1H), 2.40 (br. s, 1H), 2.37 (ddd, J=13.9, 9.6, 5.6 Hz, 1H), 2.24 (td, J=11.4, 4.4 Hz, 1H), 2.05 (s, 3H), 2.07-2.00 (m, 2H), 1.87-1.77 (m, 4H), 1.71-1.63 (m, 2H), 1.58 (qd, J=12.4, 4.9 Hz, 1H), 1.43 (qd, J=12.1, 5.9 Hz, 1H), 1.33 (s, 9H), 0.93 (s, 3H). $^{13}$C-NMR (126 MHz, methylene chloride-d$_2$) δ 177.7, 170.8, 154.4, 149.9, 138.9, 136.0, 126.9, 123.3, 122.3, 90.9, 80.3, 78.3, 69.4, 53.2, 49.8, 48.4, 44.0, 39.5, 39.2, 34.7, 34.1, 33.4, 27.4, 26.3, 23.3, 21.9, 13.0. $[α]_D^{24}$=+25.1 (c=0.94, CHCl$_3$). HRMS (TOF ESI+) m/z calculated for C$_{29}$H$_{36}$O$_7$Na [M+Na]$^+$: 519.2359, found 519.2355.

Assignment of stereochemistry: 5.97 (dd, J=4.4, 2.1 Hz, 1H) is assigned as the benzylic proton bearing OAc substitution based on HMBC and HSQC $^1$H-$^{13}$C 2D NMRs. The small coupling constants (4.4 Hz and 2.1 Hz) suggests the benzylic proton is in pseudo-equatorial conformation. This assignment can be further confirmed by the single crystal structure of the remote oxidation product.

Remote C12 Methylene Oxidation of (−)-70

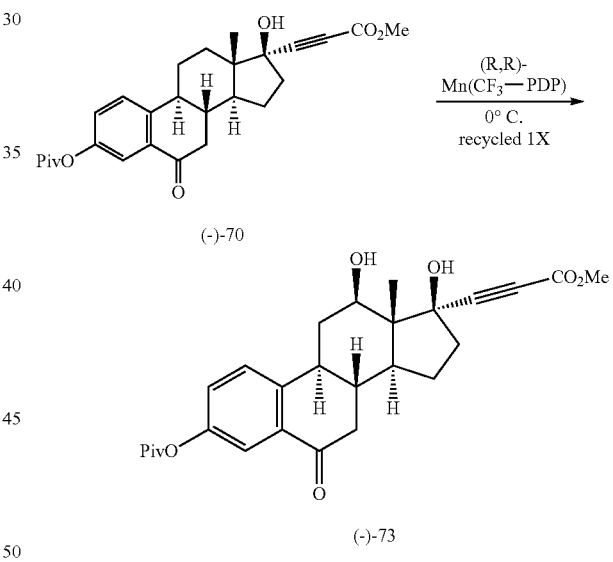

(−)-Methyl 3-((8R,9S,12R,13R,14S,17R)-12,17-dihydroxy-13-methyl-6-oxo-3-(pivaloyloxy)-7,8,9,11,12,13,14,15,16,17-decahydro-6H-cyclopenta[α]phenanthren-17-yl)propiolate [(−)-73]. The reaction was run with General Method A: Single Catalyst Addition Protocol with 1× recycle of the recovered starting material: methyl 3-(8R,9S,13S,14S,17S)-17-hydroxy-13-methyl-6-oxo-3-(pivaloyloxy)-7,8,9,11,12,13,14,15,16,17-decahydro-6H-cyclopenta[α]phenanthren-17-yl)propiolate (−)-70 (135.8 mg, 0.300 mmol, 1.0 equiv), (R,R)—Mn(CF$_3$-PDP) (40.7 mg, 0.030 mmol, 10 mol %), ClCH$_2$CO$_2$H (425 mg, 4.50 mmol, 15.0 equiv.), 50% wt. H$_2$O$_2$ (204 mg, 3.0 mmol, 10.0 equiv.), 4:1 MeCN:DCM mixture (0.6 mL in 40 mL vial, 3.75 mL with oxidant). The reaction was run at 0° C. with ice bath and worked up with 9 mL saturated NaHCO$_3$ and DCM as described in General Method A. Flash column chromatography on silica (35 mm fritted glass column, 150 mm SiO$_2$) using 20% acetone/hexanes→25% acetone/hexanes→40% acetone/hexanes as eluent afforded remote oxidation product (−)-73 and recovered starting material as white solids. The recovered starting material was transferred into a 2-dram vial and re-subjected to single catalyst addition C—H oxidation conditions: (R,R)—Mn(CF$_3$-PDP) (10 mol %), ClCH$_2$CO$_2$H (15.0 equiv.), 50% wt. H$_2$O$_2$ (10.0 equiv.), 4:1 MeCN:DCM mixture (0.25 M with starting material in 2-dram vial to enable full dissolvation of starting material, 1.25 mL per 0.1 mmol starting material with oxidant).

Run 1: cycle 1: (55.6 mg, 0.119 mmol, 39.6% yield), (30.5 mg, 0.067 mmol, 22.5% rsm); cycle 2: (11.5 mg, 0.025 mmol, 36.4% yield), (<5 mg, rsm); overall: (67.1 mg, 0.143 mmol, 47.7% yield), <5% rsm. Run 2: cycle 1: (55.3 mg, 0.118 mmol, 39.3% yield), (31.1 mg, 0.069 mmol, 22.9% rsm); cycle 2: (10.1 mg, 0.022 mmol, 31.3% yield), (<5 mg, rsm); overall: (65.4 mg, 0.140 mmol, 46.5% yield), <5% rsm. Average: 47.1% yield, <5% rsm.

$^1$H-NMR (749 MHz, methylene chloride-d$_2$) δ 7.67 (d, J=2.6 Hz, 1H), 7.45 (d, J=8.6 Hz, 1H), 7.25 (dd, J=8.5, 2.7 Hz, 1H), 4.30 (dd, J=11.2, 4.7 Hz, 1H), 3.77 (s, 3H), 2.80 (br. s, 1H), 2.76-2.71 (m, 2H), 2.56 (dt, J=12.5, 4.7 Hz, 1H), 2.38 (ddd, J=13.9, 9.5, 5.6 Hz, 1H), 2.26 (dd, J=16.9, 13.4 Hz, 1H), 2.16 (br. s, 1H), 2.08 (ddd, J=13.9, 11.9, 4.0 Hz, 1H), 2.00 (dtd, J=13.3, 11.0, 3.5 Hz, 1H), 1.85 (dddd, J=12.1, 9.4, 7.7, 4.0 Hz, 1H), 1.77 (td, J=11.4, 7.7 Hz, 1H), 1.70 (td, J=12.4, 11.2 Hz, 1H), 1.55 (qd, J=12.1, 5.6 Hz, 1H), 1.35 (s, 9H), 0.95 (s, 3H). $^{13}$C-NMR (126 MHz, methylene chloride-d$_2$) δ 196.7, 177.6, 154.3, 150.6, 143.6, 134.0, 127.6, 127.1, 120.4, 90.2, 80.3, 78.5, 74.9, 55.3, 52.0, 49.1, 43.9, 42.1, 39.9, 39.5, 38.4, 34.8, 27.4, 23.0, 7.7. [α]$_D^{24}$=−63.3 (c=1.00, CHCl$_3$). HRMS (TOF ESI+) m/z calculated for C$_{27}$H$_{33}$O$_7$ [M+H]$^+$: 469.2226, found 469.2221.

The site of remote oxidation was assigned based on 2D NMR analysis including DQCOSY, HSQC, HMBC and NOESY. The assignment was further confirmed by the crystal structure of the remote oxidation product (−)-73.

Crystal Structure for (−)-73. Ethanol was added dropwisely to a half dram vial containing 5 mg of (−)-73 with ~0.2 mL hexanes until the material fully dissolved. The vial was loosely capped allowing n-pentane to diffuse into the mixture. Single crystal for X-ray crystallography analysis was obtained in ~2 days. Crystallographic data for 73 can be obtained with deposit number CCDC 1869258. The hydroxyl group protons were located in the difference map and assigned to the most reasonable H-bonding geometries. H1D points toward a void space that is likely at least partially occupied by ethanol, which can act as the acceptor for H1D.

Remote C12 Methylene Oxidation of (+)-72

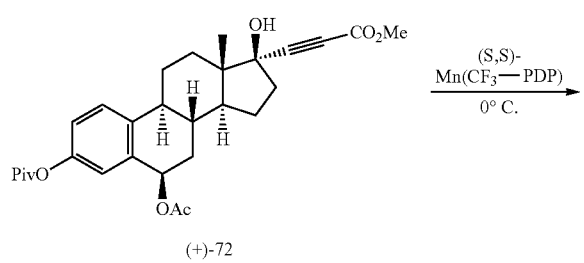

(+)-72

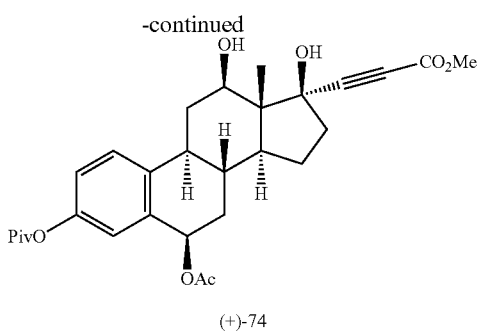

(+)-74

(+)-Methyl 3-((6R,8R,9S,12R,13R,14S,17R)-6-acetoxy-12,17-dihydroxy-13-methyl-3-(pivaloyloxy)-7,8,9,11,12, 13,14,15,16,17-decahydro-6H-cyclopenta[α]phenanthren-17-yl)propiolate [(+)-74]. The reaction was run with General Method A: Single Catalyst Addition Protocol: methyl 3-((6R,8R,9S,13S,14S,17S)-6-acetoxy-17-hydroxy-13-methyl-3-(pivaloyloxy)-7,8,9,11,12,13,14,15,16,17-decahydro-6H-cyclopenta[α]phenanthren-17-yl)propiolate (+)-72 (99.3 mg, 0.200 mmol, 1.0 equiv), (R,R)—Mn(CF$_3$-PDP) (27.1 mg, 0.020 mmol, 10 mol %), ClCH$_2$CO$_2$H (284 mg, 3.00 mmol, 15.0 equiv.), 50% wt. H$_2$O$_2$ (136 mg, 2.0 mmol, 10.0 equiv.), 4:1 MeCN:DCM mixture (0.4 mL in 40 mL vial, 2.50 mL with oxidant). The reaction was run at 0° C. with ice bath. The reaction was worked up with 9 mL saturated NaHCO$_3$ and DCM as described in General Method A. Flash column chromatography on silica (35 mm fritted glass column, 150 mm SiO$_2$) using 20% acetone/hexanes→30% acetone/hexanes→50% acetone/hexanes as eluent afforded remote oxidation product (+)-74 and recovered starting material as white solids.

Run 1: (31.3 mg, 0.061 mmol, 30.5% remote alcohol (+)-74 yield), (16.7 mg, 0.034 mmol, 16.8% rsm); Run 2: (35.1 mg, 0.068 mmol, 34.2% remote alcohol (+)-74 yield), (15.6 mg, 0.031 mmol, 15.7% rsm); Run 3: (31.3 mg, 0.061 mmol, 30.5% remote alcohol (+)-74 yield), (17.7 mg, 0.036 mmol, 17.8% rsm). Average: 31.7%±2.1% remote alcohol (+)-74 yield, 16.8%±1.1% rsm.

$^1$H-NMR (749 MHz, methylene chloride-d$_2$) δ 7.35 (dd, J=8.5, 1.2 Hz, 1H), 6.99 (dd, J=8.5, 2.6 Hz, 1H), 6.97 (d, J=2.5 Hz, 1H), 5.99 (dd, J=4.6, 2.0 Hz, 1H), 4.23 (dd, J=11.1, 4.7 Hz, 1H), 3.76 (s, 3H), 2.92 (br. s, 1H), 2.52 (dt, J=12.5, 4.6 Hz, 1H), 2.38-2.32 (m, 2H), 2.26 (br. s, 1H), 2.09-2.05 (m, 1H), 2.06 (s, 3H), 2.02 (dt, J=14.2, 2.4 Hz, 1H), 1.83 (dtdd, J=13.0, 9.4, 6.4, 3.3 Hz, 1H), 1.77 (ddd, J=13.5, 11.0, 2.6 Hz, 1H), 1.65-1.60 (m, 3H), 1.54 (qd, J=12.0, 5.5 Hz, 1H), 1.33 (s, 9H), 0.98 (s, 3H). $^{13}$C-NMR (126 MHz, methylene chloride-d$_2$) δ 177.7, 170.8, 154.4, 150.1, 138.0, 136.0, 126.7, 123.4, 122.4, 90.6, 80.4, 78.3, 75.3, 69.3, 53.3, 52.4, 48.7, 42.8, 39.5, 38.5, 35.2, 33.9, 33.9, 27.4, 23.1, 21.9, 7.8. [α]$_D^{25}$=+2.7 (c=0.78, CHCl$_3$). HRMS (TOF ESI+) m/z calculated for C$_{29}$H$_{36}$O$_8$Na [M+Na]$^+$: 535.2308, found 535.2304.

The site of remote oxidation was assigned based on 2D NMR analysis including DQCOSY, HSQC, HMBC and NOESY. The assignment was further confirmed by the crystal structure of the remote oxidation product (+)-74.

Crystal structure for (+)-74. Ethyl acetate was added dropwisely to a half dram vial containing 5 mg of (+)-74 with ~0.2 mL n-pentane until the material fully dissolved. The vial was loosely capped allowing n-pentane to diffuse into the mixture. Single crystal for X-ray crystallography analysis was obtained in ~2 days. Crystallographic data for 74 can be obtained with deposit number CCDC 1869259.

Oxidation of (+)-72 with TFDO

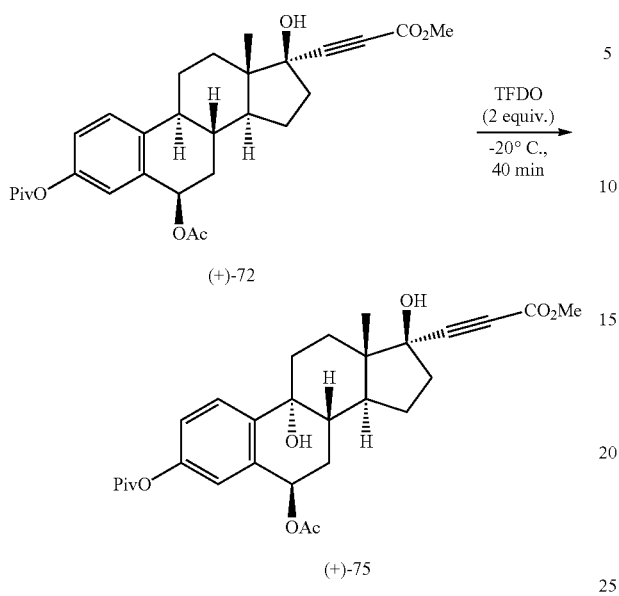

(+)-Methyl 3-((6R,8S,9R,13S,14S,17S)-6-acetoxy-9,17-dihydroxy-13-methyl-3-(pivaloyloxy)-7,8,9,11,12,13,14,15,16,17-decahydro-6H-cyclopenta[a]phenanthren-17-yl)propiolate [(+)-75]. To a 1 dram vial charged with methyl 3-((6R,8R,9S,13S,14S,17S)-6-acetoxy-17-hydroxy-13-methyl-3-(pivaloyloxy)-7,8,9,11,12,13,14,15,16,17-decahydro-6H-cyclopenta[α]phenanthren-17-yl)propiolate (+)-72 (24.8 mg, 0.05 mmol, 1.0 equiv) in 0.5 mL anhydrous DCM (0.1 M). 0.25 mL freshly made TFDO (0.4 M in trifluoroacetone, 0.1 mmol, 2.0 equiv.) was added in 1-2 portions at −20° C. The reaction was wrapped with aluminum foil and allowed to stir at −20° C. The reaction as monitored by TLC and full conversion of starting material was reached after 40 min. The reaction was concentrated and purified by CombiFlash (12 g column) to yield tertiary benzylic alcohol product (+)-75 as white solid.

Run 1: 21.7 mg, 0.042 mmol, 84.6% yield. Run 2: 21.2 mg, 0.041 mmol, 82.7% yield. Average: 83.7% yield.

$^1$H-NMR (500 MHz, methylene chloride-$d_2$) δ 7.59 (d, J=8.6 Hz, 1H), 7.05 (dd, J=8.6, 2.5 Hz, 1H), 7.00 (d, J=2.5 Hz, 1H), 5.98 (dd, J=4.6, 1.9 Hz, 1H), 3.76 (s, 3H), 2.51-2.33 (m, 3H), 2.06 (s, 3H), 2.22-2.02 (m, 5H), 1.86 (td, J=13.7, 4.3 Hz, 1H), 1.78-1.69 (m, 2H), 1.64 (ddd, J=12.7, 4.3, 2.6 Hz, 1H), 1.58 (br. s, 1H), 1.42 (tt, J=12.1, 6.1 Hz, 1H), 1.34 (s, 9H), 0.94 (s, 3H). $^{13}$C-NMR (126 MHz, methylene chloride-$d_2$) δ 177.5, 170.9, 154.4, 151.3, 140.6, 136.0, 126.6, 123.9, 123.0, 91.1, 80.2, 78.2, 69.9, 69.2, 53.3, 48.3, 43.1, 39.5, 39.3, 37.6, 32.9, 29.5, 27.9, 27.4, 23.2, 21.8, 12.3. $[\alpha]_D^{25}$=+17.9 (c=0.61, CHCl$_3$). HRMS (TOF ESI+) m/z calculated for $C_{29}H_{36}O_8Na$ [M+Na]$^+$: 535.2308, found 535.2305.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A complex of Formula III:

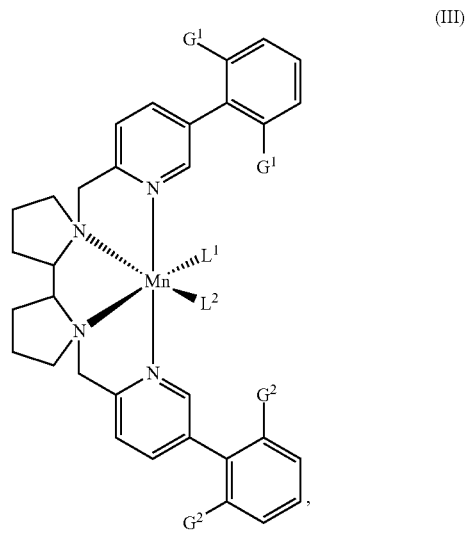

(III)

wherein
L$^1$ and L$^2$ are each independently halo or a ligand;
each G$^1$ and each G$^2$ is independently halo, —(C$_1$-C$_6$)alkyl, —O(C$_1$-C$_6$)alkyl, or —C(=O)O(C$_1$-C$_6$)alkyl, wherein the (C$_1$-C$_6$)alkyl moiety of —(C$_1$-C$_6$)alkyl, —O(C$_1$-C$_6$)alkyl and —C(=O)O(C$_1$-C$_6$)alkyl are optionally substituted with one to three halo groups; wherein each —(C$_1$-C$_6$)alkyl is unbranched or optionally branched;
or salt thereof.

2. The complex of claim 1 wherein the complex is an (S,S) enantiomer.

3. The complex of claim 1 wherein the complex is an (R,R) enantiomer.

4. The complex of claim 1 wherein the complex is a salt and the anion of the salt is Cl$^-$, Br$^-$, AcO$^-$, TfO$^-$, CF$_3$CO$_2^-$, BF$_4^-$, ClO$_4^-$, ReO$_4^-$, AsF$_6^-$, PF$_6^-$, or SbF$_6^-$.

5. The complex of claim 1 wherein L$^1$ and L$^2$ are each independently chloro, acetone, acetonitrile, or a terminal oxo bridge; or L$^1$ and L$^2$ together are a carboxylate group.

6. The complex of claim 1 wherein each G$^1$ and each G$^2$ is independently —(C$_1$-C$_6$)alkyl substituted with one or more halo groups.

7. The complex of claim 1 wherein each G$^1$ is independently chloro, methyl, ethyl, isopropyl, tert-butyl, —OCH$_3$, —C(=O)OCH$_3$, —C(=O)OC(CH$_3$)$_3$, —CF$_3$, —CF$_2$CH$_3$, or —CF$_2$CF$_3$.

8. The complex of claim 1 wherein each G$^1$ and each G$^2$ is independently chloro, methyl, ethyl, isopropyl, tert-butyl, —OCH$_3$, —C(=O)OCH$_3$, —C(=O)OC(CH$_3$)$_3$, —CF$_3$, —CF$_2$CH$_3$, or —CF$_2$CF$_3$.

9. The complex of claim 8 wherein the complex is (R,R)—Mn(CF$_3$-PDP):

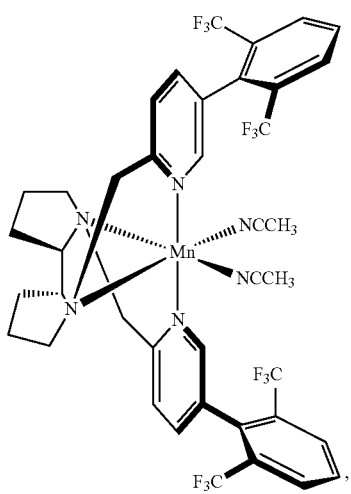

, or salt thereof.

10. A composition comprising a complex of claim 9 in combination with one or more counter ions.

11. The composition of claim 10 wherein the one or more counter ions are $Cl^-$, $Br^-$, $AcO^-$, $TfO^-$, $CF_3CO_2^-$, $BF_4^-$, $ClO_4^-$, $ReO_4^-$, $AsF_6^-$, $PF_6^-$, or $SbF_6^-$; or
the composition in combination with an oxidant and optionally an acid.

12. The composition of claim 11 wherein the oxidant comprises hydrogen peroxide, ozone, a peracid, an alkyl hydroperoxide, a periodinane, or a combination thereof.

13. A method of oxidizing a substrate comprising contacting a substrate with an effective amount of a composition of claim 10, wherein the substrate comprises an aromatic moiety and methylene moiety, and the methylene moiety is selectively oxidized.

14. The method of claim 13 further comprising contacting the substrate with an effective amount of a Lewis acid, a halogenated organic acid, or a combination thereof; or
wherein the methylene moiety comprises an unactivated $sp^3$-hybridized C—H bond.

15. The method of claim 14 wherein the C—H bond is sterically unhindered and is selectively oxidized to an alcohol moiety or a carbonyl moiety.

16. The method of claim 15 wherein the composition is enantiomerically enriched and matched or mismatched to the substrate, the substrate has at least one stereocenter and the C—H bond is selectively oxidized to an alcohol moiety, and the alcohol moiety has the (S)- or (R)-configuration.

17. The complex of claim 1 wherein the complex is $(R,R)$—$Mn(CF_3$-PDP$)Cl_2$:

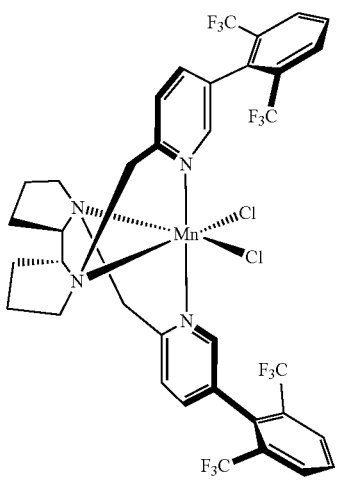

18. The complex of claim 1 wherein the complex is an $SbF_6$ salt.

19. A catalyst wherein the catalyst is $(R,R)$—$Mn(CF_3$-PDP$)(SbF_6)_2$:

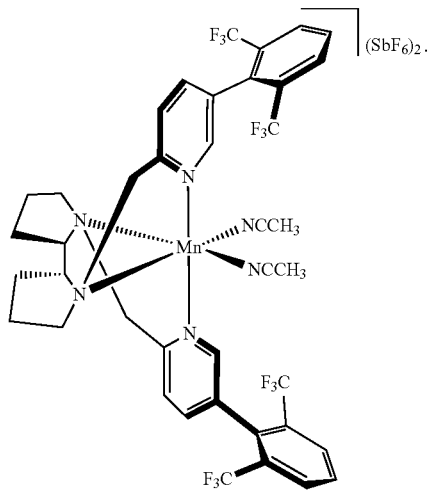

* * * * *